(12) United States Patent
Herndler-Brandstetter et al.

(10) Patent No.: US 11,576,356 B2
(45) Date of Patent: *Feb. 14, 2023

(54) GENETICALLY MODIFIED NON-HUMAN ANIMALS AND METHODS OF USE THEREOF

(71) Applicants: Regeneren Pharmaceuticals, Inc., Tarrytown, NY (US); Yale University, New Haven, CT (US); Institute for Research in Biomedicine (IRB), Bellinzona (CH)

(72) Inventors: Dietmar Herndler-Brandstetter, New Haven, CT (US); Richard A. Flavell, Guilford, CT (US); Davor Frleta, Tarrytown, NY (US); Cagan Gurer, Tarrytown, NY (US); Markus Gabriel Manz, Zollikon (CH); Andrew J. Murphy, Croton-on-Hudson, NY (US); Noah W. Palm, New Haven, CT (US); Liang Shan, New Haven, CT (US); Sean Stevens, Del Mar, CA (US); Till Strowig, Braunschweig (DE); George D. Yancopoulos, Yorktown Heights, NY (US); Marcel de Zoete, Amersfoort (NL)

(73) Assignees: Regeneron Pharmaceuticals, Inc., Tarrytown, NY (US); Yale University, New Haven, CT (US); Institute for Research in Biomedicine (IRB), Bellinzona (CH)

(*) Notice: Subject to any disclaimer, the term of this patent is extended or adjusted under 35 U.S.C. 154(b) by 425 days.

This patent is subject to a terminal disclaimer.

(21) Appl. No.: 16/782,708

(22) Filed: Feb. 5, 2020

(65) Prior Publication Data
US 2020/0229410 A1     Jul. 23, 2020

Related U.S. Application Data

(63) Continuation of application No. 15/954,450, filed on Apr. 16, 2018, now Pat. No. 10,561,126, which is a continuation of application No. 15/097,239, filed on Apr. 12, 2016, now Pat. No. 10,123,518.

(60) Provisional application No. 62/146,938, filed on Apr. 13, 2015, provisional application No. 62/148,667, filed on Apr. 16, 2015, provisional application No. 62/287,842, filed on Jan. 27, 2016.

(51) Int. Cl.
| A01K 67/00 | (2006.01) |
| A01K 67/027 | (2006.01) |
| A61K 49/00 | (2006.01) |

(52) U.S. Cl.
CPC ...... *A01K 67/0278* (2013.01); *A01K 67/0271* (2013.01); *A61K 49/0008* (2013.01); *A01K 2207/12* (2013.01); *A01K 2217/072* (2013.01); *A01K 2217/15* (2013.01); *A01K 2227/105* (2013.01); *A01K 2267/0331* (2013.01); *A01K 2267/0337* (2013.01)

(58) Field of Classification Search
None
See application file for complete search history.

(56) References Cited

U.S. PATENT DOCUMENTS

| 4,736,866 A | 4/1988 | Leder et al. |
| 4,870,009 A | 9/1989 | Evans et al. |
| 5,222,982 A | 6/1993 | Ommaya |
| 5,385,582 A | 1/1995 | Ommaya |
| 5,573,930 A | 11/1996 | Ladner et al. |
| 5,583,278 A | 12/1996 | Alt et al. |
| 5,633,426 A | 5/1997 | Namikawa et al. |
| 5,652,373 A | 7/1997 | Reisner et al. |
| 5,663,481 A | 9/1997 | Gallinger et al. |
| 5,681,729 A | 10/1997 | Kudo et al. |
| 5,709,843 A | 1/1998 | Reisner et al. |
| 5,750,826 A | 5/1998 | Borkowski et al. |
| 5,849,288 A | 12/1998 | Reisner et al. |
| 5,866,757 A | 2/1999 | Reisner et al. |
| 6,018,096 A | 1/2000 | Keating et al. |

(Continued)

FOREIGN PATENT DOCUMENTS

| CN | 1748143 | 3/2006 |
| CN | 101250553 | 8/2008 |

(Continued)

OTHER PUBLICATIONS

Wallace, et al (2007) "Manipulating the Mouse Genome to Engineer Precise Functional Syntenic Replacements with Human Sequence"; Cell vol. 128, Issue 1; pp. 197-209.

(Continued)

*Primary Examiner* — Michael D Burkhart
(74) *Attorney, Agent, or Firm* — Trisha Agrawal; Brian E. Davy; Bozicevic, Field & Francis LLP

(57) ABSTRACT

Genetically modified non-human animals expressing human SIRPα and human IL-15 from the non-human animal genome are provided. Also provided are methods for making non-human animals expressing human SIRPα and human IL-15 from the non-human animal genome, and methods for using non-human animals expressing human SIRPα and human IL-15 from the non-human animal genome. These animals and methods find many uses in the art, including, for example, in modeling human T cell and/or natural killer (NK) cell development and function, in modeling human pathogen infection of human T cells and/or NK cells, and in various in vivo screens.

20 Claims, 56 Drawing Sheets
(23 of 56 Drawing Sheet(s) Filed in Color)
Specification includes a Sequence Listing.

(56) References Cited

U.S. PATENT DOCUMENTS

| | | |
|---|---|---|
| 6,248,721 B1 | 6/2001 | Chang |
| 6,353,150 B1 | 3/2002 | Dick et al. |
| 6,455,756 B1 | 9/2002 | Chen et al. |
| 6,586,251 B2 | 7/2003 | Economides et al. |
| 7,273,753 B2 | 9/2007 | Crawford et al. |
| 7,294,754 B2 | 11/2007 | Poueymirou et al. |
| 7,576,259 B2 | 8/2009 | Poueymirou et al. |
| 7,659,442 B2 | 2/2010 | Poueymirou et al. |
| 7,759,541 B2 | 7/2010 | Wolf et al. |
| 8,541,646 B2 | 9/2013 | Stevens et al. |
| 8,692,052 B2 | 4/2014 | Stevens et al. |
| 8,847,004 B2 | 9/2014 | Murphy et al. |
| 8,878,001 B2 | 11/2014 | Wang et al. |
| 9,127,292 B2 | 9/2015 | Murphy et al. |
| 9,155,290 B2 | 10/2015 | Rojas |
| 9,193,977 B2 | 11/2015 | Murphy et al. |
| 9,301,509 B2 | 4/2016 | Stevens et al. |
| 9,402,377 B2 | 8/2016 | Flavell |
| 9,462,794 B2 | 10/2016 | Murphy et al. |
| 9,554,563 B2 | 1/2017 | Stevens et al. |
| 9,655,352 B2 | 5/2017 | Murphy et al. |
| 9,820,476 B2 | 11/2017 | Flavell et al. |
| 9,901,082 B2 | 2/2018 | Flavell et al. |
| 9,986,724 B2 | 6/2018 | Flavell et al. |
| 10,433,527 B2 | 10/2019 | Flavell et al. |
| 10,561,126 B2 | 2/2020 | Herndler-Brandstetter et al. |
| 2002/0037523 A1 | 3/2002 | Ruben et al. |
| 2003/0028911 A1 | 2/2003 | Huang et al. |
| 2005/0208474 A1 | 9/2005 | Lau et al. |
| 2007/0254842 A1 | 11/2007 | Bankiewicz |
| 2008/0081064 A1 | 4/2008 | Jelle et al. |
| 2008/0311095 A1 | 12/2008 | Holmes et al. |
| 2009/0196903 A1 | 8/2009 | Kliman |
| 2011/0200982 A1 | 8/2011 | Stevens et al. |
| 2012/0157667 A1 | 6/2012 | Chen |
| 2013/0022996 A1 | 1/2013 | Stevens et al. |
| 2013/0024957 A1 | 1/2013 | Stevens et al. |
| 2013/0042330 A1 | 2/2013 | Murphy et al. |
| 2013/0117873 A1 | 5/2013 | Wang et al. |
| 2014/0090095 A1 | 3/2014 | Stevens et al. |
| 2014/0134662 A1 | 5/2014 | Flavell et al. |
| 2015/0047061 A1 | 2/2015 | Murphy et al. |
| 2015/0089678 A1 | 3/2015 | Murphy et al. |
| 2015/0089679 A1 | 3/2015 | Murphy et al. |
| 2015/0208622 A1 | 7/2015 | Flavell et al. |
| 2015/0327524 A1 | 11/2015 | Murphy et al. |
| 2016/0050896 A1 | 10/2016 | Murphy et al. |
| 2016/0295844 A1 | 10/2016 | Herndler-Brandstetter et al. |
| 2016/0366862 A1 | 12/2016 | Flavell et al. |
| 2016/0374321 A1 | 12/2016 | Murphy et al. |
| 2017/0172121 A1 | 6/2017 | Murphy et al. |
| 2017/0273285 A1 | 9/2017 | Murphy et al. |
| 2018/0020647 A1 | 1/2018 | Flavell et al. |
| 2018/0049413 A1 | 2/2018 | Flavell et al. |
| 2018/0295820 A1 | 10/2018 | Herndler-Brandstetter et al. |
| 2019/0297862 A1 | 10/2019 | Stevens et al. |
| 2020/0093105 A1 | 3/2020 | Flavell et al. |
| 2021/0368752 A1 | 12/2021 | Flavell et al. |
| 2022/0000084 A1 | 1/2022 | Murphy et al. |

FOREIGN PATENT DOCUMENTS

| | | |
|---|---|---|
| EP | 0322240 | 6/1989 |
| EP | 0438053 | 7/1991 |
| EP | 0517199 | 12/1992 |
| EP | 1452093 | 9/2004 |
| GB | 2434578 A | 8/2007 |
| JP | 2002501375 | 1/2002 |
| JP | 2009542253 | 12/2009 |
| RU | 2425880 | 2/2011 |
| WO | WO 1988003173 | 5/1988 |
| WO | WO 1989012823 | 12/1989 |
| WO | WO 1991016910 | 11/1991 |
| WO | WO 1991018615 | 12/1991 |
| WO | WO 1993005796 | 4/1993 |
| WO | WO 200115521 | 3/2001 |
| WO | WO 2002066630 | 8/2002 |
| WO | WO 2003018744 | 3/2003 |
| WO | WO 2003039232 | 5/2003 |
| WO | WO 2004005496 | 1/2004 |
| WO | WO 2004022738 | 3/2004 |
| WO | WO 2004044003 | 5/2004 |
| WO | WO 2004060052 | 7/2004 |
| WO | WO 2008069659 | 6/2008 |
| WO | WO 2008153742 | 12/2008 |
| WO | WO 2009034328 | 3/2009 |
| WO | WO 2009042917 | 4/2009 |
| WO | WO 2008010100 | 12/2009 |
| WO | WO 2011002721 | 1/2011 |
| WO | WO 2011002727 | 1/2011 |
| WO | WO 2011044050 | 4/2011 |
| WO | WO 2012040207 | 3/2012 |
| WO | WO 2012051572 | 4/2012 |
| WO | WO 2012112544 | 8/2012 |
| WO | WO 2013063556 | 5/2013 |
| WO | WO 2014039782 | 3/2014 |
| WO | WO 2014071397 | 5/2014 |
| WO | WO 2015042557 | 3/2015 |
| WO | WO 2015179317 | 11/2015 |

OTHER PUBLICATIONS

Lee, et al (2018) "Differences between immunodeficient mice generated by classical gene targeting and CRISPR/Cas9-mediated gene knockout"; Transgenic research, vol. 27, No. 3, pp. 241-251.

Abadie V., et al; (2014) "IL-15: a central regulator of celiac disease immunopathology"; Immunol Rev. 260(1):221-34.

Abboud et al., "Analysis of the Mouse CSF-1 Gene Promoter in a Transgenic Mouse Model" *The Journal of Histochemistry & Cytochemistry*, 51(7):941-949 (2003).

Alves et al.; "Characterization of the thymic IL-7 niche in vivo"; *Proceedings of the National Academy of Sciences*, 1 06(5); pp. 1512-1517, (2009).

Angulo-Barturen Inigo, et al; "A Murine Model of falciparum-Malaria by In Vivo Selection of Competent Strains in Non-Myelodepleted Mice Engrafted with Human Erythrocytes"; *PLoS One*, vol. 3. No. 5; May 2008, pp. 1-14; XP055166984.

Appenheimer et al (2007) "Conservation of IL-6 trans-signaling mechanisms controlling L-selectin adhesion by fever-range thermal stress"; Eur J Immunol. 37(10):2856-67.

Arranz Eduardo and Garrote Jose A. (2011) "IL-15 modulates the effect of retinoic acid, promoting inflammation rather than oral tolerance to dietary antigen"; *Expert Rev. Gastroenterol. Hepatol.* 5(3); pp. 315-317.

Auffray et al., (2009), "Blood monocytes: development, heterogeneity, and relationship with dendritic cells"; *Annual review of immunology* 27, 669-692.

Badell et al. (2000) "Human malaria in immunocompromised mice: an in vivo model to study defense mechanisms against Plasmodium falciparum"; *JEM* 192(11): pp. 1653-1659.

Baenziger et al., (2006), "Disseminated and Sustained HIV Infection in CD34+ Cord Blood Cell-Transplanted Rag2—/—γc—/— Mice"; *Proc Natl Acad Sci USA* 103: pp. 15951-15956.

Bartley, T.D. et al. (1994) Identification and cloning of a megakaryocyte growth and development factor that is a ligand for the cytokine receptor Mpl, *Cell* 77:1117-1124. (Abstract).

Becker et al., (2010), "Generation of Human Antigen-Specific Monoclonal IgM Antibodies Using Vaccinated Human Immune System Mice"; *PLoS One* 5(10); pp. 1-10.

Bergsagel et al.; (2005); "Cyclin D dysregulation: an early and unifying pathogenic event in multiple myeloma"; *Blood* 106: pp. 296-303.

Bernard, et al; "Establishing humanized mice using stem cells: maximizing the potential"; Clinical & Experimental Immunology vol. 152, Issue 3, pp. 406-414, (Jun. 2008).

Biedzka-Sarek; et al. "How to outwit the enemy: dendritic cells face *Salmonella*", *APMIS* 114 (9); (Sep. 2006): pp. 589-600.

Billerbeck, et al (2011) "Development of human CD4+FoxP3+ regulatory T cells in human stem cell factor-, granulocyte-

(56) References Cited

OTHER PUBLICATIONS macrophage colony-stimulating factor-, and interleukin-3-expressing NOD-SCID IL2Rγ(null) humanized mice"; Blood 117(11); pp. 3076-3086.

Bingle et al., (2002), "The role of tumour-associated macrophages in tumour progression: implications for new anticancer therapies"; T Journal of pathology 196: pp. 254-265.

Bird et al., (1988), "Single-Chain Antigen-Binding Proteins"; Science 242: pp. 423-426.

Bock; et al. "Improved Engraftment of Humanized Hematopoeitic Cells in Severe Combined Immunodeficient (SCID) Mice Carrying Human Cytokine Transgenes", Journal of Exp. Med. 182; (Dec. 1995),:pp. 2037-2043.

Bosma et al. (1989), "The mouse mutation severe combined immune deficiency (scid) is on chromosome 16"; Immunogenetics 29: pp. 54-56.

Brehm; et al."Parameters for establishing humanized mouse models to study human immunity: Analysis of human hematopoeitic stem cell engraftment in three immunodeficient strains of mice bearing the IL2rγ null mutation", Clinical Immunology 135; (2010): pp. 84-98.

Brehm et al., (2012), "Engraftment of human HSCs in nonirradiated newborn NOD-scid IL2rγ$^{null}$ mice is enhanced by transgenic expression of membrane-bound human SCF", Blood 119: pp. 2778-2788.

Burger et al., (2001) "Gp130 and ras mediated signaling in human plasma cell line INA-6: a cytokine-regulated tumor model for plasmacytoma"; Hematol J, 2(1): pp. 42-53.

Campbell et al., "Neurologic disease induced in transgenic mice by cerebral overexpression of interleukin 6," Proc. Natl. Acad. Sci. USA, 90: pp. 10061-10065; (1993).

Calvi; et al. "Osteoblastic cells regulate the haematopoietic stem cell niche", Nature 425 (Oct. 2003),:841-846.

Carstea, et al. (2009) "Germline competence of mouse ES and iPS cell lines: Chimera technologies and genetic background"; World Journals of Stem Cells, vol. 1, No. 1; pp. 22-29.

Chang, et al (2015) "Anti-CCR4 monoclonal antibody enhances antitumor immunity by modulating tumor-infiltrating Tregs in an ovarian cancer xenograft humanized mouse model"; Oncoimmunology 5(3):e1090075. 14 pages.

Chen et al., "Expression of human cytokines dramatically improves reconstitution of specific human-blood lineage cells in humanized mice" PNAS 106(51): (Dec. 22, 2009) 21783-21788.

Chen et al., (2012) "Human extramedullary bone marrow in mice: a novel in vivo model of genetically controlled hematopoietic microenvironment"; Blood 119(21); pp. 4971-4980.

Cheng et al., "Therapeutic Antibodies Targeting CSF1 Impede Macrophage Recruitment in a Xenograft Model of Tenosynovial Giant Cell Tumor" Sarcoma, Article ID 174528, pp. 1-7 (2010).

Chicha et al. "Human Adaptive Immune System Rag2-/- γc -/- Mice"; Annals of NY Academy of Science 104; (2005); pp. 236-243.

Chng et al., (2005), "A validated FISH trisomy index demonstrates the hyperdiploid and nonhyperdiploid dichotomy in MGUS" Blood 106(6): pp. 2156-2161.

Chow et al., (2011), "Studying the mononuclear phagocyte system in the molecular age" Nature reviews Immunology 11: pp. 788-798.

Clark, et al.; "A future for transgenic livestock", Natures Reviews, vol. 4; (Oct. 2003); pp. 825-833.

Cocco; et al. "CD34+ Cord Blood Cell-Transplanted Rag2-/-γc-/- Mice as a Model for Epstein-Barr Virus Infection"; The American Journal of Pathology 173(5): (Nov. 2008), 1369-1378.

Coussens et al.,(2013) "Neutralizing tumor-promoting chronic inflammation: a magic bullet?"; Science 339: pp. 286-291.

Cros et al., (2010), "Human CD14$^{dim}$ Monocytes Patrol and Sense Nucleic Acids and Viruses via TLR7 and TLR8 Receptors"; Immunity 33: pp. 375-386.

Cuende, et al (2015) "Monoclonal antibodies against GARP/TGF-β1 complexes inhibit the immunosuppressive activity of human regulatory T cells in vivo"; Sci Transl Med. 7(284):284ra56; pp. 1-13.

Dai et al., "Incomplete restoration of colony-stimulating factor 1 (CSF-1) function in CSF-1-deficient Csf1op/Csf1op mice by transgenic expression of cell surface CSF-1" Blood 103(3):1114-1123 (Feb. 1, 2004).

Danos et al. (1988) "Safe and efficient generation of recombinant retroviruses with amphotropic and ecotropic host ranges"; PNAS 85(17): pp. 6460-6464.

Dao; et al. "Immunodeficient mice as models of human hematopoietic stem cell engraftment", Current Opinion in Immunol 11: (1999), 532-537.

Das, et al (2016) "Microenvironment-dependent growth of preneoplastic and malignant plasma cells in humanized mice"; Nat Med. 22(11); pp. 1351-1357.

Denning, et al (2001) "Deletion of the alpha(1,3)galactosyl transferase (GGTA1) gene and the prion protein (PrP) gene in sheep"; Nat Biotech;19; pp. 559-562.

Dennis Melvin B. (2002) "Welfare issues of genetically modified animals"; ILAR Journal, vol. 43, No. 2, pp. 100-109.

Denton PW, et al. (2012) "IL-2 receptor γ-chain molecule is critical for intestinal T-cell reconstitution in humanized mice"; Mucosal Immunol; 5(5); pp. 555-566.

Depaolo, et al. (2011) "Co-adjuvant effects of retinoic acid and IL-15 induce inflammatory immunity to dietary antigens"; Nature. 471; pp. 220-224.

De Raeve and Vanderkerken, (2005), "The role of the bone marrow microenvironment in multiple myeloma"; Histol Histopathol. 20: pp. 1227-1250.

De Sauvage, F.J. et al. (1994) "Stimulation of megakaryocytopoiesis and thrombopoiesis by the c-Mpl ligand"; Nature 369: pp. 533-538.

Dewan et al., (2004), "Prompt tumor formation and maintenance of constitutive NF-κB activity of multiple myeloma cells in NOD/SCID/γc$^{null}$ mice"; Cancer Sci. 95:564-568.

Dhodapkar, (2009), "Myeloid neighborhood in myeloma: Cancer's underbelly" Am J Hematol. 84: pp. 395-396.

Diminici et al. (2006) "Minimal criteria for defining multipotent mesenchymal stromal cells, The International Society for Cellular Therapy position statement"; Cytotherapy 8: pp. 315-317.

Drake, et al. (2012) "Engineering humanized mice for improved hematopoietic reconstitution"; Cell Mol Immunol. 9(3); pp. 215-224.

Egeblad et al., (2010), "Tumors as organs: complex tissues that interface with the entire Organism"; Developmental Cell 18: pp. 884-901.

Eisenbarth et al.; "Development and Characterization of a Human IL-7 Transgenic Humanized Mouse Model,"; iwhm2, 2nd International Workshop on Humanized Mice, Program & Abstract Book; Sint Olofskapel, Amsterdam, The Netherlands, Apr. 3-6, 2009, Abstract #19.

El-Ad et al. (2013) "viSNE enables visualization of high dimensional single-cell data and reveals phenotypic heterogeneity of leukemia"; Nat. Biotechnol. 31(6); pp. 545-552.

Erta M. et al., (2012) "Interleukin-6, a major cytokine in the central nervous system"; Int J Biol Sci. 8(9):1254-66. doi: 10.7150/ijbs. 4679. Epub Oct. 25, 2012.

Epstein et al., (2005), "The SCID-hu myeloma model"; Methods Mol Med, 113: pp. 183-190.

Extended European Search Report for EP Application No. 16157878.6 dated May 23, 2016.

Fattori, et al., (1994) "Development of Progressive Kidney Damage and Myeloma Kidney in Interleukin-6 Transgenic Mice," Blood, 83(9): 2570-2579.

Fattori et al., (1995)"IL-6 Expression in Neurons of Transgenic Mice Causes Reactive Astrocytosis and Increase in Ramified Microglial Cells but no Neuronal Damage," European Journal of D Neuroscience, 7: 2441-2449.

Felix, R. et al. (1990) "Macrophage colony stimulating factor restores In Vivo bone resorption in the OP/OP osteopetrotic mouse"; Endocrinology 127: pp. 2592-2594.

Fisher et al.; (1993) "Lymphoprolierative Disorders in an IL-7 Transgenic Mouse Line"; Leukemia, 7(2): pp. 566-568.

Flavell, Richard A. "Tissue-resident T cells in a novel humanized mouse model" Presentation: CSH Meeting, Apr. 16, 2015; 23 pages.

(56) References Cited

OTHER PUBLICATIONS

Fonseca et al., (2002), "Genomic abnormalities in monoclonal gammopathy of undetermined significance" *Blood* 100: pp. 1417-1424.
Foss et al; "Frequent Expression of IL-7 Gene Transcripts in Tumor Cells of Classical Hodgkin's Disease"; *American Journal of Pathology*, 146(1): pp. 33-39, (1995).
Fox, N., et al. (2002) "Thrombopoietin expands hematopoietic stem cells after transplantation"; *J Clin Invest* 110: pp. 389-394.
Freeden Jeffry et al.; "Lymphopenia in Interleukin (IL)-7 Gene-deleted Mice Identifies IL-7 as a Nonredundant Cytokine"; *J. Exp. Med.*, 181; pp. 1519-1526, (1995).
Fry et al., "A potential role for interleukin-7 in T-cell homeostasis," *Blood*, 97: 2983-2990, (2001).
Fry et al., "IL-7 comes of age," *Blood*, 107(1): pp. 2587-2588, (2006).
Fry et al., "The Many Faces of IL-7: From Lymphopoiesis to Peripheral T Cell Maintenance,"; *Journal of Immunology*, 174: pp. 6571-6576, (2005).
Fry, et al., "Interleukin-7: from bench to clinic," *Blood*, 99(11): pp. 3892-3904, (2002).
Fukuchi, Y., et al., "Cytokine dependent growth of human TF-1 leukemic cell line in human GMCSF and IL-3 producing transgenic SCID mice"; *Leukemia Research*, vol. 22; (1998); pp. 837-843.
Galán J.E. & Curtiss, R. (1991) Distribution of the invA, -B, -C, and -D genes of *S. thyphimurium* among other *Salmonella*. Serovars: invA mutants of *Salmonella typhi* are deficient for entry into mammalian cells; *Infect. Immun.* 59(9): pp. 2901-2908.
Garcia, Sylvie, et al; "Humanized mice: Current states an perspectives"; *Immunology Letters*, Elsevier BV, NL, vol. 146, No. 1-2; Aug. 30, 2012; pp. 1-7; XP002681730.
Geiselhart et al., "IL-7 Administration Alters the CD4: CD8 Ratio, Increases T Cell Numbers, and Increases T Cell Function in the Absence of Activation," *The Journal of Immunology*, 166: 3019-3027; (2001).
Goldman; et al. "BMP4 regulates the hematopoietic stem cell niche", *Blood* 114(20); (Nov. 2009) pp. 4393-4401.
Goodwin et al.; "Human interleukin 7: Molecular cloning and growth factor activity on human and murine B-lineage cells"; *Proc. Natl. Acad. Sci. USA*, 86: pp. 302-306, (1989).
Goldman, et al. (2004) "Transgenic animals in medicine: integration and expression of foreign genes, theoretical and applied aspects"; *Med Sci Monit*, vol. 10, No. 11; pp. RA274-285.
Gorantla; et al. "Human Immunodeficiency Virus Type 1 Pathobiology Studied in Humanized BALB/c-Rag2-/-Yc-/- Mice", *Journal of Virology* 81(6): (Mar. 2007), 2700-2712.
Goya et al., "Sustained interleukin-6 signalling leads to the development of lymphoid organ-like structures in the lung": *Journal of Pathology*, 200: pp. 82-87, (2003).
Greenblatt, et al. (2012) "Graft versus host disease in the bone marrow, liver and thymus humanized mouse model"; *PLoS One* 7(9); e44664.
Greiner; et al. "Improved Engraftment of Human Spleen Cells in NOD/LtSz-scid/scid Mice as Compared with C. B-17-scid/scid Mice", *American Journal of Pathology* 146(4): (Apr. 1995), 888-902.
Groen, R. W. J., et al; "Reconstructing the human hematopoietic niche in immunodeficient mice: opportunities for studying primary multiple myeloma"; *Blood*, vol. 120, No. 3, May 31, 2012; pp. e9-e16, XP055113167.
Guimond et al.; "Cytokine Signals in T-Cell Homeostasis"; *J. Immunother*, 28; (2005); pp. 289-294.
Haley, (2003), "Species differences in the structure and function of the immune System"; *Toxicology* 188: pp. 49-71.
Hao et al., (2012), Macrophages in tumor microenvironments and the progression of tumors; *Clinical & developmental immunology* 2012: 948098.
Hayakawa J., et al, (2009), "Busulfan produces efficient human cell engraftment in NOD/LtSz-Scid IL2Rgamma(null) mice"; *Stem Cells*, 27(1): pp. 175-182.

Hayday Adrian and Viney Joanne L. (2000) "The ins and outs of body surface immunology"; *Science* 290(5489); pp. 97-100.
Heinrich et al., "Interleukin-6 and the acute phase response," *Biochem. J.*, 265: 621-636, (1990).
Hideshima et al., (2007), "Understanding multiple myeloma pathogenesis in the bone marrow to identify new therapeutic targets"; *Nat Rev Cancer.* 7: pp. 585-598.
Hiramatsu, Hidefumi, et al. (2003) "Complete reconstitution of human lymphocytes from cord blood CD34+ cells using the NOD/SCID/γcnull mice model"; *Blood*, vol. 102, No. 3; Aug. 1, 2003; pp. 873-880.
Hirano et al., Purification to homogeneity and characterization of human B-cell differentiation factor (BCDF or BSFp-2), Proc. *Natl. Acad. Sci. USA*, 82: pp. 5490-5494, (1985).
Hirano et al., "Complementary DNA for a novel human interleukin (BSF-2) that induces B lymphocytes to produce immunoglobulin," *Nature*, 324: pp. 73-76, (1986).
Hirano et al., "Biological and clinical aspects of interleukin 6"; *Immunology*, 11: pp. 443-449, (1990).
Hirota et al., "Continuous activation of gp130, a signal-transducing receptor component for interleukin 6-related cytokines, causes myocardial hypertrophy in mice"; *Proc. Natl. Acad. Sci. D USA*, 92: pp. 4862-4866, (1995).
Hofer; et al. "RAG2-/-yc-/-Mice Transplanted with CD34+ Cells from Human Cord Blood Show Low Levels of Intestinal Engraftment and Are Resistant to Rectal Transmission of Human Immunodeficiency Virus", *Journal of Virology* 82(24): (Dec. 2008), 12145-12153.
Hofker Marten H., et al., Transgenic mouse methods and protocols, Methods in molecular biology, vol. 209 (2002-2003), p. 51-58.
Holyoake et al. (1999) "Functional differences between transplantable human hematopoietic stem cells from fetal liver, cord blood, and adult marrow"; *Exp Hematol.* 27(9): pp. 1418-1427.
Houdebine, Louis-Marie (2007) "Transgenic animal models in biomedical research"; *Methods in Molecular Biology*, vol. 360; pp. 163-202.
Houdebine Louis-Marie (2009) "Methods to Generate Transgenic Animals"; *Genetic Engineering in Livestock: New Applications and Interdisciplinary Perspectives*; pp. 31-48.
Hu, Z. et al; "Macrophages prevent human red blood cell reconstitution in immunodeficient mice"; *Blood*, vol. 118, No. 22; Nov. 24, 2011; pp. 5938-5946.
Huo; et al. "Humanized Mouse Model of Cooley's Anemia", *J. Biol. Chem* 284(8): (Feb. 2009), 4889-4896.
Huntington et al., (2009), "IL-15 trans-presentation promotes human NK cell development and differentiation in vivo"; *Journal of experimental medicine* 206(1); pp. 25.
Huston et al., (1988), "Protein engineering of antibody binding sites: recovery of specific activity in an anti-digoxin single-chain Fv analogue produced in *Escherichia coli*"; *Proc. Natl. Acad. Sci. USA* 85(16): pp. 5879-5883.
Inagaki et al. (2000) "SHPS-1 regulates integrin-mediated cytoskeletal reorganization and cell motility"; EMBO J. 19(24); pp. 6721-6731.
Irvine et al., "Colony-stimulating factor-1 (CSF-1) delivers a proatherogenic signal to human macrophages" *Journal of Leukocyte Biology*, 85:278-288 (Feb. 2009).
Ishikawa et al. (2005), "Development of functional human blood and immune systems in NOD/SCID/IL2 receptor {gamma} chain-(null) mice"; *Blood.* 106(5); Sep. 1, 2005: 1565-73. Epub May 26, 2005.
Ito et al., "NOD/SCID/gamma(c)(null) mouse: an excellent recipient mouse model for engraftment of human cells" *Blood* 100(9); Nov. 1, 2002; pp. 3175-3182.
Ito, et al (2013) "Establishment of a human allergy model using human IL-3/GM-CSF-transgenic NOG mice"; *The Journal of Immunology* 191(6); pp. 2890-2899.
IWHM2 2nd International Workshop on Humanized Mice, Colorado State University, Program & Abstract Book. (Apr. 3-6, 2009), Sint Olofskapei/Amsterdam, NL.
The Jackson Laboratory, "Strain Name: C; 129S4-Rag2tm1.1Flv; Csf1tm1.1(CSF1)Flv; Il2rgtm1.1Flv/J" JAX Mice Database, http://jaxmic.jax.org/strain/107708.html, 6 pages (Jan. 26, 2012).

(56) References Cited

OTHER PUBLICATIONS

Jacob et al: (2010) "Gene targeting in the rat: advances and opportunities"; Trends Genet. 26(12):510-8. doi: 10.1016/j.tig.2010. 08.006. Epub Oct. 1, 2010.
Jacobs et al., "IL-7 Is Essential for Homeostatic Control of T Cell Metabolism In Vivo" The *Journal of Immunology*, 184: 3461-3469, (2010).
Jimenez-Diaz et al. (2009) "Improved murine model of malaria using Plasmodium falciparum competent strains and non-myelodepleted NOD-scid IL2Rgnull mice engrafted with human erythrocytes. Antimicrob Agents"; *Chemother* 53: pp. 4533-4536.
Kalueff A.V. et al., (2004) "Intranasal administration of human IL-6 increases the severity of chemically induced seizures in rats." *Neurosci Lett.* 365(2):106-10.
Kamel-Reid and Dick, "Engraftment of immune-deficient mice with human hematopoietic stem cells"; *Science.* 242 (4886): Dec. 23, 1988; 1706-1709.
Kandalaft et al., "Angiogenesis and the tumor vasculature as antitumor immune modulators: the role of vascular endothelial growth factor and endothelin"; *Curr Top Microbiol Immunol.* (2011); 344: 129-48.
Kang et al., "Defective Development of y/o T Cells in Interleukin 7 Receptor-deficient Mice Is Due to Impaired Expression of T Cell Receptor y Genes," *J. Exp. Med.*, 190(7): 973-982, (1999).
Katano, I. et al. (2015) "Predominant development of mature and functional human NK cells in a novel human IL-2-producing transgenic NOG mouse"; Journal of Immunology,194(7); pp. 3513-3525.
Kaufmann et al., (2004), "Both IGH translocations and chromosome 13q deletions are early events in monoclonalgammopathy of undetermined significance and do not evolve during transition to multiple myeloma" *Leukemia.* 18: pp. 1879-1882.
Kaushansky, K. et al. (1994) "Promotion of megakaryocyte progenitor expansion and differentiation by the c-Mpl ligand thrombopoietin", *Nature* 369: pp. 568-571.
Kaushansky, K. (1998) "Thrombopoietin", *N Engl J Med* 339: pp. 746-754.
Kaushansky, K. (2005) "The molecular mechanisms that control thrombopoiesis", *J Clin Invest* 115: pp. 3339-3347.
Kaushansky, K. (2008) "Historical review: megakaryopoiesis and thrombopoiesis", *Blood* 111: pp. 981-986.
Keefer (2015) "Artificial cloning of domestic animals"; PNAS 112; pp. 8874-8878.
Keller et al., "Molecular and Cellular Biology of Interleukin-6 and its Receptor," *Frontiers in Bioscience*, 1: 340-357, 1996.
Kieper et al., "Overexpression of Interleukin (IL)-7 Leads to IL-15-independent Generation of Memory Phenotype CD+T Cells" *J. Exp. Med.*, 195(12): 1533-1539, (2002).
Kieran, Seay et al. (2015) In Vivo Activation of Human NK Cells by Treatment with an Interleukin-15 Superagonist Potently Inhibits Acute InVivo HIV-1 Infection in Humanized Mice; *Journal of Virology*, vol. 89. No. 12; pp. 6264-6274.
Kim et al., "Seeing is Believing: Illuminating the Source of In Vivo Interleukin-7"; *Immune Network*, 11(1): pp. 1-7, (2011).
Kim, D. K., et al., Engraftment of human myelodysplastic syndrome derived cell line in transgenic severe combined immunodeficient (TG-SCID) mice expressing human GM-CSF and IL-3; *European Journal of Haematology*, vol. 61 (1998); pp. 93-99.
Kinoshita Ichiro, et al (2008) "Molecular pathophysiology of lung cancer-identification of lung cancer stem cells"; *Nippon Rinsho*, vol. 66, Suppl 6; pp. 95-99 (w/partial English translation).
Kirito, K. et al. (2003) "Thrombopoietin stimulates Hoxb4 expression: an explanation for the favorable effects of TPO on hematopoietic stem cells"; *Blood* 102:3172-3178.
Kishimoto, Tadamitsu, "The Biology of lnterleukin-6"; *Blood*, 74(1): pp. 1-10, (1989).
Kishimoto, Tadamitsu, "IL-6: from its discovery to clinical applications"; International *Immunology*, 22(5): pp. 347-352, (2010).
Kirma et al., "Overexpression of the Colony-Stimulating Factor (CSF-1) and/or Its Receptor c-fms in Mammary Glands of Transgenic Mice Results in Hyperplasia and Tumor Formulation" *Cancer Resesarch*, 64:4162-4170 (Jun. 15, 2004).
Kondo; et al. "Lymphocyte development from hematopoietic stem cells", *Current Opn Gen & Dev* 11; (2001): 520-526.
Kosco-Vilbois; et al. "A mightier mouse with human adaptive immunity", *Nature Biotechnology* (Jun. 2004), 22 (6):684-685.
Kovalchuk et al., "IL-6 transgenic mouse model for extraosseous plasmacytoma" *PNAS*, 99(3): pp. 1509-1514, (2002).
Kraus et al. (2010), "A more cost effective and rapid high percentage germ-line transmitting chimeric mouse generation procedure via microinjection of 2-cell, 4-cell, and 8-cell embryos with ES and iPS cells" *Genesis* 48(6): pp. 394-399.
Kuehl and Bergsagel, (2002), "Multiple myeloma: evolving genetic events and host interactions"; *Nat Rev Cancer.* 2(3): pp. 175-187.
Kukreja et al., (2006) "Enhancement of clonogenicity of human multiple myeloma by dendritic cells", *J Exp Med.* 203(8): pp. 1859-1865.
Kuruvilla; et al, "Dengue virus infection and immune response in humanized RAG2-1-yc-1-(RAG-hu) mice", *Virology* (2007), 369:143-152.
Kuter, D.J. & Rosenberg, R.D. (1995) "The reciprocal relationship of thrombopoietin (c-Mpl ligand) to changes in the platelet mass during busulfan-induced thrombocytopenia in the rabbit", *Blood* 85: pp. 2720-2730.
Landgren et al., (2009), "Monoclonal gammopathy of undetermined significance (MGUS) consistently precedes multiple myeloma: a prospective study"; *Blood* 113(22): pp. 5412-5417.
Lapidot et al., (1992) "Cytokine stimulation of multilineage hematopoiesis from immature human cells engrafted in SCID mice", *Science* 255(5048):Feb. 28, 1992; 1137-41.
Lebrec Herve, et al. (2013) "Homeostasis of human NK cells is not IL-15 dependent"; *J Immunol.* 191(11); pp. 5551-5558.
Legrand; et al. "Experimental Models to Study Development and Function of the Human Immune System in Vivo", *The Journal of Immunology* (2006), 176: 2053-2058.
Legrand; et al. "Humanized Mice for Modeling Human Infectious Disease: Challenges, Progress, and Outlook", *Cell Host & Microbe*, vol. 6, No. 1; (Jul. 2009); pp. 5-9. XP00258476.
Legrand et al., (2011) "Functional CD47/signal regulatory protein alpha (SIRP(alpha)) interaction is required for optimal human T- and natural killer-(NK) cell homeostasis in vivo", *Proc Natl Acad Sci USA* 108(32): pp. 13224-13229.
Lemay L.G. et al: (1990) "Role of interleukin 6 in fever in rats"; Am J Physiol. 258(3 Pt 2):R798-803.
Libby; et al. "Humanized nonobese diabelic-scid IL2ry null mice are susceptible to lethal *Salmonella typhi* infection", *PNAS* 107(35): (Aug. 2010), 15589-15594.
Lie and Petropoulos (1998) "Advances in quantitative PCR technology: 5' nuclease assays"; Curr. Opin. Biotechnology 9(1); pp. 43-48.
Liton et al., (2005), "Specific Targeting of Gene Expression to a Subset of Human Trabecular Meshwork Cells Using the Chitinase 3-Like 1 Promoter"; Invest Ophthalmol Vis Sci.46(1):183-90.
Lombard-Platet et al., "Expression of Functional MHC Class II Molecules by a Mouse Pro-B Cell Clone," *Developmental Immunology*, 4: 85-92, (1995).
Lok, S. et al. (1994) "Cloning and expression of murine thrombopoietin cDNA and stimulation of platelet production in vivo", Nature 369: pp. 565-568.
Lu et al. (2009) "Epitope-tagged receptor knock-in mice reveal that differential desensitization of alpha2-adrenergic responses is because of ligand-selective internalization"; J. Bioi. Chem., vol. 284(19), 13233-13243.
Luo; et al., "Knock-in mice with chimeric human/murine p53 gene develop normally and show wild-type p53 responses to DNA damaging agents: a new biomedical research tool", *Oncogene* (2001), 20:320-328.
Lupton et al., "Characterization of the Human and Murine IL-7 Genes," *The Journal of Immunology*, 144(9): 3592-3601, 1990.
Ma et al., (2006), "Diverse functions of IL-2, IL-15, and IL-7 in lymphoid homeostasis"; *Annu Rev Immunol.* 24: 657-79.
MacBride Megan M.; "Meeting report: International Workshop on Humanized Mice 5"; Mar. 8, 2016; XP002758867.

(56) References Cited

OTHER PUBLICATIONS

Macchiarini, et al. "Humanized mice: are we there yet?"; *Journal of Experimental Medicine*, vol. 202, No. 10; (Nov. 2005); pp. 1307-1311; XP002559426.
Mahajan et al., "Homeostasis of T Cell Diversity," *Cellular & Molecular Immunology*, 2(1): 1-10, 2005.
Maione et al., "Coexpression of IL-6 and soluble IL-6R causes nodular regenerative hyperplasia and adenomas of the liver"; *The EMBO Journal*, 17(19): 5588-5597, (1998).
Majumder et al. (1996) "Xenogeneic expression of human stem cell factor in transgenic mice mimics codominant c-kit mutations", *Blood* 87(8):Apr. 15, 1996; 3203-11.
Maksimenko, et al (2013) "Use of transgenic animals in biotechnology: prospects and problems"; *Acta Naturae*, vol. 5, No. 1; pp. 33-46.
Manz Markus M., et al.; "Human-Hemato-Lymphoid-System Mice: Opportunities and Challenges", *Immunity*, vol. 26, No. 5; (May 2007); pp. 537-541.
Manz; et al. "Renaissance for mouse models of human hematopoiesis and immunobiology", *Nature Immun.* 10(10): (Oct. 2009), 1039-1042.
Mason; et al. "Alcohol Exacerbates Murine Pulmonary Tuberculosis", *Infection and Immunity* 72 (5): (May 2004):2556-2563.
Mazurier; et al. "A Novel Immunodeficient Mouse Model-RAG2 X Common Cytokine Receptor y Chain Double Mutants—Requiring Exogenous Cytokine Administration for Human Hematopoietic Stem Cell Engraftment", *Journal of Interferon and Cytokine Research* (1999), 19:533-541.
Mazzucchelli et al., "Interleukin-7 receptor expression: intelligent design," *Nature*, 7: 144-154, (2007).
Mazzucchelli et al., "Visualization and Identification of IL-7 Producing Cells in Reporter Mice" *PLoS One*, 4(11): p. e7637, 2009.
McBurney et al. "Murine PGK-1 promoter drives widespread but not uniform expression in transgenic mice"; *Dev Dyn*.200(4): (Aug. 1994); 278-93.
McCune et al., "The SCID-hu mouse: murine model for the analysis of human hematolymphoid differentiation and function" *Science* 241(4873): Sep. 23, 1988; 1632-9.
Mestas & Hughes, "Of mice and not men: differences between mouse and human immunology"; *J Immunol.* 172(5): Mar. 1, 2004; 2731-8.
Mertsching et al., "IL-7 transgenic mice: analysis of the role of IL-7 in teh differentiation of thymocytes in vivo and in vitro"; *International Immunology*, 7(3): 401-414, (1995).
Meyer et al. "Gene targeting by homologous recombination in mouse zygotes mediated by zinc-finger nucleases"; *Proc Natl Acad Sci U S A.* Aug. 24, 2010; 107(34):15022-6. doi: 10.1073/pnas.1009424107. Epub Aug. 4, 2010.
Miller et al. "Generation of helper-free amphotropic retroviruses that transduce a dominant-acting, methotrexate-resistant dihydrofolate reductase gene"; *Mol Cell Biol.*5(3):Mar. 1985. 431-7 . . . .
Miller et al. "Redesign of retrovirus packaging cell lines to avoid recombination leading to helper virus production"; *Mol Cell Biol.* 6(8): (Aug. 1986); 2895-902.
Mittrucker; et al. "Cutting Edge: Role of B Lymphocytes in Protective Immunity Against *Salmonella typhimurium* Infection", *J. Immunol.*164 (2000),:1648-1652.
Miyakawa et al.; "Establishment of a new model of human multiple myeloma using NOD/SCID/y$_c^{null}$ (NOG) mice"; *Biochem. Biophys. Res. Comm.*, vol. 313, (2004); pp. 258-262.
Mlecnik Bernhard, et al. (2014) "Functional network pipeline reveals genetic determinants associated with in situ lymphocyte proliferation and survival of cancer patients"; Sci Transl Med. 6:228ra37.
Moreadith et al. (1997) "Gene targeting in embryonic stem cells: the new physiology and metabolism"; J. Mol. Med.75(3); pp. 208-216.
Moreno et al. (2006) The course of infections and pathology in immunomodulated NOD/LtSz-SCID mice inoculated with Plasmodium falciparum laboratory lines and clinical isolates. *Int. J. Parasitol.* 36:361-369).

Mosier et al., "Transfer of a functional human immune system to mice with severe combined immunodeficiency"; *Nature* 335(6187): Sep. 15, 1988; 256-9.
Motz and Coukos, "Deciphering and reversing tumor immune suppression"; *Immunity* 39(1):Jul. 25, 2013; 61-73.
Mullins (1996) "Transgenesis in the rat and larger mammals"; J Clin Invest,97; pp. 1557 15-60.
Munitic et al., "Dynamic regulation of IL-7 receptor expression is required for normal thymopoiesis" *Blood*, 104: 4165-4172, (2004).
Munoz et al., "Constraints to Progress in Embryonic Stem Cells from Domestic Species," Stem Cell Rev, and Rep., 5:6-9, 2009.
Murphy et al. (1993) "Antitumor Effects of Interleukin-7 and Adoptive Immunotherapy on Human Colon Carcinoma Xenografts"; *J. Clin. Invest.*, 92; pp. 1918-1924.
Murphy, D., BAC-based Modifications of the Mouse Genome: The Big and the Backward, Wellcome Trust Advanced Course: Genetic Manipulation of ES Cells, 58 pages (2009).
Murphy, D. MFA: the turducken of alleles*, Wellcome Trust Advanced Course: Genetic Manipulation of ES Cells, 76 pages (2010).
Murray; et al. "Thrombopoietin mobilizes CD34+ cell subsets into peripheral blood and expands multilineage progenitors in bone marrow of cancer patients with normal hematopoiesis", *Exp Hematol* 26(3): (Mar. 1998), 207-216.
Nagy et al. "Embryonic stem cells alone are able to support fetal development in the mouse"; *Development.* Nov. 1990;110(3):815-21.
Naka et al., "The paradigm of IL-6: from basic science to medicine," *Arthritis Research*, 4(3): S233-S242, 2002.
Nelson and Bissell, "Of extracellular matrix, scaffolds, and signaling: tissue architecture regulates development, homeostasis, and cancer"; *Annu Rev Cell Dev Biol.* 2006;22:287-309.
Nevus Biologicals—a Bio-Techne Brand, "Human IL-6 Protein 5 µg", NBP2-34901 (4 pages) (2016).
Nicolini; et al. "NOD/SCID mice engineered to express human IL-3, GM-CSF and Steel factor constitutively mobilize engrafted human progenitors and compromise human stem cell regeneration", *Leukemia* (2004), 18:341-347.
Niemann et al., "Transgenic farm animals: present and future," *Rev. Sci. Tech. Off. Int. Epiz.*, 24(1):285-298, (2005).
Nishimura, et al; (2000) "Differential Roles of Interleukin 15 mRNA Isoforms Generated by Alternative Splicing in Immune Responses In Vivo"; J Exp Med. 191(1); pp. 157-170.
Nochi T, et al. (2013) "Cryptopatches are essential for the development of human GALT"; Cell Rep; 3(6); pp. 1874-1884.
Northemann, et al (1989) "Structure of the Rat Interleukin 6 Gene and Its Expression in Macrophage-derived Cell" *J Biol Chem.* Sep. 25, 1989;264(27):16072-82.
O'Connell et al., "Lentiviral Vector Delivery of Human Interleukin-7 (hiL-7) to Human Immune System (HIS) Mice Expands T Lymphocyte Populations," *PLoS One*, 5(8): 1-10, (2010).
Palm NW, et al. (2014) "Immunoglobulin A coating identifies colitogenic bacteria in inflammatory bowel disease"; Cell; 158(10); pp. 1000-1010.
Papanicolaou Dimitris et al., "The Pathophysiologic Roles of Interleukin-6 in Human Disease," *Ann Intern Med.*, 128: 127-137, (1998).
Patil et al.(2011) "Transgenic animals and drug development: A review"; Indian Journal of Public Health research & Development, vol. 2, No. 1; pp. 106-109.
Pear et al. "Production of high-titer helper-free retroviruses by transient transfection"; Proc Natl *Acad Sci U S A.* Sep. 15, 1993; 90(18):8392-6.
Pearson et al. (2008), "Creation of "Humanized" Mice to Study Human Immunity"; Curr. *Protoc. Immunol.* 81: pp. 1-15.
Pek et al., "Characterization and IL-15 dependence of NK cells in humanized mice"; *Immunobiology.* Jan.-Feb. 2011;216(1-2):218-24. doi: 10.1016/j.imbio.2010.04.008. Epub May 13, 2010.
Peters et al., "The Function of the Soluble Interleukin 6 (IL-6) Receptor In Vivo: Sensitization of Human Soluble IL-6 Receptor Transgenic Mice Towards IL-6 and Prolongation of the Plasma D Half-life ofiL-6" *J. Exp. Med.*, 183:1399-1406, (1996).

(56) References Cited

OTHER PUBLICATIONS

Pierfrancesco Tassone, et al: "A clinically relevant SCID-hu in vivo model of human multiple myeloma"; *Blood. American Society Of Hematology.* US. vol. 106. No. 2; Jul. 15, 2005; pp. 713-716; XP002633148.

Pixley et al., "CSF-1 regulation of the wandering macrophage: complexity in action" Trends in *Cell Biology,* 14(11): 628-638 (Nov. 2004).

Pleiman et al., "Organization of the Murine and Human Interleukin-7 Receptor Genes: Two mRNAs Generated by Differential Splicing and Presence of a Type 1-Interferon-Inducible Promoter" *Molecular and Cellular Biology,* 11 (6): 3052-3059, 1991.

Polejaeva et al (2000) "Cloned pigs produced by nuclear transfer from adult somatic cells"; Nature 407; pp. 86-90.

Pollard, Jeffrey W.; "Tumour-educated macrophages promote tumour progression and metastasis"; *Nature Reviews,* 4; (Jan. 2004); pp. 71-78.

Poueymirou et al. (2007) "F0 generation mice that are essentially fully derived from the donor gene-targeted ES cells allowing immediate phenotypic analyses," *Nat Biot* 25(1):91-99.

Prelle et al., "Pluripotent Stem Cells—Model of Embryonic Development, Tool for Gene Targeting, and Basis of Cell Therapy," *Anal. Histol. Embryol.* 31; (2002); pp. 169-186.

Qian, H. et al. (2007) "Critical role of thrombopoietin in maintaining adult quiescent hematopoietic stem cells," *Cell Stem Cell* 1:671-684.

Qian and Pollard, "Macrophage diversity enhances tumor progression and metastasis" (2010), *Cell* 141(1) pp. 39-51.

Rämer Patrick C. et al. (2011) "Mice with human immune system components as in vivo models for infections with human pathogens"; *Immunol Cell Biol.* 89(3):408-16.

Rathinam et al., "Efficient differentiation and function of human macrophages in humaized CSF-1 mice" *Blood,* 118(11):3119-3132 (Sep. 15, 2011).

Rathinam et al., "Efficient differentiation and function of human macrophages in humaized CSF-1 mice" *Blood,* 118(11):3119-3128 (Sep. 15, 2011)—Supplemental Figures.

Raulet, 2006, "Missing self recognition and self tolerance of natural killer (NK) cells" *Seminars in immunology* 18(3):145-50.

Repass et al., "IL7-hCD25 and IL7-Cre BAC transgenic mouse lines: New tools for analysis of IL-7 expressing cells," *Genesis,* 47(4): 281-287, 2009.

Rich et al., "Cutaneous Lymphoproliferation and Lymphomas in Interleukin 7 Transgenic Mice," *J. Exp. Med.,* 177: 305-316, 1993.

Rieger et al.; "Hematopoietic Cytokines Can Instruct Lineage Choice"; *Science,* 325; (Jul. 10, 2009); pp. 217-218.

Ring, Aaron M. et al. (2012) "Mechanistic and structural insight into the functional dichotomy between IL-2 and IL-15"; *Nat Immunol.* 13(12): pp. 1187-1195.

Rohrschneider, L.R. et al. (1997) "Growth and differentiation signals regulated by the MCSF receptor", *Mol. Reprod. Dev.* 46:96-103.

Rongvaux, Anthony; "Improvement of human-hemato-lymphoid-system mice: the human Thrombopoietin knock-in mouse"; IWHM2 2nd International Workshop on Humanized Mice, PowerPoint Presentation; Apr. 3-6, 2009; Sint Olofskapei/Amsterdam, NL; pp. 1-20.

Rongvaux; "Human Thrombopoietin knockin mice efficiently support human hematopoiesis", Flavell Lab, Yale University (ASH—Dec. 6, 2010).

Rongvaux, A., et al.; "Human thrombopoietin knockin mice efficiently support human hematopoiesis in vivo", PNAS, vol. 108, No. 6; (Feb. 2011); pp. 2378-2383.

Rongvaux et al., (2013), "Human hemato-lymphoid system mice: current use and future potential for medicine," *Annu Rev Immunol.* 31: 2013; 635-74. doi: 10.1146/annurev-immunol-032712-095921. Epub Jan. 16, 2013.

Rongvaux Anthony et al: "Development and function of human innate immune cells in a humanized mouse model"; *Nature Biotechnology,* vol. 32. No. 4; (Apr. 2014) pp. 364-372.

Rongvaux A. et al.: (2012) "MISTRG: a novel humanised mouse model to study human hematopoiesis and myeloid development and function in vivo"; Immunology, vol. 137, No. 1, Suppl. 1; pp. 184.

Roychowdhury, Sameek, et al. (2005) "IL-15 but not IL-2 rapidly induces lethal xenogeneic graft-versus-host disease"; Blood 106(7); pp. 2433-2435.

Ryan et al., "Rescue of the colony-stimulating factor 1 (CSF-1)-nullizygous mouse (Csflop/Csflop) phenotype with CSF-1 transgene and identification of sites of local CSF-1 synthesis" *Blood,* 98(1):74-84 (Jul. 2001).

Rybchin C. N., "Principles of Genetic Engineering"; Saint-Petersburg, Publisher SPbGTU, 2002; p. 411-413.

Saha et al; (2009); "Technical challenges in using human induced pluripotent stem cells to model disease"; Cell Stem Cell.5(6); pp. 584-595.

Samaridis et al., "Development of lymphocytes in intereleukin 7-transgenic mice" Eur. J. *Immunol.,* 21: 453-460, (1991).

Sanmamed, et al (2015) "Nivolumab and Urelumab Enhance Antitumor Activity of Human T Lymphocytes Engrafted in Rag2-/-IL2Rγnull Immunodeficient Mice"; Cancer Res. 75(17); pp. 3466-3478.

Sanmamed, et al (2016) "Defining the optimal murine models to investigate immune checkpoint blockers and their combination with other immunotherapies"; Ann Oncol. 27(7); pp. 1190-1198.

Sarrazin et al., "MafB Restricts M-CSF-Dependent Myeloid Commitment Divisions of Hematopoietic Stem Cells" *Cell,* 138:300-313 (Jul. 24, 2009).

Sawamura D. et al.; (1998) "Induction of keratinocyte proliferation and lymphocytic infiltration by in vivo introduction of the IL-6 gene into keratinocytes and possibility of keratinocyte gene therapy for inflammatory skin diseases using IL-6 mutant genes"; J Immunol. 161(10): 5633-9.

Schluns et al.; "Interleukin-7 mediates the homeostasis of naive and memory COST cells in vivo"; *Nature Immunology,*1(5); (2000); pp. 426-432.

Schorpp et al. 1996, "The human ubiquitin C promoter directs high ubiquitous expression of transgenes in mice," *Nucleic Acids Res.* May 1, 1996; 24(9):1787-8.

Scudellari, Megan; "The innate debate over HSCs"; *Nature Reports Stem Cells*; (published online Aug. 6, 2009 / doi: 10.1038/stemcells. 2009.103). 1 page.

Selsby et al (2015) "Porcine Models of Muscular Dystrophy"; ILAR Journal, vol. 56, No. 1; pp. 116-126.

Semenza, G. L. et al; "Polycythemia in transgenic mice expressing the human erythropoietin gene"; *Proceedings of The National Academy of Sciences,* vol. 86, No. 7; (Apr. 1989); pp. 2301-2305.

Semenza Gregg L., et al; "Cell-type-specific and hypoxia-inducible expression of the human erythropoietin gene in transgenic mice"; *Genetics,* vol. 88; (Oct. 1991); pp. 8725-8729.

Setty, Mala, et al. (2015) "Distinct and Synergistic Contributions of Epithelial Stress and Adaptive Immunity to Functions of Intraepithelial Killer Cells and Active Celiac Disease"; Gastroenterology 149(3):681-91.

Shalapour et al.; "Commensal microflora and interferon-[gamma] promote steady-state interleukin-7 production in vivo"; *European Journal of Immunology,* 40(9); (2010); pp. 2391-2399.

Sherr, C.J. et al. (1988) "Macrophage colony-stimulating factor, CSF-1, and its proto-oncogeneencoded receptor," *Cold Spring Harb. Symp. Quant. Biol.* 53 Pt 1:521-530.

Shinobara et al. (2007) "Active integration: new strategies for transgenesis"; *Transgenic research,* vol. 16, pp. 333-339.

Shultz et al., 2000, "NOD/LtSz-Rag1null mice: an immunodeficient and radioresistant model for engraftment of human hematolymphoid cells, HIV infection, and adoptive transfer of NOD mouse diabetogenic T cells" *J Immunol.* Mar. 1, 2000; 164(5):2496-507.

Shultz; et al."Human Lymphoid and Myeloid Cell Development in NOD/LtSz-scid IL2Ry null Mice Engrafted with Mobilized Human Hempoietic Stem Cells", *J Immunol* (2005), 174:6477-6489.

Shultz, Leonard D., et al; "Humanized mice for immune system investigation: progress, promise and challenges"; *Nature Reviews Immunology,* vol. 12, No. 11; (Nov. 1, 2012); pp. 786-798. XP055064740.

(56) References Cited

OTHER PUBLICATIONS

Shultz L D et al; "Humanized mice in translational biomedical research"; *The Journal of Immunology. Nature Pub. Group. GB*, vol. 7. No. 2; (Feb. 2007) pp. 118-130. XP002493022.
Silva et al.; "IL-7 Contributes to the Progression of Human T-cell Acute Lymphoblastic Leukemias"; *Cancer Research*, 71(14); (2011); pp. 4780-4789.
Skjot et al. (2002) "Epitope mapping of the immunodominant antigen TB10.4 and the two homologous proteins TB10.3 and TB12.9, which constitute a subfamily of the esat-6 gene family," *Infect. Immun.* 70:5446-5453.
Socolovsky, M. et al. (1998) "Cytokines in hematopoiesis: specificity and redundancy in receptor function," *Adv. Protein Chem.* 52:141-198.
Soderquest et al., 2011, "Monocytes control natural killer cell differentiation to effector phenotypes," *Blood.* Apr. 28, 2011;117(17):4511-8. doi: 10.1182/blood-2010-10-312264. Epub Mar. 9, 2011.
Sohn B; et al. "Expression and characterization of bioactive human thrombopoietin in the milk of transgenic mice", *DNA Cell Biol* (Nov. 1999), 18(11):845-852.
Song; et al. "A Mouse Model for the Human Pathogen *Salmonella typhi*", *Cell Host & Microbe* (Oct. 2010), 17(8):369-376.
Spits, Hergen; "New models of human immunity"; *Nature Biotechnology* vol. 32, No. 4; (Apr. 2014), pp. 335-336.
Stanley, E. Richard, "Lineage Commitment: Cytokines Instruct, At Last!" *Cell Stem Cell*, 5; (Sep. 4, 2009); pp. 234-236.
Stanley, E.R. et al. (1997) "Biology and action of colony—stimulating factor-1," *Mol. Reprod. Dev.* 1997; 46:4-10.
Strowig et al., "Transgenic expression of human signal regulatory protein alpha in Rag2—/—γc—/—mice improves engraftment of human hematopoietic cells in humanized mice", *PNAS* 108(32); (2011); pp. 13218-13223.
Strowig Till et al; "Humanized mouse models of infectious diseases"; *Drug Discovery Today: Disease Models.*; Jan. 2012; pp. e11-e16; XP055166844.
Strowig et al., 2010, "Human NK cells of mice with reconstituted human immune system components require preactivation to acquire functional competence," *Blood.* Nov. 18, 2010;116(20):4158-67. doi: 10.1182/blood-2010-02-270678. Epub Jul. 29, 2010.
Suematsu et al.; "IgG1 plasmacytosis in interleukin 6 transgenic mice"; *Proc. Natl. Acad. Sci. USA*, 86; (1989); pp. 7547-7551.
Suematsu et al.; "Generation of plasmacytomas with the chromosomal translocation t(12;15) in interleukin 6 transgenic mice"; *Proc. Natl. Acad. Sci. USA*, 89; (1992); pp. 232-235.
Sugita et al.; "Functional Murine Interleukin 6 Receptor with the Intracisternal a Particle Gene Product at its Cytoplasmic Domain"; *J. Exp. Med.*, 171; (1990); pp. 2001-2009.
Takagi et al., 2012, "Membrane-bound human SCF/KL promotes in vivo human hematopoietic engraftment and myeloid differentiation," *Blood.* Mar. 22, 2012; 119(12):2768-77. doi: 10.1182/blood-2011-05-353201. Epub Jan. 25, 2012.
Takenaka et al., (2007), Polymorphism in Sirpa modulates engraftment of human hematopoietic stem cells; *Nature Immunology* 8: 1313-1323.
Takizawa & Manz, 2007, "Macrophage tolerance: CD47-SIRP-alpha-mediated signals matter," *Nat Immunol.* Dec. 2007; 8(12):1287-9.
Tan et al.; "IL-7 is critical for homeostatic proliferation and survival of naive T cells"; *PNAS*, 98(15); (2001); pp. 8732-8737.
Tanabe et al.; "Genomic Structure of the Murine IL-6 Gene—High Degree Conservation of Potential Regulatory Sequences between Mouse and Human"; *The Journal of Immunology*, D 141; (1988); pp. 3875-3881.
Tang, 2013, "Tumor-associated macrophages as potential diagnostic and prognostic biomarkers in breast cancer," *Cancer Lett.* May 10, 2013; 332(1):3-10. doi: 10.1016/j.canlet.2013.01.024. Epub Jan. 21, 2013.
Tassone et al., 2005, "A clinically relevant SCID-hu in vivo model of human multiple myeloma," *Blood.* Jul. 15, 2005; 106(2):713-6. Epub Apr. 7, 2005.
Tong et al; "Production of p53 gene knockout rats by homologous recombination in embryonic stem cells"; *Nature.* Sep. 9, 2010; pp. 211-215.
Theocharides, et al; (2012) "Disruption of SIRPα signaling in macrophages eliminates human acute myeloid leukemia stem cells in xenografts"; *J Exp Med.* 209(10); pp. 1883-1899.
Theocharides et al (2016) "Humanized hemato-lymphoid system mice"; Haematologica. (1); 5-19.
Traggiai; et al. "Development of a Human Adaptive Immune System in Cord Blood Cell-Transplanted Mice", *Science* (Apr. 2004), 304:104-107.
Tsantikos et al.; "Autoimmune Disease in Lyn-Deficient Mice is Dependent on an Inflammatory Environment Established by IL-6"; *The Journal of Immunology*, 184; (2010); pp. 1348-1360.
Tsujinaka et al.; "Muscle Undergoes Atrophy in Associate with Increase of Lysosomal Cathepsin Activity in Interleukin-6 Transgenic Mouse"; *Biochemical and Biophysical Research Communication*, 207(1); (1995); pp. 168-174.
Tsujinaka et al.; "Interleukin 6 Receptor Antibody Inhibits Muscle Atrophy and Modulates Proteolytic Systems in Interleukin 6 Transgenic Mice"; *J. Clin. Invest.*, 97(1); (1996); pp. 244-249.
Tsuruta, Lisako, et al, "Transcriptional Regulation of Cytokine Genes"; *Cytokines & Cytokine Receptors: Physiology and Pathological Disorders*, Chapter 23, (2003); pp. 383-403.
Ueda, Otoya et al; "Novel genetically-humanized mouse model established to evaluate efficacy of therapeutic agents to human interleukin-6 receptor"; *Scientific Reports. Nature Publishing Group, GB*, vol. 3; Jan. 1, 2013; pp. 1196; XP002692003.
Uehira et al.; "Immunologic Abnormalities Exhibited in IL-7 Transgenic Mice with Dermatitis"; *J. Invest Dermatol*, 110; (1998); pp. 740-745.
Uehira et al.; "The development of dermatitis infiltrated by γδ T cells in IL-7 transgenic mice"; *International Immunology*, 5(12); (1993); pp. 1619-1627.
Valenzuela et al. (2003) "High-throughput engineering of the mouse genome coupled with high-resolution expression analysis," *Nat Biot* 21 (6):652-659.
Valmori et al., 1998, "Enhanced Generation of Specific Tumor-Reactive CTL In Vitro by Selected Melan-A/MART-1 Immunodominant Peptide Analogues" *Journal of Immunology* 160:1750-1758.
Van De Wiele et al.; "Impaired thymopoiesis in interleukin-7 receptor transgenic mice is not corrected by Bcl-2"; *Cellular Immunology*, 250; (2007); pp. 31-39.
Van Der Weyden et al., "Tools for Targeted Manipulation of the Mouse Genome" *Physiological Genomics* 11; (2002); pp. 133-164.
Van Lent et al.,2009, "IL-7 enhances thymic human T cell development in "human immune system" Rag2-/-IL-2Rgammac-/- mice without affecting peripheral T cell homeostasis" *J Immunol.* Dec. 15, 2009;183(12):7645-55. doi: 10.4049/jimmunol.0902019.
Vaughan, Ashley M. et al; "Development of humanized mouse models to study human malaria parasite infection"; *Future Microbiology*, vol. 7, No. 5; (May 2012); pp. 657-665.
Verstegen et al. "Thrombopoietin is a major limiting factor for selective outgrowth of human umbilical cord blood cells in non-obese diabetic/severe combined immunodeficient recipient mice" *British Journal of Hematology* 122; (2003) pp. 837-846.
Vivier et al., 2008, "Functions of natural killer cells," *Nat Immunol.* May 2008; 9(5):503-10. doi: 10.1038/ni1582.
Vudattu, et al (2014) "Humanized mice as a model for aberrant responses in human T cell immunotherapy"; J Immunol. 193(2): pp. 587-596.
Waldron-Lynch, et al. (2012) "Teplizumab induces human gut-tropic regulatory cells in humanized mice and patients"; Sci Transl Med. 4(118):118ra12; pp. 1-12.
Wall (1997) "Transgenic dairy cattle: genetic engineering on a large scale"; J Dairy Sci;80: pp. 2213-2224.
Watanabe (1997), "GM-CSF-mobilized peripheral blood CD34+ cells differ from steady-state bone marrow CD34+ cells in adhesion molecule expression"; *Bone Marrow Transplant.* Jun. 1997; 19(12):1175-81.

(56) References Cited

OTHER PUBLICATIONS

Watanabe et al.; "Interleukin 7 Transgenic Mice Develop Chronic Colitis with Decreased Interleukin 7 Protein Accumulation in the Colonic Mucosa"; *J. Exp. Med.*, 187(3); (1998); pp. 389-402.
Watanabe Takeshi (2008) "Development of Humanized Mouse and Its Application"; Chemistry and Biology, vol. 46, No. 9, pp. 614-620 (Partial English translation attached).
Watanabe et al., 2009, "The analysis of the functions of human B and T cells in humanized NOD/shi-scid/gammac(null) (NOG) mice (hu-HSC NOG mice)," *Int Immunol.* Jul. 2009; 21(7):843-58. doi: 10.1093/intimm/dxp050. Epub Jun. 10, 2009.
Wei et al., "Transgenic expression of CSF-1 in CSF-1 receptor-expressing cells lead to macrophage activation, osteoporosis, and early death" *Journal of Leukocyte Biology*, 80:1445-1453 (Dec. 2006).
Weissenbach et al;. "Two interferon mRNAs in human fibroblasts: In vitro translation and D *Escherichia coli* cloning studies"; *Proc. Natl. Acad. Sci. USA*, 77(12); (1980); pp. 7152-7156.
Wendling, F. et al. (1994) "cMpl ligand is a humoral regulator of megakaryocytopoiesis," *Nature* 369:571-574.
Wheeler et al.; "Transgenic Technology and Applications in Swine"; *Theriogenology*, 56; (2001); pp. 1345-1369.
Wiktor-Jedrzejczak, W. et al. (1990) "Total absence of colony-stimulating factor 1 in the macrophage-deficient osteopetrotic (op/op) mouse" *Proc. Natl Acad. Sci. USA* 87:4828-4832.
Williams, et al.; "IL-7 Overexpression in Transgenic Mouse Keratinocytes Causes a Lymphoproliferative Skin Disease Dominated by Intermediate TCR Cells"; *The Journal of Immunology*, 159; (1997); pp. 3044-3056.
Willinger Tim; "A new flavor of the humanized mouse: The human IL-3/GM-CSF knock-in mouse"; IWHM2 2nd International Workshop on Humanized Mice, PowerPoint Presentation; Apr. 3-6, 2009; Sint Olofskapei/Amsterdam, NL; pp. 1-23.
Willinger, et al; "Human IL-3/GM-CSF knock-in mice support human alveolar macrophage development and human immune responses in the lung", *PNAS* 108(6); (Feb. 2011); pp. 2390-2395.
Willinger et al.; "Improving human hemato-lymphoid-system mice by cytokine knock-in gene replacement"; *Trends in Immunology*, 32(7); (2011); pp. 321-327.
Wilmut (2003) "Dolly—her life and legacy"; Cloning Stem Cell 5; pp. 99-1 00.
Woodroofe et al.; "Long-Term Consequences of Interleukin-6 Overexpression in Transgenic Mice"; *DNA and Cell Biology*, 11(8); (1992); pp. 587-592.
Yaccoby et al., 1998, "Primary myeloma cells growing in SCID-hu mice: a model for studying the biology and treatment of myeloma and its manifestations" *Blood.* Oct. 15, 1998; 92(8):2908-13.
Yaccoby and Epstein, 1999, "The proliferative potential of myeloma plasma cells manifest in the SCID-hu host" *Blood.* Nov. 15, 1999;94(10):3576-82.
Yajima et al., "A new humanized mouse model of Epstein-Barr virus infection that reproduces persistent infection, lymphoproliferative disorder, and cell-mediated and humoral immune responses," *J Infect Dis.* Sep. 1, 2008; 198(5):673-82. doi: 10.1086/590502.
Yamasaki et al.; "Cloning and Expression of the Human Interleukin-6 (BSF-2/IFNβ 2) Receptor"; *Science*, 241; (1988); pp. 825-828.
Yanagimachi (2002) "Cloning: experience from the mouse and other animals"; Mol Cell Endocrinol. 187; pp. 241-248.
Yao et al. (2014) "CyTOF supports efficient detection of immune cell subsets from small samples"; J. of Immunological Methods 415; pp. 1-5.
Yasukawa et al.; "Structure and expression of human B cell stimulatory factor-2 (BSF-2/IL-6) gene"; *The EMBO Journal*, 6(10); (1987); pp. 2939-2945.

Yeung, Y.G. and Stanley, E.R. (2003) "Proteomic approaches to the analysis of early events in colony-stimulating factor-1 signal transduction," *Mol. Cell. Proteomics* 2:1143-1155.
Yoshihara, H. et al. "Thrombopoietin/MPL signaling regulates hematopoietic stem cell quiescence and interaction with the osteoblastic niche," *Cell Stem Cell.* Dec. 13, 2007; 1(6):685-97. doi: 10.1016/j.stem.2007.10.020. Epub Nov. 20, 2007.
Yoshida, H. et al. (1990) "The murine mutation osteopetrosis is in the coding region of the macrophage colony stimulating factor gene," *Nature* 345:442-444.
Young; et al. "Infectious disease: Tuberculosis", *Eur. J. Immunol* (2009), 39:1991-2058. U.S. Appl. No. 14/469,308.
Yu et al., "CSF-1 receptor structure/function in MacCsf1r-/- macrophages: regulation of proliferation, differentiation, and morphology" *Journal of Leukocyte Biology*, 84: (Sep. 2008). pp. 852-863.
Yu et al (2017) "A novel humanized mouse model with significant improvement of class-switched, antigen-specific antibody production"; Blood. 129(8); pp. 959-969.
Zang, WP et al. "Transfer and Expression of Recombinant Human Thrombopoietin Gene in COS-7 Cells and Mice In Vivo", [Article in Chinese] Zhongguo Shi Yan Xue Ye Xue Za Zhi 9(1): (Mar. 2001), English Abstract.
Zang, W, et al. "Thrombopoietic effect of recombinant human thrombopoietin gene transferred to mice mediated by electric pulse on normal and experimental thrombocytopenia mice", [Article in Chinese] *Zhonghua Xue Ye Xue Za Zhi.* 22(3): (Mar. 2001), English Abstract.
Zhan et al., "The molecular classification of multiple myeloma"; *Blood.* Sep. 15, 2006; 108(6):2020-8. Epub May 25, 2006.
Zhao; et al."Thrombopoietin: a potential T-helper lymphocyte stimulator. Change in T-lymphocyte composition and blood cytokine levels in thrombopoietin eDNA transferred mice", *Haematolgica* (Jun. 1998), 83(6):572-573.
Zhou et al., "Transgenic Mice Overexpressing Human c-mpl Ligand Exhibit Chronic Thrombocytosis and Display Enhanced Recovery From 5-Fluorouracil or Antiplatelet Serum Treatment" *Blood* (1997) 89:1551-1559.
Zhou Hongxia, et al. (2009) "Developing tTA transgenic rats for inducible and reversible gene expression"; International Journal of Biological Sciences 5, pp. 171-181.
Zilberstein et al.; "Structure and expression of cDNA and genes for human interferon-beta-2; a distinct species inducible by growth-stimulatory cytokines"; *The EMBO Journal*, 5(10); (1986); pp. 2529-2537.
Bernier et al. (2001) "M-CSF Transgenic Mice: Role of M-CSF in Infection and Autoimmunity"; Exp. Toxic Pathology. 53: pp. 165-173.
Doherty et al. (1999) "Infection of HIV-1 Transgenic Mice with *Mycobacterium avium* Induces the Expression of Infectious Virus Selectively from a Mac-1-Positive Host Cell Population"; The Journal of Immunology 163(3); pp. 1506-1515.
Jones et al (1995) "Antimicrobial Chemotherapy of Human Infection due to Listeria Monocytogenes"; Eur. J. Clin. Microbial. Infect. Dis.,14(3); pp. 165-175.
Nichterlein et al. (1991) "Effect of Various Antibiotics on Listeria monocytogenes Multiplying in L 929 Cells"; Infection 19: Supplement 4; pp. S234-S238.
Yang et al. (2016) "Mutant PFN1 causes ALS phenotypes and progressive motor neuron degeneration in mice by a gain of toxicity"; PNAS, 113(41), E6209-E6218, p. 1-10.
Budzynski, et al. (1994) "Cytotoxic cells in immunodeficient athymic mice"; *Immunopharmacol Immunotoxicol* 16(3); pp. 319-346.
Kalberer, et al. (2003) "Human NK cell development in NOD/SCID mice receiving grafts of cord blood CD34+ cells"; *Blood* 102(1); pp. 127-135,.
Figueiredo-Pontes, et al. (2021) "Improved hematopoietic stem cell transplantation upon inhibition of natural killer cell-derived interferon-gamma"; *Stem Cell Reports*, 16(8); pp. 1-5.
The Jackson Laboratory, "Immunodeficient Mouse and Xenograft Host Comparisons", 5 page web printout (Oct. 7, 2022).

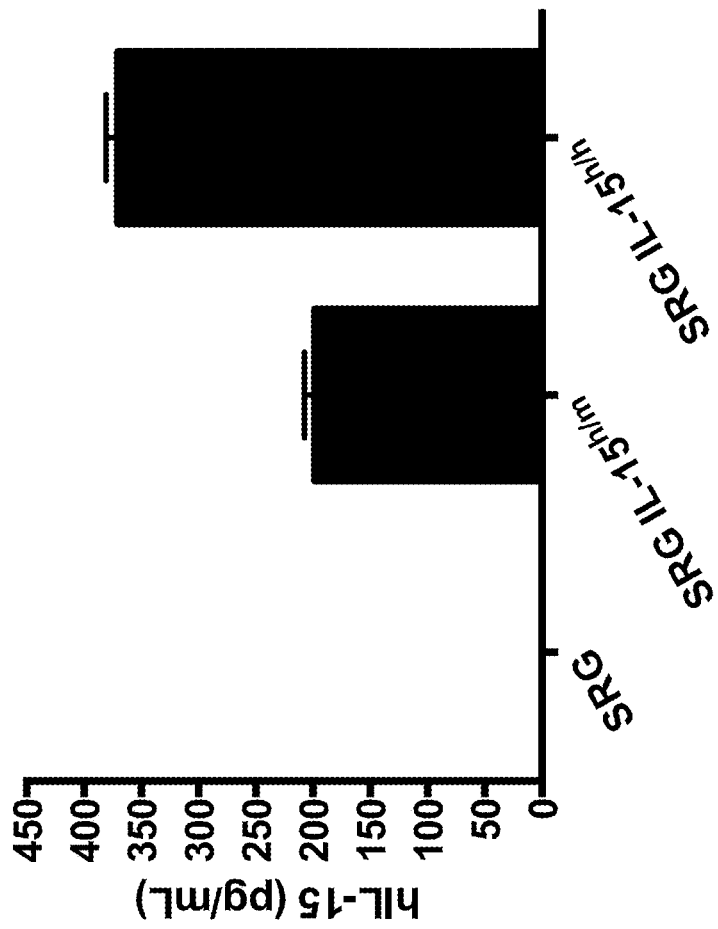

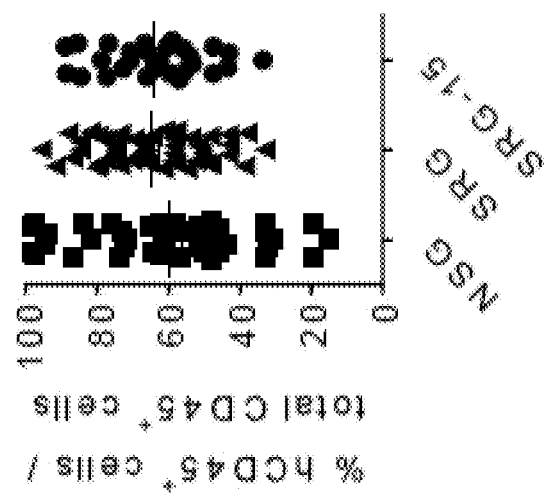

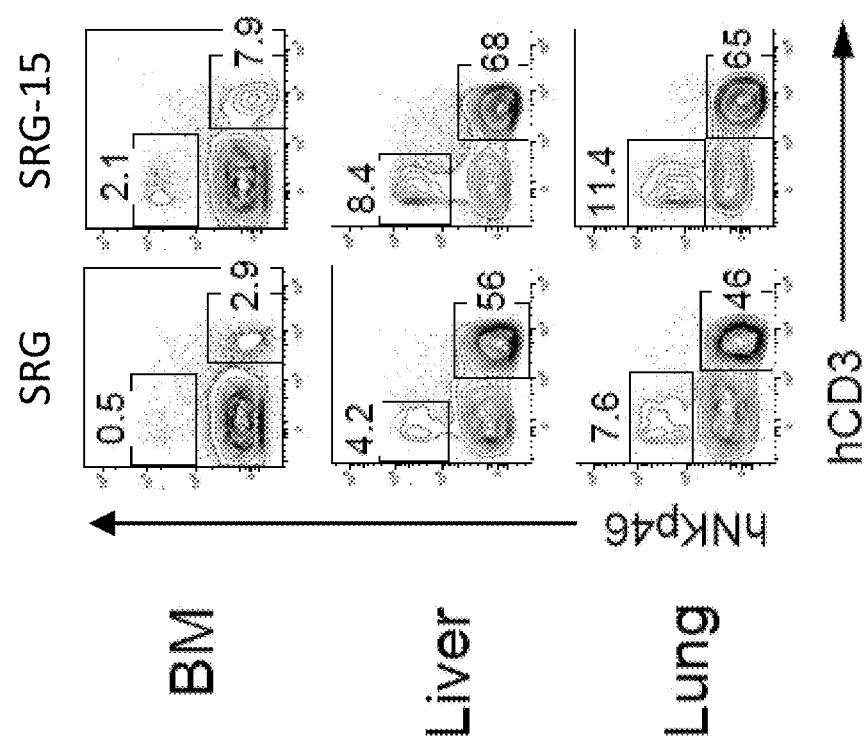

FIG. 6C
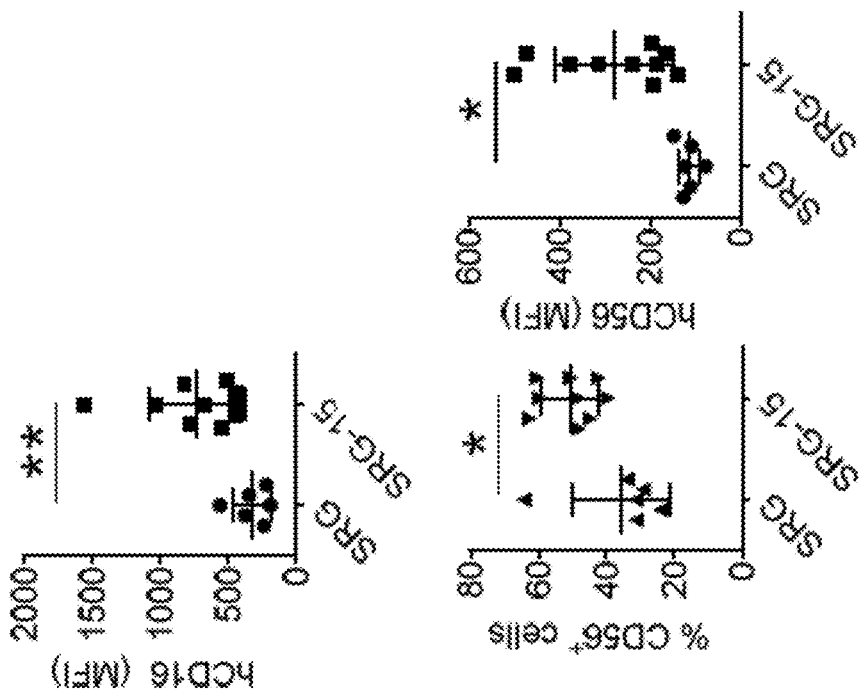
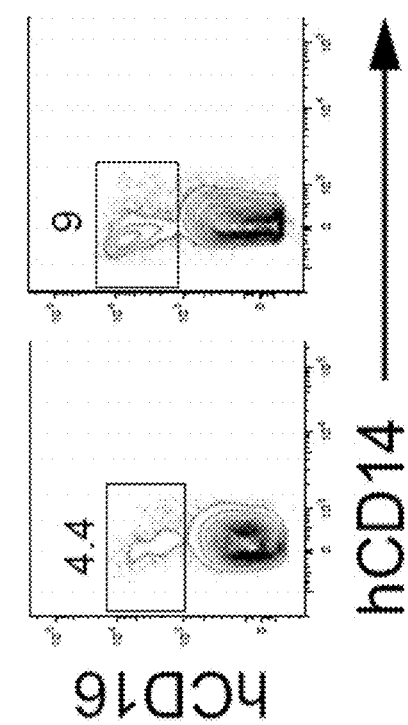
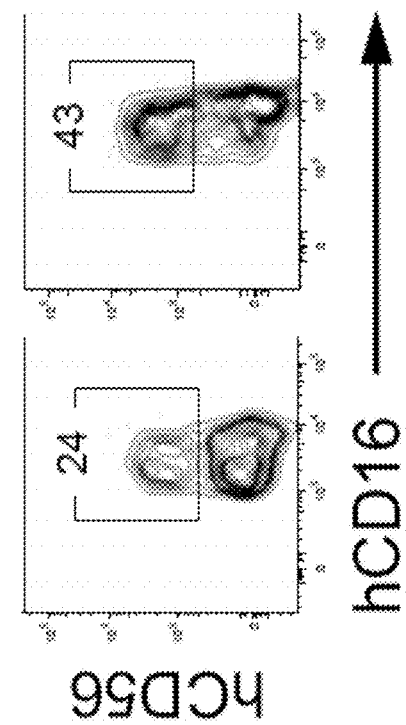

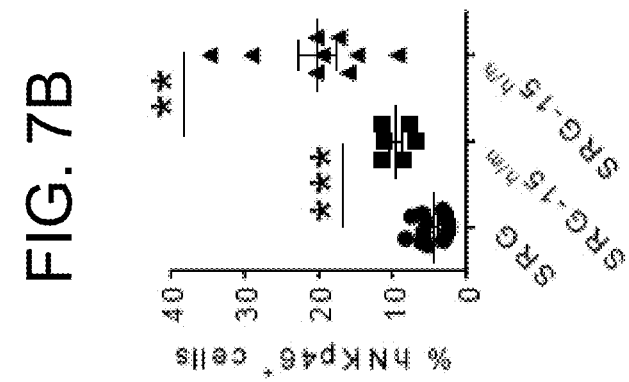
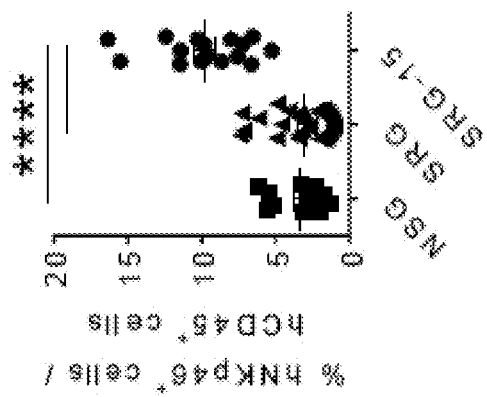

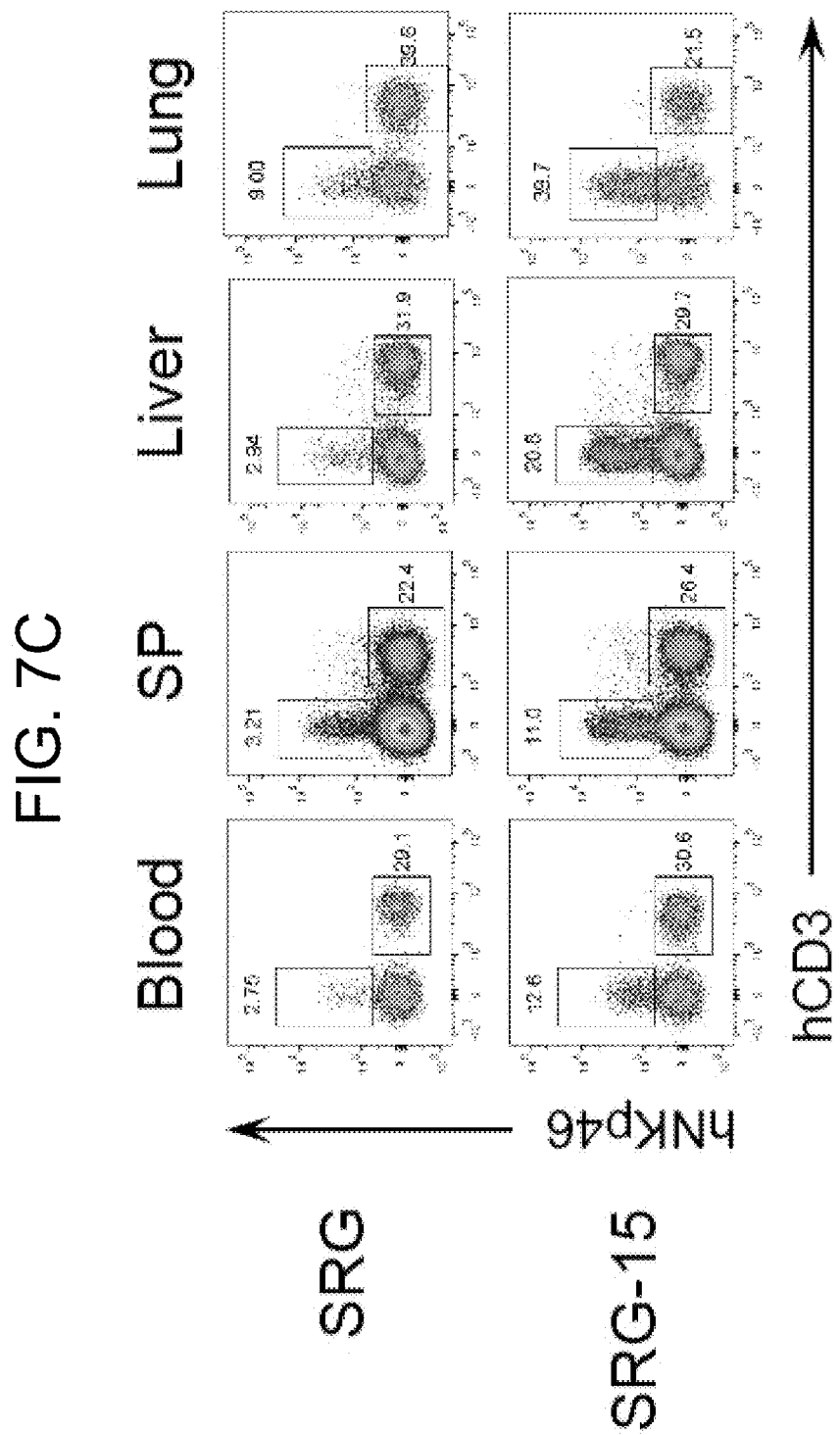

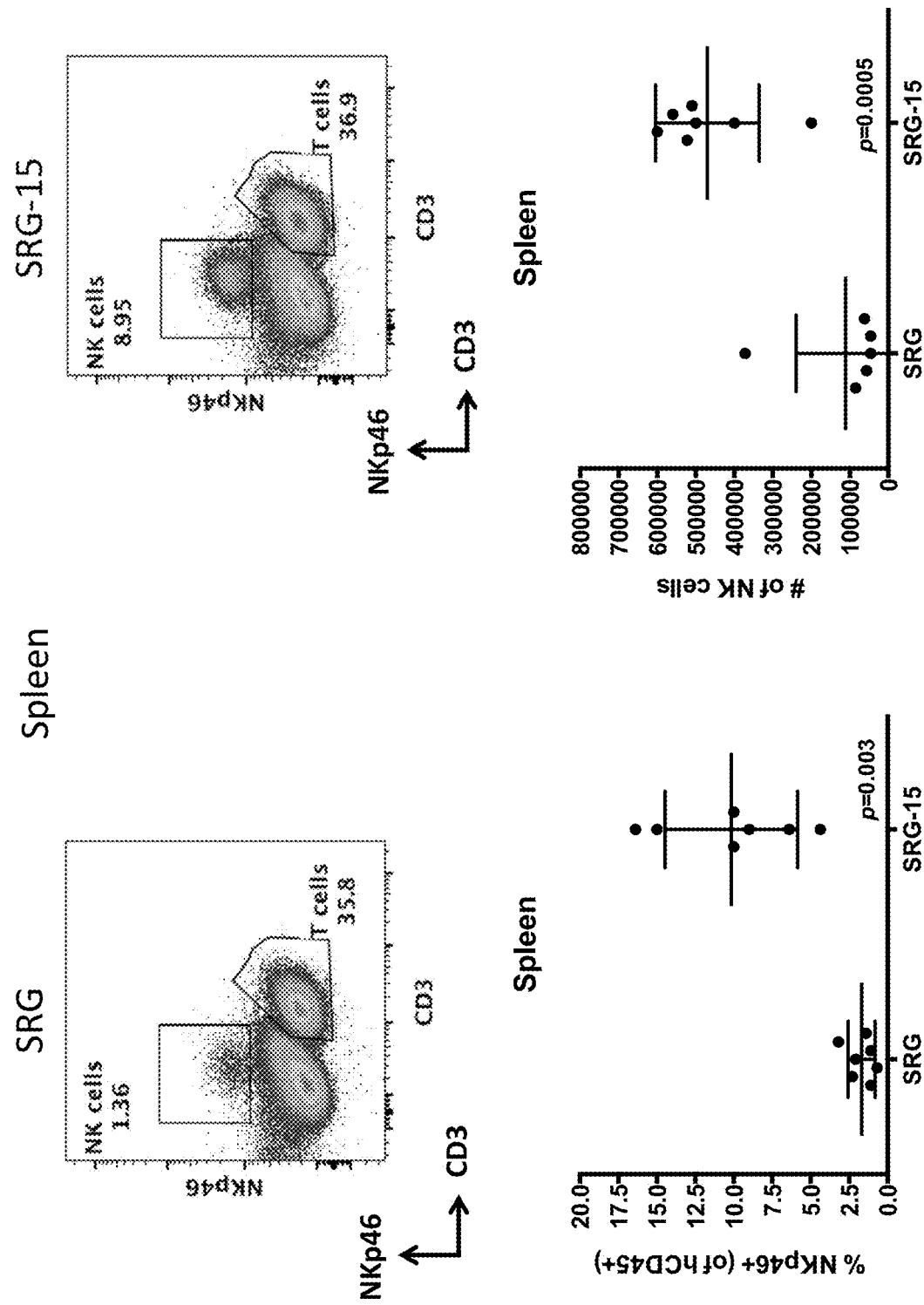

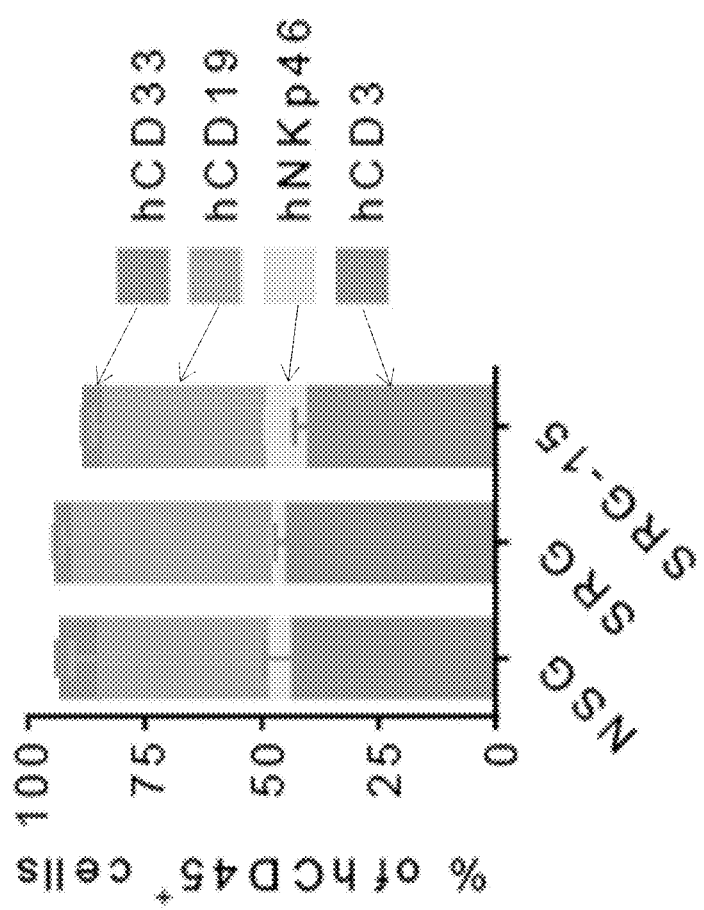

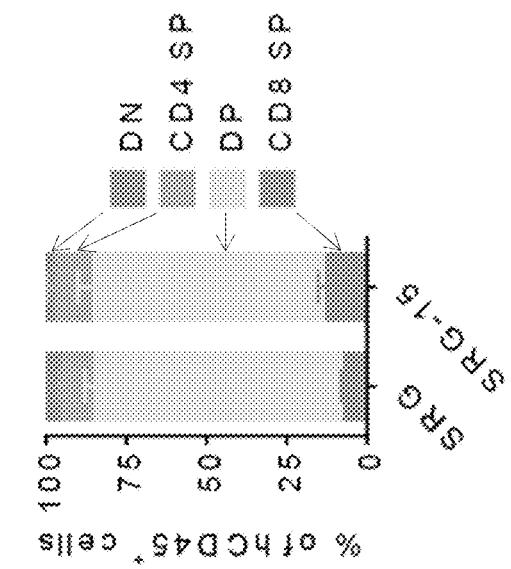
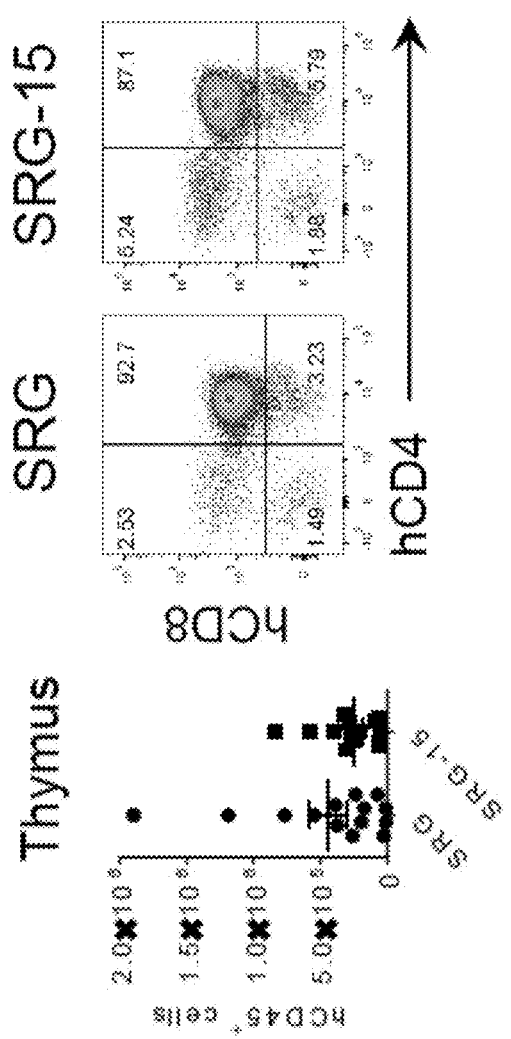
FIG. 9C  FIG. 9D  FIG. 9E

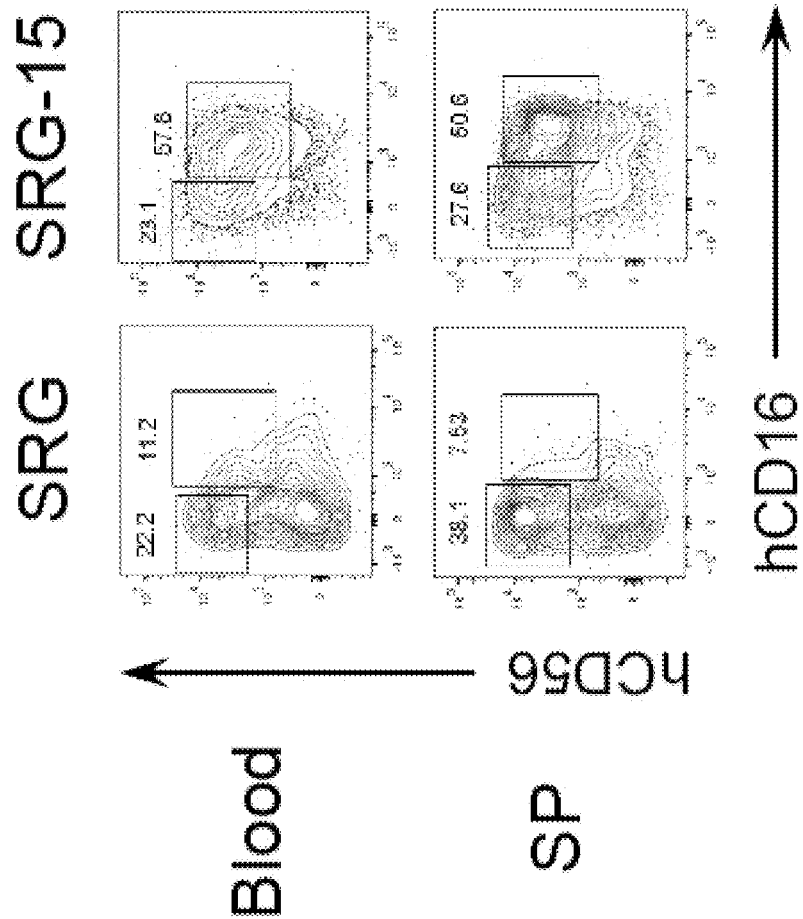

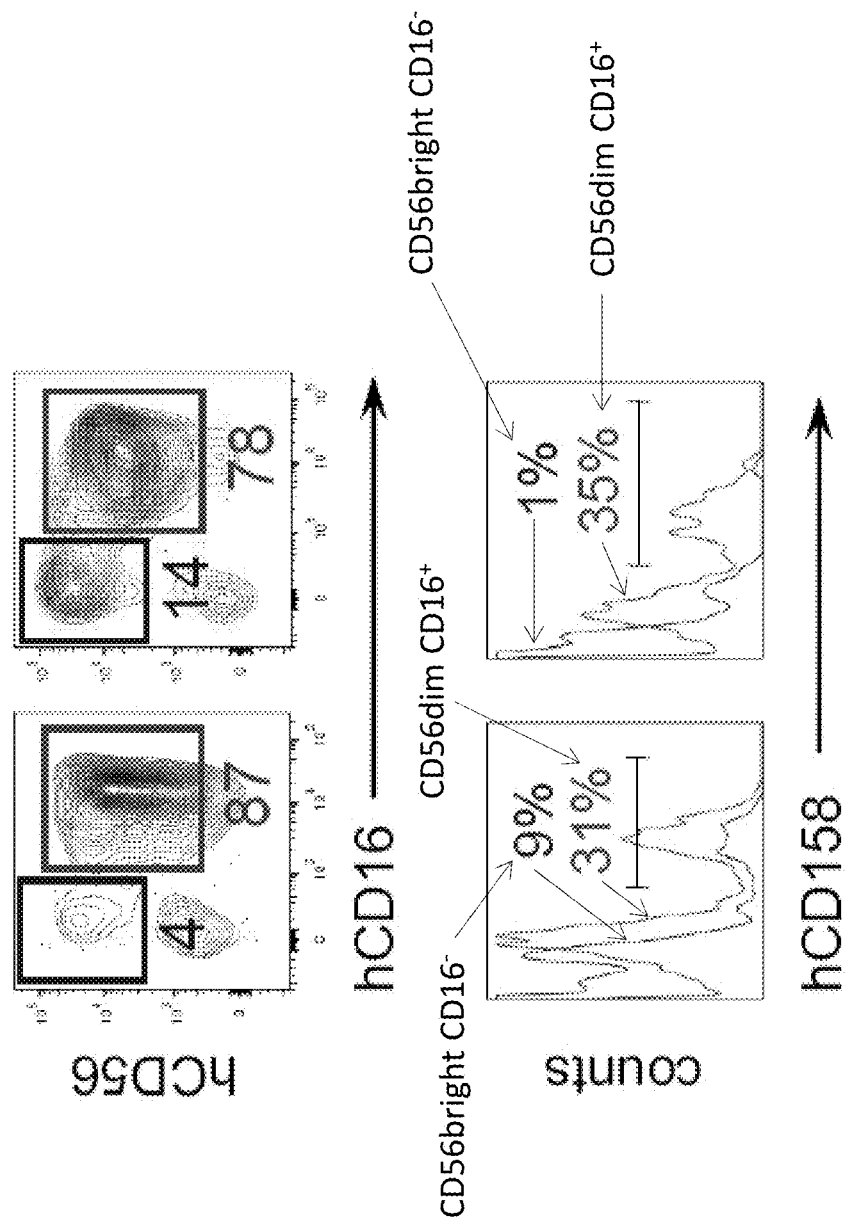

FIG. 11
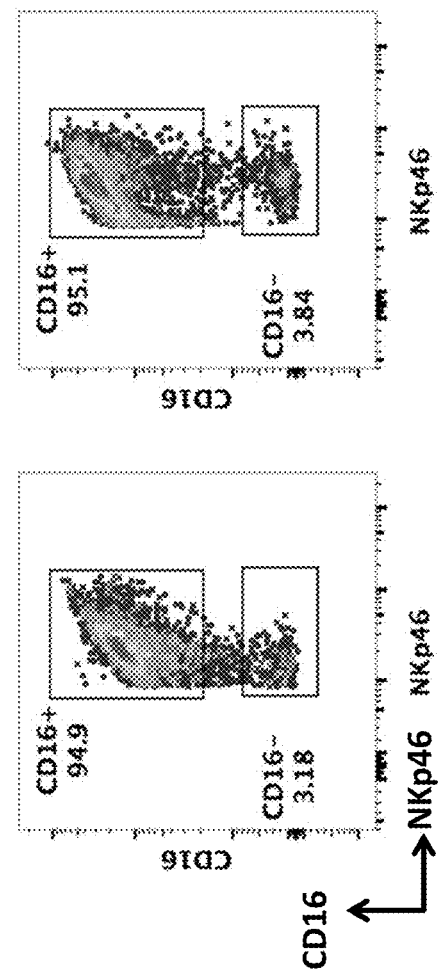
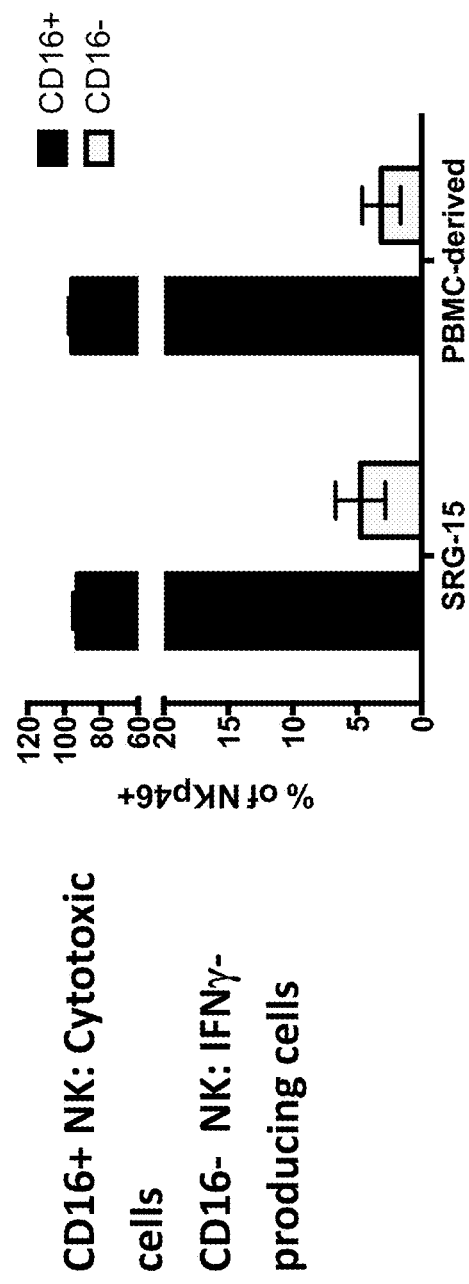
CD16+ NK: Cytotoxic cells
CD16- NK: IFNγ-producing cells FIG. 14A
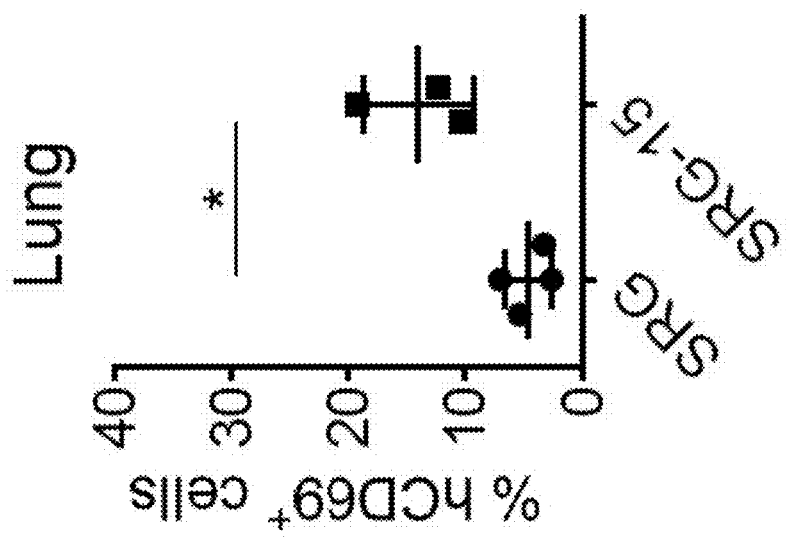
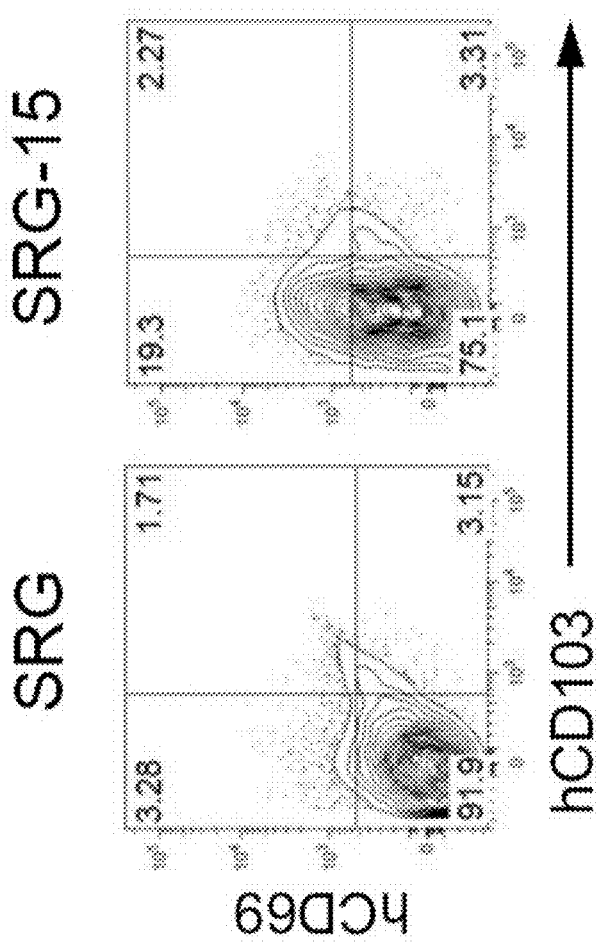

• Reflective of normal human GALT physiology

FIG. 19C
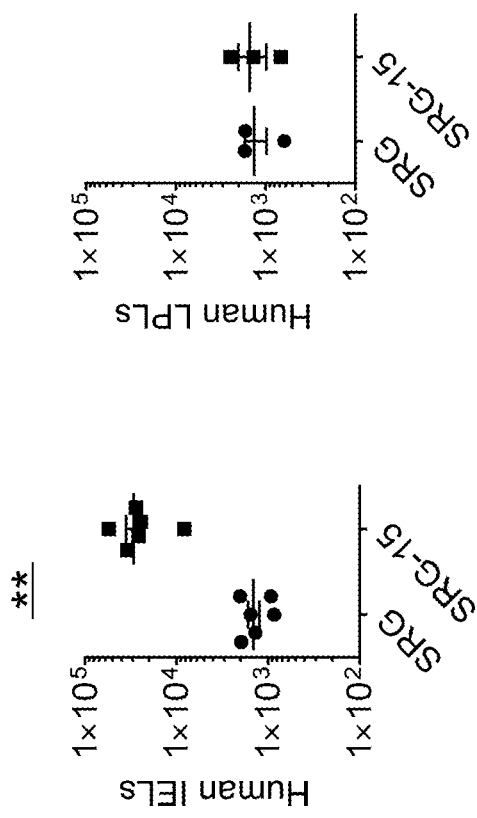
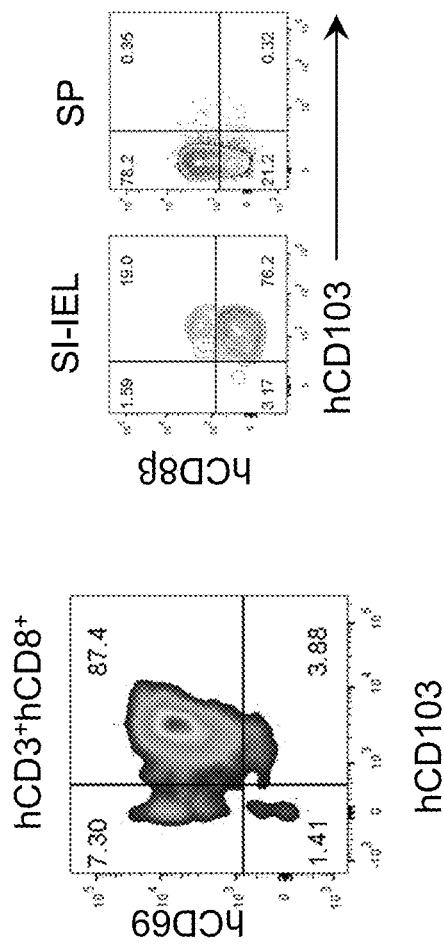

Only hIL-15hu/hu mice have discernible Peyer's Patches; pre-dominantly hCD45+

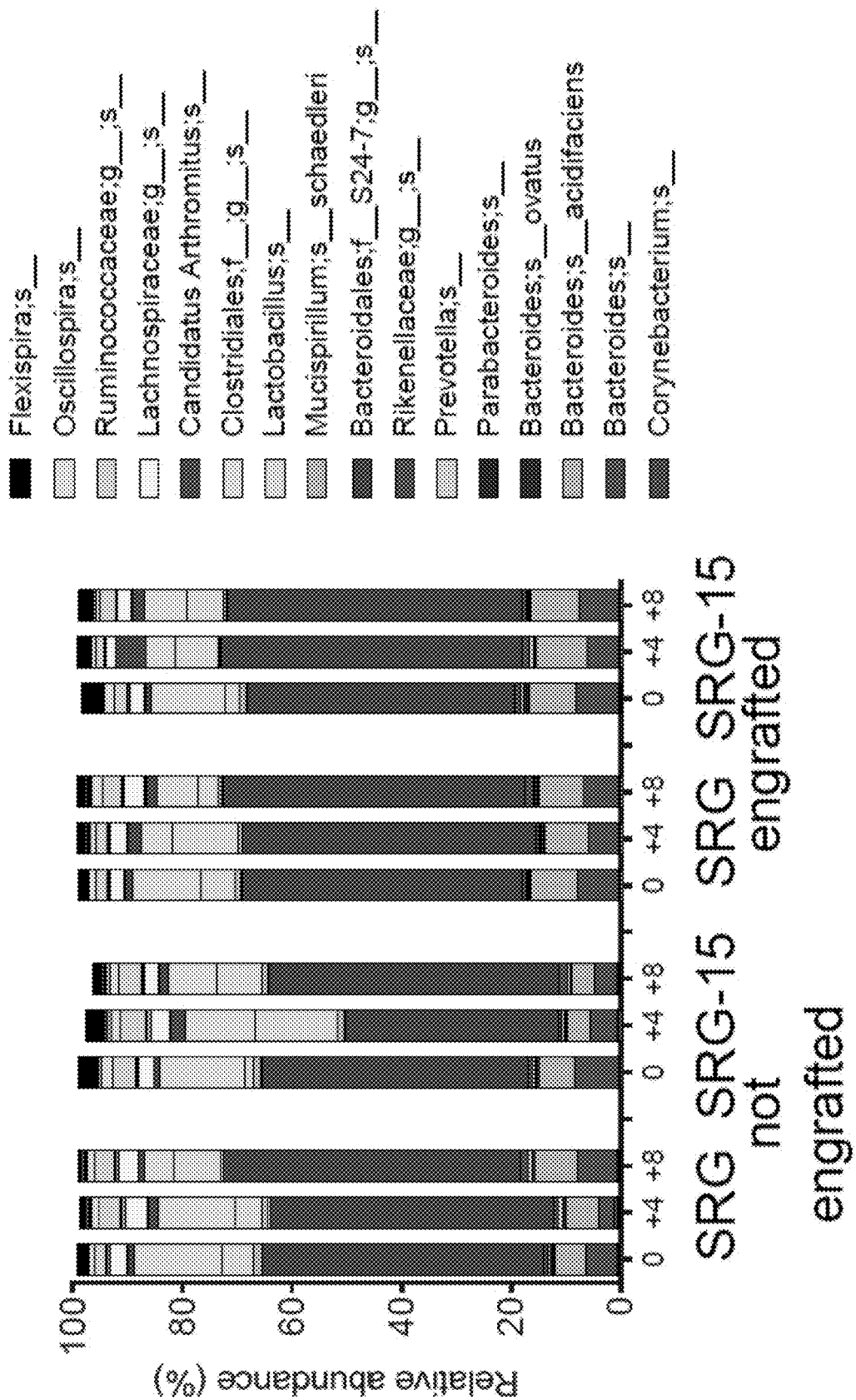

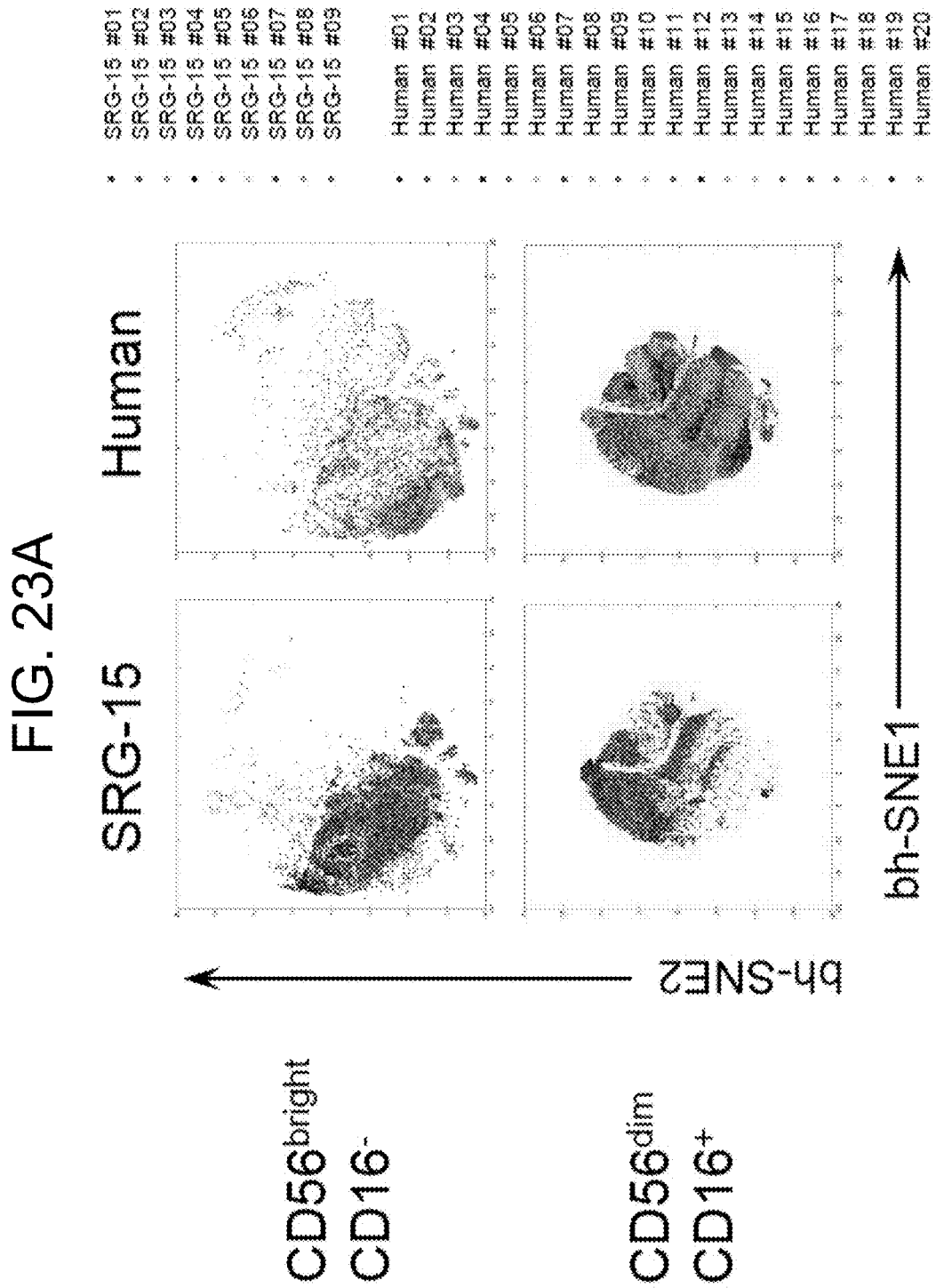

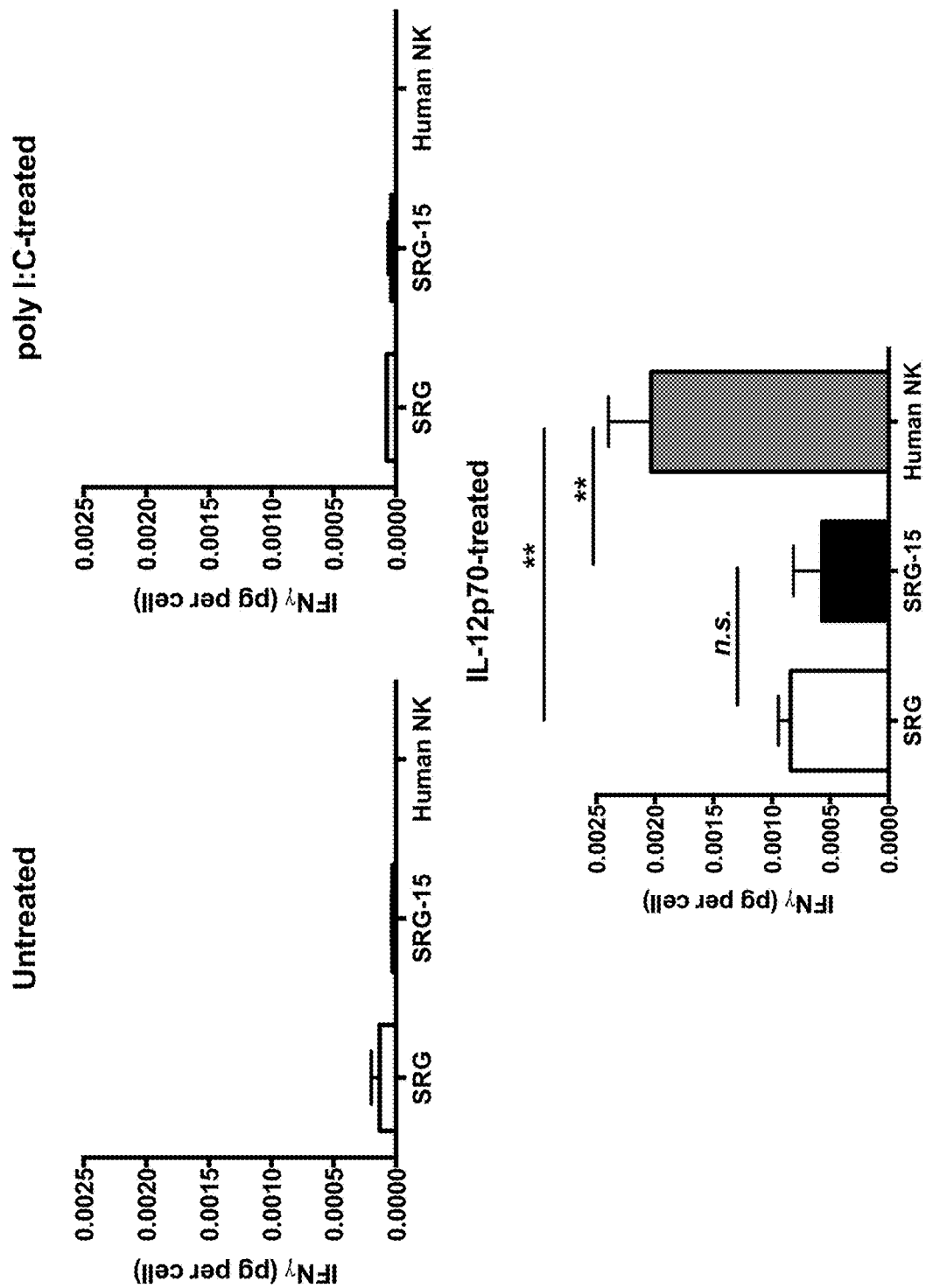

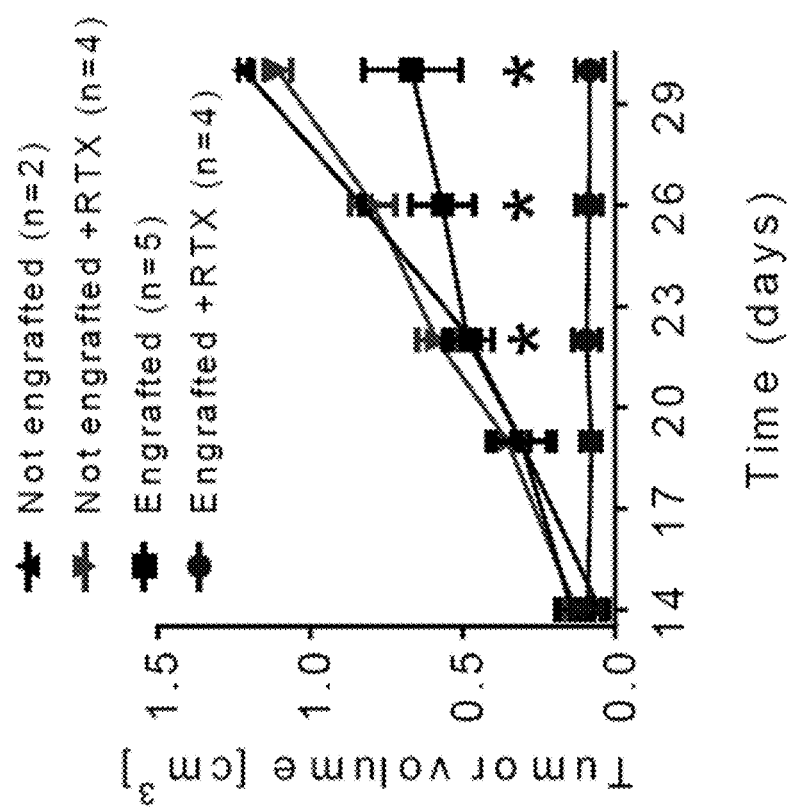

SEQUENCE LISTING

<160> NUMBER OF SEQ ID NOS: 36

<210> SEQ ID NO 1
<211> LENGTH: 200
<212> TYPE: DNA
<213> ORGANISM: Artificial sequence
<220> FEATURE:
<223> OTHER INFORMATION: synthetic polynucleotide

<400> SEQUENCE: 1

```
agctctccta ccactagact gctgagaccc gctgctctgc tcaggactcg atttccagta    60
cacaatctcc ctctttgaaa agtaccacac atcctggggt gctcttgcat tgtgtgaca    120 ctttgctagc caggctcagt cctgggttcc aggtgggac tcaaacacac tggcacgagt    180
ctacattgga tattcttggt                                                200
```

<210> SEQ ID NO 2
<211> LENGTH: 199
<212> TYPE: DNA
<213> ORGANISM: Artificial sequence
<220> FEATURE:
<223> OTHER INFORMATION: synthetic polynucleotide

<400> SEQUENCE: 2

```
gctccccatt cctcactggc ccagcccctc ttccctactc tttctagccc ctgcctcatc    60
tccctggctg ccattgggag cctgccccac tggaagccag tcgagataac ttcgtataat    120
gtatgctata cgaagttata tgcatggcct ccgcgccggg ttttggcgcc tcccgcgggc    180 gccccctcc tcacggcga                                                  199
```

<210> SEQ ID NO 3
<211> LENGTH: 200
<212> TYPE: DNA
<213> ORGANISM: Artificial sequence
<220> FEATURE:
<223> OTHER INFORMATION: synthetic polynucleotide

<400> SEQUENCE: 3

```
cattctcagt attgttttgc caagttctaa ttccatcaga cctcgacctg cagcccctag    60
ataacttcgt ataatgtatg ctatacgaag ttatgctagc tgtctcatag aggctggcga    120
tctggctcag ggacagccag tactgcaaag agtatccttg ttcataccttt ctcctagtgg   180 ccatctccct gggacagtca                                                200
```

<210> SEQ ID NO 4
<211> LENGTH: 208

```
<212> TYPE: DNA
<213> ORGANISM: Artificial sequence
<220> FEATURE:
<223> OTHER INFORMATION: synthetic polynucleotide

<400> SEQUENCE: 4
atccatttag cctttctctg atcactaagt tggacagttg dacagtcttc ctcaaattag    60
cttagactat caaaattata ctgtattttt ggtatttcca gcgatcgctt cagttacaag   120
gctgttgaat gcacagaagc aaggataaca ctgattttt cactggtcag aataaaaatt   180
attgattgct cttttgctta tagtattc                                     208

<210> SEQ ID NO 5
<211> LENGTH: 2028
<212> TYPE: DNA
<213> ORGANISM: Artificial sequence
<220> FEATURE:
<223> OTHER INFORMATION: synthetic polynucleotide

<400> SEQUENCE: 5
aatgtaacag aatctggatg caaagaatgt gaggaactgg aggaaaaaaa tattaaagaa    60
tttttgcaga gttttgtaca tattgtccaa atgttcatca acacttcttg attgcaattg   120
attcttttta aagtgtttct gttattaaca acatcactc tgctgcttag acataacaaa   180
acactcggca tttcaaatgt gctgtcaaaa caagttttc tgtcaagaag atgatcagac    240
cttggatcag atgaactctt agaaatgaag gcagaaaaat gtcattgagt aatatagtga   300
ctatgaactt ctctcagact tactttactc attttttaa tttattattg aaattgtaca    360
tatttgtgga ataatgtaaa atgttgaata aaaatatgta caagtgttgt tttttaagtt   420
gcactgatat tttacctctt attgcaaaat agcatttgtt taagggtgat agtcaaatta   480
tgtattggtg gggctgggta ccaatgctgc aggtcaacag ctatgctggt aggctcctgc   540
cagtgtggaa ccactgacta ctggctctca ttgacttcct tactaagcat agcaaacaga   600
ggaagaattt gttatcagta agaaaagaa gaactatatg tgaatcctct tctttatact   660
gtaatttagt tattgatgta taaagcaact gttatgaaat aaagaaattg caataactgg   720
catataatgt ccatcagtaa atcttggtgg tggtggcaat aataaacttc tactgatagg   780
tagaatggtg tgcaagcttg tccaatcacg gattgcaggc cacatgcggc ccaggacaac   840
tttgaatgtg gcccaacaca aattcataaa ctttcataca tctcgttttt agctcatcag   900
ctatcattag cggtagtgta tttaaagtgt ggcccaagac aattcttctt attccaatgt   960
ggcccaggga aatcaaaaga ttggatgccc ctggtataga aaactaatag tgacagtgtt  1020
catatttcat gctttcccaa atacaggtat tttattttca cattcttttt gccatgttta  1080
tataataata agaaaaacc ctgttgattt gttggagcca ttgttatctg acagaaaata  1140
attgtttata ttttttgcac tacactgtct aaaattagca agctctcttc taatggaact  1200
gtaagaaaga tgaaatattt tgtttttatt ataaatttat ttcaccttaa ttctggtaat  1260
actcactgag tgactgtggg gtgggaaatg atctcttaag aatttgattt ctttctattc  1320
catagtacaa actcgttctc tgttgaaaca ttcttctatc accccagtgc cctatccatg  1380
tacatgtgtt cttattgctc tagtcaaacg gtgcttataa atatctttca gaaagtttag  1440
gagaaatctg tatcctattt gacttccaat aatcatgtat tggctgtcag cttcttacct  1500
actctcagtc cagagaaata gtatttggca gccactcttt aaagtttatg ggttgtggat  1560
tgtggcggtt gatttatttt ttttatttca attgggatag aatttttaa tatacctgta  1620
```

```
tttttgtttt gttttatgta gcttttctat tagggagagt aggaaaagtg caccattttc    1680
ttctctaaat ttccagtcca gtctttaggg gaatgttagt cttcctgaga tgggggaagg    1740
aaaatcataa tgccagtcac tttgcaaata atattttata gtgataaatg gttcattttg    1800
gttacatagg catacaagtg ggcttaaaac ttggaattta ccagggctca aaattaaaat    1860
tcttacatta gttactcgat atggatcgct tcagttgatc ttagaaaact caaggcatag    1920
atctgcaacc tcgagataac ttcgtataat gtatgctata cgaagttata tgcatggcct    1980
ccgcgccggg ttttggcgcc tcccgcgggc gccccctcc tcacggcg               2028

<210> SEQ ID NO 6
<211> LENGTH: 200
<212> TYPE: DNA
<213> ORGANISM: Artificial sequence
<220> FEATURE:
<223> OTHER INFORMATION: synthetic polynucleotide

<400> SEQUENCE: 6
cattctcagt attgttttgc caagttctaa ttccatcaga cctcgacctg cagcccctag      60
ataacttcgt ataatgtatg ctatacgaag ttatgctagc gtgatagtcc ttcacggaaa     120
gtacaagaat acacagaaaa ctgctgttta cattagtctt tcacgttttt attttattct     180
cacaaatttt aatgcaatac                                                  200

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
agggatttga atcacgtttg                                                   20

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
tttactggca acatcaacag                                                   20

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
gcccagggaa atcaaaagat                                                   20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10
tggctccaac aaatcaacag                                                   20
```

<210> SEQ ID NO 11
<211> LENGTH: 4201
<212> TYPE: DNA
<213> ORGANISM: Homo sapiens

<400> SEQUENCE: 11

| | | | | | |
|---|---|---|---|---|---|
| tccggcccgc | acccacccc | aagaggggcc | ttcagctttg | gggctcagag | gcacgacctc | 60 |
| ctggggaggg | ttaaaaggca | gacgccccc | cgccccccgc | gccccgcgc | ccgactcct | 120 |
| tcgccgcctc | cagcctctcg | ccagtgggaa | gcggggagca | gccgcgcggc | cggagtccgg | 180 |
| aggcgagggg | aggtcggccg | caacttcccc | ggtccacctt | aagaggacga | tgtagccagc | 240 |
| tcgcagcgct | gaccttagaa | aaacaagttt | gcgcaaagtg | gagcggggac | ccggcctctg | 300 |
| ggcagccccg | gcggcgcttc | cagtgccttc | cagcccctcgc | gggcggcgca | gccgcggccc | 360 |
| atggagcccg | ccggcccggc | ccccggccgc | ctcgggccgc | tgctctgcct | gctgctcgcc | 420 |
| gcgtcctgcg | cctggtcagg | agtggcgggt | gaggaggagc | tgcaggtgat | tcagcctgac | 480 |
| aagtccgtgt | tggttgcagc | tggagagaca | gccactctgc | gctgcactgc | gacctctctg | 540 |
| atccctgtgg | ggcccatcca | gtggttcaga | ggagctggac | caggccggga | attaatctac | 600 |
| aatcaaaaag | aaggccactt | cccccgggta | acaactgttt | cagacctcac | aaagagaaac | 660 |
| aacatggact | tttccatccg | catcggtaac | atcaccccag | cagatgccgg | cacctactac | 720 |
| tgtgtgaagt | tccggaaagg | gagccccgat | gacgtggagt | ttaagtctgg | agcaggcact | 780 |
| gagctgtctg | tgcgcgccaa | accctctgcc | ccgtggtat | cgggccctgc | ggcgagggcc | 840 |
| acacctcagc | acacagtgag | cttcacctgc | gagtcccacg | gcttctcacc | cagagacatc | 900 |
| accctgaaat | ggttcaaaaa | tgggaatgag | ctctcagact | ccagaccaa | cgtggacccc | 960 |
| gtaggagaga | gcgtgtccta | cagcatccac | agcacagcca | aggtggtgct | gacccgcgag | 1020 |
| gacgttcact | ctcaagtcat | ctgcgaggtg | gcccacgtca | ccttgcaggg | ggaccctctt | 1080 |
| cgtgggactg | ccaacttgtc | tgagaccatc | cgagttccac | ccaccttgga | ggttactcaa | 1140 |
| cagcccgtga | gggcagagaa | ccaggtgaat | gtcacctgcc | aggtgaggaa | gttctacccc | 1200 |
| cagagactac | agctgacctg | gttggagaat | ggaaacgtgt | cccggacaga | aacggcctca | 1260 |
| accgttacag | agaacaagga | tggtacctac | aactggatga | gctggctcct | ggtgaatgta | 1320 |
| tctgcccaca | gggatgatgt | gaagctcacc | tgccaggtgg | agcatgacgg | gcagccagcg | 1380 |
| gtcagcaaaa | gccatgacct | gaaggtctca | gcccacccga | aggagcaggg | ctcaaatacc | 1440 |
| gccgctgaga | cactggatc | taatgaacgg | aacatctata | ttgtggtggg | tgtggtgtgc | 1500 |
| accttgctgg | tggccctact | gatggcggcc | ctctacctcg | tccgaatcag | acagaagaaa | 1560 |
| gcccagggct | ccacttcttc | tacaaggttg | catgagcccg | agaagaatgc | cagagaaata | 1620 |
| acacaggaca | caaatgatat | cacatatgca | gacctgaacc | tgcccaaggg | gaagaagcct | 1680 |
| gctcccccagg | ctgcggagcc | caacaaccac | acggagtatg | ccagcattca | gaccagcccg | 1740 |
| cagcccgcgt | cggaggacac | cctcacctat | gctgacctgg | acatggtcca | cctcaaccgg | 1800 |
| accccccaagc | agccggcccc | caagcctgag | ccgtccttct | cagagtacgc | cagcgtccag | 1860 |
| gtcccgagga | agtgaatggg | accgtggttt | gctctagcac | ccatctctac | gcgctttctt | 1920 |
| gtcccacagg | gagccgccgt | gatgagcaca | gccaacccag | ttcccggagg | gctggggcgg | 1980 |
| tgcaggctct | gggacccagg | ggccagggtg | gctcttctct | ccccacccct | ccttggctct | 2040 |
| ccagcacttc | ctgggcagcc | acggccccct | cccccacat | tgccacatac | ctggaggctg | 2100 |

```
acgttgccaa accagccagg gaaccaacct gggaagtggc cagaactgcc tggggtccaa    2160
gaactcttgt gcctccgtcc atcaccatgt gggttttgaa gaccctcgac tgcctccccg    2220
atgctccgaa gcctgatctt ccagggtggg gaggagaaaa tcccacctcc cctgacctcc    2280
accacctcca ccaccaccac caccaccacc accaccacta ccaccaccac caactggggg    2340
ctagagtggg gaagatttcc cctttagatc aaactgcccc ttccatggaa aagctggaaa    2400
aaaactctgg aacccatatc caggcttggt gaggttgctg ccaacagtcc tggcctcccc    2460
catccctagg ctaaagagcc atgagtcctg gaggaggaga ggaccccctcc caaaggactg    2520 gagacaaaac cctctgcttc cttgggtccc tccaagactc cctggggccc aactgtgttg    2580
ctccacccgg acccatctct cccttctaga cctgagcttg cccctccagc tagcactaag    2640
caacatctcg ctgtggacgc ctgtaaatta ctgagaaatg tgaaacgtgc aatcttgaaa    2700
ctgaggtgtt agaaaacttg atctgtggtg ttttgttttg ttttttttct taaaacaaca    2760
gcaacgtgat cttggctgtc tgtcatgtgt tgaagtccat ggttgggtct tgtgaagtct    2820
gaggtttaac agtttgttgt cctggaggga ttttcttaca gcgaagactt gagttcctcc    2880
aagtcccaga accccaagaa tgggcaagaa ggatcaggtc agccactccc tggagacaca    2940
gccttctggc tgggactgac ttggccatgt tctcagctga gccacgcggc tggtagtgca    3000
gccttctgtg accccgctgt ggtaagtcca gcctgcccag ggctgctgag ggctgcctct    3060
tgacagtgca gtcttatcga gacccaatgc ctcagtctgc tcatccgtaa agtggggata    3120
gtgaagatga caccccctccc caccacctct cataagcact ttaggaacac acagagggta    3180
gggatagtgg ccctggccgt ctatcctacc cctttagtga ccgcccccat cccggctttc    3240
tgagctgatc cttgaagaag aaatcttcca tttctgctct caaaccctac tgggatcaaa    3300
ctggaataaa ttgaagacag ccaggggat ggtgcagctg tgaagctcgg gctgattccc    3360
cctctgtccc agaaggttgg ccagagggtg tgacccagtt acccctttaac ccccacccctt    3420 ccagtcgggt gtgagggcct gaccgggccc agggcaagca gatgtcgcaa gcctatttta    3480
ttcagtcttc actataactc ttagagttga gacgctaatg ttcatgactc ctggccttgg    3540
gatgcccaag ggatttctgg ctcaggctgt aaaagtagct gagccatcct gcccattcct    3600
ggaggtccta caggtgaaac tgcaggagct cagcatagac ccagctctct ggggatggt    3660 cacctggtga tttcaatgat ggcatccagg aattagctga gccaacagac catgtggaca    3720
gctttggcca gagctcccgt gtggcatctg ggagccacag tgacccagcc acctggctca    3780
ggctagttcc aaaattccaaa agattggctt gtaaaccttc gtctccctct ctttacccca    3840
gagacagcac atacgtgtgc acacgcatgc acacacacat tcagtatttt aaaagaatgt    3900
tttcttggtg ccattttcat tttattttat ttttaattc ttggagggggg aaataaggga    3960 ataaggccaa ggaagatgta tagctttagc tttagcctgg caacctggag aatccacata    4020
ccttgtgtat tgaaccccag gaaaaggaag aggtcgaacc aaccctgcgg aaggagcatg    4080
gtttcaggag tttattttaa gactgctggg aaggaaacag gccccatttt gtatatagtt    4140
gcaacttaaa cttttttggct tgcaaaatat ttttgtaata aagatttctg ggtaataatg    4200
a                                                                    4201
```

<210> SEQ ID NO 12
<211> LENGTH: 504
<212> TYPE: PRT
<213> ORGANISM: Homo sapiens

<400> SEQUENCE: 12

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
    370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415
```

```
Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
        435                 440                 445

Asn His Thr Glu Tyr Ala Ser Ile Gln Thr Ser Pro Gln Pro Ala Ser
    450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500

<210> SEQ ID NO 13
<211> LENGTH: 4109
<212> TYPE: DNA
<213> ORGANISM: Homo sapiens

<400> SEQUENCE: 13
```

| | | | | | |
|---|---|---|---|---|---|
| ctctctggcc | gccectgget | ttatttctcg | cgcgcttggg | gtctctccca | gtctccgtct | 60 |
| ctccatttct | cctgggggc | ggggagggg | ggtctccaaa | aaccgcggcg | gcggcggcgg | 120 |
| ccgctccagg | cgcccgttcc | ggagtcgggg | ggaggcccag | ccgggagggg | ggaaggggg | 180 |
| gagccttagt | catttccccg | ctccagcctg | ctcccgcccg | agcgcgcact | cacggccgct | 240 |
| ctccctcctc | gctccgcagc | cgcggcccat | ggagcccgcc | ggcccggccc | ccggccgcct | 300 |
| cgggccgctg | ctctgcctgc | tgctcgccgc | gtcctgcgcc | tggtcaggag | tggcgggtga | 360 |
| ggaggagctg | caggtgattc | agcctgacaa | gtccgtgttg | gttgcagctg | gagagacagc | 420 |
| cactctcgcg | tgcactgcga | cctctctgat | ccctgtgggg | cccatccagt | ggttcagagg | 480 |
| agctggacca | ggccgggaat | taatctacaa | tcaaaaagaa | ggccacttcc | ccgggtaac | 540 |
| aactgtttca | gacctcacaa | agagaaacaa | catggacttt | tccatccgca | tcggtaacat | 600 |
| caccccagca | gatgccggca | cctactactg | tgtgaagttc | cggaaaggga | gccccgatga | 660 |
| cgtggagttt | aagtctggag | caggcactga | gctgtctgtg | cgcgccaaac | cctctgcccc | 720 |
| cgtggtatcg | ggccctgcgg | cgagggccac | acctcagcac | acagtgagct | tcacctgcga | 780 |
| gtcccacggc | ttctcacccca | gagacatcac | cctgaaatgg | ttcaaaaatg | ggaatgagct | 840 |
| ctcagacttc | cagaccaacg | tggaccccgt | aggagagagc | gtgtcctaca | gcatccacag | 900 |
| cacagccaag | gtggtgctga | cccgcgagga | cgttcactct | caagtcatct | gcgaggtggc | 960 |
| ccacgtcacc | ttgcaggggg | accctcttcg | tgggactgcc | aacttgtctg | agaccatccg | 1020 |
| agttccaccc | accttggagg | ttactcaaca | gccgtgagg | gcagagaacc | aggtgaatgt | 1080 |
| cacctgccag | gtgaggaagt | tctaccccca | gagactacag | ctgacctggt | tggagaatgg | 1140 |
| aaacgtgtcc | cggacagaaa | cggcctcaac | cgttacagag | aacaaggatg | gtacctacaa | 1200 |
| ctggatgagc | tggctcctgg | tgaatgtatc | tgcccacagg | gatgatgtga | agctcacctg | 1260 |
| ccaggtggag | catgacgggc | agccagcggt | cagcaaaagc | catgacctga | aggtctcagc | 1320 |
| ccacccgaag | gagcagggct | caaataccgc | cgctgagaac | actggatcta | atgaacggaa | 1380 |
| catctatatt | gtggtgggtg | tggtgtgcac | cttgctggtg | gccctactga | tggcggccct | 1440 |
| ctacctcgtc | cgaatcagac | agaagaaagc | ccagggctcc | acttcttcta | caaggttgca | 1500 |
| tgagcccgag | aagaatgcca | gagaaataac | acaggacaca | aatgatatca | catatgcaga | 1560 |
| cctgaacctg | cccaagggga | agaagcctgc | tccccaggct | gcggagccca | acaaccacac | 1620 |

```
ggagtatgcc agcattcaga ccagcccgca gcccgcgtcg gaggacaccc tcacctatgc    1680
tgacctggac atggtccacc tcaaccggac ccccaagcag ccggccccca agcctgagcc    1740
gtccttctca gagtacgcca gcgtccaggt cccgaggaag tgaatgggac cgtggtttgc    1800
tctagcaccc atctctacgc gctttcttgt cccacaggga gccgccgtga tgagcacagc    1860
caacccagtt cccggagggc tggggcggtg caggctctgg gacccagggg ccagggtggc    1920
tcttctctcc ccacccctcc ttggctctcc agcacttcct gggcagccac ggccccctcc    1980
ccccacattg ccacatacct ggaggctgac gttgccaaac cagccaggga accaacctgg    2040
gaagtggcca gaactgcctg ggtccaaga actcttgtgc ctccgtccat caccatgtgg    2100
gttttgaaga ccctcgactg cctccccgat gctccgaagc ctgatcttcc agggtgggga    2160
ggagaaaatc ccacctcccc tgacctccac cacctccacc accaccacca ccaccaccac    2220
caccactacc accaccaccc aactggggct agagtgggga agatttcccc tttagatcaa    2280 actgccccctt ccatggaaaa gctggaaaaa aactctggaa cccatatcca ggcttggtga    2340
ggttgctgcc aacagtcctg gcctcccccca tccctaggct aaagagccat gagtcctgga    2400
ggaggagagg acccctccca aaggactgga gacaaaaccc tctgcttcct tgggtccctc    2460
caagactccc tggggcccaa ctgtgttgct ccacccggac ccatctctcc cttctagacc    2520
tgagcttgcc cctccagcta gcactaagca acatctcgct gtggacgcct gtaaattact    2580
gagaaatgtg aaacgtgcaa tcttgaaact gaggtgttag aaaacttgat ctgtggtgtt    2640
ttgttttgtt tttttttctta aaacaacagc aacgtgatct tggctgtctg tcatgtgttg    2700
aagtccatgg ttgggtcttg tgaagtctga ggtttaacag tttgttgtcc tggagggatt    2760
ttcttacagc gaagacttga gttcctccaa gtcccagaac cccaagaatg ggcaagaagg    2820
atcaggtcag ccactccctg gagacacagc cttctggctg ggactgactt ggccatgttc    2880
tcagctgagc cacgcggctg gtagtgcagc cttctgtgac cccgctgtgg taagtccagc    2940
ctgcccaggg ctgctgaggg ctgcctcttg acagtgcagt cttatcgaga cccaatgcct    3000
cagtctgctc atccgtaaag tggggatagt gaagatgaca cccctcccca ccacctctca    3060
taagcacttt aggaacacac agagggtagg gatagtggcc ctggccgtct atcctacccc    3120
tttagtgacc gcccccatcc cggctttctg agctgatcct tgaagaagaa atcttccatt    3180
tctgctctca aaccctactg ggatcaaact ggaataaatt gaagacagcc aggggatgg    3240 tgcagctgtg aagctcgggc tgattccccc tctgtcccag aaggttggcc agagggtgtg    3300
acccagttac cctttaaccc ccacccttcc agtcgggtgt gagggcctga ccgggcccag    3360
ggcaagcaga tgtcgcaagc cctatttatt cagtcttcac tataactctt agagttgaga    3420
cgctaatgtt catgactcct ggccttggga tgcccaaggg atttctggct caggctgtaa    3480
aagtagctga gccatcctgc ccattcctgg aggtcctaca ggtgaaactg caggagctca    3540
gcatagaccc agctctctgg gggatggtca cctggtgatt tcaatgatgg catccaggaa    3600
ttagctgagc caacagacca tgtggacagc tttggccaga gctcccgtgt ggcatctggg    3660
agccacagtg acccagccac ctggctcagg ctagttccaa attccaaaag attggcttgt    3720
aaaccttcgt ctccctctct tttacccaga dacagcacat acgtgtgcac acgcatgcac    3780
acacacattc agtattttaa aagaatgttt tcttggtgcc attttcattt tatttttattt    3840 tttaattctt ggagggggaa ataagggaat aaggccaagg aagatgtata gctttagctt    3900
tagcctggca acctggagaa tccacatacc ttgtgtattg aaccccagga aaaggaagag    3960
```

```
gtcgaaccaa ccctgcggaa ggagcatggt ttcaggagtt tatttaaga ctgctgggaa    4020 ggaaacaggc cccattttgt atatagttgc aacttaaact ttttggcttg caaatatt     4080 ttgtaataaa gatttctggg taataatga                                     4109

<210> SEQ ID NO 14
<211> LENGTH: 3868
<212> TYPE: DNA
<213> ORGANISM: Homo sapiens

<400> SEQUENCE: 14
cgctcgctcg cagagaagcc gcggcccatg gagcccgccg gcccggcccc cggccgcctc      60
gggccgctgc tctgcctgct gctcgccgcg tcctgcgcct ggtcaggagt ggcgggtgag     120
gaggagctgc aggtgattca gcctgacaag tccgtgttgg ttgcagctgg agagacagcc     180
actctgcgct gcactgcgac ctctctgatc cctgtggggc ccatccagtg gttcagagga     240
gctggaccag ccgggaatt aatctacaat caaaaagaag gccacttccc ccgggtaaca      300
actgtttcag acctcacaaa gagaaacaac atggactttt ccatccgcat cggtaacatc     360
accccagcag atgccggcac ctactactgt gtgaagttcc ggaaagggag ccccgatgac     420
gtggagttta gtctggagc aggcactgag ctgtctgtgc gcgccaaacc ctctgccccc      480
gtggtatcgg ccctgcggc gagggccaca cctcagcaca cagtgagctt cacctgcgag     540
tcccacggct tctcacccag agacatcacc ctgaaatggt tcaaaaatgg gaatgagctc     600
tcagacttcc agaccaacgt ggaccccgta ggagagagcg tgtcctacag catccacagc     660
acagccaagg tggtgctgac ccgcgaggac gttcactctc aagtcatctg cgaggtggcc     720
cacgtcacct tgcaggggga ccctcttcgt gggactgcca acttgtctga ccatccga      780 gttccaccca ccttggaggt tactcaacag cccgtgaggg cagagaacca ggtgaatgtc     840
acctgccagg tgaggaagtt ctaccccag agactacagc tgacctggtt ggagaatgga      900
aacgtgtccc ggacagaaac ggcctcaacc gttacagaga caaggatgg tacctacaac     960 tggatgagct ggctcctggt gaatgtatct gcccacaggg atgatgtgaa gctcacctgc    1020
caggtggagc atgacgggca gccagcggtc agcaaaagcc atgacctgaa ggtctcagcc    1080 caccccgaagg agcagggctc aaataccgcc gctgagaaca ctggatctaa tgaacggaac    1140
atctatattg tggtgggtgt ggtgtgcacc ttgctggtgg ccctactgat ggcggccctc    1200
tacctcgtcc gaatcagaca gaagaaagcc cagggctcca cttcttctac aaggttgcat    1260
gagcccgaga agaatgccag agaaataaca caggacacaa atgatatcac atatgcagac    1320
ctgaacctgc caaggggaa gaagcctgct ccccaggctg cggagcccaa caaccacacg      1380
gagtatgcca gcattcagac cagcccgcag ccgcgtcgg aggacaccct cacctatgct      1440
gacctggaca tggtccacct caaccggacc cccaagcagc cggcccccaa gcctgagccg    1500
tccttctcag agtacgccag cgtccaggtc ccgaggaagt gaatgggacc gtggtttgct    1560
ctagcaccca tctctacgcg ctttcttgtc ccacaggag ccgccgtgat gagcacagcc      1620
aacccagttc ccggagggct ggggcggtgc aggctctggg acccaggggc cagggtggct    1680
cttctctccc caccctcct tggctctcca gcacttcctg ggcagccacg gccccctccc     1740
cccacattgc cacatacctg gaggctgacg ttgccaaacc agccagggaa ccaacctggg    1800
aagtggccag aactgcctgg ggtccaagaa ctcttgtgcc tccgtccatc accatgtggg    1860
ttttgaagac cctcgactgc ctcccgatg ctccgaagcc tgatcttcca gggtggggag      1920
gagaaaatcc cacctcccct gacctccacc acctccacca ccaccaccac caccaccacc    1980
```

| | |
|---|---|
| accactacca ccaccaccca actggggcta gagtggggaa gatttcccct ttagatcaaa | 2040 |
| ctgccccttc catggaaaag ctggaaaaaa actctggaac ccatatccag gcttggtgag | 2100 |
| gttgctgcca acagtcctgg cctcccccat ccctaggcta aagagccatg agtcctggag | 2160 |
| gaggagagga cccctcccaa aggactggag acaaaaccct ctgcttcctt gggtccctcc | 2220 |
| aagactccct ggggcccaac tgtgttgctc cacccggacc catctctccc ttctagacct | 2280 |
| gagcttgccc ctccagctag cactaagcaa catctcgctg tggacgcctg taaattactg | 2340 |
| agaaatgtga aacgtgcaat cttgaaactg aggtgttaga aaacttgatc tgtggtgttt | 2400 |
| tgttttgttt tttttcttaa aacaacagca acgtgatctt ggctgtctgt catgtgttga | 2460 |
| agtccatggt tgggtcttgt gaagtctgag gtttaacagt ttgttgtcct ggagggattt | 2520 |
| tcttacagcg aagacttgag ttcctccaag tcccagaacc ccaagaatgg gcaagaagga | 2580 |
| tcaggtcagc cactccctgg agacacagcc ttctggctgg gactgacttg gccatgttct | 2640 |
| cagctgagcc acgcggctgg tagtgcagcc ttctgtgacc ccgctgtggt aagtccagcc | 2700 |
| tgcccagggc tgctgagggc tgcctcttga cagtgcagtc ttatcgagac ccaatgcctc | 2760 |
| agtctgctca tccgtaaagt ggggatagtg aagatgacac ccctcccac cacctctcat | 2820 |
| aagcactta ggaacacaca gagggtaggg atagtggccc tggccgtcta tcctaccct | 2880 |
| ttagtgaccg cccccatccc ggctttctga gctgatcctt gaagaagaaa tcttccattt | 2940 |
| ctgctctcaa accctactgg gatcaaactg gaataaattg aagacagcca gggggatggt | 3000 |
| gcagctgtga agctcgggct gattcccct ctgtcccaga aggttggcca gagggtgtga | 3060 |
| cccagttacc ctttaacccc caccttcca gtcgggtgtg agggcctgac cgggcccagg | 3120 |
| gcaagcagat gtcgcaagcc ctatttattc agtcttcact ataactctta gagttgagac | 3180 |
| gctaatgttc atgactcctg gccttgggat gcccaaggga tttctggctc aggctgtaaa | 3240 |
| agtagctgag ccatcctgcc cattcctgga ggtcctacag gtgaaactgc aggagctcag | 3300 |
| catagaccca gctctctggg ggatggtcac ctggtgattt caatgatggc atccaggaat | 3360 |
| tagctgagcc aacagaccat gtggacagct ttggccagag ctcccgtgtg gcatctggga | 3420 |
| gccacagtga cccagccacc tggctcaggc tagttccaaa ttccaaaaga ttggcttgta | 3480 |
| aaccttcgtc tccctctctt ttacccagag acagcacata cgtgtgcaca cgcatgcaca | 3540 |
| cacacattca gtattttaaa agaatgtttt cttggtgcca tttttcatttt attttatttt | 3600 |
| ttaattcttg gaggggaaa taagggaata aggccaagga agatgtatag ctttagctttt | 3660 |
| agcctggcaa cctggagaat ccacatacct tgtgtattga acccaggaa aaggaagagg | 3720 |
| tcgaaccaac cctgcggaag gagcatggtt tcaggagttt attttaagac tgctgggaag | 3780 |
| gaaacaggcc ccattttgta tatagttgca acttaaactt tttggcttgc aaaatatttt | 3840 |
| tgtaataaag atttctgggt aataatga | 3868 |

<210> SEQ ID NO 15
<211> LENGTH: 4031
<212> TYPE: DNA
<213> ORGANISM: Mus musculus

<400> SEQUENCE: 15

| | |
|---|---|
| cgggaaggtg cgggcgcgag gaggggggcgc tcggccgggc cgccctcgcg ctggcctcgc | 60 |
| gacggctccg cacagcccgc actcgctctg cgagctgtcc ccgctcgcgc ttgctctccg | 120 |
| atctccgtcc ccgctccctc tccctcttcc tctcccctc tttccttctc cctcgctatc | 180 |

```
cgctcccccg ccccgtgcc tctggctctg cgcctggctc cctcgggtcc gctcccttt      240
cccgccggcc tggccggcg tcacgctccc ggagtctccc cgctcggcgg cgtctcattg      300
tgggagggg tcagatcacc ccgccgggcg gtggcgctgg ggggcagcgg agggggaggg      360
gccttagtcg ttcgcccgcg ccgcccgccc gcctgccgag cgcgctcacc gccgctctcc      420
ctccttgctc tgcagccgcg gcccatggag cccgccggcc cggcccctgg ccgcctaggg      480
ccgctgctgc tctgcctgct gctctccgcg tcctgtttct gtacaggagc cacggggaag      540
gaactgaagg tgactcagcc tgagaaatca gtgtctgttg ctgctgggga ttcgaccgtt      600
ctgaactgca cttttgacctc cttgttgccg gtgggaccca ttaggtggta cagaggagta      660
gggccaagcc ggctgttgat ctacagtttc gcaggagaat acgttcctcg aattagaaat      720
gtttcagata ctactaagag aaacaatatg gacttttcca tccgtatcag taatgtcacc      780
ccagcagatg ctggcatcta ctactgtgtg aagttccaga aaggatcatc agagcctgac      840
acagaaatac aatctggagg gggaacagag gtctatgtac tcgccaaacc ttctccaccg      900
gaggtatccg gcccagcaga caggggcata cctgaccaga aagtgaactt cacctgcaag      960
tctcatggct ctctccccg gaatatcacc ctgaagtggt tcaaagatgg caagaactc     1020
caccccttgg agaccaccgt gaaccctagt ggaaagaatg tctcctacaa catctccagc      1080
acagtcaggg tggtactaaa ctccatggat gttaattcta aggtcatctg cgaggtagcc      1140
cacatcacct tggatagaag ccctcttcgt gggattgcta acctgtctaa cttcatccga     1200
gttcacccca ccgtgaaggt cacccaacag tccccgacgt caatgaacca ggtgaacctc      1260
acctgccggg ctgagaggtt ctaccccgag gatctccagc tgatctggct ggagaatgga      1320
aacgtatcac ggaatgacac gcccaagaat ctcacaaaga cacggatggg gacctataat      1380
tacacaagct tgttcctggt gaactcatct gctcatagag aggacgtggt gttcacgtgc      1440
caggtgaagc acgaccaaca gccagcgatc acccgaaacc ataccgtgct gggatttgcc      1500
cactcgagtg atcaagggag catgcaaacc ttccctgata taatgctac ccacaactgg      1560
aatgtcttca tcggtgtggg cgtggcgtgt gctttgctcg tagtcctgct gatggctgct      1620
ctctacctcc tccggatcaa acagaagaaa gccaaggggt caacatcttc cacacggttg      1680
cacgagcccg agaagaacgc cagggaaata acccagatcc aggacacaaa tgacatcaac      1740
gacatcacat acgcagacct gaatctgccc aaagagaaga gcccgcacc ccgggcccct      1800
gagcctaaca accacacaga atatgcaagc attgagacag gcaaagtgcc taggccagag      1860
gataccctca cctatgctga cctggacatg gtccacctca gccgggcaca gccagccccc      1920
aagcctgagc catctttctc agagtatgct agtgtccagg tccagaggaa gtgaatgggg      1980
ctgtggtctg tactaggccc catcccccaca agttttcttg tcctacatgg agtggccatg      2040
acgaggacat ccagccagcc aatcctgtcc ccagaaggcc aggtggcacg ggtcctagga      2100
ccaggggtaa gggtggcctt tgtcttccct ccgtggctct tcaacacctc ttgggcaccc      2160
acgtccccctt cttccggagg ctgggtgttg cagaaccaga gggcgaactg gagaaagctg     2220
cctggaatcc aagaagtgtt gtgcctcggc ccatcactcg tgggtctgga tcctggtctt      2280
ggcaacccca ggttgcgtcc ttgatgttcc agagcttggt cttctgtgtg gagaagagct      2340
caccatctct acccaacttg agctttggga ccagactccc tttagatcaa accgcccat      2400
ctgtggaaga actacaccag aagtcagcaa gttttcagcc aacagtgctg gcctccccac      2460
ctcccaggct gactagccct gggggagaagg aaccctctcc tcctagacca gcagagactc      2520
cctgggcatg ttcagtgtgg ccccacctcc cttccagtcc cagcttgctt cctccagcta      2580
```

```
gcactaactc agcagcatcg ctctgtggac gcctgtaaat tattgagaaa tgtgaactgt   2640
gcagtcttaa agctaaggtg ttagaaaatt tgatttatgc tgtttagttg ttgttgggtt   2700
tcttttcttt ttaatttctt tttctttttt gattttttt ctttcccta aaacaacagc   2760 agcagcatct tggctctttg tcatgtgttg aatggttggg tcttgtgaag tctgaggtct   2820
aacagtttat tgtcctggaa ggattttctt acagcagaaa cagattttt tcaaattccc   2880 agaatcctga ggaccaagaa ggatccctca gctgctactt ccagcaccca gcgtcactgg   2940
gacgaaccag gccctgttct tacaaggcca catggctggc cctttgcctc catggctact   3000
gtggtaagtg cagccttgtc tgacccaatg ctgacctaat gttggccatt ccacattgag   3060
gggacaaggt cagtgatgcc ccccttcact cacaagcact tcagaggcat gcagagagaa   3120
gggacactcg gccagctctc tgaggtaatc agtgcaagga ggagtccgtt ttttgccagc   3180
aaacctcagc aggatcacac tggaacagaa cctggtcata cctgtgacaa cacagctgtg   3240
agccagggca aaccacccac tgtcactggc tcgagagtct gggcagaggc tctgaccctc   3300
caccctttaa actggatgcc ggggcctggc tgggcccaat gccaagtggt tatggcaacc   3360
ctgactatct ggtcttaaca tgtagctcag gaagtggagg cgctaatgtc cccaatccct   3420
ggggattcct gattccagct attcatgtaa gcagagccaa cctgcctatt tctgtaggtg   3480
cgactgggat gttaggagca cagcaaggac ccagctctgt agggctggtg acctgatact   3540
tctcataatg gcatctagaa gttaggctga gttggcctca ctggcccagc aaaccagaac   3600
ttgtctttgt ccgggccatg ttcttgggct gtcttctaat tccaaagggt tggttggtaa   3660
agctccaccc ccttctcctc tgcctaaaga catcacatgt gtatacacac acgggtgtat   3720
agatgagtta aaagaatgtc ctcgctggca tcctaatttt gtcttaagtt tttttggagg   3780
gagaaaggaa caaggcaagg gaagatgtgt agctttggct ttaaccaggc agcctgggg    3840 ctcccaagcc tatggaaccc tggtacaaag aagagaacag aagcgccctg tgaggagtgg   3900
gatttgtttt tctgtagacc agatgagaag gaaacaggcc ctgttttgta catagttgca   3960
acttaaaatt tttggcttgc aaaatatttt tgtaataaag atttctgggt aacaataaaa   4020
aaaaaaaaaa a                                                       4031
```

<210> SEQ ID NO 16
<211> LENGTH: 509
<212> TYPE: PRT
<213> ORGANISM: Mus musculus

<400> SEQUENCE: 16

```
Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Lys
            20                  25                  30

Glu Leu Lys Val Thr Gln Pro Glu Lys Ser Val Ser Val Ala Ala Gly
        35                  40                  45

Asp Ser Thr Val Leu Asn Cys Thr Leu Thr Ser Leu Leu Pro Val Gly
    50                  55                  60

Pro Ile Arg Trp Tyr Arg Gly Val Gly Pro Ser Arg Leu Leu Ile Tyr
65                  70                  75                  80

Ser Phe Ala Gly Glu Tyr Val Pro Arg Ile Arg Asn Val Ser Asp Thr
                85                  90                  95

Thr Lys Arg Asn Asn Met Asp Phe Ser Ile Arg Ile Ser Asn Val Thr
            100                 105                 110
```

Pro Ala Asp Ala Gly Ile Tyr Tyr Cys Val Lys Phe Gln Lys Gly Ser
        115                 120                 125

Ser Glu Pro Asp Thr Glu Ile Gln Ser Gly Gly Thr Glu Val Tyr
    130                 135                 140

Val Leu Ala Lys Pro Ser Pro Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
                180                 185                 190

His Pro Leu Glu Thr Thr Val Asn Pro Ser Gly Lys Asn Val Ser Tyr
                195                 200                 205

Asn Ile Ser Ser Thr Val Arg Val Val Leu Asn Ser Met Asp Val Asn
            210                 215                 220

Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255

Val Lys Val Thr Gln Gln Ser Pro Thr Ser Met Asn Gln Val Asn Leu
            260                 265                 270

Thr Cys Arg Ala Glu Arg Phe Tyr Pro Glu Asp Leu Gln Leu Ile Trp
        275                 280                 285

Leu Glu Asn Gly Asn Val Ser Arg Asn Asp Thr Pro Lys Asn Leu Thr
290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
                340                 345                 350

His Ser Ser Asp Gln Gly Ser Met Gln Thr Phe Pro Asp Asn Asn Ala
            355                 360                 365

Thr His Asn Trp Asn Val Phe Ile Gly Val Gly Val Ala Cys Ala Leu
        370                 375                 380

Leu Val Val Leu Leu Met Ala Ala Leu Tyr Leu Leu Arg Ile Lys Gln
385                 390                 395                 400

Lys Lys Ala Lys Gly Ser Thr Ser Ser Thr Arg Leu His Glu Pro Glu
                405                 410                 415

Lys Asn Ala Arg Glu Ile Thr Gln Ile Gln Asp Thr Asn Asp Ile Asn
                420                 425                 430

Asp Ile Thr Tyr Ala Asp Leu Asn Leu Pro Lys Glu Lys Lys Pro Ala
            435                 440                 445

Pro Arg Ala Pro Glu Pro Asn Asn His Thr Glu Tyr Ala Ser Ile Glu
        450                 455                 460

Thr Gly Lys Val Pro Arg Pro Glu Asp Thr Leu Thr Tyr Ala Asp Leu
465                 470                 475                 480

Asp Met Val His Leu Ser Arg Ala Gln Pro Ala Pro Lys Pro Glu Pro
                485                 490                 495

Ser Phe Ser Glu Tyr Ala Ser Val Gln Val Gln Arg Lys
            500                 505

<210> SEQ ID NO 17
<211> LENGTH: 3377

```
<212> TYPE: DNA
<213> ORGANISM: Mus musculus

<400> SEQUENCE: 17
cgggaaggtg cgggcgcgag gaggggcgc tcggccgggc cgccctcgcg ctggcctcgc    60
gacggctccg cacagcccgc actcgctctg cgagctgtcc ccgctcgcgc ttgctctccg   120
atctccgtcc ccgctccctc tccctcttcc tctccccctc tttccttctc cctcgctatc   180
cgctcccccg ccccgtgcc tctggctctg cgcctggctc cctcgggtcc gctccctt    240
cccgccggcc tggcccggcg tcacgctccc ggagtctccc cgctcggcgg cgtctcattg   300
tgggaggggg tcagatcacc ccgccgggcg gtggcgctgg ggggcagcgg agggggaggg   360
gccttagtcg ttcgcccgcg ccgcccgccc gcctgccgag cgcgctcacc gccgctctcc   420
ctccttgctc tgcagccgcg gcccatggag ccgccggcc cggcccctgg ccgcctaggg   480
ccgctgctgc tctgcctgct gctctccgcg tcctgtttct gtacaggagc cacggggaag   540
gaactgaagg tgactcagcc tgagaaatca gtgtctgttg ctgctgggga ttcgaccgtt   600
ctgaactgca ctttgaccct cttgttgccg gtgggaccca ttaggtggta cagaggagta   660
gggccaagcc ggctgttgat ctacagtttc gcaggagaat acgttcctcg aattagaaat   720
gtttcagata ctactaagag aaacaatatg gacttttcca tccgtatcag taatgtcacc   780
ccagcagatg ctggcatcta ctactgtgtg aagttccaga aaggatcatc agagcctgac   840
acagaaatac aatctggagg gggaacagag gtctatgtac tcgataataa tgctacccac   900
aactggaatg tcttcatcgg tgtgggcgtg gcgtgtgctt tgctcgtagt cctgctgatg   960
gctgctctct acctcctccg gatcaaacag aagaaagcca aggggtcaac atcttccaca  1020
cggttgcacg agcccgagaa gaacgccagg gaaataaccc agatccagga cacaaatgac  1080
atcaacgaca tcacatacgc agacctgaat ctgcccaaag agaagaagcc cgcaccccgg  1140
gcccctgagc ctaacaacca cacagaatat gcaagcattg agacaggcaa agtgcctagg  1200
ccagaggata ccctcaccta tgctgacctg gacatggtcc cctcagccg ggcacagcca  1260
gcccccaagc ctgagccatc tttctcagag tatgctagtg tccaggtcca gaggaagtga  1320
atggggctgt ggtctgtact aggccccatc cccacaagtt ttcttgtcct acatggagtg  1380
gccatgacga ggacatccag ccagccaatc ctgtccccag aaggccaggt ggcacgggtc  1440
ctaggaccag gggtaagggt ggcctttgtc ttccctccgt ggctcttcaa cacctcttgg  1500
gcacccacgt ccccttcttc cggaggctgg gtgttgcaga accagagggc gaactggaga  1560
aagctgcctg gaatccaaga agtgttgtgc ctcggcccat cactcgtggg tctggatcct  1620
ggtcttggca accccaggtt gcgtccttga tgttccagag cttggtcttc tgtgtggaga  1680
agagctcacc atctctaccc aacttgagct ttgggaccag actcccttta gatcaaaccg  1740
ccccatctgt ggaagaacta caccagaagt cagcaagttt tcagccaaca gtgctggcct  1800
ccccacctcc caggctgact agccctgggg agaaggaacc ctctcctcct agaccagcag  1860
agactccctg ggcatgttca gtgtggcccc acctcccttc cagtcccagc ttgcttcctc  1920
cagctagcac taactcagca gcatcgctct gtggacgcct gtaaattatt gagaaatgtg  1980
aactgtgcag tcttaaagct aaggtgttag aaaatttgat ttatgctgtt tagttgttgt  2040
tgggtttctt ttctttttaa ttttcttttc tttttgatt ttttttcttt cccttaaaac  2100
aacagcagca gcatcttggc tctttgtcat gtgttgaatg gttgggtctt tgaagtctg  2160
aggtctaaca gtttattgtc ctggaaggat tttcttacag cagaaacaga tttttttcaa  2220
```

```
attcccagaa tcctgaggac caagaaggat ccctcagctg ctacttccag cacccagcgt    2280
cactgggacg aaccaggccc tgttcttaca aggccacatg gctggccctt tgcctccatg    2340
gctactgtgg taagtgcagc cttgtctgac ccaatgctga cctaatgttg gccattccac    2400
attgagggga caaggtcagt gatgcccccc ttcactcaca agcacttcag aggcatgcag    2460
agagaaggga cactcggcca gctctctgag gtaatcagtg caaggaggag tccgtttttt    2520
gccagcaaac ctcagcagga tcacactgga acagaacctg gtcatacctg tgacaacaca    2580
gctgtgagcc agggcaaacc acccactgtc actggctcga gagtctgggc agaggctctg    2640
accctccacc ctttaaactg gatgccgggg cctggctggg cccaatgcca agtggttatg    2700
gcaaccctga ctatctggtc ttaacatgta gctcaggaag tggaggcgct aatgtcccca    2760
atccctgggg attcctgatt ccagctattc atgtaagcag agccaacctg cctatttctg    2820
taggtgcgac tgggatgtta ggagcacagc aaggacccag ctctgtaggg ctggtgacct    2880
gatacttctc ataatggcat ctagaagtta ggctgagttg gcctcactgg cccagcaaac    2940
cagaacttgt ctttgtccgg gccatgttct tgggctgtct tctaattcca aagggttggt    3000
tggtaaagct ccacccccctt ctcctctgcc taaagacatc acatgtgtat acacacacgg    3060
gtgtatagat gagttaaaag aatgtcctcg ctggcatcct aattttgtct taagtttttt    3120
tggaggagag aaggaacaag gcaagggaag atgtgtagct ttggctttaa ccaggcagcc    3180
tgggggctcc caagcctatg gaaccctggt acaaagaaga aacagaagc gccctgtgag    3240 gagtgggatt tgttttttctg tagaccagat gagaaggaaa caggccctgt tttgtacata    3300 gttgcaacttt aaaattttttg gcttgcaaaa tattttttgta ataaagattt ctgggtaaca    3360
ataaaaaaaa aaaaaaa                                                   3377
```

<210> SEQ ID NO 18
<211> LENGTH: 291
<212> TYPE: PRT
<213> ORGANISM: Mus musculus

<400> SEQUENCE: 18

```
Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Lys
            20                  25                  30

Glu Leu Lys Val Thr Gln Pro Glu Lys Ser Val Ser Val Ala Ala Gly
        35                  40                  45

Asp Ser Thr Val Leu Asn Cys Thr Leu Thr Ser Leu Leu Pro Val Gly
    50                  55                  60

Pro Ile Arg Trp Tyr Arg Gly Val Gly Pro Ser Arg Leu Leu Ile Tyr
65                  70                  75                  80

Ser Phe Ala Gly Glu Tyr Val Pro Arg Ile Arg Asn Val Ser Asp Thr
                85                  90                  95

Thr Lys Arg Asn Asn Met Asp Phe Ser Ile Arg Ile Ser Asn Val Thr
            100                 105                 110

Pro Ala Asp Ala Gly Ile Tyr Tyr Cys Val Lys Phe Gln Lys Gly Ser
        115                 120                 125

Ser Glu Pro Asp Thr Glu Ile Gln Ser Gly Gly Thr Glu Val Tyr
    130                 135                 140

Val Leu Asp Asn Asn Ala Thr His Asn Trp Asn Val Phe Ile Gly Val
145                 150                 155                 160

Gly Val Ala Cys Ala Leu Leu Val Val Leu Leu Met Ala Ala Leu Tyr
```

```
                165                 170                 175
Leu Leu Arg Ile Lys Gln Lys Lys Ala Lys Gly Ser Thr Ser Ser Thr
            180                 185                 190

Arg Leu His Glu Pro Glu Lys Asn Ala Arg Glu Ile Thr Gln Ile Gln
        195                 200                 205

Asp Thr Asn Asp Ile Asn Asp Ile Thr Tyr Ala Asp Leu Asn Leu Pro
    210                 215                 220

Lys Glu Lys Lys Pro Ala Pro Arg Ala Pro Glu Pro Asn Asn His Thr
225                 230                 235                 240

Glu Tyr Ala Ser Ile Glu Thr Gly Lys Val Pro Arg Pro Glu Asp Thr
                245                 250                 255

Leu Thr Tyr Ala Asp Leu Asp Met Val His Leu Ser Arg Ala Gln Pro
            260                 265                 270

Ala Pro Lys Pro Glu Pro Ser Phe Ser Glu Tyr Ala Ser Val Gln Val
        275                 280                 285

Gln Arg Lys
    290

<210> SEQ ID NO 19
<211> LENGTH: 4043
<212> TYPE: DNA
<213> ORGANISM: Mus musculus

<400> SEQUENCE: 19
cgggaaggtg cgggcgcgag gaggggcgc tcggccgggc cgccctcgcg ctggcctcgc      60
gacggctccg cacagcccgc actcgctctg cgagctgtcc ccgctcgcgc ttgctctccg     120
atctccgtcc ccgctccctc tccctcttcc tctccccctc tttccttctc cctcgctatc    180
cgctcccccg ccccgtgcc tctggctctg cgcctggctc cctcgggtcc gctcccttt      240
cccgccggcc tggcccggcg tcacgctccc ggagtctccc cgctcggcgg cgtctcattg    300
tgggaggggg tcagatcacc ccgcggggcg gtggcgctgg gggcagcgg aggggaggg      360
gccttagtcg ttcgcccgcg ccgcccgccc gcctgccgag cgcgctcacc gccgctctcc    420
ctccttgctc tgcagccgcg gcccatggag ccgccggcc cggcccctgg ccgcctaggg     480
ccgctgctgc tctgcctgct gctctccgcg tcctgtttct gtacaggagc cacggggaag    540
gaactgaagg tgactcagcc tgagaaatca gtgtctgttg ctgctgggga ttcgaccgtt    600
ctgaactgca cttgacctc cttgttgccg gtgggaccca ttaggtggta cagaggagta    660
gggccaagcc ggctgttgat ctacagtttc gcaggagaat acgttcctcg aattagaaat    720
gtttcagata ctactaagag aaacaatatg gacttttcca tccgtatcag taatgtcacc    780
ccagcagatg ctggcatcta ctactgtgtg aagttccaga aggatcatc agagcctgac    840
acagaaatac aatctggagg gggaacagag gtctatgtac tcgccaaacc ttctccaccg    900
gaggtatccg gcccagcaga caggggcata cctgaccaga agtgaactt cacctgcaag    960
tctcatggct tctctccccg gaatatcacc ctgaagtggt tcaaagatgg gcaagaactc   1020
caccccttgg agaccaccgt gaaccctagt ggaaagaatg tctcctacaa catctccagc   1080
acagtcaggg tggtactaaa ctccatggat gttaattcta aggtcatctg cgaggtagcc   1140
cacatcacct tggatagaag ccctcttcgt gggattgcta acctgtctaa cttcatccga   1200
gtttcaccca ccgtgaaggt cacccaacag tccccgacgt caatgaacca ggtgaacctc   1260
acctgccggg ctgagaggtt ctaccccgag atctccagc tgatctggct ggagaatgga   1320
aacgtatcac ggaatgacac gcccaagaat ctcacaaaga acacggatgg gacctataat   1380
```

-continued

```
tacacaagct tgttcctggt gaactcatct gctcatagag aggacgtggt gttcacgtgc    1440
caggtgaagc acgaccaaca gccagcgatc acccgaaacc ataccgtgct gggatttgcc    1500
cactcgagtg atcaagggag catgcaaacc ttccctgata taatgctac ccacaactgg     1560 aatgtcttca tcggtgtggg cgtggcgtgt gctttgctcg tagtcctgct gatggctgct    1620
ctctacctcc tccggatcaa acagaagaaa gccaaggggt caacatcttc cacacggttg    1680
cacgagcccg agaagaacgc cagggaaata acccaggtac agtctttgat ccaggacaca    1740
aatgacatca acgacatcac atacgcagac ctgaatctgc ccaaagagaa gaagcccgca    1800
cccgggcccc tgagcctaa caaccacaca gaatatgcaa gcattgagac aggcaaagtg     1860
cctaggccag aggatacct cacctatgct gacctggaca tggtccacct cagccgggca     1920
cagccagccc ccaagcctga gccatctttc tcagagtatg ctagtgtcca ggtccagagg    1980
aagtgaatgg ggctgtggtc tgtactaggc cccatcccca caagttttct tgtcctacat    2040
ggagtggcca tgacgaggac atccagccag ccaatcctgt ccccagaagg ccaggtggca    2100
cgggtcctag gaccaggggt aagggtggcc tttgtcttcc ctccgtggct cttcaacacc    2160
tcttgggcac ccacgtcccc ttcttccgga ggctgggtgt tgcagaacca gagggcgaac    2220
tggagaaagc tgcctggaat ccaagaagtg ttgtgcctcg gcccatcact cgtgggtctg    2280
gatcctggtc ttggcaaccc caggttgcgt ccttgatgtt ccagagcttg gtcttctgtg    2340
tggagaagag ctcaccatct ctacccaact tgagctttgg gaccagactc cctttagatc    2400
aaaccgcccc atctgtggaa gaactacacc agaagtcagc aagttttcag ccaacagtgc    2460
tggcctcccc acctcccagg ctgactagcc ctggggagaa ggaaccctct cctcctagac    2520
cagcagagac tccctgggca tgttcagtgt ggccccacct cccttccagt cccagcttgc    2580
ttcctccagc tagcactaac tcagcagcat cgctctgtgg acgcctgtaa attattgaga    2640
aatgtgaact gtgcagtctt aaagctaagg tgttagaaaa tttgatttat gctgtttagt    2700
tgttgttggg tttctttttct ttttaatttc tttttcttt ttgatttttt ttctttccct    2760
taaaacaaca gcagcagcat cttggctctt tgtcatgtgt tgaatggttg ggtcttgtga    2820
agtctgaggt ctaacagttt attgtcctgg aaggatttc ttacagcaga aacagatttt     2880
tttcaaattc ccagaatcct gaggaccaag aaggatccct cagctgctac ttccagcacc    2940
cagcgtcact gggacgaacc aggccctgtt cttacaaggc acatggctg gcccttgcc     3000 tccatggcta ctgtggtaag tgcagccttg tctgacccaa tgctgaccta atgttggcca    3060
ttccacattg aggggacaag gtcagtgatg ccccccttca ctcacaagca cttcagaggc    3120
atgcagagag aagggacact cggccagctc tctgaggtaa tcagtgcaag gaggagtccg    3180
ttttttgcca gcaaacctca gcaggatcac actggaacag aacctggtca tacctgtgac    3240
aacacagctg tgagccaggg caaaccaccc actgtcactg gctcgagagt ctgggcagag    3300
gctctgaccc tccacccttt aaactggatg ccggggcctg gctgggccca atgccaagtg    3360
gttatggcaa ccctgactat ctggtcttaa catgtagctc aggaagtgga ggcgctaatg    3420
tccccaatcc ctggggattc ctgattccag ctattcatgt aagcagagcc aacctgccta    3480
tttctgtagg tgcgactggg atgttaggag cacagcaagg acccagctct gtagggctgg    3540
tgacctgata cttctcataa tggcatctag aagttaggct gagttggcct cactggccca    3600
gcaaaccaga acttgtcttt gtccgggcca tgttcttggg ctgtcttcta attccaaagg    3660
gttggttggt aaagctccac ccccttctcc tctgcctaaa gacatcacat gtgtatacac    3720
```

-continued

```
acacgggtgt atagatgagt taaaagaatg tcctcgctgg catcctaatt ttgtcttaag      3780 ttttttttgga gggagaaagg aacaaggcaa gggaagatgt gtagctttgg ctttaaccag     3840
gcagcctggg ggctcccaag cctatggaac cctggtacaa agaagagaac agaagcgccc     3900
tgtgaggagt gggatttgtt tttctgtaga ccagatgaga aggaaacagg ccctgttttg     3960
tacatagttg caacttaaaa ttttttggctt gcaaatatt tttgtaataa agatttctgg     4020
gtaacaataa aaaaaaaaaa aaa                                              4043
```

```
<210> SEQ ID NO 20
<211> LENGTH: 513
<212> TYPE: PRT
<213> ORGANISM: Mus musculus

<400> SEQUENCE: 20
```

| | | | | | | | | | | | | | | | |
|---|---|---|---|---|---|---|---|---|---|---|---|---|---|---|---|
| Met | Glu | Pro | Ala | Gly | Pro | Ala | Pro | Gly | Arg | Leu | Gly | Pro | Leu | Leu | Leu |
| 1 | | | | 5 | | | | | 10 | | | | | 15 | |
| Cys | Leu | Leu | Leu | Ser | Ala | Ser | Cys | Phe | Cys | Thr | Gly | Ala | Thr | Gly | Lys |
| | | | 20 | | | | | 25 | | | | | 30 | | |
| Glu | Leu | Lys | Val | Thr | Gln | Pro | Glu | Lys | Ser | Val | Ser | Val | Ala | Ala | Gly |
| | | | 35 | | | | | 40 | | | | | 45 | | |
| Asp | Ser | Thr | Val | Leu | Asn | Cys | Thr | Leu | Thr | Ser | Leu | Leu | Pro | Val | Gly |
| | 50 | | | | | 55 | | | | | 60 | | | | |
| Pro | Ile | Arg | Trp | Tyr | Arg | Gly | Val | Gly | Pro | Ser | Arg | Leu | Leu | Ile | Tyr |
| 65 | | | | | 70 | | | | | 75 | | | | | 80 |
| Ser | Phe | Ala | Gly | Glu | Tyr | Val | Pro | Arg | Ile | Arg | Asn | Val | Ser | Asp | Thr |
| | | | | 85 | | | | | 90 | | | | | 95 | |
| Thr | Lys | Arg | Asn | Asn | Met | Asp | Phe | Ser | Ile | Arg | Ile | Ser | Asn | Val | Thr |
| | | | 100 | | | | | 105 | | | | | 110 | | |
| Pro | Ala | Asp | Ala | Gly | Ile | Tyr | Tyr | Cys | Val | Lys | Phe | Gln | Lys | Gly | Ser |
| | | | 115 | | | | | 120 | | | | | 125 | | |
| Ser | Glu | Pro | Asp | Thr | Glu | Ile | Gln | Ser | Gly | Gly | Gly | Thr | Glu | Val | Tyr |
| | 130 | | | | | 135 | | | | | 140 | | | | |
| Val | Leu | Ala | Lys | Pro | Ser | Pro | Pro | Glu | Val | Ser | Gly | Pro | Ala | Asp | Arg |
| 145 | | | | | 150 | | | | | 155 | | | | | 160 |
| Gly | Ile | Pro | Asp | Gln | Lys | Val | Asn | Phe | Thr | Cys | Lys | Ser | His | Gly | Phe |
| | | | | 165 | | | | | 170 | | | | | 175 | |
| Ser | Pro | Arg | Asn | Ile | Thr | Leu | Lys | Trp | Phe | Lys | Asp | Gly | Gln | Glu | Leu |
| | | | 180 | | | | | 185 | | | | | 190 | | |
| His | Pro | Leu | Glu | Thr | Thr | Val | Asn | Pro | Ser | Gly | Lys | Asn | Val | Ser | Tyr |
| | | | 195 | | | | | 200 | | | | | 205 | | |
| Asn | Ile | Ser | Ser | Thr | Val | Arg | Val | Val | Leu | Asn | Ser | Met | Asp | Val | Asn |
| | 210 | | | | | 215 | | | | | 220 | | | | |
| Ser | Lys | Val | Ile | Cys | Glu | Val | Ala | His | Ile | Thr | Leu | Asp | Arg | Ser | Pro |
| 225 | | | | | 230 | | | | | 235 | | | | | 240 |
| Leu | Arg | Gly | Ile | Ala | Asn | Leu | Ser | Asn | Phe | Ile | Arg | Val | Ser | Pro | Thr |
| | | | | 245 | | | | | 250 | | | | | 255 | |
| Val | Lys | Val | Thr | Gln | Gln | Ser | Pro | Thr | Ser | Met | Asn | Gln | Val | Asn | Leu |
| | | | 260 | | | | | 265 | | | | | 270 | | |
| Thr | Cys | Arg | Ala | Glu | Arg | Phe | Tyr | Pro | Glu | Asp | Leu | Gln | Leu | Ile | Trp |
| | | | 275 | | | | | 280 | | | | | 285 | | |
| Leu | Glu | Asn | Gly | Asn | Val | Ser | Arg | Asn | Asp | Thr | Pro | Lys | Asn | Leu | Thr |
| | 290 | | | | | 295 | | | | | 300 | | | | |
| Lys | Asn | Thr | Asp | Gly | Thr | Tyr | Asn | Tyr | Thr | Ser | Leu | Phe | Leu | Val | Asn |
| 305 | | | | | 310 | | | | | 315 | | | | | 320 |

```
Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
            340                 345                 350

His Ser Ser Asp Gln Gly Ser Met Gln Thr Phe Pro Asp Asn Asn Ala
        355                 360                 365

Thr His Asn Trp Asn Val Phe Ile Gly Val Gly Val Ala Cys Ala Leu
    370                 375                 380

Leu Val Val Leu Leu Met Ala Ala Leu Tyr Leu Arg Ile Lys Gln
385                 390                 395                 400

Lys Lys Ala Lys Gly Ser Thr Ser Ser Thr Arg Leu His Glu Pro Glu
                405                 410                 415

Lys Asn Ala Arg Glu Ile Thr Gln Val Gln Ser Leu Ile Gln Asp Thr
            420                 425                 430

Asn Asp Ile Asn Asp Ile Thr Tyr Ala Asp Leu Asn Leu Pro Lys Glu
        435                 440                 445

Lys Lys Pro Ala Pro Arg Ala Pro Glu Pro Asn Asn His Thr Glu Tyr
    450                 455                 460

Ala Ser Ile Glu Thr Gly Lys Val Pro Arg Pro Glu Asp Thr Leu Thr
465                 470                 475                 480

Tyr Ala Asp Leu Asp Met Val His Leu Ser Arg Ala Gln Pro Ala Pro
                485                 490                 495

Lys Pro Glu Pro Ser Phe Ser Glu Tyr Ala Ser Val Gln Val Gln Arg
            500                 505                 510

Lys
```

<210> SEQ ID NO 21
<211> LENGTH: 3845
<212> TYPE: DNA
<213> ORGANISM: Mus musculus

<400> SEQUENCE: 21

```
aagctcccct gccgcgggca gcctcttgcc cactggagtc taaggactgg ccgggtgaga     60
ggccgagacc agggggcgat cggccgccac ttccccagtc cacccttaaga ggaccaagta   120
gccagcccgc cgcgccgacc tcagaaaaac aagtttgcgc aaagtggtgc gcggccagcc   180
tctgggcaga gggagcggtg cttccaccgc ctggcagccc tgcgcgcggc ggcgcagccg   240
cggcccatgg agcccgccgg cccggccccct ggccgctagg ggccgctgct gctctgcctg   300
ctgctctccg cgtcctgttt ctgtacagga gccacgggga aggaactgaa ggtgactcag   360
cctgagaaat cagtgtctgt tgctgctggg gattcgaccg ttctgaactg cactttgacc   420
tccttgttgc cggtgggacc cattaggtgg tacagaggag tagggccaag ccggctgttg   480
atctacagtt tcgcaggaga atacgttcct cgaattagaa atgtttcaga tactactaag   540
agaaacaata tggacttttc catccgtatc agtaatgtca ccccagcaga tgctggcatc   600
tactactgtg tgaagttcca gaaggatca tcagagcctg acacagaaat acaatctgga   660
gggggaacag aggtctatgt actcgccaaa ccttctccac cggaggtatc cggcccagca   720
gacagggca tacctgacca gaaagtgaac ttcacctgca gtctcatgg cttctctccc   780
cggaatatca ccctgaagtg gttcaaagat gggcaagaac tccacccctt ggagaccacc   840
gtgaaccta gtgaaagaa tgtctcctac aacatctcca gcacagtcag ggtggtacta   900
aactccatgg atgttaattc taaggtcatc tgcgaggtag cccacatcac cttggataga   960
```

```
agccctcttc gtgggattgc taacctgtct aacttcatcc gagtttcacc caccgtgaag    1020
gtcacccaac agtccccgac gtcaatgaac caggtgaacc tcacctgccg ggctgagagg    1080
ttctaccccg aggatctcca gctgatctgg ctggagaatg gaaacgtatc acggaatgac    1140
acgcccaaga atctcacaaa gaacacggat gggacctata attacacaag cttgttcctg    1200
gtgaactcat ctgctcatag agaggacgtg gtgttcacgt gccaggtgaa gcacgaccaa    1260
cagccagcga tcacccgaaa ccataccgtg ctgggatttg cccactcgag tgatcaaggg    1320
agcatgcaaa ccttccctga taataatgct acccacaact ggaatgtctt catcggtgtg    1380
ggcgtggcgt gtgctttgct cgtagtcctg ctgatggctg ctctctacct cctccggatc    1440
aaacagaaga aagccaaggg gtcaacatct tccacacggt tgcacgagcc cgagaagaac    1500
gccagggaaa taacccaggt acagtctttg atccaggaca caaatgacat caacgacatc    1560
acatacgcag acctgaatct gcccaaagag aagaagcccg caccccgggc ccctgagcct    1620
aacaaccaca cagaatatgc aagcattgag acaggcaaag tgcctaggcc agaggatacc    1680
ctcacctatg ctgacctgga catggtccac ctcagccggg cacagccagc ccccaagcct    1740
gagccatctt tctcagagta tgctagtgtc caggtccaga ggaagtgaat ggggctgtgg    1800
tctgtactag gccccatccc cacaagtttt cttgtcctac atggagtggc catgacgagg    1860
acatccagcc agccaatcct gtccccagaa ggccaggtgg cacgggtcct aggaccaggg    1920
gtaagggtgg cctttgtctt ccctccgtgg ctcttcaaca cctcttgggc acccacgtcc    1980
ccttcttccg gaggctgggt gttgcagaac cagagggcga actggagaaa gctgcctgga    2040
atccaagaag tgttgtgcct cggcccatca ctcgtgggtc tggatcctgg tcttggcaac    2100
cccaggttgc gtccttgatg ttccagagct tggtcttctg tgtggagaag agctcaccat    2160
ctctacccaa cttgagcttt gggaccagac tcccttaga tcaaaccgcc ccatctgtgg    2220
aagaactaca ccagaagtca gcaagttttc agccaacagt gctggcctcc ccacctccca    2280
ggctgactag ccctggggag aaggaaccct ctcctcctag accagcagag actccctggg    2340
catgttcagt gtggccccac ctcccttcca gtcccagctt gcttcctcca gctagcacta    2400
actcagcagc atcgctctgt ggacgcctgt aaattattga gaaatgtgaa ctgtgcagtc    2460
ttaaagctaa ggtgttagaa aatttgattt atgctgttta gttgttgttg ggtttctttt    2520 cttttaatt tctttttctt ttttgatttt ttttctttcc cttaaaacaa cagcagcagc    2580
atcttggctc tttgtcatgt gttgaatggt tgggtcttgt gaagtctgag gtctaacagt    2640
ttattgtcct ggaaggattt tcttacagca gaaacagatt tttttcaaat tcccagaatc    2700
ctgaggacca agaaggatcc ctcagctgct acttccagca cccagcgtca ctgggacgaa    2760
ccaggccctg ttcttacaag gccacatggc tggccctttg cctccatggc tactgtggta    2820
agtgcagcct tgtctgaccc aatgctgacc taatgttggc cattccacat tgagggaca    2880 aggtcagtga tgcccccctt cactcacaag cacttcagag gcatgcagag agaagggaca    2940
ctcggccagc tctctgaggt aatcagtgca aggaggagtc cgttttttgc cagcaaacct    3000
cagcaggatc acactggaac agaacctggt catacctgtg acaacacagc tgtgagccag    3060
ggcaaaccac ccactgtcac tggctcgaga gtctgggcag aggctctgac cctccaccct    3120
ttaaactgga tgccggggcc tggctgggcc caatgccaag tggttatggc aaccctgact    3180
atctggtctt aacatgtagc tcaggaagtg gaggcgctaa tgtccccaat ccctggggat    3240
tcctgattcc agctattcat gtaagcagag ccaacctgcc tatttctgta ggtgcgactg    3300
ggatgttagg agcacagcaa ggacccagct ctgtagggct ggtgacctga tacttctcat    3360
```

```
aatggcatct agaagttagg ctgagttggc tcactggcc cagcaaacca gaacttgtct    3420
ttgtccgggc catgttcttg ggctgtcttc taattccaaa gggttggttg gtaaagctcc    3480 accccttct cctctgccta aagacatcac atgtgtatac acacgggt gtatagatga      3540 gttaaagaa tgtcctcgct ggcatcctaa ttttgtctta agttttttg gagggagaaa    3600 ggaacaaggc aagggaagat gtgtagcttt ggctttaacc aggcagcctg ggggctccca   3660
agcctatgga accctggtac aaagaagaga acagaagcgc cctgtgagga gtgggatttg   3720
tttttctgta gaccagatga aaggaaaca ggccctgttt tgtacatagt tgcaacttaa    3780
aatttttggc ttgcaaaata tttttgtaat aaagatttct gggtaacaat aaaaaaaaaa   3840
aaaaa                                                              3845

<210> SEQ ID NO 22
<211> LENGTH: 3389
<212> TYPE: DNA
<213> ORGANISM: Mus musculus

<400> SEQUENCE: 22
cgggaaggtg cgggcgcgag gaggggcgc tcggccgggc cgccctcgcg ctggcctcgc      60
gacggctccg cacagcccgc actcgctctg cgagctgtcc ccgctcgcgc ttgctctccg    120
atctccgtcc ccgctccctc tccctcttcc tctccccctc tttccttctc cctcgctatc   180 cgctccccg ccccgtgcc tctggctctg cgcctggctc cctcgggtcc gctccccttt     240
cccgccggcc tggccggcg tcacgctccc ggagtctccc cgctcggcgg cgtctcattg    300
tgggaggggg tcagatcacc ccgccgggcg gtggcgctgg ggggcagcgg aggggaggg    360 gccttagtcg ttcgcccgcg ccgcccgccc gcctgccgag cgcgctcacc gccgctctcc   420
ctccttgctc tgcagccgcg gcccatggag cccgccggcc cggcccctgg ccgcctaggg   480
ccgctgctgc tctgcctgct gctctccgcg tcctgtttct gtacaggagc cacggggaag   540
gaactgaagg tgactcagcc tgagaaatca gtgtctgttg ctgctgggga ttcgaccgtt   600
ctgaactgca ctttgaccte cttgttgccg gtgggaccca ttaggtggta cagaggagta    660
gggccaagcc ggctgttgat ctacagtttc gcaggagaat acgttcctcg aattagaaat    720
gtttcagata ctactaagag aaacaatatg gacttttcca tccgtatcag taatgtcacc    780
ccagcagatg ctggcatcta ctactgtgtg aagttccaga aaggatcatc agagcctgac    840
acagaaatac aatctggagg gggaacagag gtctatgtac tcgataataa tgctacccac    900
aactggaatg tcttcatcgg tgtgggcgtg gcgtgtgctt tgctcgtagt cctgctgatg    960
gctgctctct acctcctccg gatcaaacag aagaaagcca aggggtcaac atcttccaca   1020
cggttgcacg agcccgagaa gaacgccagg gaaataaccc aggtacagtc tttgatccag   1080
gacacaaatg acatcaacga catcacatac gcagacctga atctgccaa agagaagaag   1140 cccgcacccc gggcccctga gcctaacaac cacacagaat atgcaagcat tgagacaggc   1200
aaagtgccta ggccagagga taccctcacc tatgctgacc tggacatggt ccacctcagc   1260
cgggcacagc cagcccccaa gcctgagcca tctttctcag agtatgctag tgtccaggtc   1320
cagaggaagt gaatgggget gtggtctgta ctaggcccca tccccacaag ttttcttgtc   1380
ctacatggag tggccatgac gaggacatcc agccagccaa tcctgtcccc agaaggccag   1440
gtggcacggg tcctaggacc agggtaagg gtggcctttg tcttccctcc gtggctcttc   1500
aacacctctt gggcacccac gtccccttct tccggaggct gggtgttgca gaaccagagg   1560
```

```
gcgaactgga gaaagctgcc tggaatccaa gaagtgttgt gcctcggccc atcactcgtg    1620
ggtctggatc ctggtcttgg caaccccagg ttgcgtcctt gatgttccag agcttggtct    1680
tctgtgtgga gaagagctca ccatctctac ccaacttgag ctttgggacc agactccctt    1740
tagatcaaac cgccccatct gtggaagaac tacaccagaa gtcagcaagt tttcagccaa    1800
cagtgctggc ctccccacct cccaggctga ctagccctgg ggagaaggaa ccctctcctc    1860
ctagaccagc agagactccc tgggcatgtt cagtgtggcc ccacctccct tccagtccca    1920
gcttgcttcc tccagctagc actaactcag cagcatcgct ctgtggacgc ctgtaaatta    1980
ttgagaaatg tgaactgtgc agtcttaaag ctaaggtgtt agaaaatttg atttatgctg    2040
tttagttgtt gttgggtttc ttttcttttt aatttctttt tcttttttga ttttttttct    2100
ttcccttaaa acaacagcag cagcatcttg gctctttgtc atgtgttgaa tggttgggtc    2160
ttgtgaagtc tgaggtctaa cagtttattg tcctggaagg attttcttac agcagaaaca    2220
gatttttttc aaattcccag aatcctgagg accaagaagg atccctcagc tgctacttcc    2280
agcacccagc gtcactggga cgaaccaggc cctgttctta caaggccaca tggctggccc    2340
tttgcctcca tggctactgt ggtaagtgca gccttgtctg acccaatgct gacctaatgt    2400
tggccattcc acattgaggg gacaaggtca gtgatgcccc ccttcactca caagcacttc    2460
agaggcatgc agagagaagg acactcggc cagctctctg aggtaatcag tgcaaggagg    2520
agtccgtttt tgccagcaa acctcagcag gatcacactg aacagaacc tggtcatacc    2580
tgtgacaaca cagctgtgag ccagggcaaa ccacccactg tcactggctc gagagtctgg    2640
gcagaggctc tgaccctcca cccttttaaac tggatgccgg ggcctggctg ggcccaatgc    2700
caagtggtta tggcaaccct gactatctgg tcttaacatg tagctcagga agtggaggcg    2760
ctaatgtccc caatccctgg ggattcctga ttccagctat tcatgtaagc agagccaacc    2820
tgcctatttc tgtaggtgcg actgggatgt taggagcaca gcaaggaccc agctctgtag    2880
ggctggtgac ctgatacttc tcataatggc atctagaagt taggctgagt tggcctcact    2940
ggcccagcaa accagaactt gtctttgtcc gggccatgtt cttgggctgt cttctaattc    3000
caaagggttg gttggtaaag ctccaccccc ttctcctctg cctaaagaca tcacatgtgt    3060
atacacacac gggtgtatag atgagttaaa agaatgtcct cgctggcatc ctaattttgt    3120
cttaagtttt tttggaggga gaaaggaaca aggcaaggga agatgtgtag ctttggcttt    3180
aaccaggcag cctgggggct cccaagccta tggaaccctg gtacaaagaa gagaacagaa    3240
gcgccctgtg aggagtggga tttgtttttc tgtagaccag atgagaagga acaggcccc    3300
gttttgtaca tagttgcaac ttaaaatttt tggcttgcaa atattttg taataaagat    3360
ttctgggtaa caataaaaaa aaaaaaaaa                                     3389
```

<210> SEQ ID NO 23
<211> LENGTH: 295
<212> TYPE: PRT
<213> ORGANISM: Mus musculus

<400> SEQUENCE: 23

```
Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Lys
            20                  25                  30

Glu Leu Lys Val Thr Gln Pro Glu Lys Ser Val Ser Val Ala Ala Gly
        35                  40                  45
```

```
Asp Ser Thr Val Leu Asn Cys Thr Leu Thr Ser Leu Leu Pro Val Gly
    50                  55                  60

Pro Ile Arg Trp Tyr Arg Gly Val Gly Pro Ser Arg Leu Leu Ile Tyr
65                  70                  75                  80

Ser Phe Ala Gly Glu Tyr Val Pro Arg Ile Arg Asn Val Ser Asp Thr
                85                  90                  95

Thr Lys Arg Asn Asn Met Asp Phe Ser Ile Arg Ile Ser Asn Val Thr
            100                 105                 110

Pro Ala Asp Ala Gly Ile Tyr Tyr Cys Val Lys Phe Gln Lys Gly Ser
            115                 120                 125

Ser Glu Pro Asp Thr Glu Ile Gln Ser Gly Gly Thr Glu Val Tyr
    130                 135                 140

Val Leu Asp Asn Asn Ala Thr His Asn Trp Asn Val Phe Ile Gly Val
145                 150                 155                 160

Gly Val Ala Cys Ala Leu Leu Val Val Leu Leu Met Ala Ala Leu Tyr
                165                 170                 175

Leu Leu Arg Ile Lys Gln Lys Lys Ala Lys Gly Ser Thr Ser Ser Thr
            180                 185                 190

Arg Leu His Glu Pro Glu Lys Asn Ala Arg Glu Ile Thr Gln Val Gln
    195                 200                 205

Ser Leu Ile Gln Asp Thr Asn Asp Ile Asn Asp Ile Thr Tyr Ala Asp
    210                 215                 220

Leu Asn Leu Pro Lys Glu Lys Lys Pro Ala Pro Arg Ala Pro Glu Pro
225                 230                 235                 240

Asn Asn His Thr Glu Tyr Ala Ser Ile Glu Thr Gly Lys Val Pro Arg
                245                 250                 255

Pro Glu Asp Thr Leu Thr Tyr Ala Asp Leu Asp Met Val His Leu Ser
            260                 265                 270

Arg Ala Gln Pro Ala Pro Lys Pro Glu Pro Ser Phe Ser Glu Tyr Ala
    275                 280                 285

Ser Val Gln Val Gln Arg Lys
    290                 295

<210> SEQ ID NO 24
<211> LENGTH: 3020
<212> TYPE: DNA
<213> ORGANISM: Mus musculus

<400> SEQUENCE: 24
cgggaaggtg cgggcgcgag gaggggggcgc tcggccgggc cgccctcgcg ctggcctcgc      60
gacggctccg cacagcccgc actcgctctg cgagctgtcc ccgctcgcgc ttgctctccg     120
atctccgtcc ccgctcccte tccctcttcc tctcccccte tttccttctc cctcgctatc     180
cgctcccccg ccccegtgcc tctggctctg cgcctggctc cctcgggtcc gctcccctit     240 cccgccggcc tggccggcg tcacgctccc ggagtctccc cgctcggcgg cgtctcattg      300 tgggagggggg tcagatcacc ccgccgggcg gtggcgctgg ggggcagcgg aggggggaggg   360 gccttagtcg ttcgcccgcg ccgcccgccc gcctgccgag cgcgctcacc gccgctctcc    420
ctccttgctc tgcagccgcg gcccatggag ccgccggcc cggcccctgg ccgcctaggg      480
ccgctgctgc tctgcctgct gctctccgcg tcctgtttct gtacagataa taatgctacc    540
cacaactgga atgtcttcat cggtgtgggc gtggcgtgtg ctttgctcgt agtcctgctg    600
atggctgctc tctacctcct ccggatcaaa cagaagaaag ccaaggggtc aacatcttcc    660
acacggttgc acgagcccga gaagaacgcc aggaaaataa cccagatcca ggacacaaat    720
```

```
gacatcaacg acatcacata cgcagacctg aatctgccca aagagaagaa gcccgcaccc    780
cgggcccctg agcctaacaa ccacacagaa tatgcaagca ttgagacagg caaagtgcct    840
aggccagagg ataccctcac ctatgctgac ctggacatgg tccacctcag ccgggcacag    900
ccagccccca agcctgagcc atctttctca gagtatgcta gtgtccaggt ccagaggaag    960
tgaatggggc tgtggtctgt actaggcccc atccccacaa gttttcttgt cctacatgga   1020
gtggccatga cgaggacatc cagccagcca atcctgtccc cagaaggcca ggtggcacgg   1080
gtcctaggac caggggtaag ggtggccttt gtcttccctc cgtggctctt caacacctct   1140
tgggcaccca cgtccccttc ttccggaggc tgggtgttgc agaaccagag ggcgaactgg   1200
agaaagctgc ctggaatcca agaagtgttg tgcctcggcc catcactcgt gggtctggat   1260
cctggtcttg gcaaccccag gttgcgtcct tgatgttcca gagcttggtc ttctgtgtgg   1320
agaagagctc accatctcta cccaacttga gctttgggac cagactccct ttagatcaaa   1380 ccgcccatc tgtggaagaa ctacaccaga agtcagcaag ttttcagcca acagtgctgg   1440
cctccccacc tcccaggctg actagccctg ggagaagga  accctctcct cctagaccag   1500
cagagactcc ctgggcatgt tcagtgtggc cccacctccc ttccagtccc agcttgcttc   1560
ctccagctag cactaactca gcagcatcgc tctgtggacg cctgtaaatt attgagaaat   1620
gtgaactgtg cagtcttaaa gctaaggtgt tagaaaattt gatttatgct gtttagttgt   1680
tgttgggttt cttttctttt taatttcttt ttctttttg atttttttc tttcccttaa    1740 aacaacagca gcagcatctt ggctctttgt catgtgttga atggttgggt cttgtgaagt   1800
ctgaggtcta acagtttatt gtcctggaag gattttctta cagcagaaac agattttttt   1860
caaattccca gaatcctgag gaccaagaag gatccctcag ctgctacttc cagcacccag   1920
cgtcactggg acgaaccagg ccctgttctt acaaggccac atggctggcc ctttgcctcc   1980
atggctactg tggtaagtgc agccttgtct gacccaatgc tgacctaatg ttggccattc   2040
cacattgagg ggacaaggtc agtgatgccc cccttcactc acaagcactt cagaggcatg   2100
cagagagaag ggacactcgg ccagctctct gaggtaatca gtgcaaggag gagtccgttt   2160
tttgccagca aacctcagca ggatcacact ggaacagaac ctggtcatac ctgtgacaac   2220
acagctgtga gccagggcaa accacccact gtcactggct cgagagtctg gcagaggct    2280 ctgaccctcc acccttttaaa ctggatgccg gggcctggct gggcccaatg ccaagtggtt   2340
atggcaaccc tgactatctg gtcttaacat gtagctcagg aagtggaggc gctaatgtcc   2400
ccaatccctg gggattcctg attccagcta ttcatgtaag cagagccaac ctgcctattt   2460
ctgtaggtgc gactgggatg ttaggagcac agcaaggacc cagctctgta gggctggtga   2520
cctgatactt ctcataatgg catctagaag ttaggctgag ttggcctcac tggcccagca   2580
aaccagaact tgtctttgtc cgggccatgt tcttgggctg tcttctaatt ccaaagggtt   2640
ggttggtaaa gctccacccc cttctcctct gcctaaagac atcacatgtg tatacacaca   2700
cgggtgtata gatgagttaa aagaatgtcc tcgctggcat cctaattttg tcttaagttt   2760
ttttggaggg agaaaggaac aaggcaaggg aagatgtgta gctttggctt taaccaggca   2820 gcctggggc tcccaagcct atggaaccct ggtacaaaga agagaacaga agcgccctgt   2880
gaggagtggg attttgttttt ctgtagacca gatgagaagg aaacaggccc tgttttgtac   2940
atagttgcaa cttaaaattt ttggcttgca aaatattttt gtaataaaga tttctgggta   3000
acaataaaaa aaaaaaaaaa                                               3020
```

<210> SEQ ID NO 25
<211> LENGTH: 172
<212> TYPE: PRT
<213> ORGANISM: Mus musculus

<400> SEQUENCE: 25

```
Met Glu Pro Ala Gly Pro Ala Pro Gly Arg Leu Gly Pro Leu Leu Leu
1               5                   10                  15

Cys Leu Leu Ser Ala Ser Cys Phe Cys Thr Asp Asn Asn Ala Thr
            20                  25                  30

His Asn Trp Asn Val Phe Ile Gly Val Gly Val Ala Cys Ala Leu Leu
            35                  40                  45

Val Val Leu Leu Met Ala Ala Leu Tyr Leu Leu Arg Ile Lys Gln Lys
        50                  55                  60

Lys Ala Lys Gly Ser Thr Ser Ser Thr Arg Leu His Glu Pro Glu Lys
65                  70                  75                  80

Asn Ala Arg Glu Ile Thr Gln Ile Gln Asp Thr Asn Asp Ile Asn Asp
                85                  90                  95

Ile Thr Tyr Ala Asp Leu Asn Leu Pro Lys Glu Lys Lys Pro Ala Pro
            100                 105                 110

Arg Ala Pro Glu Pro Asn Asn His Thr Glu Tyr Ala Ser Ile Glu Thr
        115                 120                 125

Gly Lys Val Pro Arg Pro Glu Asp Thr Leu Thr Tyr Ala Asp Leu Asp
    130                 135                 140

Met Val His Leu Ser Arg Ala Gln Pro Ala Pro Lys Pro Glu Pro Ser
145                 150                 155                 160

Phe Ser Glu Tyr Ala Ser Val Gln Val Gln Arg Lys
                165                 170
```

<210> SEQ ID NO 26
<211> LENGTH: 3393
<212> TYPE: DNA
<213> ORGANISM: Mus musculus

<400> SEQUENCE: 26

| | | | | | |
|---|---|---|---|---|---|
| actctaccct | gcagccttca | gcttggcaca | aactaaacag | tgactcttcc | ccaagtgccg | 60 |
| agtttaattc | ctggcttggc | cgaaaggatt | cagagaggga | taagcagccc | ctctggcctt | 120 |
| cagtgccaaa | ataagaaaga | gtatttcaca | tccacaagcg | ggaagtacac | ttcataccto | 180 |
| tctaagataa | aagacctatt | cacaatcaaa | aatgtccctg | cagatggtaa | cagtgggtca | 240 |
| taacatagcc | ttaattcaac | caggcttctc | acttatgaat | tttgatggcc | aagttttctt | 300 |
| ctttggccag | aaaggctggc | ctaagagatc | ctgtcctact | ggagtctttc | attttgatat | 360 |
| aaaacaaaat | catctcaaac | tgaagcctgc | aatcttctct | aaagattcct | gctacctccc | 420 |
| acctcttcgt | tatccagcta | cttgctcata | caaaggcagc | atagactctg | acaagcatca | 480 |
| atatatcatt | cacggaggga | aaacaccaaa | caatgagctt | tccgataaga | tttatatcat | 540 |
| gtctgtcgct | tgcaagaata | caaaaaagt | tactttccgt | tgcacagaga | aagacttagt | 600 |
| aggagatgtc | cctgaaccca | gatacggcca | ttccattgac | gtggtgtata | gtcgagggaa | 660 |
| aagcatgggt | gttctctttg | gaggacgttc | atacatgcct | tctacccaga | gaaccacaga | 720 |
| aaaatggaat | agtgtagctg | actgcctacc | ccatgttttc | ttgatagatt | ttgaatttgg | 780 |
| gtgtgctaca | tcatatattc | tcccagaact | tcaggatggg | ctgtctttc | atgtttctat | 840 |
| tgccagaaac | gataccgttt | atattttggg | aggacactca | cttgccagta | atatacgccc | 900 |

```
tgctaacttg tatagaataa gagtggacct tccccctgggt accccagcag tgaattgcac    960
agtcttgcca ggaggaatct ctgtctccag tgcaatcctc actcaaacaa acaatgatga   1020
atttgttatt gtgggtggtt atcagctgga aaatcagaaa aggatggtct gcagccttgt   1080
ctctctaggg gacaacacga ttgaaatcag tgagatggag actcctgact ggacctcaga   1140
tattaagcat agcaaaatat ggtttggaag caacatggga aacgggacta ttttccttgg   1200
cataccagga gacaataagc aggctatgtc agaagcattc tatttctata ctttgagatg   1260
ctctgaagag gatttgagtg aagatcagaa aattgtctcc aacagtcaga catcaacaga   1320
agatcctggg gactccactc cctttgaaga ctcagaggaa ttttgtttca gtgctgaagc   1380
aaccagtttt gatggtgacg atgaatttga cacctacaat gaagatgatg aagatgacga   1440
gtctgtaacc ggctactgga taacatgttg ccctacttgt gatgttgaca tcaatacctg   1500
ggttccgttc tattcaacgg agctcaataa acccgccatg atctattgtt ctcatgggga   1560
tgggcactgg gtacatgccc agtgcatgga tttggaagaa cgcacactca tccacttgtc   1620
agaaggaagc aacaagtatt attgcaatga acatgtacag atagcaagag cattgcaaac   1680
tcccaaaaga aacccccccct tacaaaaacc tccaatgaaa tccctccaca aaaaaggctc   1740
tgggaaagtc ttgactcctg ccaagaaatc cttccttaga agactgtttg attaatttag   1800
caaaagcccc tcagactcag gtatattgct ctctgaatct actttcaatc ataaacatta   1860
ttttgatttt tgtttactga aatctctatg ttatgtttta gttatgtgaa ttaagtgctg   1920
ttgtgattta ttgttaagta taactattct aatgtgtgtt ttttaacatc ttatccagga   1980
atgtcttaaa tgagaaatgt tatacagttt tccattaagg atatcagtga taagtatag    2040
aactcttaca ttattttgta acaatctaca tattgaatag taactaaata ccaataaata   2100
aactaatgca caaaaagtta agttcttttg tgtaataagt agcctatagt tggtttaaac   2160
agttaaaacc aacagctata tcccacacta ctgctgttta taaatttttaa ggtggcctct   2220
ggtttatact tatgagcaga attatatata ttggtcaata ccatgaagaa aaatttaatt   2280
ctatatcaag ccaggcatgg tgatggtgat acatgcctgt aatcctggca cttaggaagt   2340
ggaagaagga agtttgtgag tttgatgctt gttgaggtat gacctttttgc tatgtattgt   2400
agtgtatgag ccccaagacc tgcttgaccc agagacaaga gagtccacac atagatccaa   2460
gtaatgctat gtgaccttgc cccccggtta cttgtgatta ggtgaataaa gatgtcaaca   2520
gccaatagct gggcagaaga gccaaaagtg gggattgagg gtaccctggc ttgatgtagg   2580
aggagaccat gaggaaaggg gagaaaaaag tgatggagga ggagaaagat gccatgagct   2640
aggagttaag aaagcatggc catgagtgct ggccaattgg agttaagagc agcccagatg   2700
aaacatagta agtaataact cagggttatc gatagaaaat agatttagt gccgtactct     2760
ccccagccct agagctgact atggcttact gtaaatataa agtttgtatg tgtcttttat   2820
ccaggaacta aatggtcaaa ggtggagtag aaactctgga ttgggattaa attttctac    2880
aacaaatgct ggcctgggct agattttatc tcatatccga aggctgacag aacacagagc   2940
actggtaaca ttgccacctg ccatgcacaa agacctgagt ctaatactgt ggacattttc   3000
ttgaagtatc tacatgtact tctggagtga aaacatattc caacaatatg cctttgttta   3060
aatcactcac tcactttggg ccctcacatt atatcctttc aaaatcaatg gttcaccct    3120
ttgaaaatgc ttagccatag tccctcatct tccttaaaga cagttgtcat ctctggaaat   3180
agtcacatgt cattccaaggt ccaatactgt gcagctctga agtatggcat taccacttta   3240
agtgaaaagt gaaatatgaa catgagctca gacaaaggtt tgggactatc actctcaagg   3300
```

```
aggctctact gctaagtcct gaactgcttt cacatgaata cagaaattat aacaaaaaat    3360
atgtaatcaa taaaaagaaa actttcatat tcc                                 3393
```

<210> SEQ ID NO 27
<211> LENGTH: 527
<212> TYPE: PRT
<213> ORGANISM: Mus musculus

<400> SEQUENCE: 27

```
Met Ser Leu Gln Met Val Thr Val Gly His Asn Ile Ala Leu Ile Gln
1               5                   10                  15

Pro Gly Phe Ser Leu Met Asn Phe Asp Gly Gln Val Phe Phe Phe Gly
            20                  25                  30

Gln Lys Gly Trp Pro Lys Arg Ser Cys Pro Thr Gly Val Phe His Phe
        35                  40                  45

Asp Ile Lys Gln Asn His Leu Lys Leu Lys Pro Ala Ile Phe Ser Lys
    50                  55                  60

Asp Ser Cys Tyr Leu Pro Pro Leu Arg Tyr Pro Ala Thr Cys Ser Tyr
65                  70                  75                  80

Lys Gly Ser Ile Asp Ser Asp Lys His Gln Tyr Ile Ile His Gly Gly
                85                  90                  95

Lys Thr Pro Asn Asn Glu Leu Ser Asp Lys Ile Tyr Ile Met Ser Val
            100                 105                 110

Ala Cys Lys Asn Asn Lys Lys Val Thr Phe Arg Cys Thr Glu Lys Asp
        115                 120                 125

Leu Val Gly Asp Val Pro Glu Pro Arg Tyr Gly His Ser Ile Asp Val
    130                 135                 140

Val Tyr Ser Arg Gly Lys Ser Met Gly Val Leu Phe Gly Gly Arg Ser
145                 150                 155                 160

Tyr Met Pro Ser Thr Gln Arg Thr Thr Glu Lys Trp Asn Ser Val Ala
                165                 170                 175

Asp Cys Leu Pro His Val Phe Leu Ile Asp Phe Glu Phe Gly Cys Ala
            180                 185                 190

Thr Ser Tyr Ile Leu Pro Glu Leu Gln Asp Gly Leu Ser Phe His Val
        195                 200                 205

Ser Ile Ala Arg Asn Asp Thr Val Tyr Ile Leu Gly Gly His Ser Leu
    210                 215                 220

Ala Ser Asn Ile Arg Pro Ala Asn Leu Tyr Arg Ile Arg Val Asp Leu
225                 230                 235                 240

Pro Leu Gly Thr Pro Ala Val Asn Cys Thr Val Leu Pro Gly Gly Ile
                245                 250                 255

Ser Val Ser Ser Ala Ile Leu Thr Gln Thr Asn Asn Asp Glu Phe Val
            260                 265                 270

Ile Val Gly Gly Tyr Gln Leu Glu Asn Gln Lys Arg Met Val Cys Ser
        275                 280                 285

Leu Val Ser Leu Gly Asp Asn Thr Ile Glu Ile Ser Glu Met Glu Thr
    290                 295                 300

Pro Asp Trp Thr Ser Asp Ile Lys His Ser Lys Ile Trp Phe Gly Ser
305                 310                 315                 320

Asn Met Gly Asn Gly Thr Ile Phe Leu Gly Ile Pro Gly Asp Asn Lys
                325                 330                 335

Gln Ala Met Ser Glu Ala Phe Tyr Phe Tyr Thr Leu Arg Cys Ser Glu
            340                 345                 350
```

Glu Asp Leu Ser Glu Asp Gln Lys Ile Val Ser Asn Ser Gln Thr Ser
            355                 360                 365

Thr Glu Asp Pro Gly Asp Ser Thr Pro Phe Glu Asp Ser Glu Phe
        370                 375                 380

Cys Phe Ser Ala Glu Ala Thr Ser Phe Asp Gly Asp Asp Glu Phe Asp
385                 390                 395                 400

Thr Tyr Asn Glu Asp Asp Glu Asp Glu Ser Val Thr Gly Tyr Trp
            405                 410                 415

Ile Thr Cys Cys Pro Thr Cys Asp Val Asp Ile Asn Thr Trp Val Pro
            420                 425                 430

Phe Tyr Ser Thr Glu Leu Asn Lys Pro Ala Met Ile Tyr Cys Ser His
        435                 440                 445

Gly Asp Gly His Trp Val His Ala Gln Cys Met Asp Leu Glu Glu Arg
        450                 455                 460

Thr Leu Ile His Leu Ser Glu Gly Ser Asn Lys Tyr Tyr Cys Asn Glu
465                 470                 475                 480

His Val Gln Ile Ala Arg Ala Leu Gln Thr Pro Lys Arg Asn Pro Pro
            485                 490                 495

Leu Gln Lys Pro Pro Met Lys Ser Leu His Lys Lys Gly Ser Gly Lys
        500                 505                 510

Val Leu Thr Pro Ala Lys Lys Ser Phe Leu Arg Arg Leu Phe Asp
        515                 520                 525

<210> SEQ ID NO 28
<211> LENGTH: 1612
<212> TYPE: DNA
<213> ORGANISM: Mus musculus

<400> SEQUENCE: 28
gacacagact acacccagag aaagaagagc aagcaccatg ttgaaactat tattgtcacc      60
tagatccttc ttagtccttc agctgctcct gctgagggca gggtggagct ccaaggtcct     120
catgtccagt gcgaatgaag acatcaaagc tgatttgatc ctgacttcta cagcccctga     180
acacctcagt gctcctactc tgcccccttcc agaggttcag tgctttgtgt tcaacataga    240
gtacatgaat tgcacttgga atagcagttc tgagcctcag gcaaccaacc tcacgctgca     300
ctataggtac aaggtatctg ataataatac attccaggag tgcagtcact atttgttctc     360
caaagagatt acttctggct gtcagataca aaaagaagat atccagctct accagacatt     420
tgttgtccag ctccaggacc cccagaaacc ccagaggcga gctgtacaga agctaaacct     480
acagaatctt gtgatcccac gggctccaga aaatctaaca ctcagcaatc tgagtgaatc     540
ccagctagag ctgagatgga aaagcagaca tattaaagaa cgctgtttac aatacttggt     600
gcagtaccgg agcaacagag atcgaagctg acggaacta atagtgaatc atgaacctag     660
attctccctg cctagtgtgg atgagctgaa acggtacaca tttcgggttc ggagccgcta     720
taacccaatc tgtggaagtt ctcaacagtg gagtaaatgg agccagcctg tccactgggg     780
gagtcatact gtagaggaga tccttccctt gtttgcactg gaagctgtgc ttatccctgt     840
tggcaccatg gggttgatta ttaccctgat ctttgtgtac tgttggttgg aacgaatgcc     900
tccaattccc cccatcaaga atctagagga tctggttact gaataccaag ggaacttttc     960
ggcctggagt ggtgtgtcta aagggctgac tgagagtctg cagccagact acagtgaacg    1020
gttctgccac gtcagcgaga ttcccccccaa aggaggggcc ctaggagagg ggcctggagg    1080
ttctccttgc agcctgcata gcccttactg gcctcccccca tgttattctc tgaagccgga    1140

```
agcctgaaca tcaatccttt gatggaacct caaagtccta tagtcctaag tgacgctaac    1200
ctcccctact caccttggca atctggatcc aatgctcact gccttccctt ggggctaagt    1260
ttcgatttcc tgtcccatgt aactgctttt ctgttccata tgccctactt gagagtgtcc    1320
cttgccctct ttccctgcac aagccctccc atgcccagcc taacacctttc ccactttctt    1380 tgaagagagt cttaccctgt agcccagggt ggctgggagc tcactatgta ggccaggttg    1440
gcctccaact cacaggctat cctcccacct ctgcctcata agagttgggg ttactggcat    1500
gcaccaccac acccagcatg gtccttctct tttataggat tctccctccc ttttctacc    1560 tatgattcaa ctgtttccaa atcaacaaga aataaagttt ttaaccaatg at            1612
```

<210> SEQ ID NO 29
<211> LENGTH: 369
<212> TYPE: PRT
<213> ORGANISM: Mus musculus

<400> SEQUENCE: 29

```
Met Leu Lys Leu Leu Ser Pro Arg Ser Phe Leu Val Leu Gln Leu
1               5                   10                  15

Leu Leu Arg Ala Gly Trp Ser Ser Lys Val Leu Met Ser Ser Ala
            20                  25                  30

Asn Glu Asp Ile Lys Ala Asp Leu Ile Leu Thr Ser Thr Ala Pro Glu
        35                  40                  45

His Leu Ser Ala Pro Thr Leu Pro Leu Pro Glu Val Gln Cys Phe Val
    50                  55                  60

Phe Asn Ile Glu Tyr Met Asn Cys Thr Trp Asn Ser Ser Ser Glu Pro
65                  70                  75                  80

Gln Ala Thr Asn Leu Thr Leu His Tyr Arg Tyr Lys Val Ser Asp Asn
                85                  90                  95

Asn Thr Phe Gln Glu Cys Ser His Tyr Leu Phe Ser Lys Glu Ile Thr
            100                 105                 110

Ser Gly Cys Gln Ile Gln Lys Glu Asp Ile Gln Leu Tyr Gln Thr Phe
        115                 120                 125

Val Val Gln Leu Gln Asp Pro Gln Lys Pro Gln Arg Arg Ala Val Gln
    130                 135                 140

Lys Leu Asn Leu Gln Asn Leu Val Ile Pro Arg Ala Pro Glu Asn Leu
145                 150                 155                 160

Thr Leu Ser Asn Leu Ser Glu Ser Gln Leu Glu Leu Arg Trp Lys Ser
                165                 170                 175

Arg His Ile Lys Glu Arg Cys Leu Gln Tyr Leu Val Gln Tyr Arg Ser
            180                 185                 190

Asn Arg Asp Arg Ser Trp Thr Glu Leu Ile Val Asn His Glu Pro Arg
        195                 200                 205

Phe Ser Leu Pro Ser Val Asp Glu Leu Lys Arg Tyr Thr Phe Arg Val
    210                 215                 220

Arg Ser Arg Tyr Asn Pro Ile Cys Gly Ser Ser Gln Gln Trp Ser Lys
225                 230                 235                 240

Trp Ser Gln Pro Val His Trp Gly Ser His Thr Val Glu Glu Asn Pro
                245                 250                 255

Ser Leu Phe Ala Leu Glu Ala Val Leu Ile Pro Val Gly Thr Met Gly
            260                 265                 270

Leu Ile Ile Thr Leu Ile Phe Val Tyr Cys Trp Leu Glu Arg Met Pro
        275                 280                 285

Pro Ile Pro Pro Ile Lys Asn Leu Glu Asp Leu Val Thr Glu Tyr Gln
```

```
                    290                 295                 300
Gly Asn Phe Ser Ala Trp Ser Gly Val Ser Lys Gly Leu Thr Glu Ser
305                 310                 315                 320

Leu Gln Pro Asp Tyr Ser Glu Arg Phe Cys His Val Ser Glu Ile Pro
                325                 330                 335

Pro Lys Gly Gly Ala Leu Gly Glu Gly Pro Gly Gly Ser Pro Cys Ser
            340                 345                 350

Leu His Ser Pro Tyr Trp Pro Pro Cys Tyr Ser Leu Lys Pro Glu
        355                 360                 365

Ala

<210> SEQ ID NO 30
<211> LENGTH: 2012
<212> TYPE: DNA
<213> ORGANISM: Homo sapiens

<400> SEQUENCE: 30
```

| | | | | | |
|---|---|---|---|---|---|
| gttgggactc | cgggtggcag | gcgcccgggg | gaatcccagc | tgactcgctc | actgccttcg | 60 |
| aagtccggcg | cccccggga | gggaactggg | tggccgcacc | ctcccggctg | cggtggctgt | 120 |
| cgcccccac | cctgcagcca | ggactcgatg | gagaatccat | tccaatatat | ggccatgtgg | 180 |
| ctctttggag | caatgttcca | tcatgttcca | tgctgctgac | gtcacatgga | gcacagaaat | 240 |
| caatgttagc | agatagccag | cccatacaag | atcgtattgt | attgtaggag | gcattgtgga | 300 |
| tggatggctg | ctggaaaccc | cttgccatag | ccagctcttc | ttcaatactt | aaggatttac | 360 |
| cgtggctttg | agtaatgaga | atttcgaaac | cacatttgag | aagtatttcc | atccagtgct | 420 |
| acttgtgttt | acttctaaac | agtcattttc | taactgaagc | tggcattcat | gtcttcattt | 480 |
| tgggctgttt | cagtgcaggg | cttcctaaaa | cagaagccaa | ctgggtgaat | gtaataagtg | 540 |
| atttgaaaaa | aattgaagat | cttattcaat | ctatgcatat | tgatgctact | ttatatacgg | 600 |
| aaagtgatgt | tcaccccagt | tgcaaagtaa | cagcaatgaa | gtgctttctc | ttggagttac | 660 |
| aagttatttc | acttgagtcc | ggagatgcaa | gtattcatga | tacagtagaa | atctgatca | 720 |
| tcctagcaaa | caacagtttg | tcttctaatg | ggaatgtaac | agaatctgga | tgcaaagaat | 780 |
| gtgaggaact | ggaggaaaaa | aatattaaag | aattttttgca | gagttttgta | catattgtcc | 840 |
| aaatgttcat | caacacttct | tgattgcaat | tgattctttt | taaagtgttt | ctgttattaa | 900 |
| caaacatcac | tctgctgctt | agacataaca | aaacactcgg | catttcaaat | gtgctgtcaa | 960 |
| aacaagtttt | tctgtcaaga | agatgatcag | accttggatc | agatgaactc | ttagaaatga | 1020 |
| aggcagaaaa | atgtcattga | gtaatatagt | gactatgaac | ttctctcaga | cttactttac | 1080 |
| tcattttttt | aatttattat | tgaaattgta | catatttgtg | gaataatgta | aatgttgaa | 1140 |
| taaaaatatg | tacaagtgtt | gttttttaag | ttgcactgat | attttacctc | ttattgcaaa | 1200 |
| atagcatttg | tttaagggtg | atagtcaaat | tatgtattgg | tggggctggg | taccaatgct | 1260 |
| gcaggtcaac | agctatgctg | gtaggctcct | gccagtgtgg | aaccactgac | tactggctct | 1320 |
| cattgacttc | cttactaagc | atagcaaaca | gaggaagaat | ttgttatcag | taagaaaaag | 1380 |
| aagaactata | tgtgaatcct | cttctttata | ctgtaattta | gttattgatg | tataaagcaa | 1440 |
| ctgttatgaa | ataaagaaat | tgcaataact | ggcatataat | gtccatcagt | aaatcttggt | 1500 |
| ggtggtggca | ataataaact | tctactgata | ggtagaatgg | tgtgcaagct | tgtccaatca | 1560 |
| cggattgcag | gccacatgcg | gcccaggaca | actttgaatg | tggcccaaca | caaattcata | 1620 |
| aactttcata | catctcgttt | ttagctcatc | agctatcatt | agcggtagtg | tatttaaagt | 1680 |

```
gtggcccaag acaattcttc ttattccaat gtggcccagg gaaatcaaaa gattggatgc    1740
ccctggtata gaaaactaat agtgacagtg ttcatatttc atgctttccc aaatacaggt    1800
attttatttt cacattcttt ttgccatgtt tatataataa taaagaaaaa ccctgttgat    1860
ttgttggagc cattgttatc tgacagaaaa taattgttta tatttttgc actacactgt     1920 ctaaaattag caagctctct tctaatggaa ctgtaagaaa gatgaaatat ttttgtttta    1980
ttataaattt atttcacctt aaaaaaaaaa aa                                  2012
```

<210> SEQ ID NO 31
<211> LENGTH: 160
<212> TYPE: PRT
<213> ORGANISM: Homo sapiens

<400> SEQUENCE: 31

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160
```

<210> SEQ ID NO 32
<211> LENGTH: 2333
<212> TYPE: DNA
<213> ORGANISM: Homo sapiens

<400> SEQUENCE: 32

```
gttgggactc cgggtggcag gcgcccgggg gaatcccagc tgactcgctc actgccttcg     60
aagtccggcg ccccccggga gggaactggg tggccgcacc ctcccggctg cggtggctgt    120
cgccccccac cctgcagcca ggactcgatg gagaatccat tccaatatat ggccatgtgg    180
ctctttggag caatgttcca tcatgttcca tgctgctgac gtcacatgga gcacagaaat    240
caatgttagc agatagccag cccatacaag atcgttttca actagtggcc ccactgtgtc    300
cggaattgat gggttcttgg tctcactgac ttcaagaatg aagccgcgga ccctcgcggt    360
gagtgttaca gctcttaagg tggcgcatct ggagtttgtt ccttctgatg ttcggatgtg    420
ttcggagttt cttccttctg gtgggttcgt ggtctcgctg gctcaggagt gaagctacag    480
accttcgcgg aggcattgtg gatggatggc tgctggaaac cccttgccat agccagctct    540
tcttcaatac ttaaggattt accgtggctt tgagtaatga gaatttcgaa accacatttg    600
```

```
agaagtattt ccatccagtg ctacttgtgt ttacttctaa acagtcattt tctaactgaa    660
gctggcattc atgtcttcat tttgggatgc agctaatata cccagttggc ccaaagcacc    720
taacctatag ttatataatc tgactctcag ttcagtttta ctctactaat gccttcatgg    780
tattgggaac catagatttg tgcagctgtt tcagtgcagg gcttcctaaa acagaagcca    840
actgggtgaa tgtaataagt gatttgaaaa aaattgaaga tcttattcaa tctatgcata    900
ttgatgctac tttatatacg gaaagtgatg ttcaccccag ttgcaaagta acagcaatga    960
agtgctttct cttggagtta caagttattt cacttgagtc cggagatgca agtattcatg   1020
atacagtaga aaatctgatc atcctagcaa acaacagttt gtcttctaat gggaatgtaa   1080
cagaatctgg atgcaaagaa tgtgaggaac tggaggaaaa aaatattaaa gaattttgc    1140
agagttttgt acatattgtc caaatgttca tcaacacttc ttgattgcaa ttgattcttt   1200
ttaaagtgtt tctgttatta acaaacatca ctctgctgct tagacataac aaaacactcg   1260
gcatttcaaa tgtgctgtca aaacaagttt ttctgtcaag aagatgatca gaccttggat   1320
cagatgaact cttagaaatg aaggcagaaa aatgtcattg agtaatatag tgactatgaa   1380
cttctctcag acttacttta ctcattttt taatttatta ttgaaattgt acatatttgt    1440
ggataatgt aaaatgttga ataaaaatat gtacaagtgt tgtttttaa gttgcactga    1500
tattttacct cttattgcaa aatagcattt gtttaagggt gatagtcaaa ttatgtattg   1560
gtggggctgg gtaccaatgc tgcaggtcaa cagctatgct ggtaggctcc tgccagtgtg   1620
gaaccactga ctactggctc tcattgactt ccttactaag catagcaaac agaggaagaa   1680
tttgttatca gtaagaaaaa gaagaactat atgtgaatcc tcttctttat actgtaattt   1740
agttattgat gtataaagca actgttatga aataaagaaa ttgcaataac tggcatataa   1800
tgtccatcag taaatcttgg tggtggtggc aataataaac ttctactgat aggtagaatg   1860
gtgtgcaagc ttgtccaatc acggattgca ggccacatgc ggcccaggac aactttgaat   1920
gtggcccaac acaaattcat aaactttcat acatctcgtt tttagctcat cagctatcat   1980
tagcggtagt gtatttaaag tgtggcccaa gacaattctt cttattccaa tgtggcccag   2040
ggaaatcaaa agattggatg cccctggtat agaaaactaa tagtgacagt gttcatattt   2100
catgctttcc caaatacagg tattttattt tcacattctt tttgccatgt ttatataata   2160
ataaagaaaa accctgttga tttgttggag ccattgttat ctgacagaaa ataattgttt   2220
atattttttg cactacactg tctaaaatta gcaagctctc ttctaatgga actgtaagaa   2280
agatgaaata tttttgtttt attataaatt tatttcacct taaaaaaaaa aaa           2333
```

<210> SEQ ID NO 33
<211> LENGTH: 135
<212> TYPE: PRT
<213> ORGANISM: Mus musculus

<400> SEQUENCE: 33

Met Val Leu Gly Thr Ile Asp Leu Cys Ser Cys Phe Ser Ala Gly Leu
1               5                   10                  15

Pro Lys Thr Glu Ala Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile

```
                    65                  70                  75                  80
His Asp Thr Val Glu Asn Leu Ile Ile Leu Ala Asn Asn Ser Leu Ser
                    85                  90                  95

Ser Asn Gly Asn Val Thr Glu Ser Gly Cys Lys Glu Cys Glu Glu Leu
                100                 105                 110

Glu Glu Lys Asn Ile Lys Glu Phe Leu Gln Ser Phe Val His Ile Val
            115                 120                 125

Gln Met Phe Ile Asn Thr Ser
        130                 135

<210> SEQ ID NO 34
<211> LENGTH: 1297
<212> TYPE: DNA
<213> ORGANISM: Mus musculus

<400> SEQUENCE: 34
ttcttgacca agacttcaat actcagtggc actgtattcc ccttctgtcc agccactctt      60
ccccagagtt ctcttcttca tcctcccccct tgcagagtag ggcagcttgc aggtcctcct    120
```
```
gcaagtctct cccaattctc tgcgcccaaa agacttgcag tgcatctcct acgcgctgc     180 agggaccttg ccagggcagg actgccccg cccagttgca gagttggacg aagacgggat     240
cctgctgtgt ttggaaggct gagttccaca tctaacagct cagagaggtc aggaaagaat     300
ccaccttgac acatggccct ctggctcttc aaagcactgc ctcttcatgg tccttgctgg     360
tgaggtcctt aagaacacag aaacccatgt cagcagataa ccagcctaca ggaggccaag     420
aagagttctg gatggatggc agctggaagc ccatcgccat agccagctca tcttcaacat     480
tgaagctctt acctgggcat taagtaatga aatttttgaa accatatatg aggaatacat     540
ccatctcgtg ctacttgtgt ttccttctaa acagtcactt tttaactgag ctggcattc     600 atgtcttcat tttgggctgt gtcagtgtag gtctccctaa aacagaggcc aactggatag     660
atgtaagata tgacctggag aaaattgaaa gccttattca atctattcat attgacacca     720
ctttatacac tgacagtgac tttcatccca gttgcaaagt tactgcaatg aactgctttc     780
tcctggaatt gcaggttatt ttacatgagt acagtaacat gactcttaat gaaacagtaa     840
gaaacgtgct ctaccttgca acagcactc tgtcttctaa caagaatgta gcagaatctg     900
gctgcaagga atgtgaggag ctggaggaga aaaccttcac agagttttg caaagcttta     960 tacgcattgt ccaaatgttc atcaacacgt cctgactgca tgcgagcctc ttccgtgttt    1020
ctgttattaa ggtacctcca cctgctgctc agaggcagca cagctccatg catttgaaat    1080
ctgctgggca aactaagctt cctaacaagg agataatgag ccacttggat cacatgaaat    1140
cttggaaatg aagagaggaa aagagctcgt ctcagactta tttttgcttg cttatttta    1200 atttattgct tcatttgtac atatttgtaa tataacagaa gatgtggaat aaagttgtat    1260
ggatatttta tcaattgaaa tttaaaaaaa aaaaaaa                              1297

<210> SEQ ID NO 35
<211> LENGTH: 160
<212> TYPE: PRT
<213> ORGANISM: Mus musculus

<400> SEQUENCE: 35

Met Lys Ile Leu Lys Pro Tyr Met Arg Asn Thr Ser Ile Ser Cys Tyr
1               5                   10                  15

Leu Cys Phe Leu Leu Asn Ser His Phe Leu Thr Glu Ala Gly Ile His
                20                  25                  30
```

```
Val Phe Ile Leu Gly Cys Val Ser Val Gly Leu Pro Lys Thr Glu Ala
         35                  40                  45

Asn Trp Ile Asp Val Arg Tyr Asp Leu Glu Lys Ile Glu Ser Leu Ile
 50                  55                  60

Gln Ser Ile His Ile Asp Thr Thr Leu Tyr Thr Asp Ser Asp Phe His
 65                  70                  75                  80

Pro Ser Cys Lys Val Thr Ala Met Asn Cys Phe Leu Leu Glu Leu Gln
                 85                  90                  95

Val Ile Leu His Glu Tyr Ser Asn Met Thr Leu Asn Glu Thr Val Arg
                100                 105                 110

Asn Val Leu Tyr Leu Ala Asn Ser Thr Leu Ser Ser Asn Lys Asn Val
            115                 120                 125

Ala Glu Ser Gly Cys Lys Glu Cys Glu Glu Leu Glu Glu Lys Thr Phe
130                 135                 140

Thr Glu Phe Leu Gln Ser Phe Ile Arg Ile Val Gln Met Phe Ile Asn
145                 150                 155                 160

<210> SEQ ID NO 36
<211> LENGTH: 1287
<212> TYPE: DNA
<213> ORGANISM: Mus musculus

<400> SEQUENCE: 36
ttcttgacca agacttcaat actcagtggc actgtattcc ccttctgtcc agccactctt      60
ccccagagtt ctcttcttca tcctccccct tgcagagtag ggcagcttgc aggtcctcct     120
gcaagtctct cccaattctc tgcgcccaaa agacttgcag tgcatctcct tacgcgctgc     180
agggaccttg ccagggcagg actgcccccg cccagttgca gagttggacg aagacgggat     240
cctgctgtgt ttggaaggct gagttccaca tctaacagct cagagagaat ccaccttgac     300
acatggcccc ctggctcttc aaagcactgc ctcttcatgg tccttgctgg tgaggtcctt     360
aagaacacag aaacccatgt cagcagataa ccagcctaca ggaggccaag aagagttctg     420
gatggatggc agctggaagc ccatcgccat agccagctca tcttcaacat tgaagctctt     480
acctgggcat taagtaatga aaattttgaa accatatatg aggaatacat ccatctcgtg     540
ctacttgtgt ttccttctaa acagtcactt tttaactgag gctggcattc atgtcttcat     600
tttgggctgt gtcagtgtag gtctccctaa aacagaggcc aactggatag atgtaagata     660
tgacctggag aaaattgaaa gccttattca atctattcat attgacacca ctttatacac     720
tgacagtgac tttcatccca gttgcaaagt tactgcaatg aactgctttc tcctggaatt     780
gcaggttatt ttacatgagt acagtaacat gactcttaat gaaacagtaa gaaacgtgct     840
ctaccttgca aacagcactc tgtcttctaa caagaatgta gcagaatctg gctgcaagga     900
atgtgaggag ctggaggaga aaaccttcac agagttttg caaagcttta tacgcattgt      960
ccaaatgttc atcaacacgt cctgactgca tgcgagcctc ttccgtgttt ctgttattaa    1020
ggtacctcca cctgctgctc agaggcagca cagctccatg catttgaaat ctgctgggca    1080
aactaagctt cctaacaagg agataatgag ccacttggat cacatgaaat cttggaaatg    1140
aagagaggaa aagagctcgt ctcagactta tttttgcttg cttattttta atttattgct    1200
tcatttgtac atatttgtaa tataacagaa gatgtggaat aaagttgtat ggatatttta    1260
tcaattgaaa tttaaaaaaa aaaaaaa                                        1287
```

GENETICALLY MODIFIED NON-HUMAN ANIMALS AND METHODS OF USE THEREOF

CROSS-REFERENCE

This application claims the benefit of U.S. Provisional Application Nos. 62/146,938, filed Apr. 13, 2015; 62/148,667, filed Apr. 16, 2015; and 62/287,842, filed Jan. 27, 2016, the disclosure of each of which is incorporated herein by reference in its entirety.

FIELD OF INVENTION

The invention relates to the field of genetically modified non-human animals.

INTRODUCTION

Genetically modified non-human animals, such as humanized mice, hold great promise for translational research, as they allow modeling and studying of human diseases in vivo. Within the last decade, considerable progress has been made in developing humanized mice by genetically inserting human genes that are essential for the proper development and function of human immune cells in the mouse. However, some limitations still restrict the utility of humanized mice in translational research. In particular, the development and survival of human T cells is suboptimal.

Although the bone marrow-liver-thymus (BLT) model has been shown to improve intestinal T cell reconstitution in NS/NSG-BLT mice (Denton P W, Nochi T, Lim A et al. *Mucosal Immunol* 2012; 5:555-566, Nochi T, Denton P W, Wahl A et al. *Cell Rep* 2013; 3:1874-1884), those mice have been shown to develop graft-versus-host disease, resulting in massive immune cell infiltration in multiple tissues (Greenblatt M B, Vrbanac V, Tivey T et al. *PLoS One* 2012; 7:e44664). Therefore, current humanized mouse models still lack proper development and function of human T cells. In particular, the absence of human tissue-resident memory T cells prevents the use of humanized mice as a preclinical tool to develop and test more efficient immunization strategies that aim to induce long-lasting mucosal immunity against pathogens such as HIV.

In order to better understand the development and survival of human tissue-resident T cells and provide a model to test novel immunization strategies to induce long-lasting T cell-dependent mucosal immunity, it would be useful to have a genetically modified non-human animal which develops human tissue-resident T cells. Such a mouse model could also be used to study the interaction of human tissue-resident immune cells with the gut microbiota, for example, how the microbiota may shape the development and survival of human immune cells in the small intestine and colon.

In addition, there is a need in the art for non-human animal models of human Natural Killer (NK) cell development and function.

SUMMARY

Genetically modified non-human animals expressing human SIRPα and human IL-15 from the non-human animal genome are provided. Also provided are methods for making non-human animals expressing human SIRPα and human IL-15 from the non-human animal genome, and methods for using non-human animals expressing human SIRPα and human IL-15 from the non-human animal genome. These animals and methods find many uses in the art, including, for example, in modeling human T cell and/or natural killer (NK) cell development and function; in modeling human pathogen infection of human T cells and/or NK cells; in in vivo screens for agents that inhibit infection by a pathogen that activates, induces and/or targets T cells and/or NK cells; in in vivo screens for agents that modulate the development and/or function of human T cells and/or NK cells, e.g. in a healthy or a diseased state; in in vivo screens for agents that are toxic to human T cells and/or NK cells; in in vivo screens for agents that prevent against, mitigate, or reverse the toxic effects of toxic agents on human T cells and/or NK cells; in in vivo screens of candidate T cell-inducing vaccines; and in in vivo and in vitro screens for agents that inhibit tumor growth and/or infection by activating NK cell-mediated antibody dependent cellular cytotoxicity (ADCC) processes.

In a first aspect, the present disclosure provides a genetically modified non-human animal, including: a nucleic acid sequence incorporated into the genome of the genetically modified non-human animal, which sequence encodes a human SIRPα protein and is operably linked to a SIRPα gene promoter; and a nucleic acid sequence incorporated into the genome of the genetically modified non-human animal, which sequence encodes a human IL-15 protein and is operably linked to an IL-15 gene promoter, wherein the genetically modified non-human animal expresses the human SIRPα protein and the human IL-15 protein.

The SIRPα gene promoter can be an endogenous non-human SIRPα gene promoter. For example, the SIRPα gene promoter can be the endogenous non-human SIRPα gene promoter at the non-human animal SIRPα gene locus. Where the SIRPα gene promoter is the endogenous non-human SIRPα gene promoter at the non-human animal SIRPα gene locus, the genetically modified non-human animal can include a null mutation in the non-human SIRPα gene at the non-human animal SIRPα gene locus. In one such embodiment, the genetically modified non-human animal is a mouse and the null mutation is a deletion of at least mouse SIRPα exons 2-4. In another such embodiment, the genetically modified non-human animal is heterozygous for the allele including the nucleic acid sequence that encodes the human SIRPα protein. In another such embodiment, the genetically modified non-human animal is homozygous for the allele including the nucleic acid sequence that encodes the human SIRPα protein.

In another embodiment of the first aspect, or in a further embodiment of any of the above embodiments thereof, the nucleic acid sequence that encodes the human SIRPα protein includes human SIRPα genomic coding and non-coding sequence.

In another embodiment of the first aspect, or in a further embodiment of any of the above embodiments thereof, the human SIRPα protein is a functional fragment of a full length human SIRPα protein. In one such embodiment, the functional fragment includes an extracellular domain of human SIRPα, e.g., an extracellular domain that includes at least amino acids 28-362 of SEQ ID NO:12.

In another embodiment of the first aspect, or in a further embodiment of any of the above embodiments thereof, the IL-15 gene promoter is an endogenous non-human IL-15 gene promoter. In one such embodiment, the IL-15 gene promoter is the endogenous non-human IL-15 gene promoter at the non-human animal IL-15 gene locus. In one embodiment, where the IL-15 gene promoter is the endogenous non-human IL-15 gene promoter at the non-human animal IL-15 gene locus, the genetically modified non-human animal includes a null mutation in the non-human IL-15 gene at the non-human animal IL-15 gene locus. In one such embodiment, the genetically modified non-human animal is a mouse and the null mutation is a deletion of at least mouse IL-15 exons 5-8. In another such embodiment, the genetically modified non-human animal is heterozygous for the allele including the nucleic acid sequence that encodes the human IL-15 protein. In another such embodiment, the genetically modified non-human animal is homozygous for the allele including the nucleic acid sequence that encodes the human IL-15 protein.

In another embodiment of the first aspect, or in a further embodiment of any of the above embodiments thereof, the nucleic acid sequence that encodes the human IL-15 protein includes human IL-15 genomic coding and non-coding sequence.

In another embodiment of the first aspect, or in a further embodiment of any of the above embodiments thereof, the human IL-15 protein is a functional fragment of a full length human IL-15 protein.

In another embodiment of the first aspect, or in a further embodiment of any of the above embodiments thereof, the genetically modified non-human animal is immunodeficient. For example, in one embodiment the genetically modified non-human animal includes a Rag2 gene knock-out. In another embodiment, the genetically modified non-human animal includes an an IL2rg gene knock-out or both a Rag2 gene knock-out and an an IL2rg gene knock-out.

In another embodiment of the first aspect, or in a further embodiment of any of the above embodiments thereof, the non-human animal is a mammal. In one such embodiment, the mammal is a rodent, e.g., a mouse.

In another embodiment of the first aspect, or in a further embodiment of any of the above embodiments thereof, the genetically modified non-human animal includes an engraftment of human hematopoietic cells. In one such embodiment, the genetically modified non-human animal includes an infection with a human pathogen. In one embodiment, where the the genetically modified non-human animal includes an infection with a human pathogen, the human pathogen activates, induces and/or targets T cells and/or natural killer (NK) cells. In another embodiment, where the the genetically modified non-human animal includes an infection with a human pathogen, the human pathogen is a pathogen that affects (e.g., by infecting) human intestine. In one such embodiment, the human pathogen is a human rotavirus. In another embodiment, where the the genetically modified non-human animal includes an infection with a human pathogen, the pathogen affects (e.g., by infecting) human lung. In one such embodiment, the human pathogen is an influenza virus. In another embodiment, where the the genetically modified non-human animal includes an infection with a human pathogen, the pathogen affects (e.g., by infecting) human liver. In yet another embodiment, a genetically modified non-human animal includes an engraftment of human hematopoietic cells and a tumor, e.g., a human tumor, e.g., transplanted human tumor.

In a second aspect, the present disclosure provides an in vivo model, including a genetically modified non-human animal including: a nucleic acid sequence incorporated into the genome of the genetically modified non-human animal, which sequence encodes a human SIRPα protein and is operably linked to a SIRPα gene promoter; a nucleic acid sequence incorporated into the genome of the genetically modified non-human animal, which sequence encodes a human IL-15 protein and is operably linked to an IL-15 gene promoter; and an engraftment of human hematopoietic cells, wherein the genetically modified non-human animal (i) expresses the human SIRPα protein and the human IL-15 protein, and (ii) includes human intraepithelial lymphocytes (IELs) in the small intestine and Peyer's patches of the genetically modified non-human animal.

In one embodiment of the second aspect, the genetically modified non-human animal includes an infection with a human pathogen, e.g., an intestinal pathogen. In one such embodiment, the intestinal pathogen is selected from: *Campylobacter jejuni, Clostridium difficile, Enterococcus faecalis, Enterococcus faecium, Escherichia coli*, Human Rotavirus, *Listeria monocytogenes*, Norwalk Virus, *Salmonella enterica, Shigella flexneri, Shigella sonnei, Shigella dysenteriae, Yersinia pestis, Yersinia enterocolitica*, and *Helicobacter pylori*.

In another embodiment of the second aspect, or in a further embodiment of any of the above embodiments thereof, the SIRPα gene promoter is an endogenous non-human SIRPα gene promoter. In one such embodiment, the SIRPα gene promoter is the endogenous non-human SIRPα gene promoter at the non-human animal SIRPα gene locus. In one embodiment, where the SIRPα gene promoter is the endogenous non-human SIRPα gene promoter at the non-human animal SIRPα gene locus, the genetically modified non-human animal includes a null mutation in the non-human SIRPα gene at the non-human animal SIRPα gene locus. In one such embodiment, the genetically modified non-human animal is a mouse and the null mutation is a deletion of at least mouse SIRPα exons 2-4. In another such embodiment, the genetically modified non-human animal is heterozygous for the allele including the nucleic acid sequence that encodes the human SIRPα protein. In another such embodiment, the genetically modified non-human animal is homozygous for the allele including the nucleic acid sequence that encodes the human SIRPα protein.

In another embodiment of the second aspect, or in a further embodiment of any of the above embodiments thereof, the nucleic acid sequence that encodes the human SIRPα protein includes human SIRPα genomic coding and non-coding sequence.

In another embodiment of the second aspect, or in a further embodiment of any of the above embodiments thereof, the human SIRPα protein is a functional fragment of a full length human SIRPα protein. In one such embodiment, the functional fragment includes an extracellular domain of human SIRPα, e.g., an extracellular domain that includes amino acids 28-362 of SEQ ID NO:12.

In another embodiment of the second aspect, or in a further embodiment of any of the above embodiments thereof, the IL-15 gene promoter is an endogenous non-human IL-15 gene promoter. In one such embodiment, the IL-15 gene promoter is the endogenous non-human IL-15 gene promoter at the non-human animal IL-15 gene locus. In one embodiment, where the IL-15 gene promoter is the endogenous non-human IL-15 gene promoter at the non-human animal IL-15 gene locus, the genetically modified non-human animal includes a null mutation in the non-human IL-15 gene at the non-human animal IL-15 gene locus. In one such embodiment, the genetically modified non-human animal is a mouse and the null mutation is a deletion of at least mouse IL-15 exons 5-8. In one such embodiment, the genetically modified non-human animal is heterozygous for the allele including the nucleic acid sequence that encodes the human IL-15 protein. In another such embodiment, the genetically modified non-human animal is homozygous for the allele including the nucleic acid sequence that encodes the human IL-15 protein.

In another embodiment of the second aspect, or in a further embodiment of any of the above embodiments thereof, the nucleic acid sequence that encodes the human IL-15 protein includes human IL-15 genomic coding and non-coding sequence.

In another embodiment of the second aspect, or in a further embodiment of any of the above embodiments thereof, the human IL-15 protein is a functional fragment of a full length human IL-15 protein.

In another embodiment of the second aspect, or in a further embodiment of any of the above embodiments thereof, the genetically modified non-human animal is immunodeficient. For example, in one embodiment the genetically modified non-human animal includes a Rag2 gene knock-out. In another embodiment, the genetically modified non-human animal includes an an IL2rg gene knock-out or both a Rag2 gene knock-out and an an IL2rg gene knock-out.

In another embodiment of the second aspect, or in a further embodiment of any of the above embodiments thereof, the non-human animal is a mammal. In one such embodiment, the mammal is a rodent, e.g., a mouse.

In a third aspect, the present disclosure provides an in vivo model, including a genetically modified non-human animal including: a nucleic acid sequence incorporated into the genome of the genetically modified non-human animal, which sequence encodes a human SIRPα protein and is operably linked to a SIRPα gene promoter; a nucleic acid sequence incorporated into the genome of the genetically modified non-human animal, which sequence encodes a human IL-15 protein and is operably linked to an IL-15 gene promoter; and an engraftment of human hematopoietic cells, wherein the genetically modified non-human animal (i) expresses the human SIRPα protein and the human IL-15 protein, and (ii) includes human intraepithelial lymphocytes (IELs) in the lung of the genetically modified non-human animal.

In one embodiment of the third aspect, the genetically modified non-human animal includes an infection with a human pathogen, e.g., a lung pathogen. In one such embodiment, the lung pathogen is selected from: *Streptococcus pyogenes, Haemophilus influenza, Corynebacterium diphtheria*, SARS coronavirus, *Bordetella pertussis, Moraxella catarrhalis*, Influenza virus (A, B, C), Coronavirus, Adenovirus, Respiratory Syncytial Virus, Parainfluenza virus, Mumps virus, *Streptococcus pneumoniae, Staphylococcus aureus, Legionella pneumophila, Klebsiella pneumoniae, Pseudomonas aeruginosa, Mycoplasma pneumonia, Mycobacterium tuberculosis, Chlamydia Pneumoniae, Blastomyces dermatitidis, Cryptococcus neoformans*, and *Aspergillus fumigatus*.

In another embodiment of the third aspect, or in a further embodiment of any of the above embodiments thereof, the SIRPα gene promoter is an endogenous non-human SIRPα gene promoter. In one such embodiment, the SIRPα gene promoter is the endogenous non-human SIRPα gene promoter at the non-human animal SIRPα gene locus. In one embodiment, where the SIRPα gene promoter is the endogenous non-human SIRPα gene promoter at the non-human animal SIRPα gene locus, the genetically modified non-human animal includes a null mutation in the non-human SIRPα gene at the non-human animal SIRPα gene locus. In one such embodiment, the genetically modified non-human animal is a mouse and the null mutation is a deletion of at least mouse SIRPα exons 2-4. In another such embodiment, the genetically modified non-human animal is heterozygous for the allele including the nucleic acid sequence that encodes the human SIRPα protein. In another such embodiment, the genetically modified non-human animal is homozygous for the allele including the nucleic acid sequence that encodes the human SIRPα protein.

In another embodiment of the third aspect, or in a further embodiment of any of the above embodiments thereof, the nucleic acid sequence that encodes the human SIRPα protein includes human SIRPα genomic coding and non-coding sequence.

In another embodiment of the third aspect, or in a further embodiment of any of the above embodiments thereof, the human SIRPα protein is a functional fragment of a full length human SIRPα protein. In one such embodiment, the functional fragment includes an extracellular domain of human SIRPα, e.g., an extracellular domain including at least amino acids 28-362 of SEQ ID NO:12.

In another embodiment of the third aspect, or in a further embodiment of any of the above embodiments thereof, the IL-15 gene promoter is an endogenous non-human IL-15 gene promoter. In one such embodiment, the IL-15 gene promoter is the endogenous non-human IL-15 gene promoter at the non-human animal IL-15 gene locus.

In one embodiment, where the IL-15 gene promoter is the endogenous non-human IL-15 gene promoter at the non-human animal IL-15 gene locus, the genetically modified non-human animal includes a null mutation in the non-human IL-15 gene at the non-human animal IL-15 gene locus. In one such embodiment, the genetically modified non-human animal is a mouse and the null mutation is a deletion of at least mouse IL-15 exons 5-8. In another such embodiment, the genetically modified non-human animal is heterozygous for the allele including the nucleic acid sequence that encodes the human IL-15 protein. In another such embodiment, the genetically modified non-human animal is homozygous for the allele including the nucleic acid sequence that encodes the human IL-15 protein.

In another embodiment of the third aspect, or in a further embodiment of any of the above embodiments thereof, the nucleic acid sequence that encodes the human IL-15 protein includes human IL-15 genomic coding and non-coding sequence.

In another embodiment of the third aspect, or in a further embodiment of any of the above embodiments thereof, the human IL-15 protein is a functional fragment of a full length human IL-15 protein.

In another embodiment of the third aspect, or in a further embodiment of any of the above embodiments thereof, the genetically modified non-human animal is immunodeficient. For example, in one embodiment the genetically modified non-human animal includes a Rag2 gene knock-out. In another embodiment, the genetically modified non-human animal includes an an IL2rg gene knock-out or both a Rag2 gene knock-out and an an IL2rg gene knock-out.

In another embodiment of the third aspect, or in a further embodiment of any of the above embodiments thereof, the non-human animal is a mammal. In one such embodiment, the mammal is a rodent, e.g., a mouse.

In a fourth aspect, the present disclosure provides a method of determining the efficacy of a candidate T-cell inducing vaccine, the method including: administering a candidate T-cell inducing vaccine to a genetically modified non-human animal, wherein the genetically modified non-human animal is deficient for an endogenous immune system and includes: (i) a nucleic acid sequence incorporated into the genome of the genetically modified non-human animal, which sequence encodes a human SIRPα protein and is operably linked to a SIRPα gene promoter, (ii) a nucleic acid sequence incorporated into the genome of the genetically modified non-human animal, which sequence encodes a human IL-15 protein and is operably linked to an IL-15 gene promoter, and (iii) an engraftment of human hematopoietic cells, wherein the genetically modified non-human animal expresses the human SIRPα protein and the human IL-15 protein; challenging the genetically modified non-human animal with a human pathogen; and determining whether the candidate T-cell inducing vaccine induces a T cell mediated immune response in the genetically modified non-human animal.

In one embodiment of the fourth aspect, the SIRPα gene promoter is an endogenous non-human SIRPα gene promoter. In one such embodiment, the SIRPα gene promoter is the endogenous non-human SIRPα gene promoter at the non-human animal SIRPα gene locus. In one embodiment, where the SIRPα gene promoter is the endogenous non-human SIRPα gene promoter at the non-human animal SIRPα gene locus, the genetically modified non-human animal includes a null mutation in the non-human SIRPα gene at the non-human animal SIRPα gene locus. In one such embodiment, the genetically modified non-human animal is a mouse and the null mutation is a deletion of at least mouse SIRPα exons 2-4. In another such embodiment, the genetically modified non-human animal is heterozygous for the allele including the nucleic acid sequence that encodes the human SIRPα protein. In another such embodiment, the genetically modified non-human animal is homozygous for the allele including the nucleic acid sequence that encodes the human SIRPα protein.

In another embodiment of the fourth aspect, or in a further embodiment of any of the above embodiments thereof, the nucleic acid sequence that encodes the human SIRPα protein includes human SIRPα genomic coding and non-coding sequence.

In another embodiment of the fourth aspect, or in a further embodiment of any of the above embodiments thereof, the human SIRPα protein is a functional fragment of a full length human SIRPα protein. In one such embodiment, the functional fragment includes an extracellular domain of human SIRPα, e.g., an extracellular domain including at least amino acids 28-362 of SEQ ID NO:12.

In another embodiment of the fourth aspect, or in a further embodiment of any of the above embodiments thereof, the IL-15 gene promoter is an endogenous non-human IL-15 gene promoter. In one such embodiment, the IL-15 gene promoter is the endogenous non-human IL-15 gene promoter at the non-human animal IL-15 gene locus. In one embodiment, where the IL-15 gene promoter is the endogenous non-human IL-15 gene promoter at the non-human animal IL-15 gene locus, the genetically modified non-human animal includes a null mutation in the non-human IL-15 gene at the non-human animal IL-15 gene locus. In one such embodiment, the genetically modified non-human animal is a mouse and the null mutation is a deletion of at least mouse IL-15 exons 5-8. In another such embodiment, the genetically modified non-human animal is heterozygous for the allele including the nucleic acid sequence that encodes the human IL-15 protein. In another such embodiment, the genetically modified non-human animal is homozygous for the allele including the nucleic acid sequence that encodes the human IL-15 protein.

In another embodiment of the fourth aspect, or in a further embodiment of any of the above embodiments thereof, the nucleic acid sequence that encodes the human IL-15 protein includes human IL-15 genomic coding and non-coding sequence.

In another embodiment of the fourth aspect, or in a further embodiment of any of the above embodiments thereof, the human IL-15 protein is a functional fragment of a full length human IL-15 protein.

In another embodiment of the fourth aspect, or in a further embodiment of any of the above embodiments thereof, the genetically modified non-human animal includes a Rag2 gene knock-out.

In another embodiment of the fourth aspect, or in a further embodiment of any of the above embodiments thereof, the genetically modified non-human animal includes an IL2rg gene knock-out.

In another embodiment of the fourth aspect, or in a further embodiment of any of the above embodiments thereof, the genetically modified non-human animal is a mammal, such as a rodent, e.g., a mouse.

In a fifth aspect, the present disclosure provides a method of identifying an agent that inhibits an infection by a pathogen that activates, induces and/or targets human T cells and/or natural killer (NK) cells, the method including: administering an agent to an genetically modified non-human animal, wherein the genetically modified non-human animal is deficient for an endogenous immune system and includes: (i) a nucleic acid sequence incorporated into the genome of the genetically modified non-human animal, which sequence encodes a human SIRPα protein and is operably linked to a SIRPα gene promoter, (ii) a nucleic acid sequence incorporated into the genome of the genetically modified non-human animal, which sequence encodes a human IL-15 protein and is operably linked to an IL-15 gene promoter, (iii) an engraftment of human hematopoietic cells, and (iv) an infection by a pathogen that activates, induces and/or targets human T cells and/or natural killer cells, wherein the genetically modified non-human animal expresses the human SIRPα protein and the human IL-15 protein; and determining whether the agent reduces the amount of the pathogen in the pathogen-infected non-human animal.

In one embodiment of the fifth aspect, the SIRPα gene promoter is an endogenous non-human SIRPα gene promoter. In one such embodiment, the SIRPα gene promoter is the endogenous non-human SIRPα gene promoter at the non-human animal SIRPα gene locus. In one embodiment, where the SIRPα gene promoter is the endogenous non-human SIRPα gene promoter at the non-human animal SIRPα gene locus, the genetically modified non-human animal includes a null mutation in the non-human SIRPα gene at the non-human animal SIRPα gene locus. In one such embodiment, the genetically modified non-human animal is a mouse and the null mutation is a deletion of at least mouse SIRPα exons 2-4. In another such embodiment, the genetically modified non-human animal is heterozygous for the allele including the nucleic acid sequence that encodes the human SIRPα protein. In another such embodiment, the genetically modified non-human animal is homozygous for the allele including the nucleic acid sequence that encodes the human SIRPα protein.

In another embodiment of the fifth aspect, or in a further embodiment of any of the above embodiments thereof, the nucleic acid sequence that encodes the human SIRPα protein includes human SIRPα genomic coding and non-coding sequence.

In another embodiment of the fifth aspect, or in a further embodiment of any of the above embodiments thereof, the human SIRPα protein is a functional fragment of a full length human SIRPα protein. In one such embodiment, the functional fragment includes an extracellular domain of human SIRPα, e.g., an extracellular domain which includes amino acids 28-362 of SEQ ID NO:12.

In another embodiment of the fifth aspect, or in a further embodiment of any of the above embodiments thereof, the IL-15 gene promoter is an endogenous non-human IL-15 gene promoter. In one such embodiment, the IL-15 gene promoter is the endogenous non-human IL-15 gene promoter at the non-human animal IL-15 gene locus. In one embodiment, where the IL-15 gene promoter is the endogenous non-human IL-15 gene promoter at the non-human animal IL-15 gene locus, the genetically modified non-human animal includes a null mutation in the non-human IL-15 gene at the non-human animal IL-15 gene locus. In one such embodiment, the genetically modified non-human animal is a mouse and the null mutation is a deletion of at least mouse IL-15 exons 5-8. In another such embodiment, the genetically modified non-human animal is heterozygous for the allele including the nucleic acid sequence that encodes the human IL-15 protein. In another such embodiment, the genetically modified non-human animal is homozygous for the allele including the nucleic acid sequence that encodes the human IL-15 protein.

In another embodiment of the fifth aspect, or in a further embodiment of any of the above embodiments thereof, the nucleic acid sequence that encodes the human IL-15 protein includes human IL-15 genomic coding and non-coding sequence.

In another embodiment of the fifth aspect, or in a further embodiment of any of the above embodiments thereof, the human IL-15 protein is a functional fragment of a full length human IL-15 protein.

In another embodiment of the fifth aspect, or in a further embodiment of any of the above embodiments thereof, the genetically modified non-human animal includes a Rag2 gene knock-out.

In another embodiment of the fifth aspect, or in a further embodiment of any of the above embodiments thereof, the genetically modified non-human animal includes an IL2rg gene knock-out.

In another embodiment of the fifth aspect, or in a further embodiment of any of the above embodiments thereof, the genetically modified non-human animal is a mammal, such as a rodent, e.g., a mouse.

In a sixth aspect, the present disclosure provides a method of making a non-human animal expressing a human IL-15 protein and a human SIRPα protein, including: introducing into a genome of a first non-human animal a nucleic acid sequence encoding a human IL-15 protein, wherein the sequence encoding the human IL-15 protein is operably linked to an IL-15 gene promoter sequence; introducing into a genome of a second non-human animal a nucleic acid sequence encoding a human SIRPα protein, wherein the sequence encoding the human SIRPα protein is operably linked to a SIRPα promoter sequence; and making a third non-human animal that includes the nucleic acid sequence encoding the human IL-15 protein and the nucleic acid sequence encoding the human SIRPα protein, wherein the third non-human animal expresses the human IL-15 protein and the human SIRPα protein.

In one embodiment of the sixth aspect, the steps of introducing include generating a non-human animal from a pluripotent stem cell including the nucleic acid encoding human IL-15 or human SIRPα.

In another embodiment of the sixth aspect, or in a further embodiment of any of the above embodiments thereof, the first animal is a different animal than the second animal, and the step of making the third animal includes breeding the first and the second animal.

In another embodiment of the sixth aspect, the first animal and the second animal are the same, the step of introducing into the genome of the first animal includes contacting a first pluripotent stem cell with the nucleic acid sequence encoding the human IL-15 protein to obtain a second pluripotent stem cell, the step of introducing into the genome of the second animal includes contacting the second pluripotent stem cell with the nucleic acid sequence encoding the human SIRPα protein to obtain a third pluripotent step cell, and the third non-human animal is made from the third pluripotent stem cell.

In an alternative version of the sixth aspect, the present disclosure provides a method of making a non-human animal expressing a human IL-15 protein and a human SIRPα protein, including: introducing into a genome of a first non-human animal a nucleic acid sequence encoding a human SIRPα protein, wherein the sequence encoding the human SIRPα protein is operably linked to an SIRPα gene promoter sequence; introducing into a genome of a second non-human animal a nucleic acid sequence encoding a human IL-15 protein, wherein the sequence encoding the human IL-15 protein is operably linked to a IL-15 promoter sequence; and making a third non-human animal that includes the nucleic acid sequence encoding the human IL-15 protein and the nucleic acid sequence encoding the human SIRPα protein, wherein the third non-human animal expresses the human IL-15 protein and the human SIRPα protein.

In yet another embodiment of the sixth aspect, the first animal and the second animal are the same, the step of introducing into the genome of the first animal includes contacting a first pluripotent stem cell with the nucleic acid sequence encoding the human SIRPα protein to obtain a second pluripotent stem cell, the step of introducing into the genome of the second animal includes contacting the second pluripotent stem cell with the nucleic acid sequence encoding the human IL-15 protein to obtain a third pluripotent step cell, and the third non-human animal is made from the third pluripotent stem cell.

In another embodiment of the sixth aspect, or in a further embodiment of any of the above embodiments thereof, the pluripotent stem cell is an ES cell or an iPS cell.

In another embodiment of the sixth aspect, or in a further embodiment of any of the above embodiments thereof, the pluripotent stem cell is deficient for Rag2.

In another embodiment of the sixth aspect, or in a further embodiment of any of the above embodiments thereof, the pluripotent stem cell is deficient for IL2rg.

In another embodiment of the sixth aspect, or in a further embodiment of any of the above embodiments thereof, the third non-human animal is deficient in one or both of Rag2 and IL2rg.

In another embodiment of the sixth aspect, or in a further embodiment of any of the above embodiments thereof, the IL-15 promoter sequence is a sequence for the human IL-15 promoter.

In another embodiment of the sixth aspect, or in a further embodiment of any of the above embodiments thereof, the IL-15 promoter sequence is a sequence for the endogenous non-human animal IL-15 promoter.

In another embodiment of the sixth aspect, or in a further embodiment of any of the above embodiments thereof, the integration results in a replacement of the non-human IL-15 gene at the non-human IL-15 gene locus.

In another embodiment of the sixth aspect, or in a further embodiment of any of the above embodiments thereof, the nucleic acid sequence that encodes the human IL-15 protein includes human IL-15 genomic coding and non-coding sequence.

In a seventh aspect, the present disclosure provides a method of engrafting a genetically modified non-human animal expressing a human IL-15 protein, including: transplanting a population of cells including human hematopoietic cells into the genetically modified non-human animal made by a method according to the sixth aspect or any embodiment thereof. In one such embodiment, the transplanting includes tail-vein injection, fetal liver injection, or retro-orbital injection.

In another embodiment of the seventh aspect, or in a further embodiment of any of the above embodiments thereof, the genetically modified non-human animal is sub-lethally irradiated prior to transplantation.

In another embodiment of the seventh aspect, or in a further embodiment of any of the above embodiments thereof, the human hematopoietic cells are CD34+ cells.

In another embodiment of the seventh aspect, or in a further embodiment of any of the above embodiments thereof, the human hematopoietic cells are from fetal liver, adult bone marrow, or umbilical cord blood.

In an eighth aspect, the present disclosure provides a method of determining the efficacy of a candidate therapeutic antibody or antigen-binding protein in killing a target cell, the method including: administering the candidate therapeutic antibody or antigen-binding protein to a genetically modified non-human animal, wherein the genetically modified non-human animal is deficient for an endogenous immune system and includes: (i) a nucleic acid sequence incorporated into the genome of the genetically modified non-human animal, which sequence encodes a human SIRPα protein and is operably linked to a SIRPα gene promoter, (ii) a nucleic acid sequence incorporated into the genome of the genetically modified non-human animal, which sequence encodes a human IL-15 protein and is operably linked to an IL-15 gene promoter, and (iii) an engraftment of human hematopoietic cells, wherein the genetically modified non-human animal expresses the human SIRPα protein and the human IL-15 protein; and determining whether the candidate therapeutic antibody or antigen-binding protein modulates an NK cell mediated antibody-dependent cellular cytotoxicity against the target cell in the genetically modified non-human animal.

In a ninth aspect, the present disclosure provides a method of determining the efficacy of a candidate therapeutic antibody or antigen-binding protein, in killing a target cell including: isolating an NK cell from a genetically modified non-human animal, wherein the genetically modified non-human animal is deficient for an endogenous immune system and includes: (i) a nucleic acid sequence incorporated into the genome of the genetically modified non-human animal, which sequence encodes a human SIRPα protein and is operably linked to a SIRPα gene promoter, (ii) a nucleic acid sequence incorporated into the genome of the genetically modified non-human animal, which sequence encodes a human IL-15 protein and is operably linked to an IL-15 gene promoter, and (iii) an engraftment of human hematopoietic cells, wherein the genetically modified non-human animal expresses the human SIRPα protein and the human IL-15 protein; contacting the isolated NK cell with the candidate therapeutic antibody or antigen-binding protein and the target cell; and determining the antibody- or the antigen-binding protein-dependent cytolytic activity of the isolated NK cell against the target cell.

In a tenth aspect, the present disclosure provides a method of screening a candidate therapeutic antibody or antigen-binding protein for improved efficacy in killing a target cell including: administering the candidate therapeutic antibody or antigen-binding protein to a genetically modified non-human animal, wherein the genetically modified non-human animal is deficient for an endogenous immune system and includes: (i) a nucleic acid sequence incorporated into the genome of the genetically modified non-human animal, which sequence encodes a human SIRPα protein and is operably linked to a SIRPα gene promoter, (ii) a nucleic acid sequence incorporated into the genome of the genetically modified non-human animal, which sequence encodes a human IL-15 protein and is operably linked to an IL-15 gene promoter, and (iii) an engraftment of human hematopoietic cells, wherein the genetically modified non-human animal expresses the human SIRPα protein and the human IL-15 protein; and determining whether the candidate therapeutic antibody or antigen-binding protein displays improved efficacy in killing the target cell in the genetically modified non-human animal.

In an embodiment of any one of the eighth, ninth and tenth aspects, the target cell is one or more of a tumor cell, a virally-infected cell, a bacterially-infected cell, a bacterial cell, a fungal cell, and a parasitic cell.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 (top) shows the mouse Sirpα locus indicating the relative location of exons 1-8. FIG. 1 (bottom) provides a schematic representation showing the final targeted allele with human exons 2-4. The encoded chimeric protein possesses an extracellular region corresponding to amino acids 28-362 of the wild-type human SIRPα protein fused to the intracellular portion of the mouse SIRPα protein. Diagonally striped shapes represent inserted human sequence.

FIG. 4 provides serum levels of human IL-15 protein in SRG, SRG IL-15$^{h/m}$ (mouse 2) and SRG IL-15$^{h/h}$ (mouse 2) mice after challenge with poly (I:C).

FIG. 5A provides a graph showing efficient engraftment of human hematopoietic cells in the blood of NSG, SRG and SRG-15 (mouse 2) mice 12-14 weeks post engraftment. All data are shown as mean±s.e.m. Statistical analyses were performed using unpaired, two-tailed Mann-Whitney U-test (*P<0.05, P<0.01, **P<0.0001).

FIG. 6A provides plots showing human T and NK cell frequencies in SRG and SRG-15 mice (mouse 1) in bone marrow (BM), liver, and lung.

FIG. 6C provides plots and graphs illustrating human NK cell maturation in the liver of SRG and SRG-15 mice (mouse 1).

FIG. 7A provides a graph showing the frequency of human NK cells in the blood of NSG, SRG and SRG-15 (mouse 2) mice 10-12 weeks post engraftment. All data are shown as mean±s.e.m. Statistical analyses were performed using unpaired, two-tailed Mann-Whitney U-test (*P<0.05, P<0.01, **P<0.0001).

FIG. 7B provides a graph showing the percentage of human $NKp46^+$ cells in the spleen 14 weeks post engraftment for SRG, SRG-15$^{h/m}$, and SRG-15$^{h/h}$. All data are shown as mean±s.e.m. Statistical analyses were performed using unpaired, two-tailed Mann-Whitney U-test (*P<0.05, P<0.01, **P<0.0001).

FIG. 7C provides plots showing the frequency of human NK cells in the blood, spleen (SP), liver and lung of SRG and SRG-15 (mouse 2) mice 14 weeks post engraftment. All data are shown as mean±s.e.m. Statistical analyses were performed using unpaired, two-tailed Mann-Whitney U-test (*P<0.05, P<0.01, **P<0.0001).

FIG. 9A provides plots showing the distribution of NK cells and T cells in the spleen and graphs showing the percentage and number of NKp46+ cells in the spleen of SRG-15 mice (mouse 2) engrafted with CD34+ huHSCs relative to SRG mice engrafted with CD34+ huHSCs.

FIG. 9B provides a graph showing human immune cell composition in the blood of NSG (n=5), SRG (n=19) and SRG-15 (mouse 2) mice (n=39) 10-12 weeks post engraftment.

FIG. 9C provides human CD45+ cell numbers in the thymus of SRG and SRG-15 (mouse 2) mice 14 weeks post engraftment.

FIG. 9D provides representative flow cytometry plots of hCD45+ cells in the thymus of an SRG and SRG-15 (mouse 2) mouse.

FIG. 9E provides a graph showing the composition of hCD45+ cells in the thymus of SRG (n=8) and SRG-15 (mouse 2) mice (n=4) 14 weeks post engraftment.

FIG. 10A provides plots showing the frequency of $CD56^{bright}$ $CD16^-$ and $CD56^{dim}$ $CD16^+$ NK cell subsets in the blood and spleen of SRG and SRG-15 (mouse 2) mice seven weeks post engraftment.

FIG. 10C provides plots and graphs showing expression of killer inhibitory receptors (KIRs) on NK cell subsets in humans and SRG-15 mice (mouse 2).

FIG. 11 provides two plots (top left and top right) showing the distribution of CD16$^+$ vs. CD16$^-$ NK cells in the blood of SRG-15 mice (mouse 2) relative to a PBMC sample. FIG. 11 also provides a graph (bottom) showing the percentage of NKp46$^+$ cells that are CD16$^+$ vs. CD16$^-$ in either blood obtained from SRG-15 mice (mouse 2) or PBMC-derived sample.

FIG. 14A provides plots and a graph showing expression of the tissue-resident marker CD69 in lung CD8$^+$ T cells of SRG and SRG-15 (mouse 1) mice.

FIG. 17A provides plots and graphs showing human CD45$^+$ cells and CD8+ T cells within the IEL fraction of SRG and SRG-15 (mouse 1) mice.

FIG. 19C provides plots and graphs showing the distribution and numbers of human IELs and human lamina propria lymphocytes (LPLs) in SRG and SRG-15 (mouse 2) mice.

FIG. 21B provides a diagram showing the relative abundance of mouse bacteria in the gut of non-engrafted and engrafted SRG and SRG-15 (mouse 1) mice.

FIG. 23A provides ViSNE plots showing CyTOF-based analysis of 42 parameters of $CD56^{bright}$ $CD16^-$ and $CD56^{dim}$ $CD16^+$ NK cell subsets in humans (n=20) and SRG-15 mice (mouse 2) (n=9). Each dot represents a single cell.

FIG. 24B provides graphs showing IFNγ production from SRG and SRG-15 (mouse 2) derived NK cells after in vitro stimulation with poly I:C or human IL-12p70. NK cells from mice are compared against NK cells derived from healthy human PBMCs. All samples are normalized for NK number.

FIG. 25A provides a graph showing that Human NK cells in SRG-15 mice (mouse 2) inhibit tumor growth following treatment with rituximab (RTX). All data are shown as mean±s.e.m. Statistical analyses were performed using unpaired, two-tailed Mann-Whitney U-test (***P<0.001).

DETAILED DESCRIPTION

Figure 1:
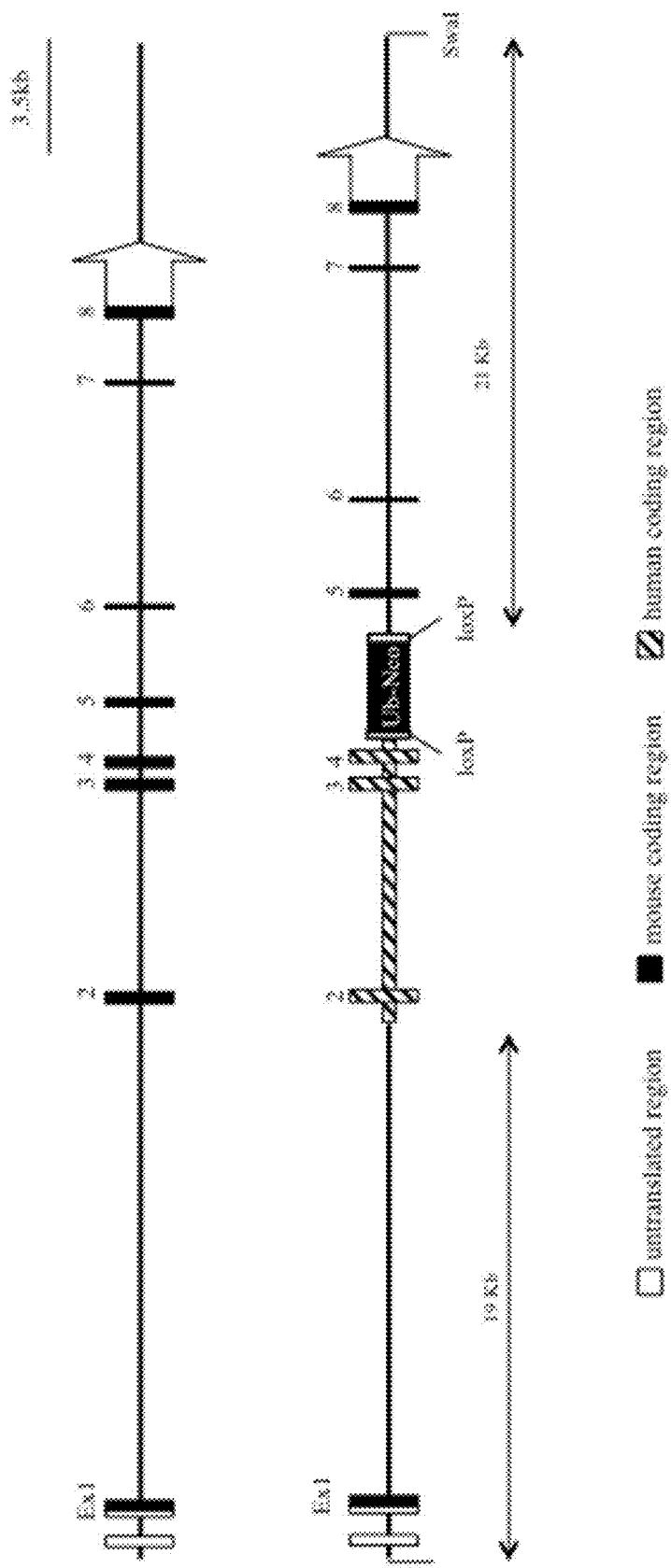
FIG. 1 provides a schematic representation of replacement of the mouse SIRPα gene with human SIRPα sequence.

Before the present methods and compositions are described, it is to be understood that this invention is not limited to particular method or composition described, as such may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, particular methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth.

The publications discussed herein are provided solely for their disclosure prior to the filing date of the present application. Nothing herein is to be construed as an admission that the present invention is not entitled to antedate such publication.

Genetically modified non-human animals expressing human SIRPα and human IL-15 from the non-human animal genome are provided. Also provided are methods for making non-human animals expressing human SIRPα and human IL-15 from the non-human animal genome, and methods for using non-human animals expressing human SIRPα and human IL-15 from the non-human animal genome. These animals and methods find many uses in the art, including, for example, in modeling human T cell and/or natural killer (NK) cell development and function; in modeling human pathogen infection, e.g., human pathogen infection of specific tissues, e.g., human gut, lung or liver pathogen infection; in modeling human pathogen infection of human T cells and/or NK cells; in in vivo screens for agents that inhibit infection by a pathogen that activates, induces and/or targets T cells and/or NK cells; in in vivo screens for agents that modulate the development and/or function of human T cells and/or NK cells, e.g. in a healthy or a diseased state; in in vivo screens for agents that are toxic to human T cells and/or NK cells; in in vivo screens for agents that prevent against, mitigate, or reverse the toxic effects of toxic agents on human T cells and/or NK cells; in in vivo screens of candidate T cell-inducing vaccines; and in in vivo and in vitro screens for agents that inhibit tumor growth and/or infection by activating NK cell-mediated antibody dependent cellular cytotoxicity (ADCC) processes.

Humanized SIRPα Non-Human Animals

In some aspects of the present disclosure, a humanized SIRPα non-human animal is provided. By a humanized SIRPα non-human animal, or "SIRPα non-human animal", is meant a non-human animal including a nucleic acid sequence that encodes a human SIRPα protein. As used herein, "human SIRPα protein" means a protein that is a wild-type (or native) human SIRPα protein or a variant of a wild-type (or native) human SIRPα protein, which retains one or more signaling and/or receptor functions of a wild-type human SIRPα protein. As used herein, the term "variant" defines either an isolated naturally occurring genetic mutant of a human polypeptide or nucleic acid sequence or a recombinantly prepared variation of a human polypeptide or nucleic acid sequence, each of which contains one or more mutations compared with the corresponding wild-type human nucleic acid or polypeptide sequence. For example, such mutations can be one or more amino acid substitutions, additions, and/or deletions. The term "variant" also includes human homologs and orthologues. In some embodiments, a variant polypeptide of the present invention has 70% or more identity, e.g. 75%, 80%, or 85% or more identity to a wild-type human polypeptide, e.g. 90%, 91%, 92%, 93%, 94%, 95%, 96%, 97%, 98% or 99% identity to a wild-type human polypeptide.

The percent identity between two sequences may be determined using any convenient technique in the art, for example, aligning the sequences using, e.g., publicly available software. Mutations can be introduced using standard molecular biology techniques, such as site-directed mutagenesis, PCR-mediated mutagenesis, directed evolution, and the like. One of skill in the art will recognize that one or more nucleic acid substitutions can be introduced without altering the amino acid sequence, and that one or more amino acid mutations can be introduced without altering the functional properties of the human protein.

Conservative amino acid substitutions can be made in human proteins to produce human protein variants. By conservative amino acid substitutions it is meant art-recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

Human variants can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, methylhistidine, and ornithine.

Human variants will typically be encoded by nucleic acids having a high degree of identity with a nucleic acid encoding the wild-type human protein. The complement of a nucleic acid encoding a human variant specifically hybridizes with a nucleic acid encoding a wild-type human under high stringency conditions. Nucleic acids encoding a human variant can be isolated or generated recombinantly or synthetically using well-known methodology. Also encompassed by the term "human SIRPα protein" are fragments of a wild-type human SIRPα protein (or a variant thereof), which retain one or more signaling and/or receptor functions of a wild-type human SIRPα protein, e.g., an extracellular domain of a human SIRPα protein.

The term "human SIRPα protein" also encompasses fusion proteins, i.e., chimeric proteins, which include one or more fragments of a wild-type human SIRPα protein (or a variant thereof) and which retain one or more signaling and/or receptor functions of a wild-type human SIRPα protein. A fusion protein which includes one or more fragments of a wild-type human SIRPα protein (or a variant thereof), e.g., in combination with one or more non-human peptides or polypeptides, may also be referred to herein as a humanized SIRPα protein. Thus, for example, a protein which includes an amino acid sequence of an extracellular domain of a wild-type human SIRPα protein fused with a signaling domain of a wild-type mouse SIRPα protein is encompassed by the term "human SIRPα protein".

In some instances, a human SIRPα protein accordingly to the present disclosure includes an amino acid sequence having at least about 70%, at least about 75%, at least about 80%, at least about 85%, at least about 90%, at least about 95%, at least about 98%, at least about 99%, or 100%, amino acid sequence identity to amino acids 28-362 of SEQ ID NO:12.

A nucleic acid sequence that encodes a human SIRPα protein is, therefore, a polynucleotide that includes a coding sequence for a human SIRPα protein, e.g., a wild-type human SIRPα protein, a variant of a wild-type human SIRPα protein, a fragment of a wild-type human SIRPα protein (or a variant thereof) which retains one or more signaling and/or receptor functions of a wild-type human SIRPα protein, or fusion proteins, i.e., chimeric proteins, which include one or more fragments of a wild-type human SIRPα protein (or a variant thereof) and which retain one or more signaling and/or receptor functions of a wild-type human SIRPα protein.

SIRPα (also known as "signal regulatory protein α" and "CD172A" in humans) is a member of the signal-regulatoryprotein (SIRP) family, and also belongs to the immunoglobulin superfamily. SIRPα has been shown to improve cell engraftment in immunodeficient mice (Strowig et al. *Proc Natl Acad Sci USA* 2011; 108:13218-13223). Polypeptide sequence for wild-type human SIRPα and the nucleic acid sequence that encodes wild-type human SIRPα may be found at Genbank Accession Nos. NM_001040022.1 (variant 1), NM_001040023.1 (variant 2), and NM_080792.2 (variant 3). The SIRPα gene is conserved in at least chimpanzee, Rhesus monkey, dog, cow, mouse, rat, and chicken. The genomic locus encoding the wild-type human SIRPα protein may be found in the human genome at Chromosome 20; NC_000020.11 (1894117-1939896). Protein sequence is encoded by exons 1 through 8 at this locus. As such, in some embodiments, a nucleic acid sequence including coding sequence for human SIRPα includes one or more of exons 1-8 of the human SIRPα gene. In some instances, the nucleic acid sequence also includes aspects of the genomic locus of the human SIRPα, e.g., introns, 3' and/or 5' untranslated sequence (UTRs). In some instances, the nucleic acid sequence includes whole regions of the human SIRPα genomic locus. In some instances, the nucleic acid sequence includes exons 2-4 of the human SIRPα genomic locus.

In the humanized SIRPα non-human animals of the subject application, the nucleic acid sequence that encodes a human SIRPα protein is operably linked to one or more regulatory sequences of a SIRPα gene, e.g., a regulatory sequence of a SIRPα gene of the non-human animal. Non-human animal, e.g., mouse, SIRPα regulatory sequences are those sequences of the non-human animal SIRPα genomic locus that regulate the non-human animal SIRPα expression, for example, 5' regulatory sequences, e.g., the SIRPα promoter, SIRPα 5' untranslated region (UTR), etc.; 3' regulatory sequences, e.g., the 3'UTR; and enhancers, etc.

A "promoter" or "promoter sequence" refers to a DNA regulatory region capable of binding RNA polymerase in a cell and initiating transcription of a downstream (3' direction) coding sequence. The promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Of particular interest to the present disclosure are DNA regulatory elements, e.g. promoters, which promote the transcription of the human protein in the same spatial and temporal expression pattern, i.e., in the same cells and tissues and at the same times, as would be observed for the corresponding endogenous protein.

Mouse SIRPα is located on chromosome 2; NC_000068.7 (129592606-129632228), and the mouse SIRPα coding sequence may be found at Genbank Accession Nos. NM_007547.4 (isoform 1), NM_001177647.2 (isoform 2), NM_001291019.1 (isoform 3), NM_001291020.1 (isoform 3), NM_001291021.1 (isoform 4), NM_001291022.1 (isoform 5). The regulatory sequences of mouse SIRPα are well defined in the art, and may be readily identified using in silico methods, e.g., by referring to the above Genbank Accession Nos. on the UCSC Genome Browser on the world wide web, or by experimental methods as described in the art. In some instances, e.g., when the nucleic acid sequence that encodes a human SIRPα protein is located at the mouse SIRPα genomic locus, the regulatory sequences operably linked to the human SIRPα coding sequence are endogenous, or native, to the mouse genome, i.e., they were present in the mouse genome prior to integration of human nucleic acid sequences.

In some instances, the humanized SIRPα non-human animal, e.g., mouse, is generated by the random integration, or insertion, of a human nucleic acid sequence encoding a human SIRPα protein (including fragments as described above), i.e., a "human SIRPα nucleic acid sequence", or "human SIRPα sequence", into the genome. Typically, in such embodiments, the location of the nucleic acid sequence encoding a human SIRPα protein in the genome is unknown. In other instances, the humanized SIRPα non-human animal is generated by the targeted integration, or insertion, of human SIRPα nucleic acid sequence into the genome, by, for example, homologous recombination. In homologous recombination, a polynucleotide is inserted into the host genome at a target locus while simultaneously removing host genomic material, e.g., 50 base pairs (bp) or more, 100 bp or more, 200 bp or more, 500 bp or more, 1 kB or more, 2 kB or more, 5 kB or more, 10 kB or more, 15 kB or more, 20 kB or more, or 50 kB or more of genomic material, from the target locus. So, for example, in a humanized SIRPα mouse including a nucleic acid sequence that encodes a human SIRPα protein created by targeting human SIRPα nucleic acid sequence to the mouse SIRPα locus, human SIRPα nucleic acid sequence may replace some or all of the mouse sequence, e.g. exons and/or introns, at the SIRPα locus. In some such instances, a human SIRPα nucleic acid sequence is integrated into the mouse SIRPα locus such that expression of the human SIRPα sequence is regulated by the native, or endogenous, regulatory sequences at the mouse SIRPα locus. In other words, the regulatory sequence(s) to which the nucleic acid sequence encoding a human SIRPα protein is operably linked are the native SIRPα regulatory sequences at the mouse SIRPα locus.

In some instances, the integration of a human SIRPα sequence does not affect the transcription of the gene into which the human SIRPα sequence has integrated. For example, if the human SIRPα sequence integrates into a coding sequence as an intein, or the human SIRPα sequence includes a 2A peptide, the human SIRPα sequence will be transcribed and translated simultaneously with the gene into which the human SIRPα sequence has integrated. In other instances, the integration of the human SIRPα sequence interrupts the transcription of the gene into which the human SIRPα sequence has integrated. For example, upon integration of the human SIRPα sequence by homologous recombination, some or all of the coding sequence at the integration locus may be removed, such that the human SIRPα sequence is transcribed instead. In some such instances, the integration of a human SIRPα sequence creates a null mutation, and hence, a null allele. A null allele is a mutant copy of a gene that completely lacks that gene's normal function. This can be the result of the complete absence of the gene product (protein, RNA) at the molecular level, or the expression of a non-functional gene product. At the phenotypic level, a null allele is indistinguishable from a deletion of the entire locus.

In some instances, the humanized SIRPα non-human animal, e.g., mouse, includes one copy of the nucleic acid sequence encoding a human SIRPα protein. For example, the non-human animal may be heterozygous for the nucleic acid sequence. In other words, one allele at a locus will include the nucleic acid sequence, while the other will be the endogenous allele. For example, as discussed above, in some instances, a human SIRPα nucleic acid sequence is integrated into the non-human animal, e.g., mouse, SIRPα locus such that it creates a null allele for the non-human animal SIRPα. In some such embodiments, the humanized SIRPα non-human animal may be heterozygous for the nucleic acid sequence encoding human SIRPα, i.e., the humanized SIRPα non-human animal includes one null allele for the non-human animal SIRPα (the allele including the nucleic acid sequence) and one endogenous SIRPα allele (wild-type or otherwise). In other words, the non-human animal is a SIRPα$^{h/m}$ non-human animal, where "h" represents the allele including the human sequence and "m" represents the endogenous allele. In other instances, the humanized SIRPα includes two copies of the nucleic acid sequence encoding a human SIRPα protein. For example, the non-human animal, e.g., mouse, may be homozygous for the nucleic acid sequence, i.e., both alleles for a locus in the diploid genome will include the nucleic acid sequence, i.e., the humanized SIRPα non-human animal includes two null alleles for the non-human animal SIRPα (the allele including the nucleic acid sequence). In other words, the non-human animal is a SIRPα$^{h/h}$ non-human animal.

In some embodiments, the humanized SIRPα non-human animal, e.g., mouse, includes other genetic modifications. In some embodiments, the humanized SIRPα non-human animal is an immunocompromised animal. For example, the humanized SIRPα non-human animal may include at least one null allele for the Rag2 gene ("recombination activating gene 2", wherein the coding sequence for the mouse gene may be found at Genbank Accession No. NM_009020.3). In some embodiments, the humanized SIRPα non-human animal includes two null alleles for Rag2. In other words, the humanized SIRPα non-human animal is homozygous null for Rag2. As another example, the humanized SIRPα non-human animal includes at least one null allele for the IL2rg gene ("interleukin 2 receptor, gamma", also known as the common gamma chain, or γC, wherein the coding sequence for the mouse gene may be found at Genbank Accession No. NM_013563.3). In some embodiments, the humanized SIRPα non-human animal includes two null alleles for IL2rg. In other words, the humanized SIRPα non-human animal is homozygous null for IL2rg, i.e., it is IL2rg$^{-/-}$ (or IL2rg$^{Y/-}$ where the IL2rg gene is located on the X chromosome as in mouse). In some embodiments, the SIRPα non-human animal includes a null allele for both Rag2 and IL2rg, i.e., it is Rag2$^{-/-}$ IL2rg$^{-/-}$ (or Rag2$^{-/-}$ IL2rg$^{Y/-}$ where the IL2rg gene is located on the X chromosome as in mouse). Other genetic modifications are also contemplated. For example, the humanized SIRPα non-human animal may include modifications in other genes associated with the development and/or function of hematopoietic cells and the immune system, e.g. the replacement of one or more other non-human animal genes with nucleic acid sequence encoding the human ortholog. Additionally or alternatively, the humanized SIRPα non-human animal may include modifications in genes associated with the development and/or function of other cells and tissues, e.g., genes associated with human disorders or disease, or genes that, when modified in a non-human animal, e.g., mice, provide for models of human disorders and disease.

Humanized IL-15 Non-Human Animals

In some aspects of the present disclosure, a humanized IL-15 non-human animal is provided. By a humanized IL-15 non-human animal, or "IL-15 non-human animal", is meant a non-human animal including a nucleic acid sequence that encodes a human IL-15 protein. As used herein, "human IL-15 protein", means a protein that is a wild-type (or native) human IL-15 protein or a variant of a wild-type (or native) human IL-15 protein, which retains one or more signaling functions of a wild-type (or native) human IL-15 protein, e.g., which allows for stimulation of (or signaling via) the human IL-15 receptor, and/or which is capable of binding to the human IL-15 receptor alpha subunit of the human IL-15 receptor, and/or which is capable of binding to IL-2R beta/IL-15R beta and the common γ-chain (γc). Also encompassed by the term "human IL-15 protein" are fragments of a wild-type human IL-15 protein (or variants thereof), which retain one or more signaling functions of a wild-type human IL-15 protein, e.g., a fragment of a human IL-15 protein, which allows for stimulation of (or signaling via) the human IL-15 receptor, and/or which is capable of binding to the human IL-15 receptor alpha subunit of the human IL-15 receptor, and/or which is capable of binding to IL-2R beta/IL-15R beta and the common γ-chain (γc).

The term "human IL-15 protein" also encompasses fusion proteins, i.e., chimeric proteins, which include one or more fragments of a wild-type human IL-15 protein (or a variant thereof) and which retain one or more signaling functions of a wild-type human IL-15 protein, e.g., as described above. A fusion protein which includes one or more fragments of a wild-type human IL-15 protein (or a variant thereof) may also be referred to herein as a humanized IL-15 protein.

A nucleic acid sequence that encodes a human IL-15 protein is, therefore, a polynucleotide that includes a coding sequence for a human IL-15 protein, i.e., a wild-type human IL-15 protein, a variant of a wild-type human IL-15 protein, a fragment of a wild-type human IL-15 protein (or a variant thereof) which retains one or more signaling functions of a wild-type human IL-15 protein, or fusion proteins, i.e., chimeric proteins, which include one or more fragments of a wild-type human IL-15 protein (or a variant thereof) and which retain one or more signaling functions of a wild-type human IL-15 protein, e.g., as described above.

IL-15 (also known as "Interleukin 15") is a cytokine that stimulates the proliferation of T lymphocytes. Polypeptide sequence for wild-type human IL-15 and the nucleic acid sequence that encodes wild-type human IL-15 may be found at Genbank Accession Nos. NM_000585.4; NP_000576.1 (isoform 1), NM_172175.2; NP_751915.1 (isoform 2). The genomic locus encoding the wild-type human IL-15 protein may be found in the human genome at Chromosome 4; NC_000004.12 (141636596-141733987). The human IL-15 locus includes 8 exons, with exons 3-8 being coding exons. As such, in some embodiments, a nucleic acid sequence including coding sequence for human IL-15 includes one or more of exons 3-8 of the human IL-15 gene (i.e., coding exons 1-6, see FIG. 2). For example, various IL-15 mRNA isoforms have been identified which are produced through the following exon usage combinations Exons 1-2-3-4-5-6-7-8; Exons 1-3-4-5-6-7-8 or Exons 1-3-4-(alternative exon 5)-5-6-7-8). In some instances, the nucleic acid sequence also includes aspects of the genomic locus of the human IL-15, e.g., introns, 3' and/or 5' untranslated sequence (UTRs). In some instances, the nucleic acid sequence includes whole regions of the human IL-15 genomic locus. In some instances, the nucleic acid sequence includes exons 5-8 of the human IL-15 genomic locus (i.e., coding exons 3-6).

In some instances, a human IL-15 protein accordingly to the present disclosure includes an amino acid sequence having at least about 70%, at least about 75%, at least about 80%, at least about 85%, at least about 90%, at least about 95%, at least about 98%, at least about 99%, or 100%, amino acid sequence identity to SEQ ID NO:31.

In the humanized IL-15 non-human animals of the subject application, the nucleic acid sequence that encodes a human IL-15 protein is operably linked to one or more regulatory sequences of an IL-15 gene, e.g., a regulatory sequence of an IL-15 gene of the non-human animal. Non-human animal, e.g., mouse, IL-15 regulatory sequences are those sequences of the non-human animal IL-15 genomic locus that regulate the non-human animal IL-15 expression, for example, 5' regulatory sequences, e.g., the IL-15 promoter, IL-15 5' untranslated region (UTR), etc.; 3' regulatory sequences, e.g., the 3'UTR; and enhancers, etc. Mouse IL-15 is located on Chromosome 8, NC_000074.6 (82331624-82403227, complement), and the mouse IL-15 coding sequence may be found at Genbank Accession Nos. NM_008357.2 (variant 1); NM_001254747.1 (variant 2). The regulatory sequences of mouse IL-15 are well defined in the art, and may be readily identified using in silico methods, e.g., by referring to the above Genbank Accession Nos. on the UCSC Genome Browser, on the world wide web at genome.ucsc.edu, or by experimental methods as described in the art. In some instances, e.g., when the nucleic acid sequence that encodes a human IL-15 protein is located at the mouse IL-15 genomic locus, the regulatory sequences operably linked to the human IL-15 coding sequence are endogenous, or native, to the mouse genome, i.e., they were present in the mouse genome prior to integration of human nucleic acid sequences.

In some instances, the humanized IL-15 non-human animal, e.g., mouse, is generated by the random integration, or insertion, of a human nucleic acid sequence encoding a human IL-15 protein (including fragments as described above), i.e., a "human IL-15 nucleic acid sequence", or "human IL-15 sequence", into the genome. Typically, in such embodiments, the location of the nucleic acid sequence encoding a human IL-15 protein in the genome is unknown. In other instances, the humanized IL-15 non-human animal is generated by the targeted integration, or insertion, of human IL-15 nucleic acid sequence into the genome, by, for example, homologous recombination. In homologous recombination, a polynucleotide is inserted into the host genome at a target locus while simultaneously removing host genomic material, e.g., 50 base pairs (bp) or more, 100 bp or more, 200 bp or more, 500 bp or more, 1 kB or more, 2 kB or more, 5 kB or more, 10 kB or more, 15 kB or more, 20 kB or more, or 50 kB or more of genomic material, from the target locus. So, for example, in a humanized IL-15 mouse including a nucleic acid sequence that encodes a human IL-15 protein created by targeting human IL-15 nucleic acid sequence to the mouse IL-15 locus, human IL-15 nucleic acid sequence may replace some or all of the mouse sequence, e.g. exons and/or introns, at the IL-15 locus. In some such instances, a human IL-15 nucleic acid sequence is integrated into the mouse IL-15 locus such that expression of the human IL-15 sequence is regulated by the native, or endogenous, regulatory sequences at the mouse IL-15 locus. In other words, the regulatory sequence(s) to which the nucleic acid sequence encoding a human IL-15 protein is operably linked are the native IL-15 regulatory sequences at the mouse IL-15 locus.

In some instances, the integration of a human IL-15 sequence does not affect the transcription of the gene into which the human IL-15 sequence has integrated. For example, if the human IL-15 sequence integrates into a coding sequence as an intein, or the human IL-15 sequence includes a 2A peptide, the human IL-15 sequence will be transcribed and translated simultaneously with the gene into which the human IL-15 sequence has integrated. In other instances, the integration of the human IL-15 sequence interrupts the transcription of the gene into which the human IL-15 sequence has integrated. For example, upon integration of the human IL-15 sequence by homologous recombination, some or all of the coding sequence at the integration locus may be removed, such that the human IL-15 sequence is transcribed instead. In some such instances, the integration of a human IL-15 sequence creates a null mutation, and hence, a null allele. A null allele is a mutant copy of a gene that completely lacks that gene's normal function. This can be the result of the complete absence of the gene product (protein, RNA) at the molecular level, or the expression of a non-functional gene product. At the phenotypic level, a null allele is indistinguishable from a deletion of the entire locus.

In some instances, the humanized IL-15 non-human animal, e.g., mouse, includes one copy of the nucleic acid sequence encoding a human IL-15 protein. For example, the non-human animal may be heterozygous for the nucleic acid sequence. In other words, one allele at a locus will include the nucleic acid sequence, while the other will be the endogenous allele. For example, as discussed above, in some instances, a human IL-15 nucleic acid sequence is integrated into the non-human animal, e.g., mouse, IL-15 locus such that it creates a null allele for the non-human animal IL-15. In some such embodiments, the humanized IL-15 non-human animal may be heterozygous for the nucleic acid sequence encoding human IL-15, i.e., the humanized IL-15 non-human animal includes one null allele for the non-human animal IL-15 (the allele including the nucleic acid sequence) and one endogenous IL-15 allele (wild-type or otherwise). In other words, the non-human animal is an IL-15$^{h/m}$ non-human animal, where "h" represents the allele including the human sequence and "m" represents the endogenous allele. In other instances, the humanized IL-15 includes two copies of the nucleic acid sequence encoding a human IL-15 protein. For example, the non-human animal, e.g., mouse, may be homozygous for the nucleic acid sequence, i.e., both alleles for a locus in the diploid genome will include the nucleic acid sequence, i.e., the humanized IL-15 non-human animal includes two null alleles for the non-human animal IL-15 (the allele including the nucleic acid sequence). In other words, the non-human animal is an IL-15$^{h/h}$ non-human animal.

Humanized SIRPα-IL-15 Non-Human Animals

By crossing humanized IL-15 non-human animals as described above with humanized SIRPα non-human animals of the same species as described above, genetically modified non-human animals expressing both human SIRPα and human IL-15 can be produced. In some embodiments, such genetically modified non-human animals are deficient for an endogenous immune system e.g., immunocompromised animals, e.g., as a result of a null allele for one or both of Rag2 and IL2rg. For example, in some embodiments a non-human animal according to the present disclosure is Rag2$^{-/-}$ and/or IL2rg$^{-/-}$ (or Rag2$^{-/-}$ and/or IL2rg$^{Y/-}$ where the IL2rg gene is located on the X chromosome as in mouse). In some embodiments, a genetically modified non-human animal, e.g., mouse, is provided wherein the genetically modified non-human animal, e.g., mouse is SIRPα$^{h/m}$ IL-15$^{h/m}$ Rag2$^{-/-}$ IL2rg$^{Y/-}$, SIRPα$^{h/h}$ IL-15$^{h/m}$ Rag2$^{-/-}$ IL2rg$^{Y/-}$, or SIRPα$^{h/m}$ IL-15$^{h/h}$ Rag2$^{-/-}$ IL2rg$^{Y/-}$.

In some embodiments, a genetically modified non-human animal, e.g., mouse, is provided which includes a nucleic acid sequence incorporated into the genome of the genetically modified non-human animal, which sequence encodes a human SIRPα protein and is operably linked to a SIRPα gene promoter; and a nucleic acid sequence incorporated into the genome of the genetically modified non-human animal, which sequence encodes a human IL-15 protein and is operably linked to an IL-15 gene promoter, wherein the genetically modified non-human animal expresses the human SIRPα protein and the human IL-15 protein.

In some embodiments, the SIRPα gene promoter is an endogenous non-human SIRPα gene promoter. In some such embodiments, the SIRPα gene promoter is the endogenous non-human SIRPα gene promoter at the non-human animal SIRPα gene locus. In another embodiment, the SIRPα gene promoter is a human SIRPα promoter.

In some embodiments, the IL-15 gene promoter is an endogenous non-human IL-15 gene promoter. In some such embodiments, the IL-15 gene promoter is the endogenous non-human IL-15 gene promoter at the non-human animal IL-15 gene locus. In another embodiment, the IL-15 promoter is a human IL-15 promoter.

In some embodiments, a genetically modified non-human animal as described herein expresses human IL-15 mRNA in the liver, lung, bone marrow (BM), small intestine (SI) and colon.

In some embodiments, a genetically modified non-human animal, e.g., mouse, expressing both human SIRPα and human IL-15 as described herein exhibits a higher percentage and number of human T cells and NK cells than a genetically modified non-human animal, e.g., mouse, expressing only human SIRPα, following engraftment with human hematopoietic cells, e.g., CD45+ cells. In some embodiments, a genetically modified non-human animal, e.g., mouse, expressing both human SIRPα and human IL-15 as described herein exhibits a higher percentage and number of NK cells in blood and spleen. In some embodiments a genetically modified non-human animal, e.g., mouse, expressing both human SIRPα and human IL-15 as described herein includes both human NK cell subsets, CD56$^{bright}$CD16$^-$ and CD56$^{dim}$CD16$^+$, in the blood, spleen and liver, following engraftment with human hematopoietic cells, e.g., CD45+ cells. In some embodiments, a genetically modified non-human animal, e.g., mouse, expressing both human SIRPα and human IL-15 as described herein exhibits similar distribution of CD16+ versus CD16− NK cells in blood as the distribution of CD16+ versus CD16− NK cells in PBMCs obtained from human subjects.

In some embodiments a genetically modified non-human animal, e.g., mouse, expressing both human SIRPα and human IL-15 as described herein includes NK cells in the liver of the genetically modified non-human animal which exhibit a higher expression level of CD16 and CD56, indicating increased NK cell maturation, relative to a genetically modified non-human animal, e.g., mouse, expressing only human SIRPα, following engraftment with human hematopoietic cells, e.g., CD45+ cells.

In some embodiments a genetically modified non-human animal, e.g., mouse, expressing both human SIRPα and human IL-15 as described herein, and engrafted with human hematopoietic cells, e.g., CD45+ cells, includes NK cells in the spleen which exhibit a distinct expression level of killer inhibitory receptors, with the CD56$^{dim}$CD16$^+$ NK cell population including the higher percentage of CD158-expressing cells, similar to what is found for NK cell subsets in the blood of humans.

In some embodiments a genetically modified non-human animal, e.g., mouse, expressing both human SIRPα and human IL-15 as described herein, and engrafted with human hematopoietic cells, e.g., CD45+ cells, exhibits a higher frequency of human CD45+ and CD8+ T cells in the intraepithelial lymphocyte population relative to a genetically modified non-human animal, e.g., mouse, expressing only human SIRPα. In some embodiments, a genetically modified non-human animal, e.g., mouse, expressing both human SIRPα and human IL-15 as described herein, and engrafted with human hematopoietic cells, exhibits comparable CD16+ versus CD16− NK cell distribution in IELs, and more CD16+ than CD16− NK cells in blood and spleen, which is reflective of normal human physiology.

In some embodiments a genetically modified non-human animal, e.g., mouse, expressing both human SIRPα and human IL-15 as described herein, and engrafted with human hematopoietic cells, e.g., CD45+ cells, exhibits an increased number of human T cells in the lung relative to a genetically modified non-human animal, e.g., mouse, expressing only human SIRPα. In some such embodiments, such a genetically modified non-human animal, e.g., mouse, exhibits a higher level of expression of CD69 on human CD8+ T cells in the lung relative to a genetically modified non-human animal, e.g., mouse, expressing only human SIRPα.

In some embodiments a genetically modified non-human animal, e.g., mouse, expressing both human SIRPα and human IL-15 as described herein, and engrafted with human hematopoietic cells, e.g., CD45+ cells, exhibits an increased level of CD69 expression on human CD8+ T cells in the liver relative to a genetically modified non-human animal, e.g., mouse, expressing only human SIRPα.

In some embodiments, a genetically modified non-human animal, e.g., mouse, expressing both human SIRPα and human IL-15 as described herein, and engrafted with human hematopoietic cells, exhibits discernable Peyer's Patches which are predominantly human CD45+.

Any non-human mammal animal may be genetically modified according to the subject disclosure. Nonlimiting examples include laboratory animals, domestic animals, livestock, etc., e.g., species such as murine, rodent, canine, feline, porcine, equine, bovine, ovine, non-human primates, etc.; for example, mice, rats, rabbits, hamsters, guinea pigs, cattle, pigs, sheep, goats and other transgenic animal species, particularly-mammalian species, as known in the art. In other embodiments, the non-human animal may be a bird, e.g., of Galliformes order, such as a chicken, a turkey, a quail, a pheasant, or a partridge; e.g., of Anseriformes order, such as a duck, a goose, or a swan, e.g., of Columbiformes order, such as a pigeon or a dove. In various embodiments, the subject genetically modified animal is a mouse, a rat or a rabbit.

In some embodiments, the non-human animal is a mammal. In some such embodiments, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, white-tailed rats, Malagasy rats and mice), Platacanthomyidae (e.g., spiny dormice), and Spalacidae (e.g., mole rats, bamboo rats, and zokors). In a specific embodiment, the genetically modified rodent is selected from a true mouse or rat (family Muridae), a gerbil, a spiny mouse, and a crested rat.

In one embodiment, the subject genetically modified non-human animal is a rat. In one such embodiment, the rat is selected from a Wistar rat, an LEA strain, a Sprague Dawley strain, a Fischer strain, F344, F6, and Dark Agouti. In another embodiment, the rat strain is a mix of two or more strains selected from the group consisting of Wistar, LEA, Sprague Dawley, Fischer, F344, F6, and Dark Agouti.

In another embodiment, the subject genetically modified non-human animal is a mouse, e.g. a mouse of a C57BL strain (e.g. C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, C57BL/Ola, etc.); a mouse of the 129 strain (e.g. 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2); a mouse of the BALB strain; e.g., BALB/c; and the like. See, e.g., Festing et al. (1999) Mammalian Genome 10:836, see also, Auerbach et al (2000) Establishment and Chimera Analysis of 129/SvEv- and C57BL/6-Derived Mouse Embryonic Stem Cell Lines). In another embodiment, a mouse is a mix of the aforementioned strains.

In some embodiments, the subject genetically modified non-human animal is also immunodeficient. "Immunodeficient," includes deficiencies in one or more aspects of an animal's native, or endogenous, immune system, e.g. the animal is deficient for one or more types of functioning host immune cells, e.g. deficient for non-human B cell number and/or function, non-human T cell number and/or function, non-human NK cell number and/or function, etc.

One method to achieve immunodeficiency in the subject animals is sublethal irradiation. For example, newborn genetically modified mouse pups can be irradiated sublethally, e.g., 2×200 cGy with a four hour interval. Alternatively, immunodeficiency may be achieved by any one of a number of gene mutations known in the art, any of which may be bred either alone or in combination into the subject genetically modified non-human animals of the present disclosure or which may be used as the source of stem cells into which the genetic modifications of the subject disclosure may be introduced. Non-limiting examples include X-linked SCID, associated with IL2rg gene mutations and characterized by the lymphocyte phenotype T(−) B(+) NK(−); autosomal recessive SCID associated with Jak3 gene mutations and characterized by the lymphocyte phenotype T(−) B(+) NK(−); ADA gene mutations characterized by the lymphocyte phenotype T(−) B(−) NK(−); IL-7R alpha-chain mutations characterized by the lymphocyte phenotype T(−) B(+) NK(+); CD3 delta or epsilon mutations characterized by the lymphocyte phenotype T(−) B(+) NK(+); RAG1 and RAG2 mutations characterized by the lymphocyte phenotype T(−) B(−) NK(+); Artemis gene mutations characterized by the lymphocyte phenotype T(−) B(−) NK(+), CD45 gene mutations characterized by the lymphocyte phenotype T(−) B(+) NK(+); and Prkdcscid mutations characterized by the lymphocyte phenotype T(−), B(−). As such, in some embodiments, the genetically modified immunodeficient non-human animal has one or more deficiencies selected from an IL2 receptor gamma chain (Il2rg$^{y/-}$) deficiency, a Jak3 deficiency, an ADA deficiency, an IL7R deficiency, a CD3 deficiency, a RAG1 and/or RAG2 deficiency, an Artemis deficiency, a CD45 deficiency, and a Prkdc deficiency. These and other animal models of immunodeficiency will be known to the ordinarily skilled artisan, any of which may be used to generate immunodeficient animals of the present disclosure.

In some embodiments, genetically modified non-human animals in accordance with the invention find use as recipients of human hematopoietic cells that are capable of developing human immune cells from engrafted human hematopoietic cells. As such, in some aspects of the invention, the subject genetically modified animal is a genetically modified, immunodeficient, non-human animal that is engrafted with human hematopoietic cells.

Engraftment of Humanized SIRPα-Il-15 Non-Human Animals

As discussed above, in some aspects of the invention, the humanized SIRPα-IL-15 non-human animal, e.g., mouse, e.g., a Rag2$^{-/-}$IL2rg$^{Y/-}$ hSIRPα hIL-15 mouse, or a sublethally irradiated hSIRPα hIL-15 mouse, is engrafted, or transplanted, with cells. Cells may be mitotic cells or post-mitotic cells, and include such cells of interest as pluripotent stem cells, e.g., ES cells, iPS cells, and embryonic germ cells; and somatic cells, e.g., fibroblasts, hematopoietic cells, neurons, muscle cells, bone cells, vascular endothelial cells, gut cells, and the like, and their lineage-restricted progenitors and precursors. Cell populations of particular interest include those that include hematopoietic stem or progenitor cells, which will contribute to or reconstitute the hematopoietic system of the humanized SIRPα-IL-15 non-human animal, for example, peripheral blood leukocytes, fetal liver cells, fetal bone, fetal thymus, fetal lymph nodes, vascularized skin, artery segments, and purified hematopoietic stem cells, e.g., mobilized HSCs or cord blood HSCs.

Any source of human hematopoietic cells, human hematopoietic stem cells (HSCs) and/or hematopoietic stem progenitor cells (HSPC) as known in the art or described herein may be transplanted into the genetically modified immunodeficient non-human animals of the present disclosure. One suitable source of human hematopoietic cells known in the art is human umbilical cord blood cells, in particular CD34-positive (CD34$^+$) cells. Another source of human hematopoietic cells is human fetal liver. Another source is human bone marrow. Also encompassed are induced pluripotent stem cells (iPSC) and induced hematopoietic stem cells (iHSC) produced by the de-differentiation of somatic cells, e.g., by methods known in the art.

Cells may be from any mammalian species, e.g., murine, rodent, canine, feline, equine, bovine, ovine, primate, human, etc. Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e., splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

If the cells are primary cells, they may be harvested from an individual by any convenient method. For example, cells, e.g., blood cells, e.g., leukocytes, may be harvested by apheresis, leukocytapheresis, density gradient separation, etc. As another example, cells, e.g., skin, muscle, bone marrow, spleen, liver, pancreas, lung, intestine, stomach tissue, etc. may be harvested by biopsy. An appropriate solution may be used for dispersion or suspension of the harvested cells. Such solution will generally be a balanced salt solution, e.g., normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

In some instances, a heterogeneous population of cells will be transplanted into the humanized non-human animal, e.g., mouse. In other instances, a population of cells that is enriched for a particular type of cell, e.g., a progenitor cell, e.g., a hematopoietic progenitor cell, will be engrafted into the humanized non-human animal, e.g., mouse. Enrichment of a cell population of interest may be by any convenient separation technique. For example, the cells of interest may be enriched by culturing methods. In such culturing methods, particular growth factors and nutrients are typically added to a culture that promotes the survival and/or proliferation of one cell population over others. Other culture conditions that affect survival and/or proliferation include growth on adherent or non-adherent substrates, culturing for particular lengths of time, etc. Such culture conditions are well known in the art. As another example, cells of interest may be enriched for by separation the cells of interest from the initial population by affinity separation techniques. Techniques for affinity separation may include magnetic separation using magnetic beads coated with an affinity reagent, affinity chromatography, "panning" with an affinity reagent attached to a solid matrix, e.g., plate, cytotoxic agents joined to an affinity reagent or used in conjunction with an affinity reagent, e.g., complement and cytotoxins, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the cells of interest.

For example, using affinity separation techniques, cells that are not the cells of interest for transplantation may be depleted from the population by contacting the population with affinity reagents that specifically recognize and selectively bind markers that are not expressed on the cells of interest. For example, to enrich for a population of hematopoietic progenitor cells, one might deplete cells expressing mature hematopoietic cell markers. Additionally or alternatively, positive selection and separation may be performed using by contacting the population with affinity reagents that specifically recognize and selectively bind markers associated with hematopoietic progenitor cells, e.g. CD34, CD133, etc. By "selectively bind" is meant that the molecule binds preferentially to the target of interest or binds with greater affinity to the target than to other molecules. For example, an antibody will bind to a molecule including an epitope for which it is specific and not to unrelated epitopes. In some embodiments, the affinity reagent may be an antibody, i.e. an antibody that is specific for CD34, CD133, etc. In some embodiments, the affinity reagent may be a specific receptor or ligand for CD34, CD133, etc., e.g., a peptide ligand and receptor; effector and receptor molecules, a T-cell receptor specific for CD34, CD133, etc., and the like. In some embodiments, multiple affinity reagents specific for the marker of interest may be used.

Antibodies and T cell receptors that find use as affinity reagents may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art. Of particular interest is the use of labeled antibodies as affinity reagents. Conveniently, these antibodies are conjugated with a label for use in separation. Labels include magnetic beads, which allow for direct separation; biotin, which can be removed with avidin or streptavidin bound to a support; fluorochromes, which can be used with a fluorescence activated cell sorter; or the like, to allow for ease of separation of the particular cell type. Fluorochromes that find use include phycobiliproteins, e.g., phycoerythrin and allophycocyanins, fluorescein and Texas red. Frequently each antibody is labeled with a different fluorochrome, to permit independent sorting for each marker.

The initial population of cells are contacted with the affinity reagent(s) and incubated for a period of time sufficient to bind the available cell surface antigens. The incubation will usually be at least about 5 minutes and usually less than about 60 minutes. It is desirable to have a sufficient concentration of antibodies in the reaction mixture, such that the efficiency of the separation is not limited by lack of antibody. The appropriate concentration is determined by titration, but will typically be a dilution of antibody into the volume of the cell suspension that is about 1:50 (i.e., 1 part antibody to 50 parts reaction volume), about 1:100, about 1:150, about 1:200, about 1:250, about 1:500, about 1:1000, about 1:2000, or about 1:5000. The medium in which the cells are suspended will be any medium that maintains the viability of the cells. A preferred medium is phosphate buffered saline containing from 0.1 to 0.5% BSA or 1-4% goat serum. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, goat serum etc.

The cells in the contacted population that become labeled by the affinity reagent are selected for by any convenient affinity separation technique, e.g., as described above or as known in the art. Following separation, the separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for a cell type of interest, e.g., hematopoietic cells, are achieved in this manner. The cells will be about 70%, about 75%, about 80%, about 85% about 90% or more of the cell composition, about 95% or more of the enriched cell composition, and will preferably be about 95% or more of the enriched cell composition. In other words, the composition will be a substantially pure composition of cells of interest.

The cells to be transplanted into the humanized SIRPα-IL-15 non-human animals, e.g., mice, be they a heterogeneous population of cells or an enriched population of cells, may be transplanted immediately. Alternatively, the cells may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells. Additionally or alternatively, the cells may be cultured in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

The cells may be genetically modified prior to transplanting to the SIRPα-IL-15 non-human animals, e.g., mice, e.g., to provide a selectable or traceable marker, to induce a genetic defect in the cells (e.g., for disease modeling), to repair a genetic defect or ectopically express a gene in the cells (e.g., to determine if such modifications will impact the course of a disease), etc. Cells may be genetically modified by transfection or transduction with a suitable vector, homologous recombination, or other appropriate technique, so that they express a gene of interest, or with an antisense mRNA, siRNA or ribozymes to block expression of an undesired gene. Various techniques are known in the art for the introduction of nucleic acids into target cells. To prove that one has genetically modified the cells, various techniques may be employed. The genome of the cells may be restricted and used with or without amplification. The polymerase chain reaction; gel electrophoresis; restriction analysis; Southern, Northern, and Western blots; sequencing; or the like, may all be employed. General methods in molecular and cellular biochemistry for these and other purposes disclosed in this application can be found in such standard textbooks as Molecular Cloning: A Laboratory Manual, 3rd Ed. (Sambrook et al., Cold Spring Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

The cells may be transplanted in the humanized SIRPα-IL-15 non-human animals, e.g., mice, by any convenient method, including, for example, intra-hepatic injection, tail-vein injection, retro-orbital injection, and the like. Typically, about $0.5 \times 10^5$-$2 \times 10^6$ pluripotent or progenitor cells are transplanted, e.g. about $1 \times 10^5$-$1 \times 10^6$ cells, or about $2 \times 10^5$-$5 \times 10^5$ cells. In some instances, the non-human animal, e.g., mouse, is sublethally irradiated prior to transplanting the human cells. In other words, the non-human animal, e.g., mouse, is exposed to a sublethal dose of radiation, e.g., as well-known in the art. The engrafted humanized SIRPα-IL-15 non-human animals, e.g., mice, are then maintained under laboratory animal husbandry conditions for at least 1 week, e.g., 1 week or more, or two weeks or more, sometimes 4 weeks or more, and in some instances 6 weeks or more, such as 10 weeks or more or 15 weeks or more, to allow sufficient reconstitution of the immune system with the engrafted cells.

The humanized SIRPα-IL-15 non-human animals, e.g., mice, and humanized SIRPα-IL-15 non-human animals, e.g., mice, engrafted with human hematopoietic cells, e.g., engrafted $Rag2^{-/-}IL2rg^{Y/-}$ hSIRPα hIL-15 mice, and optionally other genetic modifications are useful in many applications. For example, these non-human animals, e.g., mice, provide a useful system for modeling human immune diseases and human pathogens. For example, the subject non-human animals, e.g., mice, are useful for modeling, for example, human T cell and/or natural killer (NK) cell development and function; human pathogen infection of specific tissues and/or cells, e.g., human pathogen infection of the gut or lungs, and/or human pathogen infection of or response to human T cells and/or NK cells. Such non-human animals also find use in in vivo screens for agents that inhibit infection by a pathogen, e.g., a pathogen that affects (e.g., by infecting) a specific tissue or cell type, e.g., a human pathogen of the gut or lungs, e.g., a human pathogen that activates, induces and/or targets T cells and/or NK cells; in in vivo screens for agents that modulate the development and/or function of human T cells and/or NK cells, e.g. in a healthy or a diseased state; in in vivo screens for agents that are toxic to human T cells and/or NK cells; in in vivo screens for agents that prevent against, mitigate, or reverse the toxic effects of toxic agents on human T cells and/or NK cells; in in vivo screens of candidate T cell-inducing vaccines; and in in vivo and in vitro screens for agents that inhibit tumor growth and/or infection by activating NK cell-mediated antibody dependent cellular cytotoxicity (ADCC) processes.

The present disclosure provides unexpected results demonstrating that humanized SIRPα-IL-15 non-human animals, e.g., mice, engrafted with human hematopoietic cells, e.g., engrafted $Rag2^{-/-}IL2rg^{Y/-}$ hSIRPα hIL-15 mice, develop tissue-resident lymphocytes, e.g., intraepithelial lymphocytes, in the gut and lung. Accordingly, the present disclosure provides previously unavailable animal models which enable the monitoring and testing of such tissue-resident lymphocytes. Such animal models are particularly useful in modeling the immune response of tissue-resident lymphocytes, e.g., T cells and NK cells, to human pathogens which affect (e.g., by infecting) the gut and/or lung and for screening therapeutics and vaccines which target such pathogens and/or induce or improve a tissue-resident lymphocyte response. In addition, the presence of these tissue-resident lymphocytes also allows for modeling of human immune cell driven autoimmune diseases that affect the gastrointestinal tract such as celiac diseases and IBD.

Accordingly, in some embodiments, the present disclosure provides an in vivo model, including a genetically modified non-human animal including a nucleic acid sequence incorporated into the genome of the genetically modified non-human animal, which sequence encodes a human SIRPα protein and is operably linked to a SIRPα gene promoter. The genetically modified non-human animal also includes a nucleic acid sequence incorporated into the genome of the genetically modified non-human animal, which sequence encodes a human IL-15 protein and is operably linked to an IL-15 gene promoter. Finally, the genetically modified non-human animal includes an engraftment of human hematopoietic cells, wherein the genetically modified non-human animal (i) expresses the human SIRPα protein and the human IL-15 protein, and (ii) includes human tissue-resident lymphocytes, e.g., intraepithelial lymphocytes (IELs), in the gut of the genetically modified non-human. In some such embodiments, the genetically modified non-human animal is infected with a human pathogen, e.g., a human pathogen which affects (e.g., by infecting) the gut.

Human pathogens which can affect (e.g., by infecting) the gut include, but are not limited to, *Campylobacter jejuni, Clostridium difficile, Enterococcus faecalis, Enterococcus faecium, Escherichia coli*, Human Rotavirus, *Listeria monocytogenes*, Norwalk Virus, *Salmonella enterica, Shigella flexneri, Shigella sonnei, Shigella dysenteriae, Yersinia pestis, Yersinia enterocolitica*, and *Helicobacter pylori*.

In other embodiments, the present disclosure provides an in vivo model, including a genetically modified non-human animal including a nucleic acid sequence incorporated into the genome of the genetically modified non-human animal, which sequence encodes a human SIRPα protein and is operably linked to a SIRPα gene promoter. The genetically modified non-human animal also includes a nucleic acid sequence incorporated into the genome of the genetically modified non-human animal, which sequence encodes a human IL-15 protein and is operably linked to an IL-15 gene promoter. Finally, the genetically modified non-human animal includes an engraftment of human hematopoietic cells, wherein the genetically modified non-human animal (i) expresses the human SIRPα protein and the human IL-15 protein, and (ii) includes human tissue-resident lymphocytes, e.g., intraepithelial lymphocytes (IELs), in the lung of the genetically modified non-human. In some such embodiments, the genetically modified non-human animal is infected with a human pathogen, e.g., a human pathogen which affects (e.g., by infecting) the lung.

Human pathogens which can affect (e.g., by infecting) the lung include, but are not limited to, *Streptococcus pyogenes, Haemophilus influenza, Corynebacterium diphtheria*, SARS coronavirus, *Bordetella pertussis, Moraxella catarrhalis*, Influenza virus (A, B, C), Coronavirus, Adenovirus, Respiratory Syncytial Virus, Parainfluenza virus, Mumps virus, *Streptococcus pneumoniae, Staphylococcus aureus, Legionella pneumophila, Klebsiella pneumoniae, Pseudomonas aeruginosa, Mycoplasma pneumonia, Mycobacterium tuberculosis, Chlamydia Pneumoniae, Blastomyces dermatitidis, Cryptococcus neoformans*, and *Aspergillus fumigatus*.

New therapeutics, new vaccines, and new ways of testing efficacy of therapeutics and vaccines are needed. A non-human animal, e.g., mouse, which supports efficient human T and NK cell engraftment, for example, would be useful to identify new therapeutics and new vaccines, particularly for a human pathogen which infects human T cells and/or NK cells. New therapeutics and new vaccines could be tested in such a non-human animal, e.g., mouse, by, e.g., determining the amount of a human pathogen, e.g., a virus, in the non-human animal (in blood or a given tissue) in response to treatment with a putative anti-viral agent, or by inoculating the mouse with a putative vaccine followed by exposure to an infective administration of a human pathogen, e.g., HIV, and observing any change in infectivity due to inoculation by the putative vaccine as compared to a control not inoculated with the vaccine but infected with HIV.

Such non-human animal, e.g., mouse, models of pathogen infection are useful in research, e.g., to better understand the progression of human infection. Such mouse models of infection are also useful in drug discovery, e.g. to identify candidate agents that protect against or treat infection.

Engrafted genetically modified animals of the present disclosure find use in screening candidate agents to identify those that will treat infections by human pathogens, e.g., human pathogens that target human T and/or NK cells. The terms "treat", "treatment", "treating" and the like are used herein to generally include obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein include any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease.

The terms "individual," "subject," "host," and "patient," are used interchangeably herein and include any mammalian subject for whom diagnosis, treatment, or therapy is desired, particularly humans.

Humanized SIRPα-IL-15 non-human animals, e.g., mice, engrafted with human hematopoietic cells provide a useful system for screening candidate agents for other desired activities in vivo as well, for example, for agents that are able to modulate (i.e., promote or suppress) development and/or activity of human T cells and NK cells, e.g., in a healthy or a diseased state, e.g., to identify novel therapeutics and/or develop a better understanding of the molecular basis of the development and function of the immune system; for agents that are toxic to T cells and/or NK cells and progenitors thereof; and for agents that prevent against, mitigate, or reverse the toxic effects of toxic agents on T cells, NK cells, and progenitors thereof; for antibodies or antigen-binding proteins that mediate NK cell dependent ADCC processes, etc. As yet another example, the genetically modified mice described herein provide a useful system for predicting the responsiveness of an individual to a disease therapy, e.g., by providing an in vivo platform for screening the responsiveness of an individual's immune system to an agent, e.g., a therapeutic agent, to predict the responsiveness of an individual to that agent.

In screening assays for biologically active agents, humanized SIRPα-IL-15 non-human animals, e.g., mice, e.g., engrafted Rag2$^{-/-}$IL2rg$^{Y/-}$ hSIRPα hIL-15 mice, that have been engrafted with human hematopoietic cells and in some instances, infected with human pathogens, or cells to be engrafted into a humanized SIRPα-IL-15 non-human animal, e.g., mouse, are contacted with a candidate agent of interest and the effect of the candidate agent is assessed by monitoring one or more output parameters. These output parameters may be reflective of the viability of the cells, e.g. the total number of hematopoietic cells or the number of cells of a particular hematopoietic cell type, or of the apoptotic state of the cells, e.g. the amount of DNA fragmentation, the amount of cell blebbing, the amount of phosphatidylserine on the cell surface, and the like by methods that are well known in the art. Alternatively or additionally, the output parameters may be reflective of the differentiation capacity of the cells, e.g. the proportions of differentiated cells and differentiated cell types, e.g., T cells and/or NK cells. Alternatively or additionally, the output parameters may be reflective of the function of the cells, e.g. the cytokines and chemokines produced by the cells, the ability of the cells to home to and extravasate to a site of challenge, the ability of the cells to modulate, i.e. promote or suppress, the activity of other cells in vitro or in vivo, etc. Other output parameters may be reflective of the extent of pathogen infection in the animal, e.g., the titer of pathogen in the non-human animal, e.g., mouse, etc.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Candidate agents of interest for screening include known and unknown compounds that encompass numerous chemical classes, primarily organic molecules, which may include organometallic molecules, inorganic molecules, genetic sequences, vaccines, antibiotics or other agents suspected of having antibiotic properties, peptides, polypeptides, antibodies, antigen-binding proteins, agents that have been approved pharmaceutical for use in a human, etc. An important aspect of the invention is to evaluate candidate drugs, including toxicity testing; and the like.

Candidate agents include organic molecules including functional groups necessary for structural interactions, particularly hydrogen bonding, and typically include at least an amine, carbonyl, hydroxyl or carboxyl group, frequently at least two of the functional chemical groups. The candidate agents often include cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992).

Candidate agents of interest for screening also include nucleic acids, for example, nucleic acids that encode siRNA, shRNA, antisense molecules, or miRNA, or nucleic acids that encode polypeptides. Many vectors useful for transferring nucleic acids into target cells are available. The vectors may be maintained episomally, e.g., as plasmids, minicircle DNAs, virus-derived vectors such cytomegalovirus, adenovirus, etc., or they may be integrated into the target cell genome, through homologous recombination or random integration, e.g., retrovirus derived vectors such as MMLV, HIV-1, ALV, etc. Vectors may be provided directly to the subject cells. In other words, the pluripotent cells are contacted with vectors including the nucleic acid of interest such that the vectors are taken up by the cells.

Methods for contacting cells, e.g., cells in culture or cells in a non-human animal, e.g., mouse, with nucleic acid vectors, such as electroporation, calcium chloride transfection, and lipofection, are well known in the art. Alternatively, the nucleic acid of interest may be provided to the cells via a virus. In other words, the cells are contacted with viral particles including the nucleic acid of interest. Retroviruses, for example, lentiviruses, are particularly suitable to the method of the invention. Commonly used retroviral vectors are "defective", i.e., unable to produce viral proteins required for productive infection. Rather, replication of the vector requires growth in a packaging cell line. To generate viral particles including nucleic acids of interest, the retroviral nucleic acids including the nucleic acid are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g., MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) Mol. Cell. Biol. 5:431-437); PA317 (Miller et al. (1986) Mol. Cell. Biol. 6:2895-2902); GRIP (Danos et al. (1988) PNAS 85:6460-6464). Retroviruses packaged with xenotropic envelope protein, e.g., AKR env, are capable of infecting most mammalian cell types, except murine cells. The appropriate packaging cell line may be used to ensure that the cells of interest—in some instance, the engrafted cells, in some instance, the cells of the host, i.e., the humanized SIRPα-IL-15—are targeted by the packaged viral particles.

Vectors used for providing nucleic acid of interest to the subject cells will typically include suitable promoters for driving the expression, that is, transcriptional activation, of the nucleic acid of interest. This may include ubiquitously acting promoters, for example, the CMV-b-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing reprogramming factors to the subject cells may include genes that must later be removed, e.g., using a recombinase system such as Cre/Lox, or the cells that express them destroyed, e.g., by including genes that allow selective toxicity such as herpesvirus TK, bcl-xs, etc.

Candidate agents of interest for screening also include polypeptides. Such polypeptides may optionally be fused to a polypeptide domain that increases solubility of the product. The domain may be linked to the polypeptide through a defined protease cleavage site, e.g., a TEV sequence, which is cleaved by TEV protease. The linker may also include one or more flexible sequences, e.g., from 1 to 10 glycine residues. In some embodiments, the cleavage of the fusion protein is performed in a buffer that maintains solubility of the product, e.g., in the presence of from 0.5 to 2 M urea, in the presence of polypeptides and/or polynucleotides that increase solubility, and the like. Domains of interest include endosomolytic domains, e.g., influenza HA domain; and other polypeptides that aid in production, e.g., IF2 domain, GST domain, GRPE domain, and the like. Additionally or alternatively, such polypeptides may be formulated for improved stability. For example, the peptides may be PEGylated, where the polyethyleneoxy group provides for enhanced lifetime in the blood stream. The polypeptide may be fused to another polypeptide to provide for added functionality, e.g., to increase the in vivo stability. Generally such fusion partners are a stable plasma protein, which may, for example, extend the in vivo plasma half-life of the polypeptide when present as a fusion, in particular wherein such a stable plasma protein is an immunoglobulin constant domain. In most cases where the stable plasma protein is normally found in a multimeric form, e.g., immunoglobulins or lipoproteins, in which the same or different polypeptide chains are normally disulfide and/or noncovalently bound to form an assembled multichain polypeptide, the fusions herein containing the polypeptide also will be produced and employed as a multimer having substantially the same structure as the stable plasma protein precursor. These multimers will be homogeneous with respect to the polypeptide agent they include, or they may contain more than one polypeptide agent.

The candidate polypeptide agent may be produced from eukaryotic cells, or may be produced by prokaryotic cells. It may be further processed by unfolding, e.g., heat denaturation, DTT reduction, etc., and may be further refolded, using methods known in the art. Modifications of interest that do not alter primary sequence include chemical derivatization of polypeptides, e.g., acylation, acetylation, carboxylation, amidation, etc. Also included are modifications of glycosylation, e.g., those made by modifying the glycosylation patterns of a polypeptide during its synthesis and processing or in further processing steps; e.g., by exposing the polypeptide to enzymes which affect glycosylation, such as mammalian glycosylating or deglycosylating enzymes. Also embraced are sequences that have phosphorylated amino acid residues, e.g., phosphotyrosine, phosphoserine, or phosphothreonine. The polypeptides may have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. D-amino acids may be substituted for some or all of the amino acid residues.

The candidate polypeptide agent may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like. Alternatively, the candidate polypeptide agent may be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will include at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In some cases, the candidate polypeptide agents to be screened are antibodies or antigen-binding proteins. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be either polyclonal antibodies or monoclonal antibodies. Antibodies are typically provided in the media in which the cells are cultured. Besides antibodies, antigen-binding proteins encompass polypeptides that are also designed to bind an antigen of interest and elicit a response, e.g., an immunological reaction. Antigen-binding fragments known in the art (including, e.g., Fab, Fab' F(ab')2, Fabc, and scFv) are also encompassed by the term "antigen-binding protein". The terms "antibody" and "antigen-binding protein" also include one or more immunoglobulin chains or fragments that may be chemically conjugated to, or expressed as, fusion proteins with other proteins, single chain antibodies, and bispecific antibodies.

Candidate agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by administering the agent to at least one and usually a plurality of samples, sometimes in conjunction with samples lacking the agent. The change in parameters in response to the agent is measured, and the result evaluated by comparison to reference cultures, e.g. in the presence and absence of the agent, obtained with other agents, etc. In instances in which a screen is being performed to identify candidate agents that will prevent, mitigate or reverse the effects of a toxic agent, the screen is typically performed in the presence of the toxic agent, where the toxic agent is added at the time most appropriate to the results to be determined. For example, in cases in which the protective/preventative ability of the candidate agent is tested, the candidate agent may be added before the toxic agent, simultaneously with the candidate agent, or subsequent to treatment with the candidate agent. As another example, in cases in which the ability of the candidate agent to reverse the effects of a toxic agent is tested, the candidate agent may be added subsequent to treatment with the candidate agent. As mentioned above, in some instances, the sample is the humanized SIRPα-IL-15 non-human animal, e.g., mouse, that has been engrafted with cells, i.e., a candidate agent is provided to the humanized SIRPα-IL-15 non-human animal, e.g., mouse, that has been engrafted with cells. In some instances, the sample is the cells to be engrafted, i.e., the candidate agent is provided to cells prior to transplantation.

If the candidate agent is to be administered directly to the non-human animal, e.g., mouse, the agent may be administered by any of a number of well-known methods in the art for the administration of peptides, small molecules and nucleic acids. For example, the agent may be administered orally, mucosally, topically, intradermally, or by injection, e.g. intraperitoneal, subcutaneous, intramuscular, intravenous, or intracranial injection, and the like. The agent may be administered in a buffer, or it may be incorporated into any of a variety of formulations, e.g. by combination with appropriate pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. The agent may be systemic after administration or may be localized by the use of regional administration, intramural administration, or use of an implant that acts to retain the active dose at the site of implantation. The active agent may be formulated for immediate activity or it may be formulated for sustained release. For some conditions, particularly central nervous system conditions, it may be necessary to formulate agents to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as bradykinin. A BBB disrupting agent can be co-administered with the agent when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of agents behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the agent has been reversibly affixed (see e.g. US Application Nos. 20080081064 and 20090196903, incorporated herein by reference).

If the agent(s) are provided to cells prior to transplantation, the agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e., at zero concentration or below the level of detection of the agent or at or below the concentration of agent that does not give a detectable change in the phenotype.

An analysis of the response of cells in a humanized SIRPα-IL-15 non-human animal, e.g., mouse, to the candidate agent may be performed at any time following treatment with the agent. For example, the cells may be analyzed 1, 2, or 3 days, sometimes 4, 5, or 6 days, sometimes 8, 9, or 10 days, sometimes 14 days, sometimes 21 days, sometimes 28 days, sometimes 1 month or more after contact with the candidate agent, e.g., 2 months, 4 months, 6 months or more. In some embodiments, the analysis includes analysis at multiple time points. The selection of the time point(s) for analysis will be based upon the type of analysis to be performed, as will be readily understood by the ordinarily skilled artisan.

The analysis may include measuring any of the parameters described herein or known in the art for measuring cell viability, cell proliferation, cell identity, cell morphology, and cell function, particularly as they may pertain to cells of the immune system, e.g., T cells and/or NK cells. For example, flow cytometry may be used to determine the total number of hematopoietic cells or the number of cells of a particular hematopoietic cell type. Histochemistry or immunohistochemistry may be performed to determine the apoptotic state of the cells, e.g. terminal deoxynucleotidyl transferase dUTP nick end labeling (TUNEL) to measure DNA fragmentation, or immunohistochemistry to detect Annexin V binding to phosphatidylserine on the cell surface. Flow cytometry may also be employed to assess the proportions of differentiated cells and differentiated cell types, e.g., to determine the ability of hematopoietic cells to differentiate in the presence of agent. ELISAs, Westerns, and Northern blots may be performed to determine the levels of cytokines, chemokines, immunoglobulins, etc., expressed in the engrafted humanized SIRPα-IL-15 non-human animal, e.g., mouse, e.g. to assess the function of the engrafted cells. In vivo assays to test the function of immune cells, as well as assays relevant to particular diseases or disorders of interest such as diabetes, autoimmune disease, graft v. host disease, AMD, etc., may also be performed. See, e.g. Current Protocols in Immunology (Richard Coico, ed. John Wiley & Sons, Inc. 2012) and Immunology Methods Manual (I.

Lefkovits ed., Academic Press 1997), the disclosures of which are incorporated herein by reference.

So, for example, a method is provided for determining the effect of an agent on a human pathogen, including exposing an engrafted humanized SIRPα-IL-15 non-human animal, e.g., mouse, e.g., an engrafted Rag2$^{-/-}$IL2rg$^{Y/-}$ hSIRPα hIL-15 mouse, to an effective amount of a human pathogen, the effective amount of a pathogen being the amount of pathogen required to produce an infection in the mouse; allowing the pathogen to infect the mouse; measuring a parameter of the infection over time in the presence of the agent; and comparing that measurement to the measurement from an engrafted humanized SIRPα-IL-15 non-human animal, e.g., mouse, not exposed to the agent. The agent is determined to be an antipathogenic agent if it reduces the amount of the agent in blood or a tissue of the non-human animal, e.g., mouse, by at least half following a single administration or two or more administrations of the agent over a selected period of time.

As another example, a method is provided for determining if a pathogen isolate or strain of interest is drug resistant, e.g. multidrug resistant. In these methods, an engrafted humanized SIRPα-IL-15 non-human animal, e.g., mouse, e.g., an engrafted Rag2$^{-/-}$IL2rg$^{Y/-}$ hSIRPα hIL-15 mouse, is exposed to an effective amount of a human pathogen isolate or strain of interest, the effective amount of the pathogen being the amount of pathogen required to produce an infection in the non-human animal, e.g., mouse; the pathogen is allowed to infect the non-human animal; a parameter of the infection, e.g., the titer of the isolate or strain of interest in the blood or tissue of the non-human animal, the ability of the isolate or strain of interest to maintain an infection in the non-human animal, or the ability of the isolate or strain of interest to reproduce in the non-human animal at a point in time after administration of the drug, is measured in the presence of the drug; and that measurement is compared to the measurement from an engrafted humanized SIRPα-IL-15 non-human animal, e.g., mouse infected with pathogen not exposed to the agent. Examples of drugs of interest include amoxicillin, ampicillin, cefotaxime, ceftriaxone, ceftazidime, chloramphenicol, ciprofloxacin, cotrimoxazole, ertapenem, imipenem, fluoroquinolones (e.g., ciprofloxacin, gatifloxacin, ofloxacin), streptomycin, sulfadiazine, sulfamethoxazole, tetracycline, and a combination thereof. In a specific embodiment, the administration of the drug or combination of drugs is at least a week, 10 days, two week, three weeks, or four weeks after an infection-producing exposure to the isolate or strain of interest.

In addition, humanized SIRPα-IL-15 non-human animals (e.g., mice) and humanized SIRPα-IL-15 non-human animals (e.g., mice) engrafted with human hematopoietic cells, e.g., engrafted Rag2$^{-/-}$IL2rg$^{Y/-}$ hSIRPα hIL-15 mice, and optionally having other genetic modifications are useful in studying antibody-dependent cellular cytoxicity (ADCC) mediated by NK cells (e.g., human NK cells). Such animals are also useful models for testing the ability of therapeutic drug candidates, e.g., antigen-binding proteins or antibodies, designed to target various cells (e.g., tumors or infected cells) or infectious agents, to activate NK cell pathways involved in killing such cells or infectious agents.

It is widely known that one of the mechanisms underlying monoclonal antibody therapy is its activation of NK cells through binding the NK cell Fc receptor CD16 (Fc gamma receptor IIIA). Attempts have been made to increase affinity of various known monoclonal candidates (e.g., rituximab) for Fcgamma RIIIA in order to improve ADCC (e.g., Bowles et al. Blood 2006; 108:2648-2654; Garff-Tavernier et al. Leukemia 2011; 25:202-209). As demonstrated herein, the humanized SIRPα-IL-15 engrafted non-human animals produce human NK cells that are capable of mediating ADCC; and thus, these animals present a useful in vivo model for studying ADCC mechanisms and screening various therapeutic candidates.

Thus, engrafted humanized SIRPα-IL-15 non-human animals and cells, e.g., human NK cells, isolated therefrom, may be used in screening methods designed to identify agents which improve antibody dependent cellular cytotoxicity (ADCC) activity of an engrafted cell type in the humanized non-human animal or cells, e.g., human NK cells. For example, a suitable method may include administering an agent to an engrafted humanized SIRPα-IL-15 non-human animal and determining the effect of the agent on an antibody dependent cellular cytotoxicity (ADCC) activity of an engrafted cell type in vivo in the humanized non-human animal. In one embodiment, such effect results in improved tumor killing, e.g., of a transplanted tumor, e.g., of a human tumor. In another embodiment, such effect results in improved killing of infected cell, e.g., virally-infected cell or bacterially-infected cell. In yet another embodiment, such effect results in improved killing of a bacteria, a fungus or a parasite. In various embodiments the agent is an antibody or an antigen-binding protein. In some embodiments, the antibody or the antigen-binding protein is designed to target an antigen expressed on a human tumor cell. In some embodiments, the antibody or the antigen-binding protein is designed to target an antigen expressed on a virally-infected cell or a bacterially-infected cell. In some embodiments, the antibody or the antigen-binding protein is designed to target a bacterial, a fungal, or a parasitic antigen. In some embodiments, an in vitro method is provided wherein human cells, e.g., human NK cells, are isolated from an engrafted humanized SIRPα-IL-15 non-human animal and contacted in vitro with an agent such as an antibody or an antigen-binding protein, and a target cell (e.g., tumor cell) to determine the efficacy of the agent in mediating killing of the target cell. The effect of the agent on the cytolytic activity of the human cells, e.g., human NK cells, can then be determined.

Other examples of uses for the subject mice are provided elsewhere herein. Additional applications of the genetically modified and engrafted mice described in this disclosure will be apparent to those skilled in the art upon reading this disclosure.

Methods of Making the Subject Genetically Modified Non-Human Animals

In some aspects of the invention, methods are provided for making the subject non-human animals of the present disclosure. In practicing the subject methods, a non-human animal is generated which includes a nucleic acid sequence incorporated into the genome of the genetically modified non-human animal, which sequence encodes a human SIRPα protein and is operably linked to a SIRPα gene promoter, e.g., an endogenous non-human SIRPα gene promoter; and a nucleic acid sequence incorporated into the genome of the genetically modified non-human animal, which sequence encodes a human IL-15 protein and is operably linked to an IL-15 gene promoter, e.g., an endogenous non-human IL-15 gene promoter.

The generation of a non-human animal including a nucleic acid sequence that encodes a human SIRPα protein and is operably linked to a SIRPα promoter, and/or a nucleic acid sequence that encodes a human IL-15 protein and is operably linked to an IL-15 gene promoter, may be accomplished using any convenient method for the making genetically modified animals, e.g. as known in the art or as described herein.

For example, a nucleic acid encoding a human SIRPα protein or a human IL-15 protein may be incorporated into a recombinant vector in a form suitable for insertion into the genome of the host cell and expression of the human protein in a non-human host cell. In various embodiments, the recombinant vector includes the one or more regulatory sequences operatively linked to the nucleic acid encoding the human protein in a manner which allows for transcription of the nucleic acid into mRNA and translation of the mRNA into the human protein, as described above. It will be understood that the design of the vector may depend on such factors as the choice of the host cell to be transfected and/or the amount of human protein to be expressed.

Any of various methods may then be used to introduce the human nucleic acid sequence into an animal cell to produce a genetically modified animal that expresses the human gene. Such techniques are well-known in the art and include, but are not limited to, pronuclear microinjection, transformation of embryonic stem cells, homologous recombination and knock-in techniques. Methods for generating genetically modified animals that can be used include, but are not limited to, those described in Sundberg and Ichiki (2006, Genetically Engineered Mice Handbook, CRC Press), Hofker and van Deursen (2002, Genetically modified Mouse Methods and Protocols, Humana Press), Joyner (2000, Gene Targeting: A Practical Approach, Oxford University Press), Turksen (2002, Embryonic stem cells: Methods and Protocols in Methods Mol Biol., Humana Press), Meyer et al. (2010, Proc. Nat. Acad. Sci. USA 107:15022-15026), and Gibson (2004, A Primer of Genome Science $2^{nd}$ ed. Sunderland, Mass.: Sinauer), U.S. Pat. No. 6,586,251, Rathinam et al. (2011, Blood 118:3119-28), Willinger et al., (2011, Proc Natl Acad Sci USA, 108:2390-2395), Rongvaux et al., (2011, Proc Natl Acad Sci USA, 108:2378-83) and Valenzuela et al. (2003, Nat Biot 21:652-659).

For example, the subject genetically modified animals can be created by introducing the nucleic acid encoding the human protein into an oocyte, e.g., by microinjection, and allowing the oocyte to develop in a female foster animal. In preferred embodiments, the nucleic acid is injected into fertilized oocytes. Fertilized oocytes can be collected from super ovulated females the day after mating and injected with the expression construct. The injected oocytes are either cultured overnight or transferred directly into oviducts of 0.5-day p.c. pseudopregnant females. Methods for superovulation, harvesting of oocytes, expression construct injection and embryo transfer are known in the art and described in Manipulating the Mouse Embryo (2002, A Laboratory Manual, 3rd edition, Cold Spring Harbor Laboratory Press). Offspring can be evaluated for the presence of the introduced nucleic acid by DNA analysis (e.g., PCR, Southern blot, DNA sequencing, etc.) or by protein analysis (e.g., ELISA, Western blot, etc.).

As another example, the construct including the nucleic acid sequence encoding the human protein may be transfected into stem cells (e.g., ES cells or iPS cells) using well-known methods, such as electroporation, calcium-phosphate precipitation, lipofection, etc. The cells can be evaluated for the presence of the introduced nucleic acid by DNA analysis (e.g., PCR, Southern blot, DNA sequencing, etc.) or by protein analysis (e.g., ELISA, Western blot, etc.). Cells determined to have incorporated the expression construct can then be introduced into preimplantation embryos. For a detailed description of methods known in the art useful for the compositions and methods of the invention, see Nagy et al., (2002, Manipulating the Mouse Embryo: A Laboratory Manual, 3rd edition, Cold Spring Harbor Laboratory Press), Nagy et al. (1990, Development 110:815-821), U.S. Pat. Nos. 7,576,259, 7,659,442, 7,294,754, and Kraus et al. (2010, Genesis 48:394-399).

In a preferred embodiment, a method of generating a genetically modified animal described herein utilizes a targeting construct made using VELOCIGENE® technology, introducing the construct into ES cells, and introducing targeted ES cell clones into a mouse embryo using VELOCIMOUSE® technology, as described in the Examples.

Genetically modified founder animals can be bred to additional animals carrying the genetic modification. For example, humanized SIRPα non-human animals can be bred with humanized IL-15 non-human animals of the same species to produce the hSIRPα-hIL-15 non-human animals described herein. Genetically modified animals carrying a nucleic acid encoding the human protein(s) of the present disclosure can further be bred to knockout animals, e.g., a non-human animal that is deficient for one or more proteins, e.g. does not express one or more of its genes, e.g. a Rag2-deficient animal and/or an Il2rg-deficient animal.

As discussed above, in some embodiments, the subject genetically modified non-human animal is an immunodeficient animal. Genetically modified non-human animals that are immunodeficient and include one or more human proteins, e.g. hSIRPα and/or hIL-15, may be generated using any convenient method for the generation of genetically modified animals, e.g. as known in the art or as described herein. For example, the generation of the genetically modified immunodeficient animal can be achieved by introduction of the nucleic acid encoding the human protein into an oocyte or stem cells including a mutant SCID gene allele that, when homozygous, will result in immunodeficiency as described in greater detail above and in the working examples herein. Mice are then generated with the modified oocyte or ES cells using, e.g. methods described herein and known in the art, and mated to produce the immunodeficient mice including the desired genetic modification. As another example, genetically modified non-human animals can be generated in an immunocompetent background, and crossed to an animal including a mutant gene allele that, when hemizygous or homozygous, will result in immunodeficiency, and the progeny mated to create an immunodeficient animal expressing the at least one human protein of interest.

In some embodiments, the genetically modified non-human animal is treated so as to eliminate endogenous hematopoietic cells that may exist in the genetically modified non-human animal. In one embodiment, the treatment includes irradiating the genetically modified non-human animal. In a specific embodiment, newborn genetically modified mouse pups are irradiated sublethally. In a specific embodiment, newborn pups are irradiated 2×200 cGy with a four hour interval.

Various embodiments of the invention provide genetically modified animals that include a human nucleic acid in substantially all of their cells, as well as genetically modified animals that include a human nucleic acid in some, but not all their cells. In some instances, e.g. targeted recombination, one copy of the human nucleic acid will be integrated into the genome of the genetically modified animals. In other instances, e.g. random integration, multiple copies, adjacent or distant to one another, of the human nucleic acid may be integrated into the genome of the genetically modified animals.

Thus, in some embodiments, the subject genetically modified non-human animal may be an immunodeficient animal including a genome that includes a nucleic acid encoding a human polypeptide operably linked to the corresponding non-human animal promoter, wherein the animal expresses the encoded human polypeptide. In other words, the subject genetically modified immunodeficient non-human animal includes a genome that includes a nucleic acid encoding at least one human polypeptide, wherein the nucleic acid is operably linked to the corresponding non-human promoter and a polyadenylation signal, and wherein the animal expresses the encoded human polypeptide.

Reagents, Devices and Kits

Also provided are reagents, devices and kits thereof for practicing one or more of the above-described methods. The subject reagents, devices and kits thereof may vary greatly.

In some embodiments, the reagents or kits will include one or more agents for use in the methods described herein. For example, the kit may include a humanized SIRPα-IL-15 non-human animal, e.g., mouse, e.g., a Rag2$^{-/-}$IL2rg$^{Y/-}$ hSIRPα hIL-15 mouse. The kit may include reagents for breeding humanized SIRPα-IL-15 non-human animals, e.g., mice, e.g., primers and, in some instances, reagents for genotyping humanized SIRPα-IL-15 non-human animals, e.g., mice. The kit may include human hematopoietic cells or an enriched population of human hematopoietic progenitor cells for transplantation into the humanized SIRPα-IL-15 non-human animal, e.g., mouse, or reagents for preparing a population of hematopoietic cells or an enriched population of hematopoietic cells from a human for transplantation into a humanized SIRPα-IL-15 non-human animal, e.g., mouse. Other reagents may include reagents for determining the viability and/or function of hematopoietic cells or differentiated immune cells (e.g., T cells and/or NK cells), e.g. in the presence/absence of candidate agent, e.g., one or more antibodies that are specific for markers expressed by different types of hematopoietic cells or differentiated immune cells (e.g., T cells and/or NK cells), or reagents for detecting particular cytokines, chemokine, etc. Other reagents may include culture media, culture supplements, matrix compositions, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a remote site. Any convenient means may be present in the kits.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-167 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A genetically modified non-human animal, comprising:
   a nucleic acid sequence incorporated into the genome of the genetically modified non-human animal, which sequence encodes a human SIRPα protein and is operably linked to a SIRPα gene promoter; and
   a nucleic acid sequence incorporated into the genome of the genetically modified non-human animal, which sequence encodes a human IL-15 protein and is operably linked to an IL-15 gene promoter, wherein the genetically modified non-human animal expresses the human SIRPα protein and the human IL-15 protein.
2. The genetically modified non-human animal according to 1, wherein the SIRPα gene promoter is an endogenous non-human SIRPα gene promoter.
3. The genetically modified non-human animal according to 2, wherein the SIRPα gene promoter is the endogenous non-human SIRPα gene promoter at the non-human animal SIRPα gene locus.
4. The genetically modified non-human animal according to 3, comprising a null mutation in the non-human SIRPα gene at the non-human animal SIRPα gene locus.
5. The genetically modified non-human animal according to 4, wherein the genetically modified non-human animal is a mouse and the null mutation is a deletion of at least mouse SIRPα exons 2-4.
6. The genetically modified non-human animal according to 4, wherein the genetically modified non-human animal is heterozygous for the allele comprising the nucleic acid sequence that encodes the human SIRPα protein.
7. The genetically modified non-human animal according to 4, wherein the genetically modified non-human animal is homozygous for the allele comprising the nucleic acid sequence that encodes the human SIRPα protein.
8. The genetically modified non-human animal according to any one of 1-7, wherein the nucleic acid sequence that encodes the human SIRPα protein comprises human SIRPα genomic coding and non-coding sequence.
9. The genetically modified non-human animal according to any one of 1-8, wherein the human SIRPα protein is a functional fragment of a full length human SIRPα protein.
10. The genetically modified non-human animal according to 9, wherein the functional fragment comprises an extracellular domain of human SIRPα.
11. The genetically modified non-human animal according to 10, wherein the extracellular domain comprises amino acids 28-362 of SEQ ID NO:12.
12. The genetically modified non-human animal according to any one of 1-11, wherein the IL-15 gene promoter is an endogenous non-human IL-15 gene promoter.
13. The genetically modified non-human animal according to 12, wherein the IL-15 gene promoter is the endogenous non-human IL-15 gene promoter at the non-human animal IL-15 gene locus.
14. The genetically modified non-human animal according to 13, comprising a null mutation in the non-human IL-15 gene at the non-human animal IL-15 gene locus.

15. The genetically modified non-human animal according to 14, wherein the genetically modified non-human animal is a mouse and the null mutation is a deletion of at least mouse IL-15 exons 5-8.

16. The genetically modified non-human animal according to 14, wherein the genetically modified non-human animal is heterozygous for the allele comprising the nucleic acid sequence that encodes the human IL-15 protein.

17. The genetically modified non-human animal according to 14, wherein the genetically modified non-human animal is homozygous for the allele comprising the nucleic acid sequence that encodes the human IL-15 protein.

18. The genetically modified non-human animal according to any one of 1-17, wherein the nucleic acid sequence that encodes the human IL-15 protein comprises human IL-15 genomic coding and non-coding sequence.

19. The genetically modified non-human animal according to any one of 1-18, wherein the human IL-15 protein is a functional fragment of a full length human IL-15 protein.

20. The genetically modified non-human animal according to any one of 1-19, wherein the genetically modified non-human animal is immunodeficient.

21. The genetically modified non-human animal according to 20, wherein the genetically modified non-human animal comprises a Rag2 gene knock-out.

22. The genetically modified non-human animal according to 20 or 21, wherein the genetically modified non-human animal comprises an IL2rg gene knock-out.

23. The genetically modified non-human animal according to any one of 1-22, wherein the non-human animal is a mammal.

24. The genetically modified non-human animal according to 23, wherein the mammal is a rodent.

25. The genetically modified non-human animal according to 24, wherein the rodent is a mouse.

26. The genetically modified non-human animal according to any one of 1-25, wherein the genetically modified non-human animal comprises an engraftment of human hematopoietic cells.

27. The genetically modified non-human animal according to 26, wherein the genetically modified non-human animal comprises an infection with a human pathogen.

28. The genetically modified non-human animal according to 27, wherein the human pathogen activates, induces and/or targets T cells and/or natural killer (NK) cells.

29. The genetically modified non-human animal according to 27, wherein the human pathogen is a pathogen that infects human intestine.

30. The genetically modified non-human animal according to 29, wherein the human pathogen is a human rotavirus.

31. The genetically modified non-human animal according to 27, wherein the pathogen infects human lung.

32. The genetically modified non-human animal according to 31, wherein the human pathogen is an influenza virus.

33. An animal engraftment model, comprising a genetically modified non-human animal comprising:
a nucleic acid sequence incorporated into the genome of the genetically modified non-human animal, which sequence encodes a human SIRPα protein and is operably linked to a SIRPα gene promoter;
a nucleic acid sequence incorporated into the genome of the genetically modified non-human animal, which sequence encodes a human IL-15 protein and is operably linked to an IL-15 gene promoter; and
an engraftment of human hematopoietic cells, wherein the genetically modified non-human animal (i) expresses the human SIRPα protein and the human IL-15 protein, and (ii) comprises human intraepithelial lymphocytes (IELs) in the small intestine and Peyer's patches of the genetically modified non-human animal.

34. The model according to 33, wherein the genetically modified non-human animal comprises an infection with a human pathogen.

35. The model according to 34, wherein the human pathogen is an intestinal pathogen.

36. The model according to 35, wherein the intestinal pathogen is selected from: *Campylobacter jejuni, Clostridium difficile, Enterococcus faecalis, Enterococcus faecium, Escherichia coli*, Human Rotavirus, *Listeria monocytogenes*, Norwalk Virus, *Salmonella enterica, Shigella flexneri, Shigella sonnei, Shigella dysenteriae, Yersinia pestis, Yersinia enterocolitica*, and *Helicobacter pylori*.

37. The model according to any one of 33-36, wherein the SIRPα gene promoter is an endogenous non-human SIRPα gene promoter.

38. The model according to 37, wherein the SIRPα gene promoter is the endogenous non-human SIRPα gene promoter at the non-human animal SIRPα gene locus.

39. The model according to 38, wherein the genetically modified non-human animal comprises a null mutation in the non-human SIRPα gene at the non-human animal SIRPα gene locus.

40. The model according to 39, wherein the genetically modified non-human animal is a mouse and the null mutation is a deletion of at least mouse SIRPα exons 2-4.

41. The model according to 39, wherein the genetically modified non-human animal is heterozygous for the allele comprising the nucleic acid sequence that encodes the human SIRPα protein.

42. The model according to 39, wherein the genetically modified non-human animal is homozygous for the allele comprising the nucleic acid sequence that encodes the human SIRPα protein.

43. The model according to any one of 33-42, wherein the nucleic acid sequence that encodes the human SIRPα protein comprises human SIRPα genomic coding and non-coding sequence.

44. The model according to any one of 33-43, wherein the human SIRPα protein is a functional fragment of a full length human SIRPα protein.

45. The model according to 44, wherein the functional fragment comprises an extracellular domain of human SIRPα.

46. The model according to 45, wherein the extracellular domain comprises amino acids 28-362 of SEQ ID NO:12.

47. The model according to any one of 33-46, wherein the IL-15 gene promoter is an endogenous non-human IL-15 gene promoter.

48. The model according to 47, wherein the IL-15 gene promoter is the endogenous non-human IL-15 gene promoter at the non-human animal IL-15 gene locus.

49. The model according to 48, wherein the genetically modified non-human animal comprises a null mutation in the non-human IL-15 gene at the non-human animal IL-15 gene locus.
50. The model according to 49, wherein the genetically modified non-human animal is a mouse and the null mutation is a deletion of at least mouse IL-15 exons 5-8.
51. The model according to 48, wherein the genetically modified non-human animal is heterozygous for the allele comprising the nucleic acid sequence that encodes the human IL-15 protein.
52. The model according to 48, wherein the genetically modified non-human animal is homozygous for the allele comprising the nucleic acid sequence that encodes the human IL-15 protein.
53. The model according to any one of 33-52, wherein the nucleic acid sequence that encodes the human IL-15 protein comprises human IL-15 genomic coding and non-coding sequence.
54. The model according to any one of 33-53, wherein the human IL-15 protein is a functional fragment of a full length human IL-15 protein.
55. The model according to any one of 33-54, wherein the genetically modified non-human animal is immunodeficient.
56. The model according to 55, wherein the genetically modified non-human animal comprises a Rag2 gene knock-out.
57. The model according to 55 or 56, wherein the genetically modified non-human animal comprises an IL2rg gene knock-out.
58. The model according to any one of 33-57, wherein the non-human animal is a mammal.
59. The model according to 58, wherein the mammal is a rodent.
60. The model according to 59, wherein the rodent is a mouse.
61. An animal engraftment model, comprising a genetically modified non-human animal comprising:
    a nucleic acid sequence incorporated into the genome of the genetically modified non-human animal, which sequence encodes a human SIRPα protein and is operably linked to a SIRPα gene promoter;
    a nucleic acid sequence incorporated into the genome of the genetically modified non-human animal, which sequence encodes a human IL-15 protein and is operably linked to an IL-15 gene promoter; and
    an engraftment of human hematopoietic cells, wherein the genetically modified non-human animal (i) expresses the human SIRPα protein and the human IL-15 protein, and (ii) comprises human intraepithelial lymphocytes (IELs) in the lung of the genetically modified non-human animal.
62. The model according to 61, wherein the genetically modified non-human animal comprises an infection with a human pathogen.
63. The model according to 62, wherein the human pathogen is lung pathogen.
64. The model according to 63, wherein the lung pathogen is selected from: *Streptococcus pyogenes, Haemophilus influenza, Corynebacterium diphtheria*, SARS coronavirus, *Bordetella pertussis, Moraxella catarrhalis*, Influenza virus (A, B, C), Coronavirus, Adenovirus, Respiratory Syncytial Virus, Parainfluenza virus, Mumps virus, *Streptococcus pneumoniae, Staphylococcus aureus, Legionella pneumophila, Klebsiella pneumoniae, Pseudomonas aeruginosa, Mycoplasma pneumonia, Mycobacterium tuberculosis, Chlamydia Pneumoniae, Blastomyces dermatitidis, Cryptococcus neoformans,* and *Aspergillus fumigatus*
65. The model according to any one of 61-64, wherein the SIRPα gene promoter is an endogenous non-human SIRPα gene promoter.
66. The model according to 65, wherein the SIRPα gene promoter is the endogenous non-human SIRPα gene promoter at the non-human animal SIRPα gene locus.
67. The model according to 66, wherein the genetically modified non-human animal comprises a null mutation in the non-human SIRPα gene at the non-human animal SIRPα gene locus.
68. The model according to 67, wherein the genetically modified non-human animal is a mouse and the null mutation is a deletion of at least mouse SIRPα exons 2-4.
69. The model according to 67, wherein the genetically modified non-human animal is heterozygous for the allele comprising the nucleic acid sequence that encodes the human SIRPα protein.
70. The model according to 67, wherein the genetically modified non-human animal is homozygous for the allele comprising the nucleic acid sequence that encodes the human SIRPα protein.
71. The model according to any one of 61-70, wherein the nucleic acid sequence that encodes the human SIRPα protein comprises human SIRPα genomic coding and non-coding sequence.
72. The model according to any one of 61-71, wherein the human SIRPα protein is a functional fragment of a full length human SIRPα protein.
73. The model according to 72, wherein the functional fragment comprises an extracellular domain of human SIRPα.
74. The model according to 73, wherein the extracellular domain comprises amino acids 28-362 of SEQ ID NO:12.
75. The model according to any one of 61-74, wherein the IL-15 gene promoter is an endogenous non-human IL-15 gene promoter.
76. The model according to 75, wherein the IL-15 gene promoter is the endogenous non-human IL-15 gene promoter at the non-human animal IL-15 gene locus.
77. The model according to 76, wherein the genetically modified non-human animal comprises a null mutation in the non-human IL-15 gene at the non-human animal IL-15 gene locus.
78. The model according to 77, wherein the genetically modified non-human animal is a mouse and the null mutation is a deletion of at least mouse IL-15 exons 5-8.
79. The model according to 77, wherein the genetically modified non-human animal is heterozygous for the allele comprising the nucleic acid sequence that encodes the human IL-15 protein.
80. The model according to 77, wherein the genetically modified non-human animal is homozygous for the allele comprising the nucleic acid sequence that encodes the human IL-15 protein.
81. The model according to any one of 61-80, wherein the nucleic acid sequence that encodes the human IL-15 protein comprises human IL-15 genomic coding and non-coding sequence.

82. The model according to any one of 61-80, wherein the human IL-15 protein is a functional fragment of a full length human IL-15 protein.

83. The model according to any one of 61-82, wherein the genetically modified non-human animal is immunodeficient.

84. The model according to 83, wherein the genetically modified non-human animal comprises a Rag2 gene knock-out.

85. The model according to 83 or 84, wherein the genetically modified non-human animal comprises an IL2rg gene knock-out.

86. The model according to any one of 61-85, wherein the non-human animal is a mammal.

87. The model according to 86, wherein the mammal is a rodent.

88. The model according to 87, wherein the rodent is a mouse.

89. A method of determining the efficacy of a candidate T-cell inducing vaccine, the method comprising:
    administering a candidate T-cell inducing vaccine to a genetically modified non-human animal, wherein the genetically modified non-human animal is deficient for an endogenous immune system and comprises:
        (i) a nucleic acid sequence incorporated into the genome of the genetically modified non-human animal, which sequence encodes a human SIRPα protein and is operably linked to a SIRPα gene promoter,
        (ii) a nucleic acid sequence incorporated into the genome of the genetically modified non-human animal, which sequence encodes a human IL-15 protein and is operably linked to an IL-15 gene promoter, and
        (iii) an engraftment of human hematopoietic cells, wherein the genetically modified non-human animal expresses the human SIRPα protein and the human IL-15 protein;
    challenging the genetically modified non-human animal with a human pathogen; and
    determining whether the candidate T-cell inducing vaccine induces a T cell mediated immune response in the genetically modified non-human animal.

90. The method according to 89, wherein the SIRPα gene promoter is an endogenous non-human SIRPα gene promoter.

91. The method according to 90, wherein the SIRPα gene promoter is the endogenous non-human SIRPα gene promoter at the non-human animal SIRPα gene locus.

92. The method according to 91, wherein the genetically modified non-human animal comprises a null mutation in the non-human SIRPα gene at the non-human animal SIRPα gene locus.

93. The method according to 92, wherein the genetically modified non-human animal is a mouse and the null mutation is a deletion of at least mouse SIRPα exons 2-4.

94. The method according to 92, wherein the genetically modified non-human animal is heterozygous for the allele comprising the nucleic acid sequence that encodes the human SIRPα protein.

95. The method according to 92, wherein the genetically modified non-human animal is homozygous for the allele comprising the nucleic acid sequence that encodes the human SIRPα protein.

96. The method according to any one of 89-95, wherein the nucleic acid sequence that encodes the human SIRPα protein comprises human SIRPα genomic coding and non-coding sequence.

97. The method according to any one of 89-96, wherein the human SIRPα protein is a functional fragment of a full length human SIRPα protein.

98. The method according to 97, wherein the functional fragment comprises an extracellular domain of human SIRPα.

99. The method according to 98, wherein the extracellular domain comprises amino acids 28-362 of SEQ ID NO:12.

100. The method according to any one of 89-99, wherein the IL-15 gene promoter is an endogenous non-human IL-15 gene promoter.

101. The method according to 100, wherein the IL-15 gene promoter is the endogenous non-human IL-15 gene promoter at the non-human animal IL-15 gene locus.

102. The method according to 101, wherein the genetically modified non-human animal comprises a null mutation in the non-human IL-15 gene at the non-human animal IL-15 gene locus.

103. The method according to 102, wherein the genetically modified non-human animal is a mouse and the null mutation is a deletion of at least mouse IL-15 exons 5-8.

104. The method according to 101, wherein the genetically modified non-human animal is heterozygous for the allele comprising the nucleic acid sequence that encodes the human IL-15 protein.

105. The method according to 101, wherein the genetically modified non-human animal is homozygous for the allele comprising the nucleic acid sequence that encodes the human IL-15 protein.

106. The method according to any one of 89-105, wherein the nucleic acid sequence that encodes the human IL-15 protein comprises human IL-15 genomic coding and non-coding sequence.

107. The method according to any one of 89-106, wherein the human IL-15 protein is a functional fragment of a full length human IL-15 protein.

108. The method according to any one of 89-107, wherein the genetically modified non-human animal comprises a Rag2 gene knock-out.

109. The method according to any one of 89-108, wherein the genetically modified non-human animal comprises an IL2rg gene knock-out.

110. The method according to any one of 89-109, wherein the genetically modified non-human animal is a mammal.

111. The method according to 110, wherein the mammal is a rodent.

112. The method according to 111, wherein the rodent is a mouse.

113. A method of identifying an agent that inhibits an infection by a pathogen that activates, induces and/or targets human T cells and/or natural killer (NK) cells, the method comprising:
    administering an agent to an genetically modified non-human animal, wherein the genetically modified non-human animal is deficient for an endogenous immune system and comprises:
        (i) a nucleic acid sequence incorporated into the genome of the genetically modified non-human animal, which sequence encodes a human SIRPα protein and is operably linked to a SIRPα gene promoter, (ii) a nucleic acid sequence incorporated into the genome of the genetically modified non-human animal, which sequence encodes a human IL-15 protein and is operably linked to an IL-15 gene promoter, (iii) an engraftment of human hematopoietic cells, and (iv) an infection by a pathogen that activates, induces and/or targets human T cells and/or natural killer cells, wherein the genetically modified non-human animal expresses the human SIRPα protein and the human IL-15 protein; and determining whether the agent reduces the amount of the pathogen in the pathogen-infected non-human animal.

114. The method according to 113, wherein the SIRPα gene promoter is an endogenous non-human SIRPα gene promoter.

115. The method according to 114, wherein the SIRPα gene promoter is the endogenous non-human SIRPα gene promoter at the non-human animal SIRPα gene locus.

116. The method according to 115, wherein the genetically modified non-human animal comprises a null mutation in the non-human SIRPα gene at the non-human animal SIRPα gene locus.

117. The method according to 116, wherein the genetically modified non-human animal is a mouse and the null mutation is a deletion of at least mouse SIRPα exons 2-4.

118. The method according to 116, wherein the genetically modified non-human animal is heterozygous for the allele comprising the nucleic acid sequence that encodes the human SIRPα protein.

119. The method according to 116, wherein the genetically modified non-human animal is homozygous for the allele comprising the nucleic acid sequence that encodes the human SIRPα protein.

120. The method according to any one of 113-119, wherein the nucleic acid sequence that encodes the human SIRPα protein comprises human SIRPα genomic coding and non-coding sequence.

121. The method according to any one of 113-120, wherein the human SIRPα protein is a functional fragment of a full length human SIRPα protein.

122. The method according to 121, wherein the functional fragment comprises an extracellular domain of human SIRPα.

123. The method according to 122, wherein the extracellular domain comprises amino acids 28-362 of SEQ ID NO:12.

124. The method according to any one of 113-123, wherein the IL-15 gene promoter is an endogenous non-human IL-15 gene promoter.

125. The method according to 124, wherein the IL-15 gene promoter is the endogenous non-human IL-15 gene promoter at the non-human animal IL-15 gene locus.

126. The method according to 125, the genetically modified non-human animal comprises a null mutation in the non-human IL-15 gene at the non-human animal IL-15 gene locus.

127. The method according to 126, wherein the genetically modified non-human animal is a mouse and the null mutation is a deletion of at least mouse IL-15 exons 5-8.

128. The method according to 125, wherein the genetically modified non-human animal is heterozygous for the allele comprising the nucleic acid sequence that encodes the human IL-15 protein.

129. The method according to 125, wherein the genetically modified non-human animal is homozygous for the allele comprising the nucleic acid sequence that encodes the human IL-15 protein.

130. The method according to any one of 113-129, wherein the nucleic acid sequence that encodes the human IL-15 protein comprises human IL-15 genomic coding and non-coding sequence.

131. The method according to any one of 113-130, wherein the human IL-15 protein is a functional fragment of a full length human IL-15 protein.

132. The method according to any one of 113-131, wherein the genetically modified non-human animal comprises a Rag2 gene knock-out.

133. The method according to any one of 113-132, wherein the genetically modified non-human animal comprises an IL2rg gene knock-out.

134. The method according to any one of 113-133, wherein the genetically modified non-human animal is a mammal.

135. The method according to 134, wherein the mammal is a rodent.

136. The method according to 135, wherein the rodent is a mouse.

137. A method of making a non-human animal expressing a human IL-15 protein and a human SIRPα protein, comprising:

introducing into a genome of a first non-human animal a nucleic acid sequence encoding a human SIRPα protein, wherein the sequence encoding the human SIRPα protein is operably linked to an SIRPα gene promoter sequence;

introducing into a genome of a second non-human animal a nucleic acid sequence encoding a human IL-15 protein, wherein the sequence encoding the human IL-15 protein is operably linked to a IL-15 promoter sequence; and making a third non-human animal that comprises the nucleic acid sequence encoding the human IL-15 protein and the nucleic acid sequence encoding the human SIRPα protein, wherein the third non-human animal expresses the human IL-15 protein and the human SIRPα protein.

138. The method of 137, wherein the steps of introducing comprise generating a non-human animal from a pluripotent stem cell comprising the nucleic acid encoding human IL-15 or human SIRPα.

139. The method of 137 or 138, wherein the first animal is a different animal than the second animal, and the step of making the third animal comprises breeding the first and the second animal.

140. The method of 137, wherein the first animal and the second animal are the same, the step of introducing into the genome of the first animal comprises contacting a first pluripotent stem cell with the nucleic acid sequence encoding the human SIRPα protein to obtain a second pluripotent stem cell, the step of introducing into the genome of the second animal comprises contacting the second pluripotent stem cell with the nucleic acid sequence encoding the human SIRPα protein to obtain a third pluripotent step cell, and the third non-human animal is made from the third pluripotent stem cell.

141. The method according to any one of 137-140, wherein the pluripotent stem cell is an ES cell or an iPS cell.

142. The method according to any one of 137-140, wherein the pluripotent stem cell is deficient for Rag2.

143. The method according to any one of 137-142, wherein the pluripotent stem cell is deficient for IL2rg.

144. The method according to any one of 137-143, wherein the third non-human animal is deficient in one or both of Rag2 and IL2rg.

145. The method according to any one of 137-144, wherein the IL-15 promoter sequence is a human IL-15 promoter sequence.

146. The method according to any one of 137-144, wherein the IL-15 promoter sequence is an endogenous non-human animal IL-15 promoter sequence.

147. The method according to any one of 137-144, wherein the integration results in a replacement of the non-human IL-15 gene at the non-human IL-15 gene locus.

148. The method according to any one of 137-147, wherein the nucleic acid sequence that encodes the human IL-15 protein comprises human IL-15 genomic coding and non-coding sequence.

149. A method of engrafting a genetically modified non-human animal expressing a human IL-15 protein, comprising:
  transplanting a population of cells comprising human hematopoietic cells into the genetically modified non-human animal made by a method according to any one of 137-148.

150. The method according to 149, wherein the transplanting comprises tail-vein injection, fetal liver injection, or retro-orbital injection.

151. The method according to 149 or 150, wherein the genetically modified non-human animal is sublethally irradiated prior to transplantation.

152. The method according to any one of 149-151, wherein the human hematopoietic cells are CD34+ cells.

153. The method according to any one of 149-151, wherein the human hematopoietic cells are from fetal liver, adult bone marrow, or umbilical cord blood.

154. A method of determining the efficacy of a candidate therapeutic antibody or antigen-binding protein in killing a target cell, the method comprising:
  administering the candidate therapeutic antibody or antigen-binding protein to a genetically modified non-human animal, wherein the genetically modified non-human animal is deficient for an endogenous immune system and comprises:
    (i) a nucleic acid sequence incorporated into the genome of the genetically modified non-human animal, which sequence encodes a human SIRPα protein and is operably linked to a SIRPα gene promoter,
    (ii) a nucleic acid sequence incorporated into the genome of the genetically modified non-human animal, which sequence encodes a human IL-15 protein and is operably linked to an IL-15 gene promoter, and
    (iii) an engraftment of human hematopoietic cells, wherein the genetically modified non-human animal expresses the human SIRPα protein and the human IL-15 protein; and
  determining whether the candidate therapeutic antibody or antigen-binding protein modulates an NK cell mediated antibody-dependent cellular cytotoxicity against the target cell in the genetically modified non-human animal.

155. A method of determining the efficacy of a candidate therapeutic antibody or antigen-binding protein in killing a target cell, the method comprising:
  isolating an NK cell from a genetically modified non-human animal, wherein the genetically modified non-human animal is deficient for an endogenous immune system and comprises:
    (i) a nucleic acid sequence incorporated into the genome of the genetically modified non-human animal, which sequence encodes a human SIRPα protein and is operably linked to a SIRPα gene promoter,
    (ii) a nucleic acid sequence incorporated into the genome of the genetically modified non-human animal, which sequence encodes a human IL-15 protein and is operably linked to an IL-15 gene promoter, and
    (iii) an engraftment of human hematopoietic cells, wherein the genetically modified non-human animal expresses the human SIRPα protein and the human IL-15 protein;
  contacting the isolated NK cell with the candidate therapeutic antibody or antigen-binding protein and the target cell; and
  determining the antibody- or the antigen-binding protein-dependent cytolytic activity of the isolated NK cell against the target cell.

156. A method of screening a candidate therapeutic antibody or antigen-binding protein for improved efficacy in killing a target cell comprising:
  administering the candidate therapeutic antibody or antigen-binding protein to a genetically modified non-human animal, wherein the genetically modified non-human animal is deficient for an endogenous immune system and comprises:
    (i) a nucleic acid sequence incorporated into the genome of the genetically modified non-human animal, which sequence encodes a human SIRPα protein and is operably linked to a SIRPα gene promoter,
    (ii) a nucleic acid sequence incorporated into the genome of the genetically modified non-human animal, which sequence encodes a human IL-15 protein and is operably linked to an IL-15 gene promoter, and
    (iii) an engraftment of human hematopoietic cells, wherein the genetically modified non-human animal expresses the human SIRPα protein and the human IL-15 protein; and
  determining whether the candidate therapeutic antibody or antigen-binding protein displays improved efficacy in killing the target cell in the genetically modified non-human animal.

157. The method of any one of 154-156, wherein the target cell is selected from the group consisting of a tumor cell, a virally-infected cell, a bacterially-infected cell, a bacterial cell, a fungal cell, and a parasitic cell.

158. A method of determining the efficacy a candidate therapeutic antibody or antigen-binding protein in NK-cell mediated killing of a target cell, comprising:
  administering the candidate therapeutic antibody or antigen-binding protein to a genetically modified non-human animal, wherein the genetically modified non-human animal is deficient for an endogenous immune system and comprises:
  (i) a nucleic acid sequence incorporated into the genome of the genetically modified non-human animal, which sequence encodes a human SIRPα protein and is operably linked to a SIRPα gene promoter,
  (ii) a nucleic acid sequence incorporated into the genome of the genetically modified non-human animal, which sequence encodes a human IL-15 protein and is operably linked to an IL-15 gene promoter, and
  (iii) an engraftment of human hematopoietic cells, wherein the genetically modified non-human animal expresses the human SIRPα protein and the human IL-15 protein; and determining whether the candidate therapeutic antibody or antigen-binding protein modulates (e.g., activates) NK cell antibody-dependent cellular cytotoxicity against the target cell in the genetically modified non-human animal.

159. The method of 158, wherein the target cell is selected from the group consisting of a tumor cell, a virally-infected cell, a bacterially-infected cell, a bacterial cell, a fungal cell, and a parasitic cell.

160. The method of claim 159, wherein the target cell is a tumor cell.

161. The method of claim 160, wherein the tumor cell is a B-cell lymphoma cell.

162. A model of NK cell mediated antibody-dependent cellular cytotoxicity,
  comprising a genetically modified non-human animal, wherein the genetically modified non-human animal is deficient for an endogenous immune system and comprises:
    a nucleic acid sequence incorporated into the genome of the genetically modified non-human animal, which sequence encodes a human SIRPα protein and is operably linked to a SIRPα gene promoter;
    a nucleic acid sequence incorporated into the genome of the genetically modified non-human animal, which sequence encodes a human IL-15 protein and is operably linked to an IL-15 gene promoter; and
    an engraftment of human hematopoietic cells, wherein the genetically modified non-human animal (i) expresses the human SIRPα protein and the human IL-15 protein, (ii) comprises human lymphocytes, and (iii) comprises a target cell selected from the group consisting of a tumor cell, a virally-infected cell, a bacterially-infected cell, a bacterial cell, a fungal cell, and a parasitic cell.

163. The model of claim 162, wherein the target cell is a tumor cell.

164. The model of claim 163, wherein the tumor cell is a B-cell lymphoma cell.

165. The model of claim 163 or claim 164, wherein the model comprises an exogenous candidate therapeutic antibody or antigen-binding protein.

166. The model of any one of claims 162-165, wherein the genetically modified non-human animal comprises human intraepithelial lymphocytes (IELs) in the small intestine and Peyer's patches of the genetically modified non-human animal.

167. The model of any one of claims 162-166, wherein the genetically modified non-human animal comprises human intraepithelial lymphocytes (IELs) in the lung of the genetically modified non-human animal.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Generation of Humanized SIRPα (SRG) Knock-In Mice

A human SIRPα knock-in mouse was generated, which expresses the extracellular domain of human SIRPα operably linked to the mouse SIRPα promoter (see FIG. 1). Human SIRPα is known to exist in at least 10 allelic forms. In this particular example, human SIRPα variant 1 is employed for humanizing an endogenous SIRPα gene of a mouse.

Materials and Methods

The generation of knock-in mice encoding human SIRPα into the $Rag2^{-/-}$ $Il2rg^{Y/-}$ 129×Balb/c (N2) genetic background was performed using VELOCIGENE® technology as described in greater detail below. The mice were maintained under specific pathogen-free conditions and with continuous treatment of enrofloxacin in the drinking water (Baytril; 0.27 mg/mL).

[000258] A targeting vector for humanization of an extracellular region of a SIRP (e.g., SIRPα) gene was constructed using VELOCIGENE® technology (see, e.g., U.S. Pat. No. 6,586,251 and Valenzuela et al. (2003) High-throughput engineering of the mouse genome coupled with high-resolution expression analysis, *Nature Biotech.* 21(6):652-659). Briefly, mouse bacterial artificial chromosome (BAC) clone bMQ-261H14 was modified to delete the sequence containing exons 2 to 4 of an endogenous SIRPα gene and insert exons 2 to 4 of a human SIRPα gene using human BAC clone CTD-3035H21. The genomic DNA corresponding to exons 2 to 4 of an endogenous SIRPα gene (~8555 bp) was replaced in BAC clone bMQ-261H14 with a ~8581 bp DNA fragment containing exons 2 to 4 of a human SIRPα gene from BAC clone CTD-3035H21. Sequence analysis of the human SIRPα allele contained in BAC clone CTD-3035H21 revealed the allele to correspond to human variant 1. A neomycin cassette flanked by loxP sites was added to the end of the ~8581 bp human DNA fragment containing exons 2 to 4 of the human SIRPα gene (FIG. 1 (bottom)).

Upstream and downstream homology arms were obtained from mouse BAC DNA at positions 5' and 3' of exons 2 and 4, respectively, and added to the ~8581 bp human fragment-neomycin cassette to create the final targeting vector for humanization of an endogenous SIRPα gene, which contained from 5' to 3' a 5' homology arm containing 19 kb of mouse DNA 5' of exon 2 of the endogenous SIRPα gene, a ~8581 bp DNA fragment containing exons 2 to 4 of a human SIRPα gene, a neomycin cassette flanked by loxP sites, and a 3' homology arm containing 21 kb of mouse DNA 3' of exon 4 of an endogenous SIRPα gene. Targeted insertion of the targeting vector positioned the neomycin cassette in the fifth intron of a mouse SIRPα gene between exons 4 and 5. The targeting vector was linearized by digesting with SwaI and then used in homologous recombination in bacterial cells to achieve a targeted replacement of exons 2 to 4 in a mouse SIRPα gene with exons 2 to 4 of a human SIRPα gene (FIG. 1 (bottom)).

The targeted BAC DNA (described above) was used to electroporate Rag2$^{-/-}$ IL2rg$^{y/-}$ mouse ES cells to create modified ES cells including a replacement of exons 2 to 4 in an endogenous mouse SIRPα gene with a genomic fragment including exons 2 to 4 of a human SIRPα gene. Positive ES cells containing a genomic fragment including exons 2 to 4 of a human SIRPα gene were identified by quantitative PCR using TAQMAN™ probes (Lie and Petropoulos, 1998. *Curr. Opin. Biotechnology* 9:43-48). The nucleotide sequence across the upstream insertion point included the following, which indicates endogenous mouse sequence upstream of the insertion point (contained within the parentheses below) linked contiguously to a human SIRPα genomic sequence present at the insertion point:

```
                                         (SEQ ID NO: 1)
(AGCTCTCCTACCACTAGACTGCTGAGACCCGCTGCTCTGCTCAGGACTC

GATTTCCAGTACACAATCTCCCTCTTTGAAAAGTACCACACATCCTGGGG

T)GCTCTTGCATTTGTGTGACACTTTGCTAGCCAGGCTCAGTCCTGGGTT

CCAGGTGGGGACTCAAACACACTGGCACGAGTCTACATTGGATATTCTTG

GT.
```

The nucleotide sequence across the downstream insertion point at the 5' end of the neomycin cassette included the following, which indicates human SIRPα genomic sequence contiguous with cassette sequence downstream of the insertion point (contained within the parentheses below with loxP sequence italicized):

```
                                         (SEQ ID NO: 2)
GCTCCCCATTCCTCACTGGCCCAGCCCCTCTTCCCTACTCTTTCTAGCCC

CTGCCTCATCTCCCTGGCTGCCATTGGGAGCCTGCCCCACTGGAAGCCAG (TCGAGATAACTTCGTATAATGTATGCTATACGAAGTTATATGCATGGCC

TCCGCGCCGGGTTTTGGCGCCTCCCGCGGGCGCCCCCCTCCTCACGGCG

A).
```

The nucleotide sequence across the downstream insertion point at the 3' end of the neomycin cassette included the following, which indicates cassette sequence contiguous with mouse genomic sequence 3' of exon 4 of an endogenous SIRPα gene (contained within the parentheses below):

```
                                         (SEQ ID NO: 3)
CATTCTCAGTATTGTTTTGCCAAGTTCTAATTCCATCAGACCTCGACCTG

CAGCCCCTAGATAACTTCGTATAATGTATGCTATACGAAGTTATGCTAGC (TGTCTCATAGAGGCTGGCGATCTGGCTCAGGGACAGCCAGTACTGCAAA

GAGTATCCTTGTTCATACCTTCTCCTAGTGGCCATCTCCCTGGGACAGTC

A).
```

Positive ES cell clones were then used to implant female mice using the VELOCIMOUSE® method (see, e.g., U.S. Pat. No. 7,294,754 and Poueymirou et al. 2007, F0 generation mice that are essentially fully derived from the donor gene-targeted ES cells allowing immediate phenotypic analyses, Nature Biotech. 25(1):91-99) to generate a litter of pups containing an insertion of exons 2 to 4 of a human SIRPα gene into an endogenous SIRPα gene of a mouse.

Targeted ES cells described above were used as donor ES cells and introduced into an 8-cell stage mouse embryo by the VELOCIMOUSE® method (supra). Mice bearing the humanization of exons 2 to 4 of an endogenous SIRPα gene were identified by genotyping using a modification of allele assay (Valenzuela et al., supra) that detected the presence of the human SIRPα gene sequences.

Mice bearing the humanized SIRPα gene construct (i.e., containing human SIRPα exons 2 to 4 in a mouse SIRPα gene) can be bred to a Cre deletor mouse strain (see, e.g., International Patent Application Publication No. WO 2009/114400) in order to remove any loxed neomycin cassette introduced by the targeting vector that is not removed, e.g., at the ES cell stage or in the embryo. Optionally, the neomycin cassette is retained in the mice. To obtain homozygous Sirpα mice heterozygotes are bred.

Results

Mice including a nucleic acid encoding a humanized version of the mouse SIRPα gene as described above (SRG mice) exhibit physiological expression of a humanized SIRPα protein (data not shown). These mice also exhibit human immune cell engraftment in the spleen, peripheral lymph nodes (LN) and thymus comparable to NOD scid gamma (NSG) mice (data not shown).

Example 2: Generation of Humanized SRG IL-15$^{h/h}$ (SRG-15) Knock-In Mice

Figure 2:
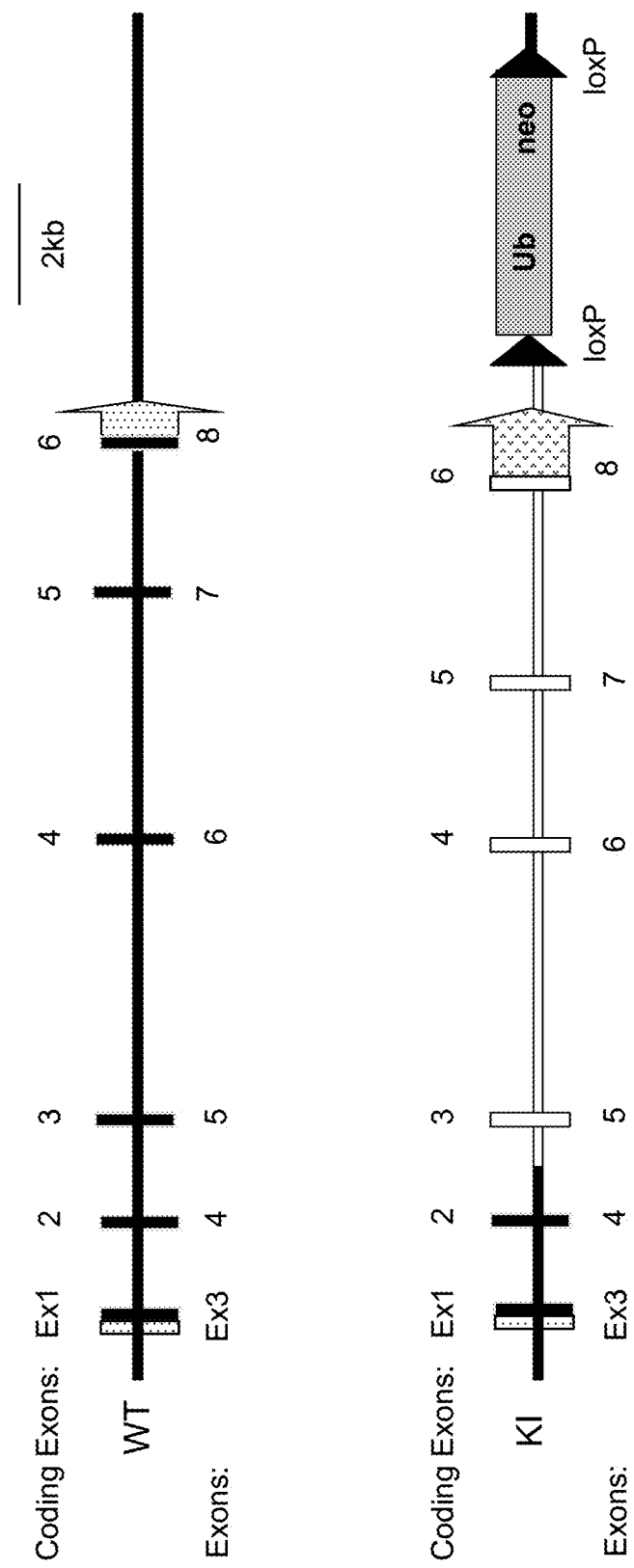
FIG. 2 provides a schematic representation illustrating targeted genomic replacement of the mouse IL-15 gene as achieved for mouse 2. Empty shapes represent inserted human sequence.

The cytokine IL-15 has been shown to be important for mouse NK cell development and memory CD9$^+$ T cell differentiation and maintenance. To study the effects of human IL-15 on the development, differentiation and maintenance of human immune cells in the context of an animal model, human IL-15 human SIRPα knock-in mice were generated as described in greater detail below. FIG. 2 shows a schematic representation of the IL-15 knock-in construct.

Materials and Methods

Mouse ES cells were modified to replace mouse IL-15 gene sequence with human IL-15 gene sequence at the endogenous mouse IL-15 locus, under control of mouse IL-15 regulatory elements, using VELOCIGENE® genetic engineering technology, to produce a humanized locus as shown in FIG. 2. Knock-in mice comprising human Il-15 were generated on Rag2$^{-/-}$ Il2rg$^{y/-}$ 129×Balb/c genetic background. FIG. 2 does not show upstream (with respect to direction of transcription of the IL-15 gene) the 5' untranslated exons of the mouse gene (exons 1 and 2); coding exon 1 (exon 3) of FIG. 2 shows a small untranslated region (unfilled) upstream of the coding exon. Except as discussed below for mouse 1, as shown in the humanization at the bottom of FIG. 2, mouse coding exons 1 and 2 (exons 3 and 4) were retained, whereas mouse coding exons 3 through 6 (exons 5-8) were replaced with human coding exons 3 through 6 (exons 5-8). At the downstream end, human coding exon 6 (exon 8) is followed by a stop codon and a human 3'-UTR, and further by human sequence found downstream of the human 3'UTR. For selection purposes, a selection cassette (foxed for removal by Cre) was included. The humanized locus of FIG. 2 expresses a mature IL-15 protein that is fully human.

Specifically, bacterial homologous recombination (BHR) was performed to construct a large targeting vector (LTVEC) containing sequences of the human IL-15 gene for targeting to the mouse IL-15 locus using standard BHR techniques (see, e.g., Valenzuela et al. (2003), supra) and gap repair BHR. Linear fragments were generated by ligating PCR-generated homology boxes to cloned cassettes followed by gel isolation of ligation products and electroporation into BHR-competent bacteria harboring the target bacterial artificial chromosome (BAC). Mouse BAC PRCI23-203P7 is used as the source of mouse sequence; human BAC RP11-103B12 is used as the source of human IL-15 gene sequence. Following a selection step, correctly recombined clones are identified by PCR across novel junctions, and by restriction analysis. An LTVEC containing homology arms and human IL-15 gene sequences was made.

The mouse IL-15 gene (mouse GeneID: 103014; RefSeq transcript: NM_008357.2; ensemble eID:16168) is modified by using genomic coordinates for deletion GRCM38: ch 8: 82331173-82343471 (minus strand); genomic coordinates for replacement GRCh37: ch4: 142642924-142655819 (plus strand). 12299 nucleotides of mouse sequence were replaced by 12896 nucleotides of human sequence. The replacement of mouse IL-15 sequence as described above is graphically presented in FIG. 2.

The LTVEC including the humanized IL-15 gene had about 13 kb of upstream mouse targeting arm flanked upstream with a MluI site, and a 27 kb downstream mouse targeting arm flanked downstream with an AscI site. The LTVEC was linearized with MluI and AscI for electroporation.

Following construction of the LTVEC, nucleotide sequence of the LTVEC across the mouse/human 5' junction, and human/mouse 3' junction is as shown in Table 1 below. SEQ ID NO:4 depicts the upstream (with respect to direction of transcription of the IL-15 gene) junction between mouse sequence and human sequence; the sequence shown begins with mouse sequence in uppercase, followed by an AsisI restriction site in lowercase, followed by human IL-15 nucleic acid sequence in uppercase. SEQ ID NO:5 indicates downstream human IL-15 coding and noncoding sequence in uppercase (human 3'UTR bolded italics), followed by an XhoI site in lowercase, followed by a lox site (uppercase, bolded italics), followed by sequence of the downstream neo selection cassette (uppercase), which extends 2.6 kb downstream (not shown). SEQ ID NO:6 is a nucleic acid sequence that depicts the junction between the downstream portion of the neo selection cassette (uppercase), with lox site (uppercase and bolded italics), followed by an NheI site (lowercase), which is followed by mouse sequence downstream of the humanization (uppercase); the selection cassette extends 2.6 kb further upstream.

TABLE 1

Junction Sequences of Humanized IL-15 Locus

| SEQ ID NO | Sequence |
|---|---|
| SEQ ID NO: 4 | ATCCATTTAGCCTTTCTCTGATCACTAAGTTGGACAGTTGGA CAGTCTTCCTCAAATTAGCTTAGACTATCAAAATTATACTGT ATTTTTGGTATTTCCAgcgatcgcTTCAGTTACAAGGCTGTTGAA TGCACAGAAGCAAGGATAACACTGATTTTTTCACTGGTCAG AATAAAAATTATTGATTGCTCTTTTGCTTATAGTATTC |
| SEQ ID NO: 5 | AATGTAACAGAATCTGGATGCAAAGAATGTGAGGAACTGG AGGAAAAAAATATTAAAGAATTTTTGCAGAGTTTTGTACAT ATTGTCCAAATGTTCATCAACACTTCTTGA*TTGCAATTGATT CTTTTTAAAGTGTTTCTGTTATTAACAAACATCACTCTGCTG CTTAGACATAACAAAACACTCGGCATTTCAAATGTGCTGTCA AAACAAGTTTTTCTGTCAAGAAGATGATCAGACCTTGGATCA GATGAACTCTTAGAAATGAAGGCAGAAAAATGTCATTGAGTA ATATAGTGACTATGAACTTCTCTCAGACTTACTTTACTCATTT TTTTAATTTATTATTGAAATTGTACATATTTGTGGAATAATGT AAAATGTTGAATAAAAATATGTACAAGTGTTGTTTTTTAAGTT GCACTGATATTTTACCTCTTATTGCAAAATAGCATTTGTTTAA GGGTGATAGTCAAATTATGTATTGGTGGGGCTGGGTACCAAT GCTGCAGGTCAACAGCTATGCTGGTAGGCTCCTGCCAGTGTG GAACCACTGACTACTGGCTCTCATTGACTTCCTTACTAAGCAT AGCAAACAGAGGAAGAATTTGTTATCAGTAAGAAAAAGAAGA ACTATATGTGAATCCTCTTCTTTATACTGTAATTTAGTTATTG ATGTATAAAGCAACTGTTATGAAATAAAGAAATTGCAATAACT GGCA*TATAATGTCCATCAGTAAATCTTGGTGGTGGTGGCAA TAATAAACTTCTACTGATAGGTAGAATGGTGTGCAAGCTTG TCCAATCACGGATTGCAGGCCACATGCGGCCCAGGACAACT TTGAATGTGGCCCAACACAAATTCATAAACTTTCATACATCT CGTTTTTAGCTCATCAGCTATCATTAGCGGTAGTGTATTTAA AGTGTGGCCCAAGACAATTCTTCTTATTCCAATGTGGCCCA GGGAAATCAAAAGATTGGATGCCCCTGGTATAGAAAACTA ATAGTGACAGTGTTCATATTTCATGCTTTCCCAAATACAGGT ATTTTATTTTCACATTCTTTTTGCCATGTTTATATAATAATAA AGAAAAACCCTGTTGATTTGTTGGAGCCATTGTTATCTGAC AGAAAATAATTGTTTATATTTTTTGCACTACACTGTCTAAAA TTAGCAAGCTCTCTTCTAATGGAACTGTAAGAAAGATGAAA TATTTTTGTTTTATTATAAATTTATTTCACCTTAATTCTGGTA ATACTCACTGAGTGACTGTGGGGTGGGAAATGATCTCTTAA GAATTTGATTTCTTTCTATTCCATAGTACAAACTCGTTCTCT GTTGAAACATTCTTCTATCACCCCAGTGCCCTATCCATGTAC ATGTGTTCTTATTGCTCTAGTCAAACGGTGCTTATAAATATC TTTCAGAAAGTTTAGGAGAAATCTGTATCCTATTTGACTTCC |

TABLE 1-continued

Junction Sequences of Humanized IL-15 Locus

| SEQ ID NO | Sequence |
|---|---|
| | AATAATCATGTATTGGCTGTCAGCTTCTTACCTACTCTCAGT<br>CCAGAGAAATAGTATTTGGCAGCCACTCTTTAAAGTTTATG<br>GGTTGTGGATTGTGGCGGTTGATTTATTTTTTTTATTTCAATT<br>GGGATAGAATTTTTTAATATACCTGTATTTTTGTTTTGTTTTA<br>TGTAGCTTTTCTATTAGGGAGAGTAGGAAAAGTGCACCATT<br>TTCTTCTCTAAATTTCCAGTCCAGTCTTTAGGGGAATGTTAG<br>TCTTCCTGAGATGGGGGAAGGAAAATCATAATGCCAGTCAC<br>TTTGCAAATAATATTTTATAGTGATAAATGGTTCATTTTGGT<br>TACATAGGCATACAAGTGGGCTTAAAACTTGGAATTTACCA<br>GGGCTCAAAATTAAAATTCTTACATTAGTTACTCGATATGG<br>ATCGCTTCAGTTGATCTTAGAAAACTCAAGGCATAGATCTG<br>CAACctcgag*ATAACTTCGTATAATGTATGTATACGAAGTTAT*A<br>TGCATGGCCTCCGCGCCGGGTTTTGGCGCCTCCCGCGGGCG<br>CCCCCCTCCTCACGGCG |
| SEQ ID NO: 6 | CATTCTCAGTATTGTTTTGCCAAGTTCTAATTCCATCAG<br>ACCTCGACCTGCAGCCCCTAG*ATAACTTCGTATAATGT*<br>*ATGCTATACGAAGTTAT*gctagcGTGATAGTCCTTCACG<br>GAAAGTACAAGAATACACAGAAAACTGCTGTTTACATT<br>AGTCTTTCACGTTTTTATTTTATTCTCACAAATTTTAATGCAA<br>TAC |

Mouse ES cells were electroporated with the LTVEC constructs, grown on selection medium, and used as donor ES cells to make humanized IL-15 mice including a replacement at the endogenous mouse IL-15 locus with human sequence as depicted in FIG. 2. Following electroporation of the ES cell, a loss of native allele assay (see, e.g., Valenzuela et al. (2003), supra) is performed to detect loss of endogenous IL-15 sequence due to the targeting.

Correctly targeted ES cells were further electroporated with a transient Cre-expressing vector to remove the Neo drug selection cassette.

Donor mouse ES cells including a humanized IL-15 locus were introduced into early stage mouse embryos by the VELOCIMOUSE® method (Poueymirou et al. (2007) F0 generation mice fully derived from gene-targeted embryonic stem cells allowing immediate phenotypic analyses, *Nat Biotechnol* 25:91-99). Heterozygous mice were obtained, and heterozygotes were bred to obtain homozygotes with respect to humanized IL-15. Two versions of humanized IL-15 mice were generated (referred to herein as mouse 1 and mouse 2). Following further analysis, the mouse 1 version was found to contain an exon duplication in its genome. In mouse 2 the endogenous mouse IL-15 locus was replaced with human sequence as depicted in FIG. 2.

Human IL-15mRNA levels were determined as follows. Reverse transcription (RT)-qPCR was performed using a 7500 Fast Real-Time PCR System (Applied Biosystems) and a SYBR® FAST universal qPCR kit (KAPA Biosystems). Sequence-specific oligonucleotide primers were designed using Primer3 software and synthesized by Sigma-Aldrich. The following primers were used: mouse Hprt forward: 5'-AGGGATTTGAATCACGTTTG-3'(SEQ ID NO:7), mouse Hprt reverse: 5'-TTTACTGGCAACAT-CAACAG-3'(SEQ ID NO:8); human Il15 forward: 5'-GCCCAGGGAAATCAAAAGAT-3'(SEQ ID NO:9), human Il15 reverse: 5'-TGGCTCCAACAAATCAACAG-3' (SEQ ID NO:10). Relative expression values were calculated using the comparative threshold cycle method and normalized to mouse Hprt.

SRG-15 mice are generated either by (1) breeding mice comprising human SIRPα replacement to mice comprising human IL-15 replacement, both on Rag2$^{-/-}$ Il2rg$^{Y/-}$ background, or by (2) introducing a large targeting vector comprising human IL-15 into an ES cell harboring human SIRPα replacement on Rag2$^{-/-}$ Il2rg$^{Y/-}$ background (described in Example 1) and generating mice from ES cells harboring both human IL-15 and SIRPα gene replacements as well as Rag2$^{-/-}$ Il2rg$^{Y/-}$ using the VELOCIMOUSE® method. Heterozygous mice are bred to homozygosity.

Results

Figure 3A:
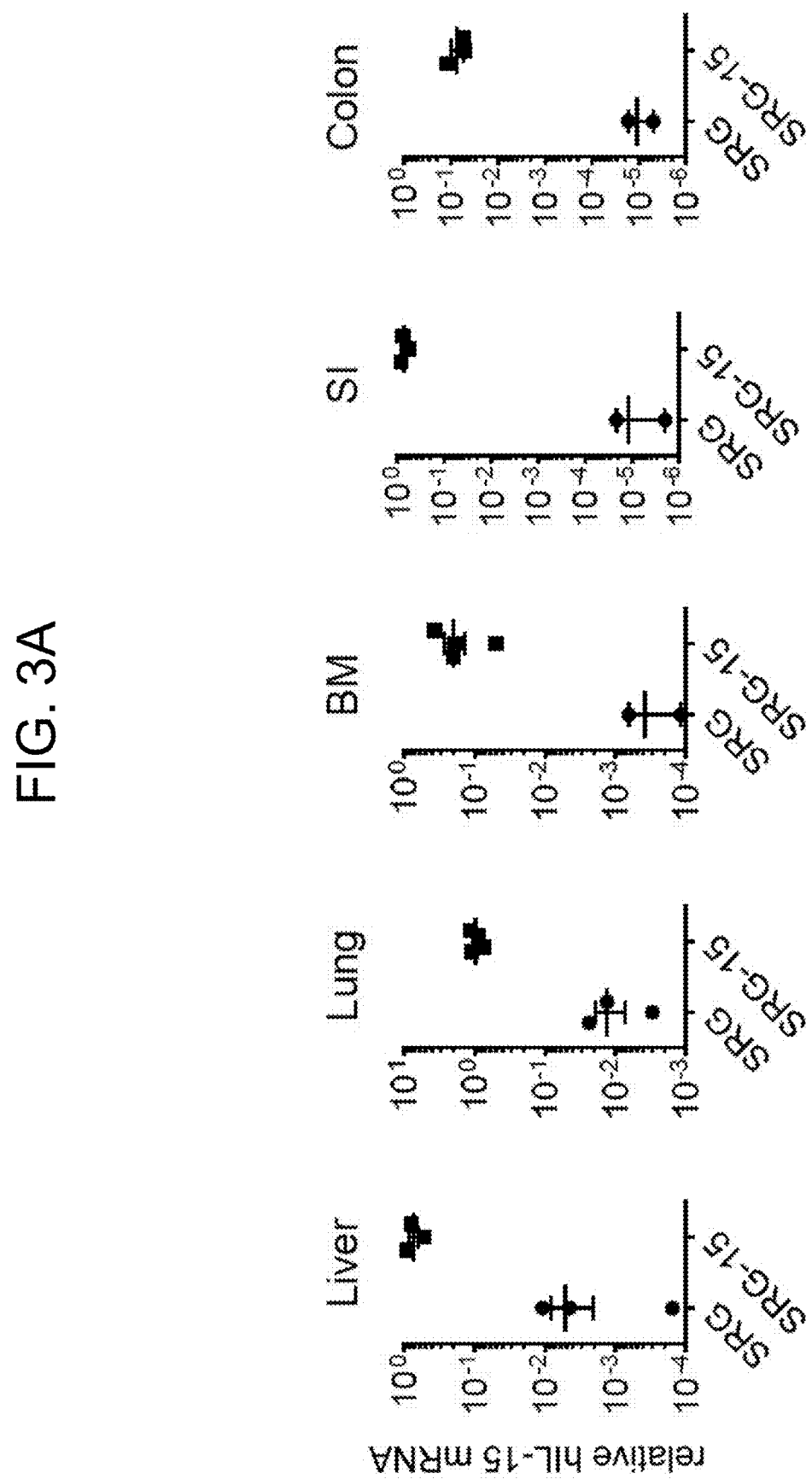
FIG. 3A provides graphs showing hIL-15 gene expression in various tissues of non-engrafted SRG (human SIRPα, Rag KO, IL-2rg KO) and SRG-15 (human SIRPα, Rag KO, IL-2rg KO, human IL-15 (mouse 1) mice. Y-axis shows level of hIL-15 mRNA relative to the housekeeping gene Hprt.
Figure 3B:
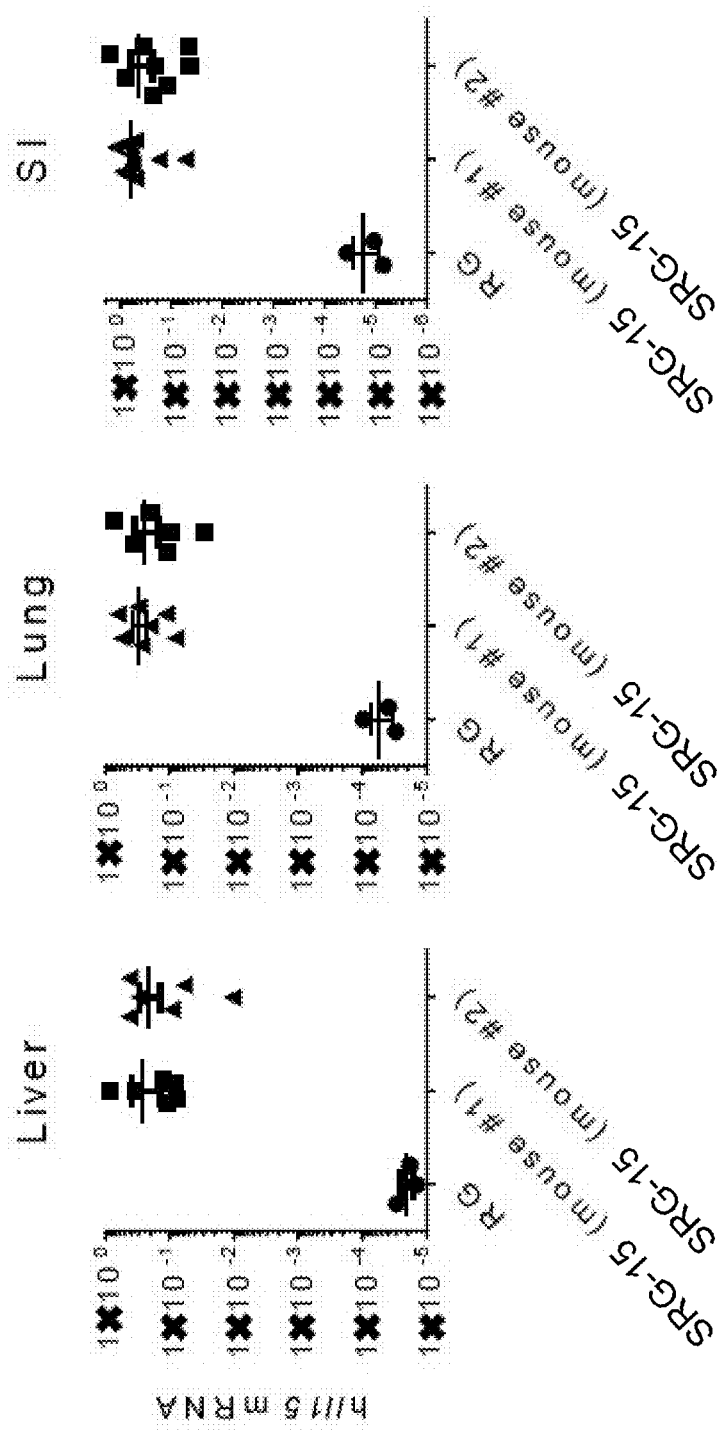
FIG. 3B provides graphs showing human hIL-15 gene expression in various tissues of non-engrafted RG (Rag KO, IL-2rg KO) and non-engrafted SRG-15 (human SIRPα, Rag KO, IL-2rg KO, human IL-15) mice (mouse #1 and mouse #2 as indicated).

As illustrated in FIGS. 3A and 3B, high levels of expression of human IL-15 mRNA were found in the liver, lung, bone marrow (BM), small intestine (SI) and colon of non-engrafted SRG-15 mouse 1. Similarly high levels of human IL-15 mRNA were found in the liver, lung and small intestine of non-engrafted SRG-15 mouse 2 (FIG. 3B). As shown in FIG. 4, upon stimulation by poly (I:C), high levels of human IL-15 protein could also be detected in the serum of SRG-15 mouse 2, wherein human exons 5-8 replace the endogenous mouse exons.

Example 3: Engraftment of SRG-15 Mice

Materials and Methods

SRG and SRG-15 mice are engrafted as described below. Neonate mice are irradiated sub-lethally without anesthesia 3-5 days post birth with 160 cGy and returned to their mothers for rest. 4-12 hours post irradiation these neonates are transplanted with CD34+ huHSCs in 25 μl PBS intrahepatically (i.h.) using a 30 G needle.

Results

Figure 5B:
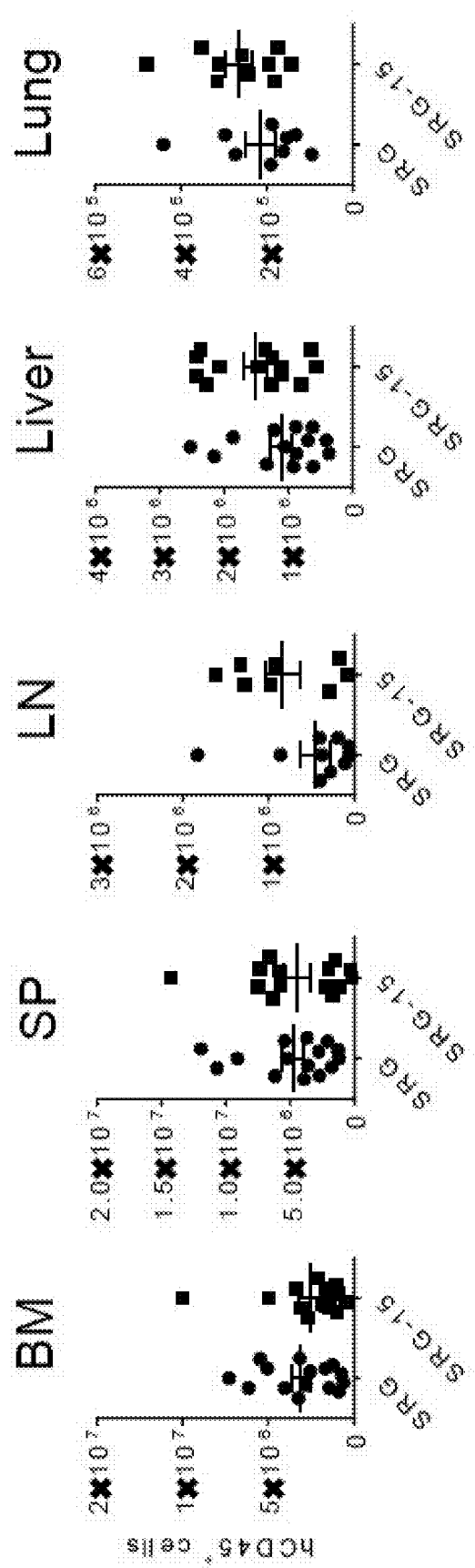
FIG. 5B provides graphs showing human CD45+ cell numbers in the BM, spleen, LN, liver and lung of SRG and SRG-15 (mouse 2) 14 weeks post engraftment.

To assess the impact of human IL-15 on immune cell development, human CD45$^+$ cell engraftment in NSG, SRG and SRG-15 mice was compared. Efficient engraftment of human hematopoietic cells in the blood of NSG, SRG and SRG-15 (mouse 2) mice was seen 12-14 weeks post engraftment as shown in FIG. 5A. A comparison showing engraftment as evidenced by human CD45+ cell numbers in the BM, spleen, LN, liver and lung of SRG and SRG-15 (mouse 2) 14 weeks post engraftment is provided in FIG. 5B.

Figure 6B:
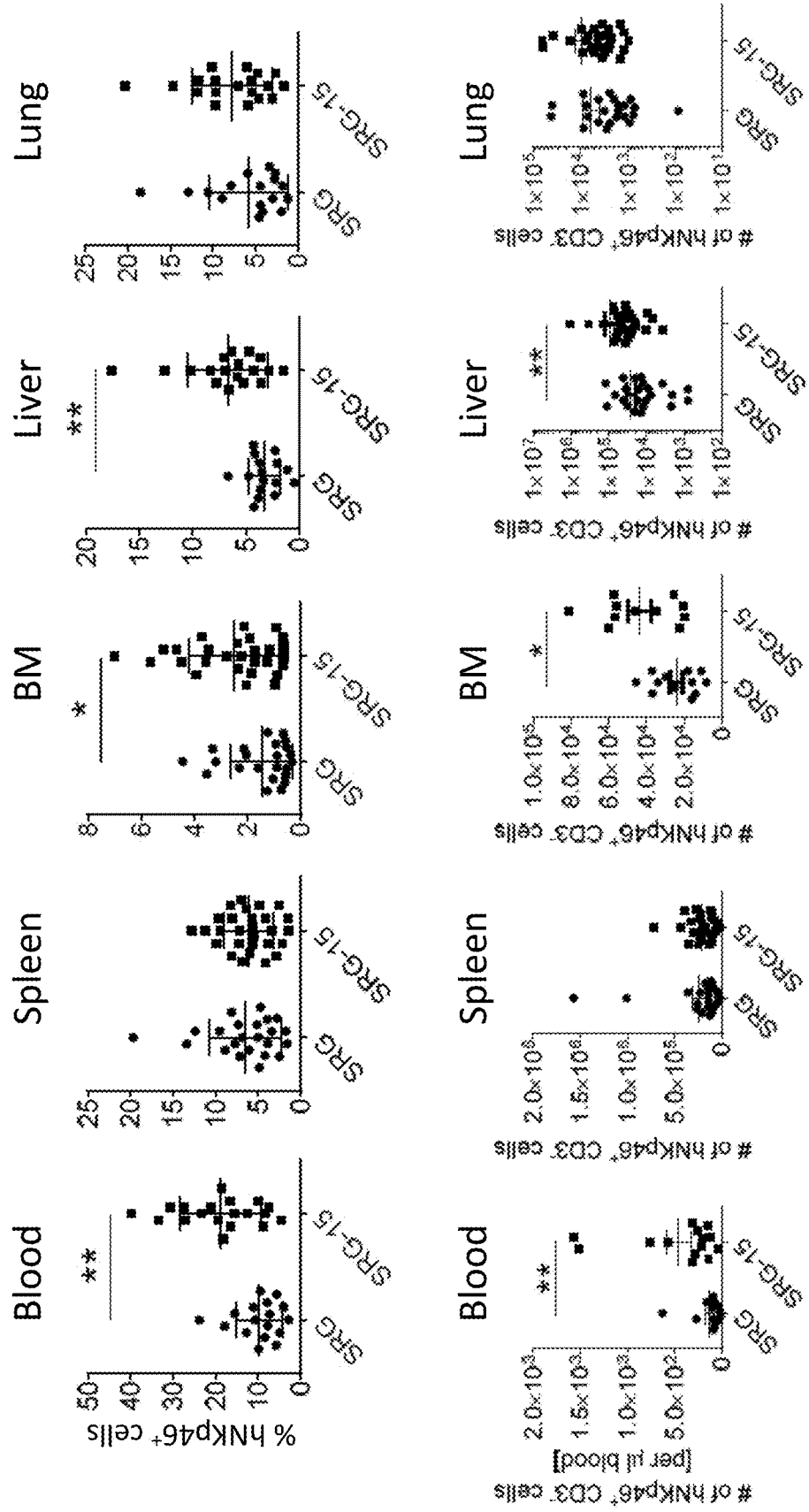
FIG. 6B provides graphs showing human NK cell frequencies in SRG and SRG-15 mice (mouse 1) in various tissues.
Figure 6D:
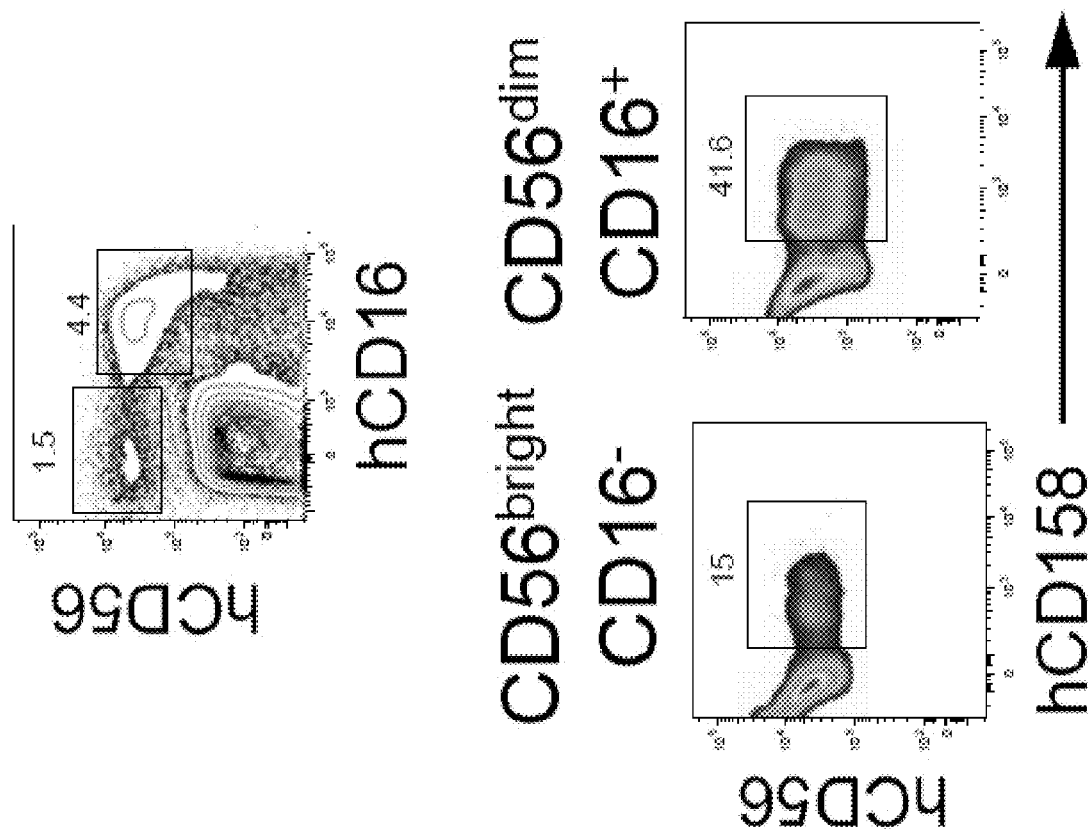
FIG. 6D provides plots showing that human $CD56^{dim}$ $CD16^+$ NK cells express high levels of human killer inhibitory receptors in the spleen of SRG-15 mice.

In mouse 1, although human CD45$^+$ cell engraftment was not different, a higher percentage and number of human NK cells was found in various tissues in SRG-15 mice compared to SRG mice, as illustrated by FIGS. 6A and 6B. IL-15 is not only important for NK cell development and survival but also for their maturation. As shown in FIG. 6C, human NK cells in the liver of SRG-15 mice (mouse 1) had a higher expression level of CD16 and CD56, indicating increased NK cell maturation in SRG-15 mice compared to SRG mice. Both human NK cell subsets, $CD56^{bright}CD16^-$ and $CD56^{dim}CD16^+$, were found to be present in the blood, spleen and liver of SRG-15 mice, as shown in FIG. 6D (spleen) (and data not shown). In addition, as shown in FIG. 6D, analysis of the two human NK cell subsets in the spleen of SRG-15 mice (mouse 1) showed that they had a distinct expression level of killer inhibitory receptors, with the $CD56^{dim}CD16^+$ NK cell population including the higher percentage of CD158-expressing cells. This resembles what is found for NK cell subsets in the blood of humans (data not shown).

Figure 7D:
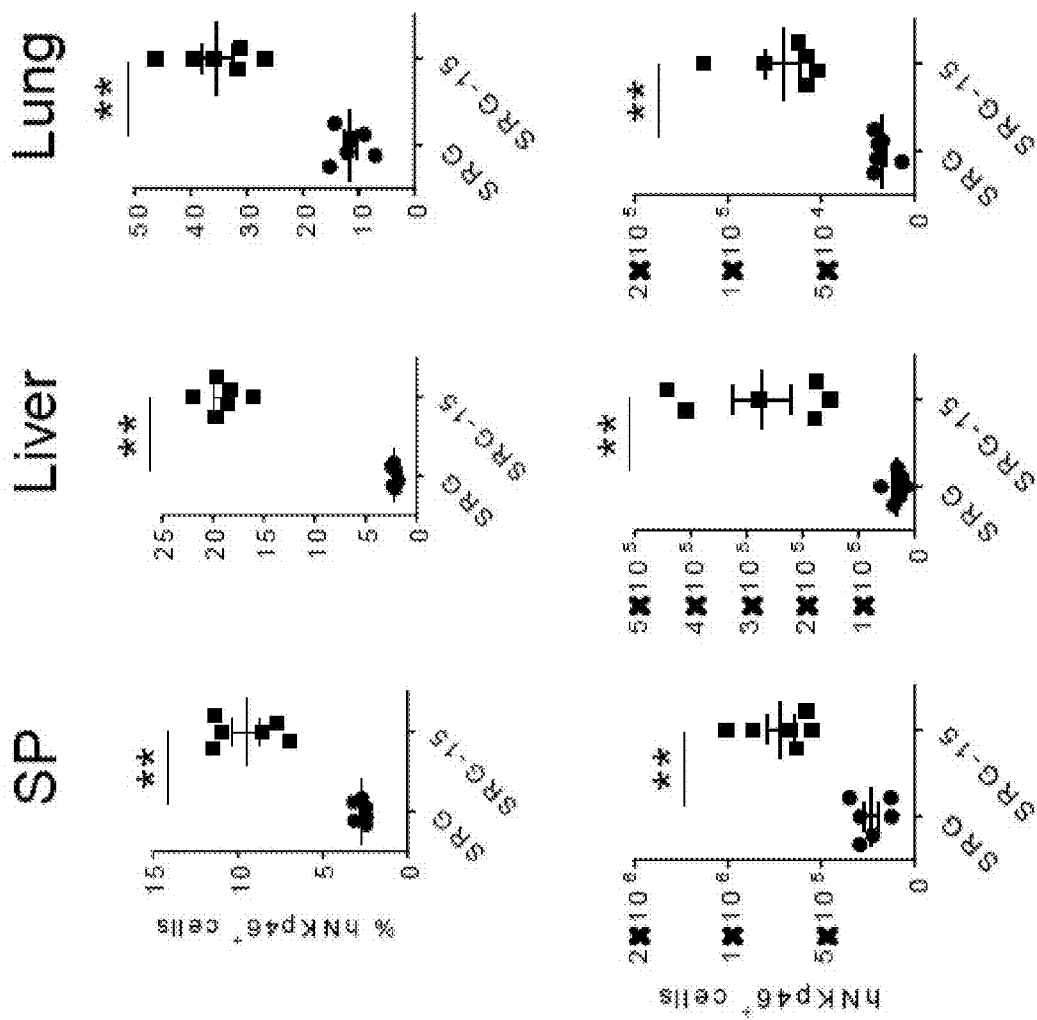
FIG. 7D provides graphs showing the frequency of human NK cells in the spleen (SP), liver and lung of SRG and SRG-15 (mouse 2) mice 14 weeks post engraftment. All data are shown as mean±s.e.m. Statistical analyses were performed using unpaired, two-tailed Mann-Whitney U-test (*P<0.05, P<0.01, **P<0.0001).

For SRG-15 mouse 2, efficient human NK cell engraftment in lymphoid and non-lymphoid tissues was seen as shown in FIGS. 7A-7D. FIGS. 7A and 7B show percentage of NK cells in blood and spleen, respectively. FIGS. 7C and 7D show the the frequency of human NK cells in the blood, spleen (SP), liver and lung of SRG and SRG-15 (mouse 2) mice 14 weeks post engraftment. Additional data showing NK cell distribution and percentage in blood and spleen of SRG and SRG-15 (mouse 2) mice from different experiments is provided in FIGS. 8 and 9A respectively. An increase in the hNKp46 fragment of hCD45+ cells in the blood of SRG-15 mice (mouse 2) is shown in FIG. 9B. FIGS. 9C-9E show relative numbers, distribution and composition of hCD45+ cells in the thymus of SRG and SRG-15 (mouse 2) mice.

Figure 10B:
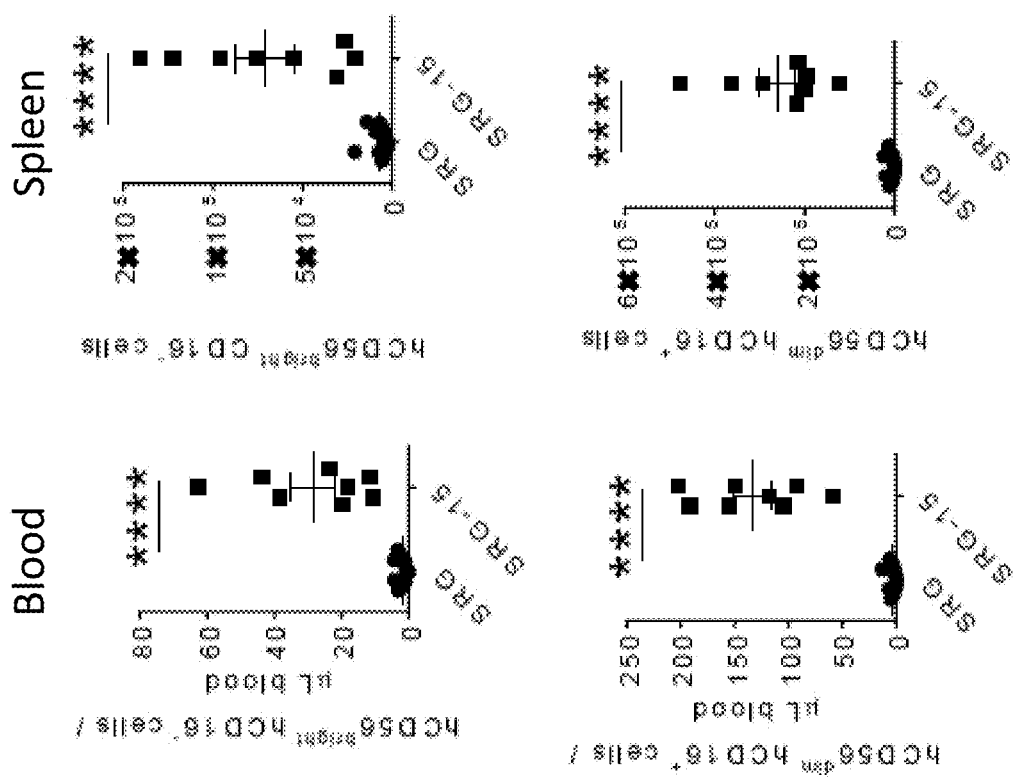
FIG. 10B provides graphs showing the frequency of $CD56^{bright}$ $CD16^-$ and $CD56^{dim}$ $CD16^+$ NK cell subsets in the blood and spleen of SRG and SRG-15 (mouse 2) mice seven weeks post engraftment.

The NK cell subsets in humans and SRG-15 mice (mouse 2) were characterized. As shown in FIGS. 10A and 10B, increased levels of both $hCD-56^{bright}$ $hCD16^-$ and $hCD56^{dim}$ $hCD16^+$ were seen in the blood and spleen of SRG-15 mice relative to SRG mice. As in human, expression of killer inhibitory receptors (KIRs) was seen on NK cell subsets in SRG-15 mice (mouse 2) (FIG. 10C). FIG. 10C shows CD56bright CD16$^-$ NK cells (left box for each plot) and CD56dim CD16$^-$ NK cells (right box for each plot). The histogram below shows CD158 expression in those subsets. CD158 (KIR2D) on NK cell subsets in SRG-15 mice is similar to what is observed in human PBMC-derived NK cells.

Human NK cell distribution in the blood of SRG-15 mice was compared to that of blood obtained from two healthy human donors. Peripheral blood mononuclear cells (PBMCs) were isolated from buffy coats of two individual donors (obtained from BioreclamationIVT, Westbury, N.Y.) over Ficoll-Paque; although greater percentage of blood NK cells was observed in engrafted SRG-15 mice than in PBMCs from human donors, a physiologically comparable distribution of cytotoxic (CD16+) NK cells versus IFN-g producing (CD16−) NK cells was observed (FIG. 11).

Figure 12:
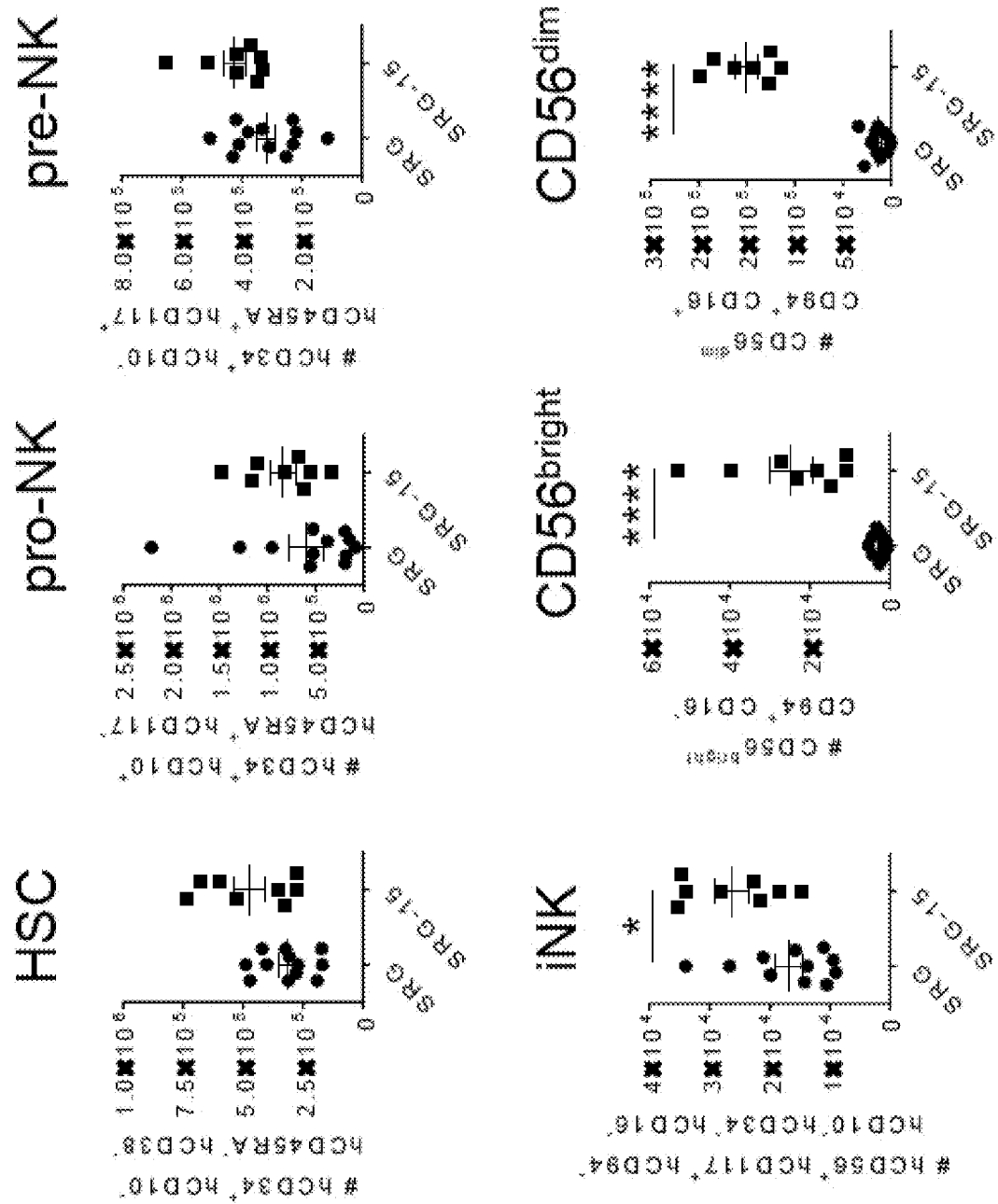
FIG. 12 provides graphs showing human NK cell development in the bone marrow of SRG and SRG-15 (mouse 2) mice seven weeks post engraftment. All data are shown as mean±s.e.m. Statistical analyses were performed using unpaired, two-tailed Mann-Whitney U-test (*P<0.05, P<0.01, **P<0.0001).

Finally, an analysis of the bone marrow of SRG and SRG-15 (mouse 2) showed increased human NK cell development in SRG-15 mice relative to SRG mice (FIG. 12).

Figure 13A:
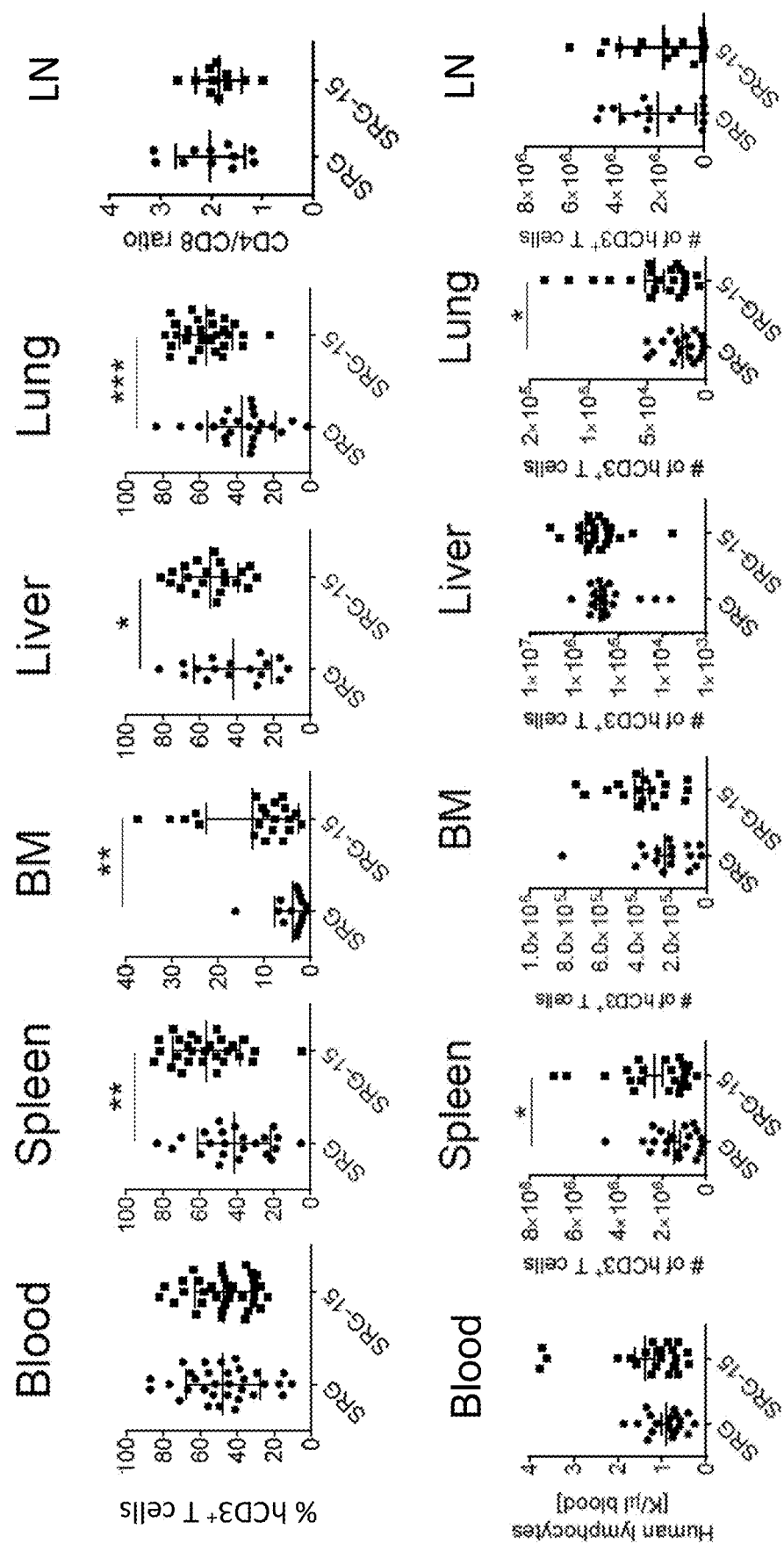
FIG. 13A provides graphs showing human T cell frequencies in SRG and SRG-15 mice (mouse 1) in various tissues. (K/μl=thousands of cells per μl).
Figure 13B:
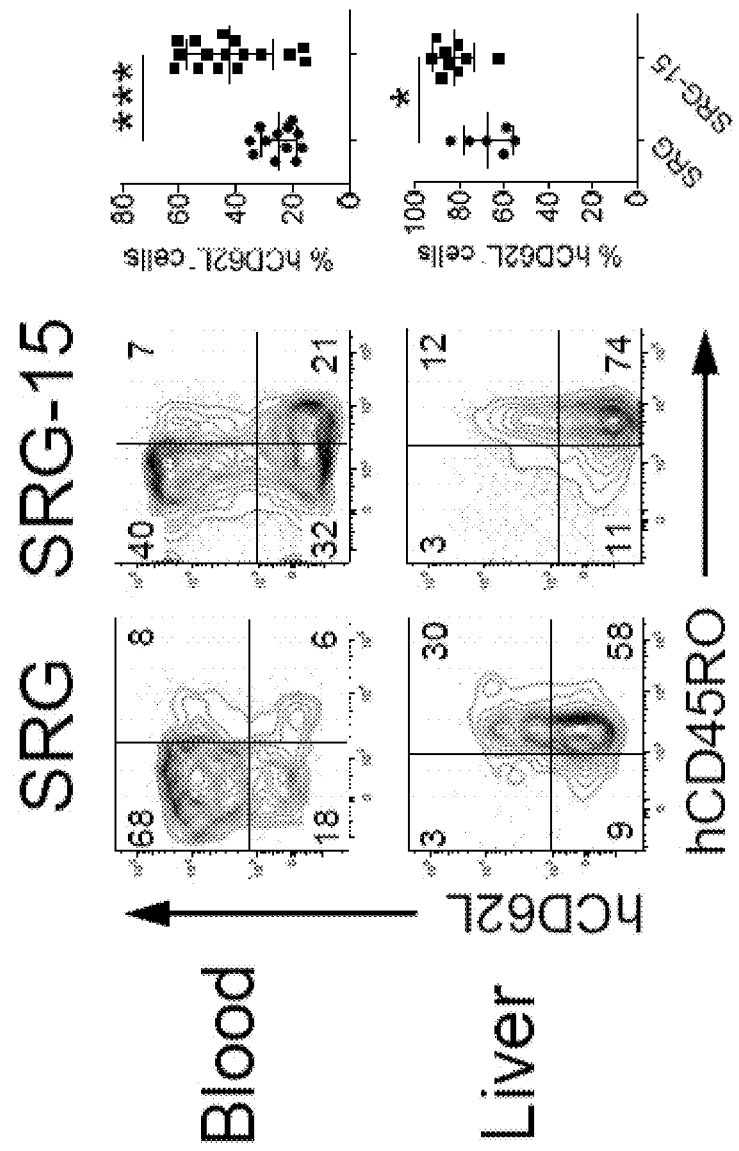
FIG. 13B provides plots and graphs showing human CD8$^+$ T cell phenotype in blood and liver for SRG and SRG-15 mice (mouse 1).

The impact of human IL-15 on human T cell development in SRG-15 mice was also assessed. A comparison of SRG-15 (mouse 1) mice relative to SRG mice showed that the effect of human IL-15 on the percentage, number and/or ratio of T cells varied depending on the tissue (FIG. 13A). The size and number of lymph nodes at week 16 post engraftment did not differ between SRG and SRG-15 mice, confirming the results that the numbers of human T cells in the lymph nodes of SRG and SRG-15 (mouse 1) mice were similar (FIG. 13A). FIG. 13B shows a human CD8$^+$ T cell phenotype in blood and liver for SRG and SRG-15 mice (mouse 1), with an increase in hCD62L$^-$ cells in SRG-15 mice (mouse 1) relative to SRG mice for both blood and liver. Additional data characterizing the T cells of the SRG-15 mice (mouse 1) relative to the SRG mice is provided in FIGS. 14A and 14B, which shows expression of the tissue-resident marker CD69 in the CD8$^+$ T cells of lung (14A) and liver (14B) of SRG and SRG-15 mice. The above data provides evidence of an increase in effector tissue-resident T cells in SRG-15 mice.

Figure 15A:
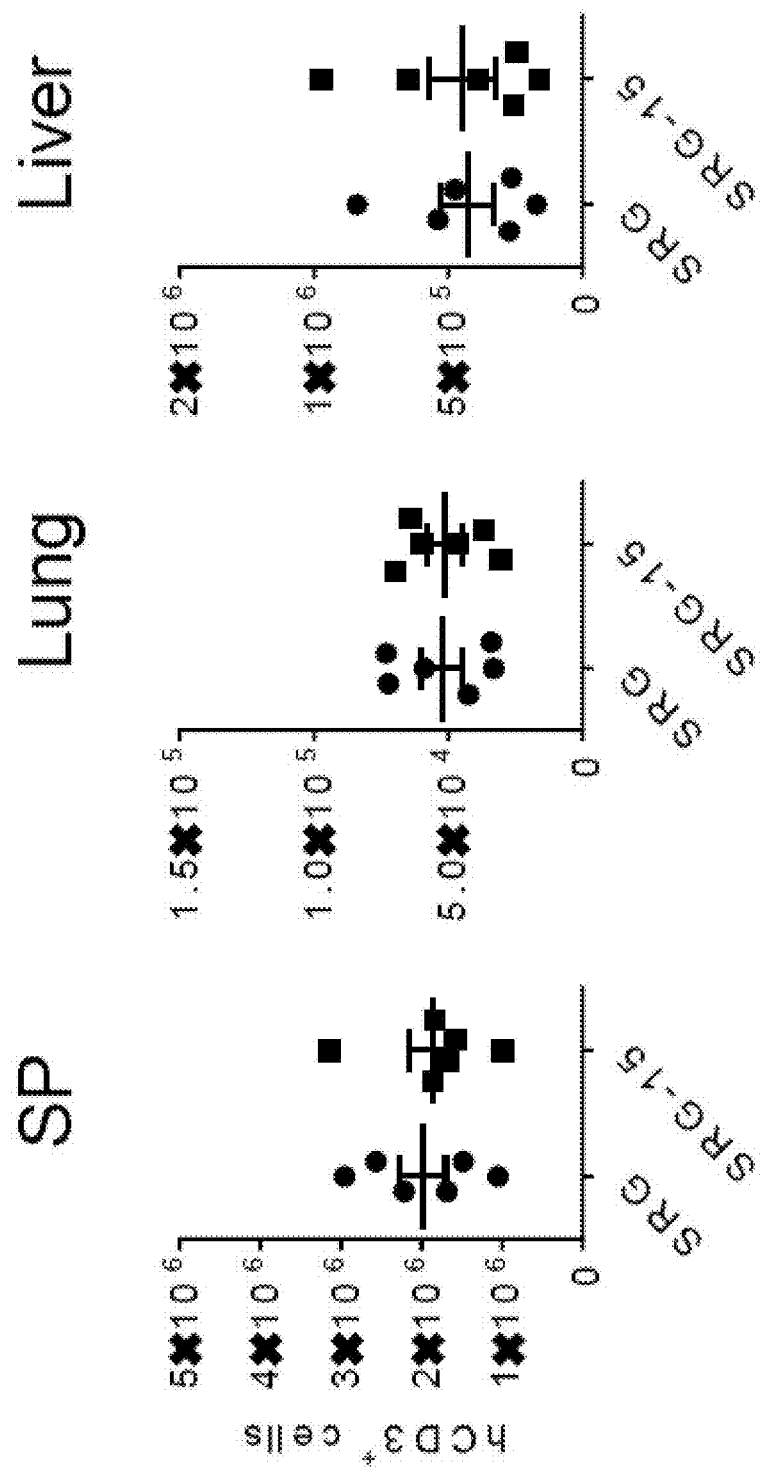
FIG. 15A provides graphs showing the frequency of hCD3$^+$ T cells in the spleen, lung and liver of SRG and SRG-15 (mouse 2) mice 16 weeks post engraftment.
Figure 15B:
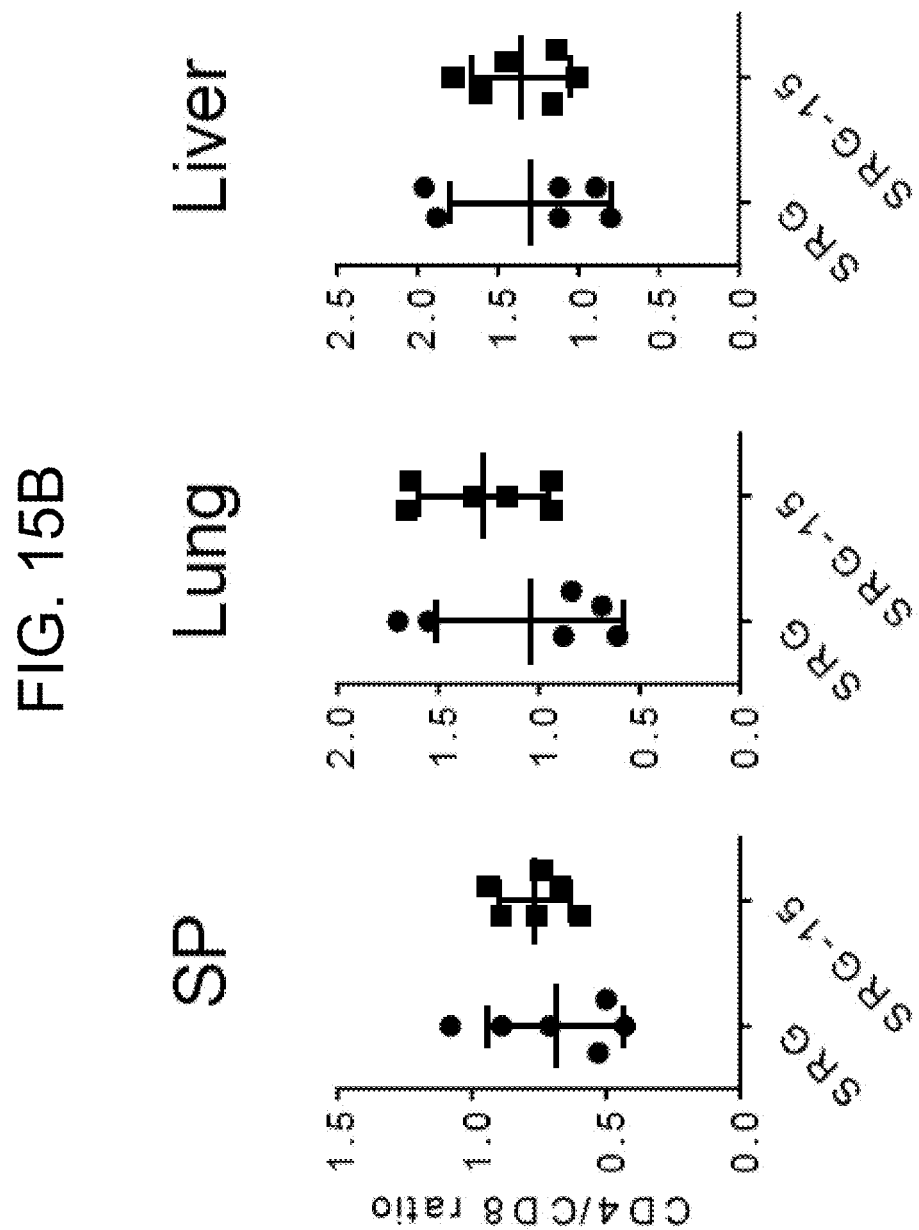
FIG. 15B provides graphs showing the CD4/CD8 ratio in the spleen, lung and liver of SRG and SRG-15 (mouse 2) mice 16 weeks post engraftment.

For mouse 2, the frequency of hCD3$^+$ T cells in the spleen, lung and liver relative to SRG mice was assessed 16 weeks post engraftment, as shown in FIGS. 15A and 15B.

Example 4: Development of Human Tissue-Resident Lymphocytes in SRG-15 Mice

Because IL-15 has been shown to be produced by epithelial cells in the gut and the lung and may play an important role for the development and survival of human tissue-resident T and NK cells, human tissue-resident T and NK cells were analyzed in SRG and SRG-15 mice.

Materials and Methods

Neonate mice are irradiated sub-lethally without anesthesia 3-5 days post birth with 160 cGy and returned to their mothers for rest. 4-12 hours post irradiation these neonates are transplanted with CD34+ huHSCs in 25 µl PBS intrahepatically (i.h.) using a 30 G needle.

Results

Figure 14B:
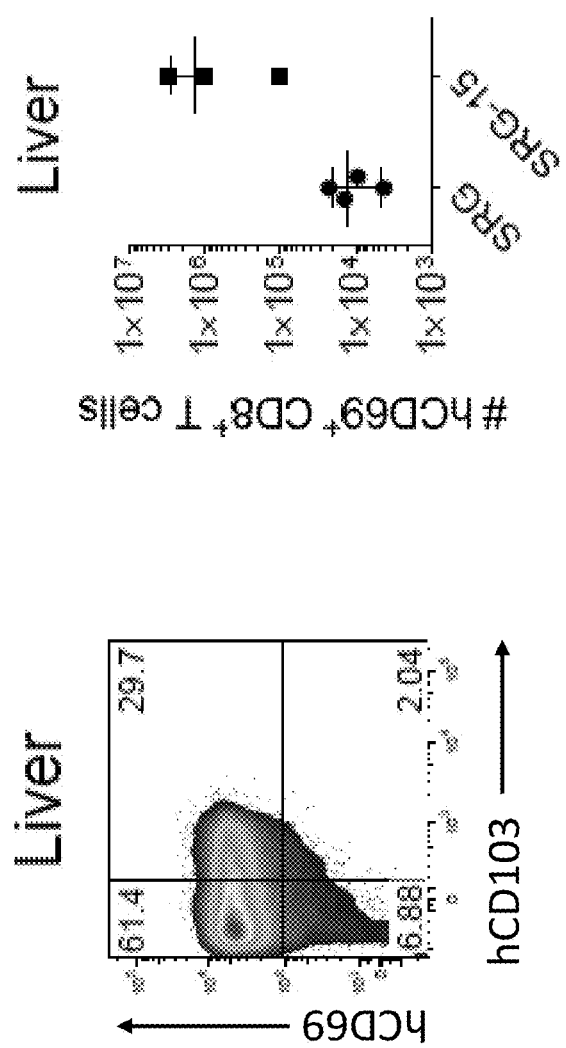
FIG. 14B provides a plot and a graph showing expression of the tissue-resident marker CD69 in liver CD8$^+$ T cells of SRG and SRG-15 (mouse 1) mice.
Figure 16A:
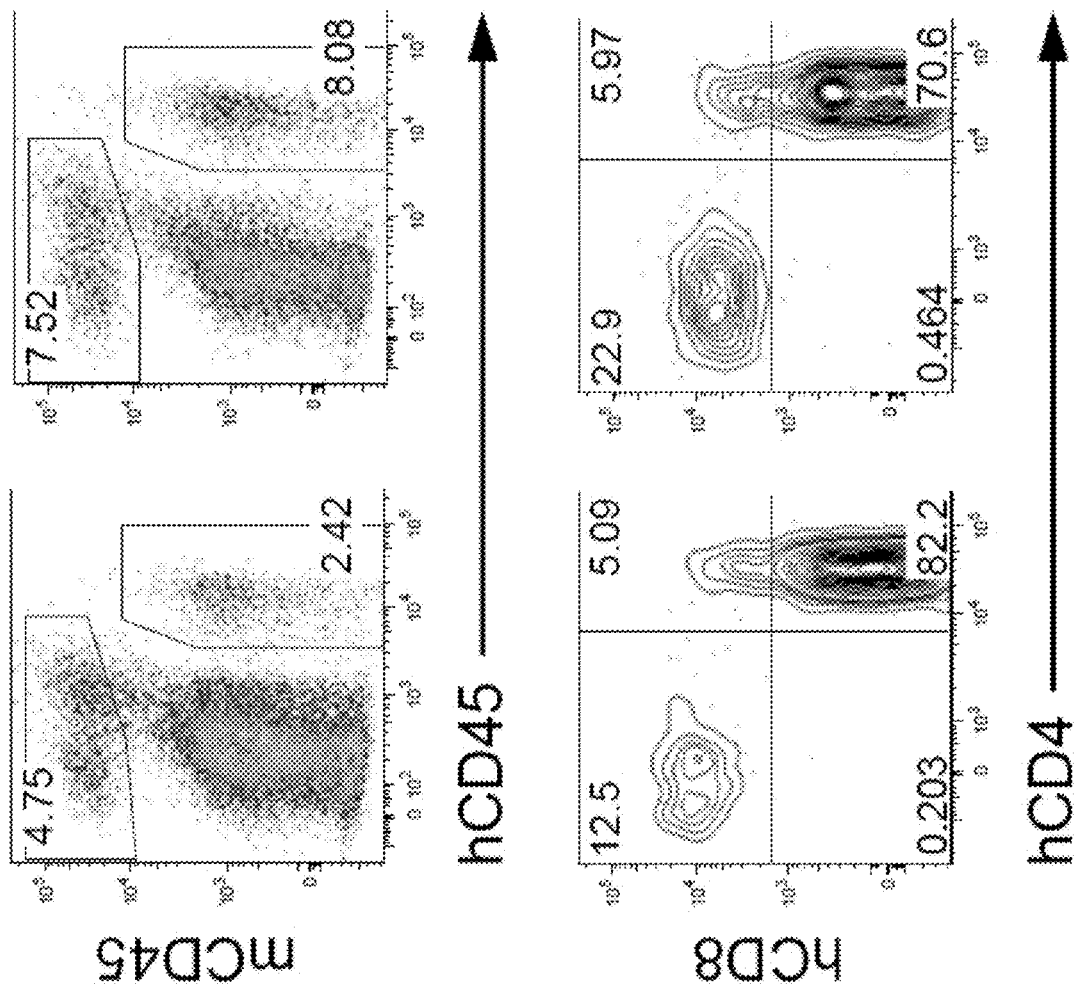
FIG. 16A provides plots illustrating the frequency of human lamina propria lymphocytes (LPLs) in the colon of SRG and SRG-15 (mouse 1) mice.
Figure 16B:
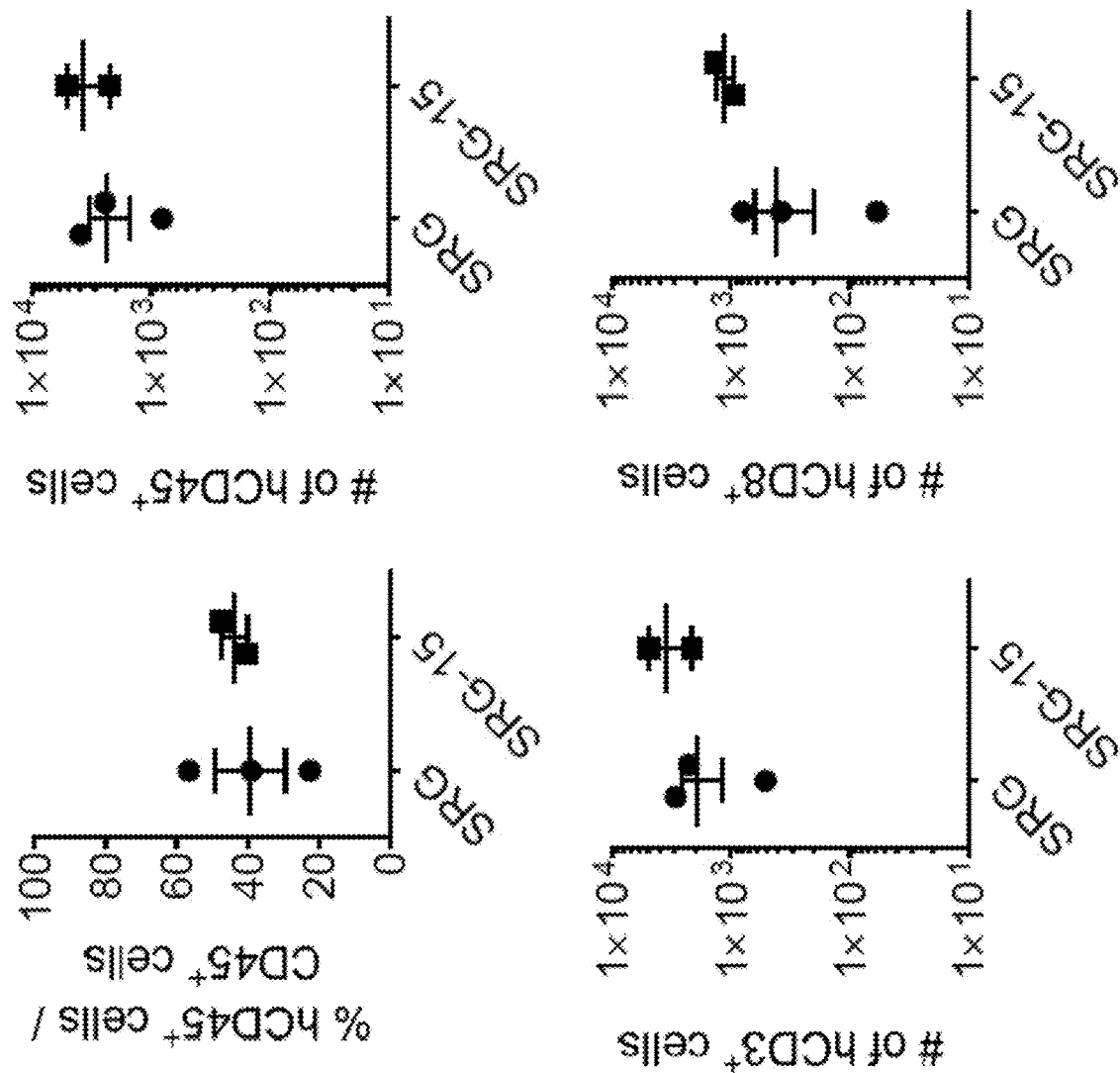
FIG. 16B provides graphs illustrating the frequency of human lamina propria lymphocytes (LPLs) in the colon of SRG and SRG-15 (mouse 1) mice.
Figure 17A:
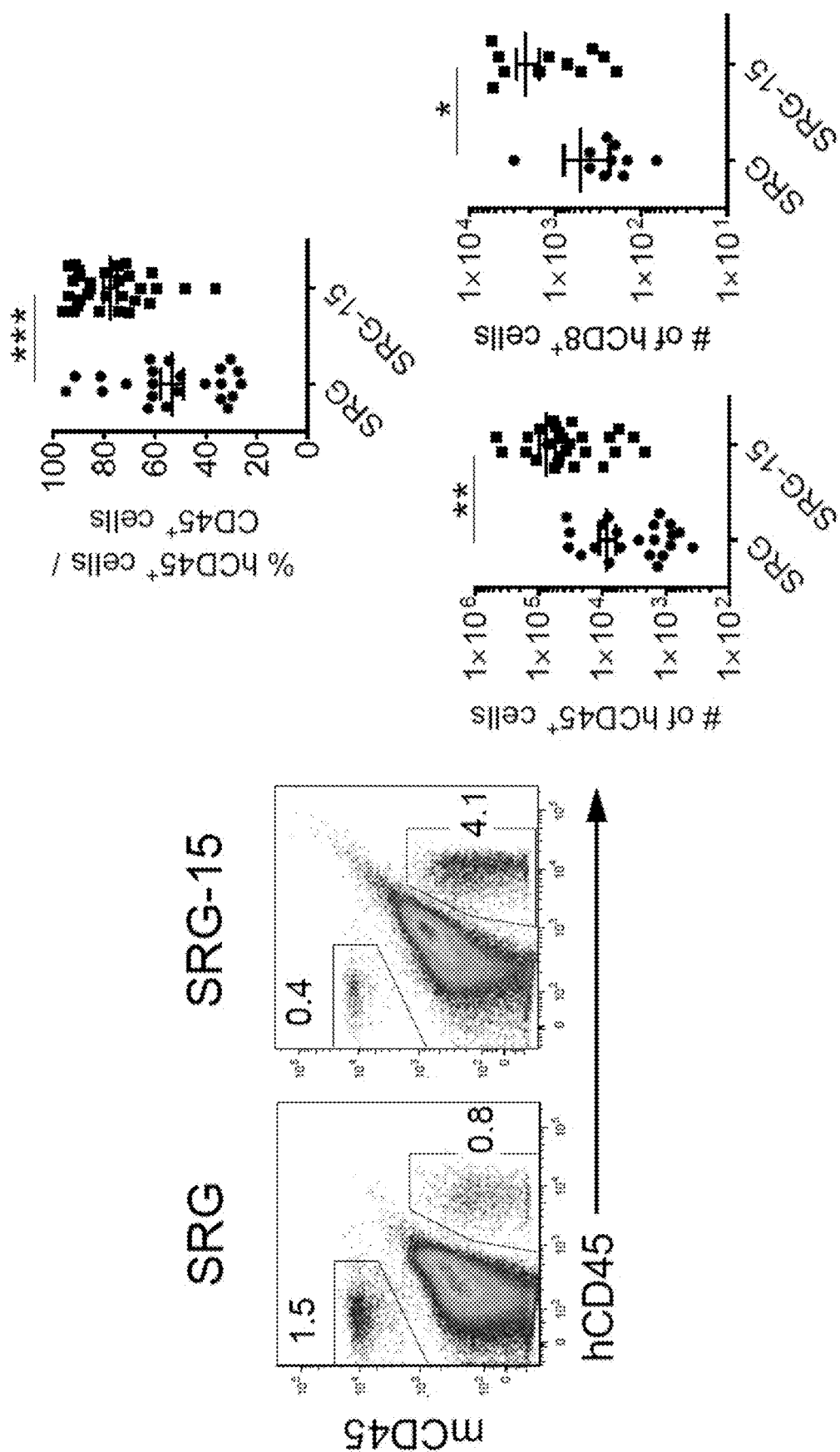
FIG. 17A together with FIGS. 17B-17C, illustrates efficient engraftment of human intraepithelial lymphocytes (IELs) in the small intestine of 16 week old SRG-15 mice (mouse 1).
Figure 17B:
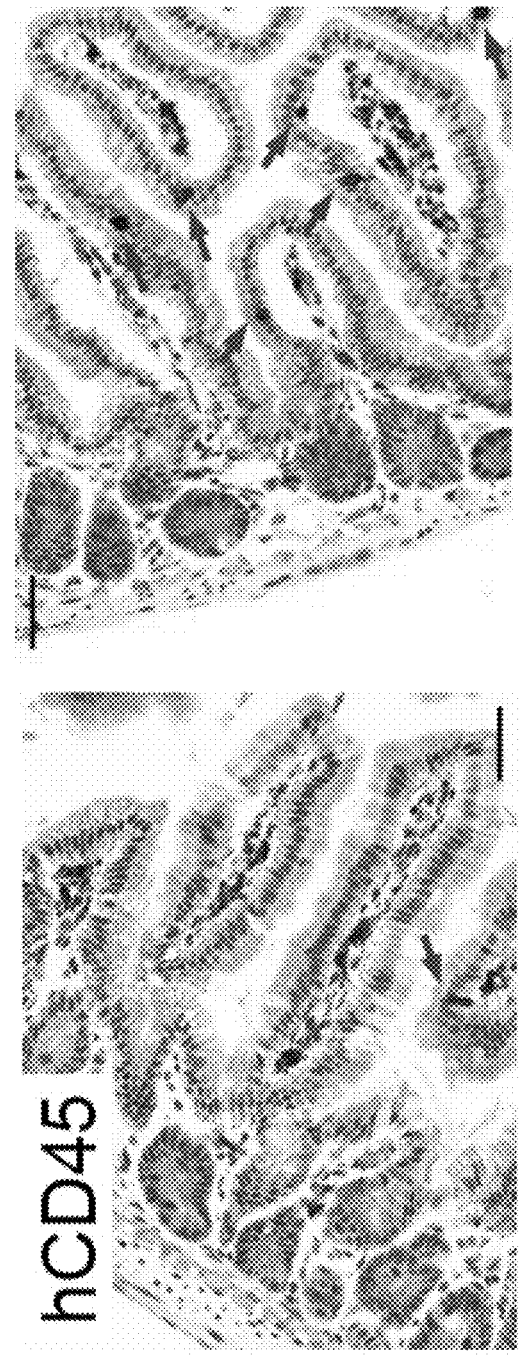
FIG. 17B provides images of immunohistochemical staining of hCD45 in the small intestine of 16 week old SRG and SRG-15 (mouse 1) mice.
Figure 17C:
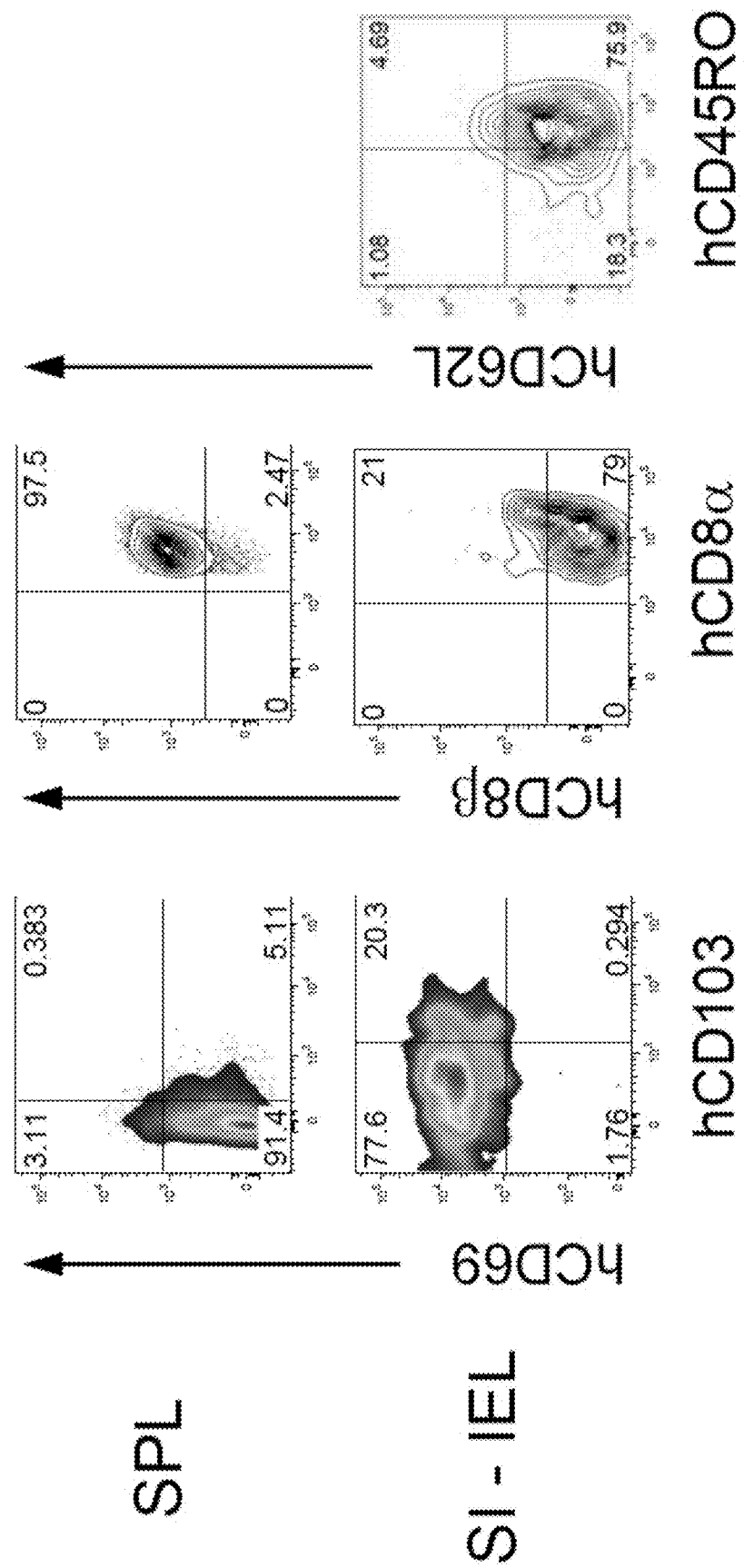
FIG. 17C provides plots showing phenotypic characteristics of human CD8$^+$ T cells in the spleen and small intestine of SRG-15 mice (mouse 1).

As shown in FIG. 17A, isolation of the intraepithelial lymphocyte population from the small intestine during steady state conditions in mouse 1 revealed a higher frequency of human CD45$^+$ cells in SRG-15 mice compared to SRG mice. Immunohistochemical analysis, as illustrated in FIG. 17B, demonstrated that the human CD45$^+$ NK cells were located in the epithelial cell layer of the small intestine of SRG-15 mice (mouse 1) (as designated by the arrows in FIG. 17B), while very few intraepithelial lymphocytes were found in SRG mice. Human CD8$^+$ IELs in SRG-15 mice showed high expression of CD69, the typical marker of tissue-resident T cells. In contrast to human IELs (Sathaliyawala T, Kubota M, Yudanin N et al. *Immunity* 2013; 38:187-197), only a subpopulation of human CD8$^+$ IELs in the SRG-15 mice expressed the tissue-resident marker CD103 (FIG. 17C). As shown in FIGS. 16A and 16B, the phenotype of increased human CD8$^-$ IELs in SRG-15 mice (mouse 1) was specific as there was little difference in the number of lamina propria cells in the colon during steady state between SRG and SRG-15 mice. In addition to the increased number of human T cells in the lung of SRG-15 mouse 1 as shown in FIG. 13A, higher expression of CD69 on human CD8$^+$ T cells in the lung of SRG-15 mice compared to SRG mice was also found as shown by FIG. 14A. In addition, FIG. 14B shows a higher level of hCD69 expressing CD8$^+$ T cells in the liver of SRG-15 mouse 1 compared to the SRG mouse.

Figure 18A:
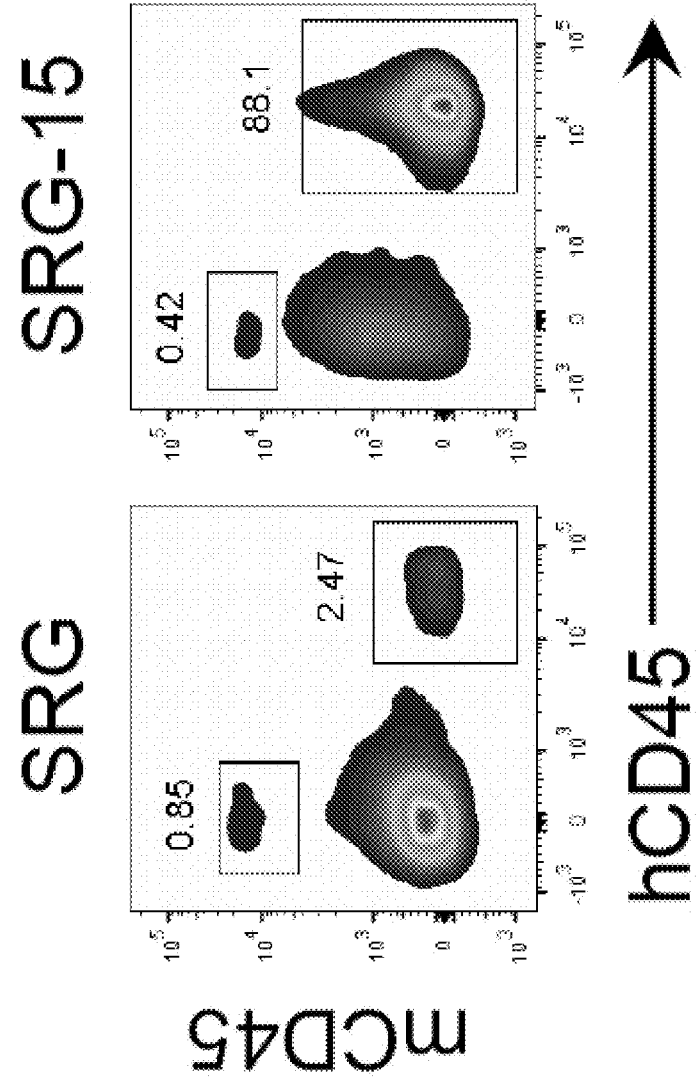
FIG. 18A provides representative FACS plots showing mouse and human CD45+ cells within the IEL fraction of SRG and SRG-15 (mouse 2) mice 16 weeks post engraftment.
Figure 18B:
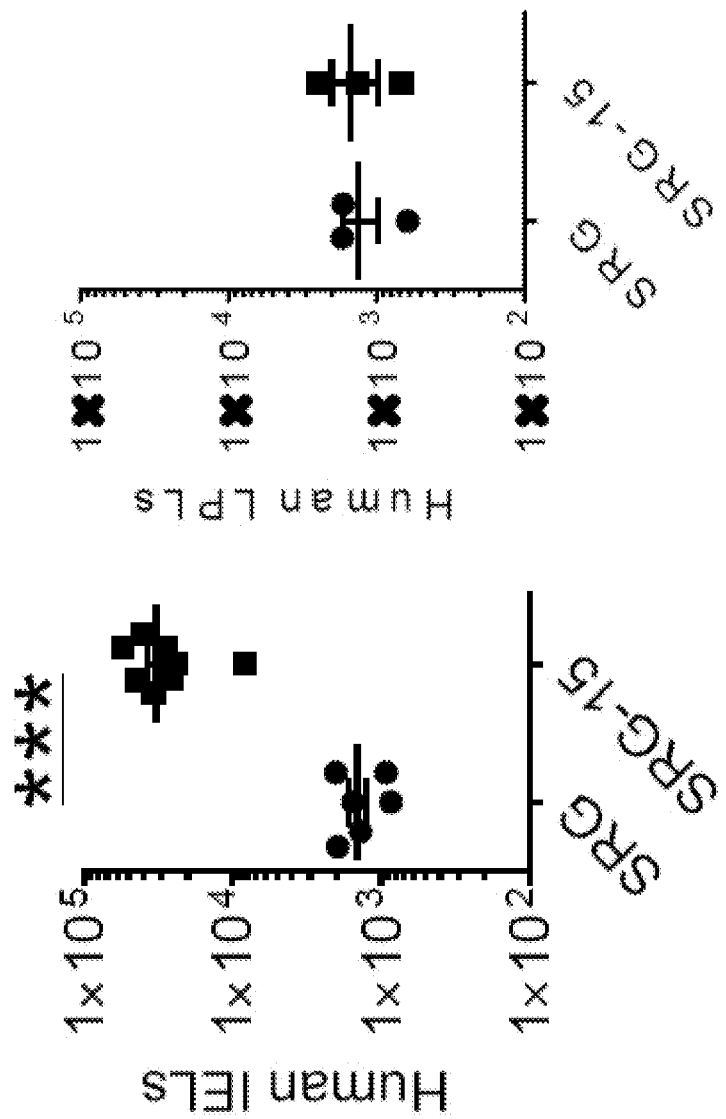
FIG. 18B provides graphs showing the number of human IELs in the small intestine of SRG relative to SRG-15 (mouse 2) mice and the number of human LPLs in the large intestine SRG relative to SRG-15 (mouse 2) mice. All data are shown as mean±s.e.m. Statistical analyses were performed using unpaired, two-tailed Mann-Whitney U-test (***P<0.001).
Figure 18C:
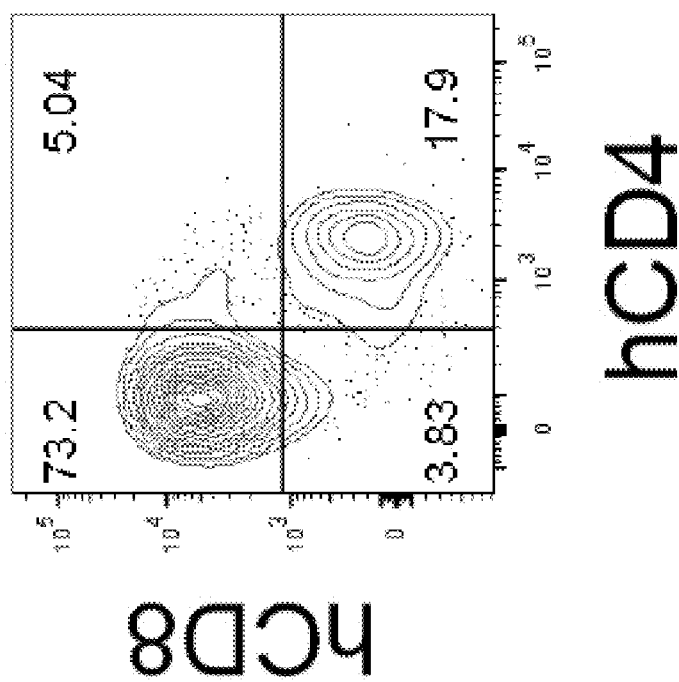
FIG. 18C provides a plot showing composition of hCD3+ cells in the small intestine of SRG-15 mice (mouse 2). One representative FACS plot of eight SRG-15 mice (mouse 2).
Figure 18D:
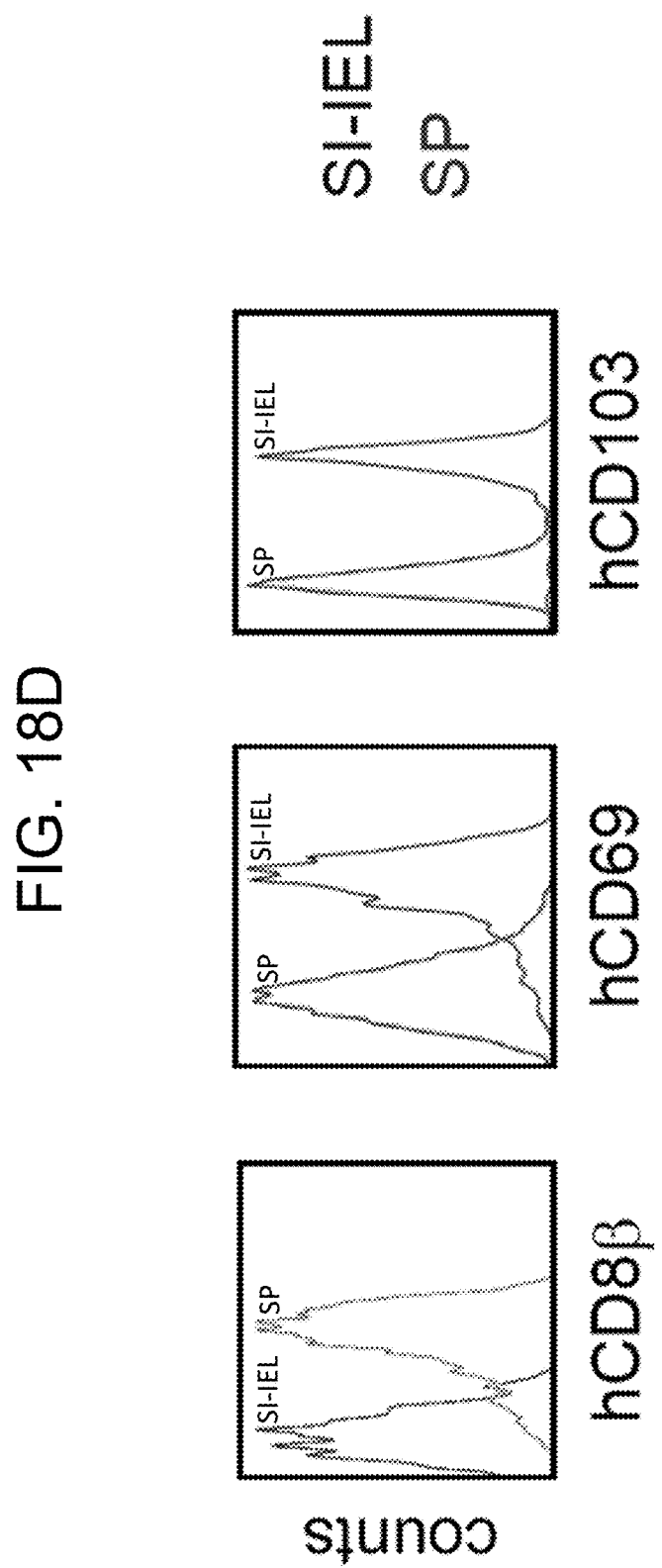
FIG. 18D provides graphs showing phenotypic characteristics of hCD3+ hCD8+ T cells in the spleen and small intestine of SRG-15 mice (mouse 2).
Figure 18E:
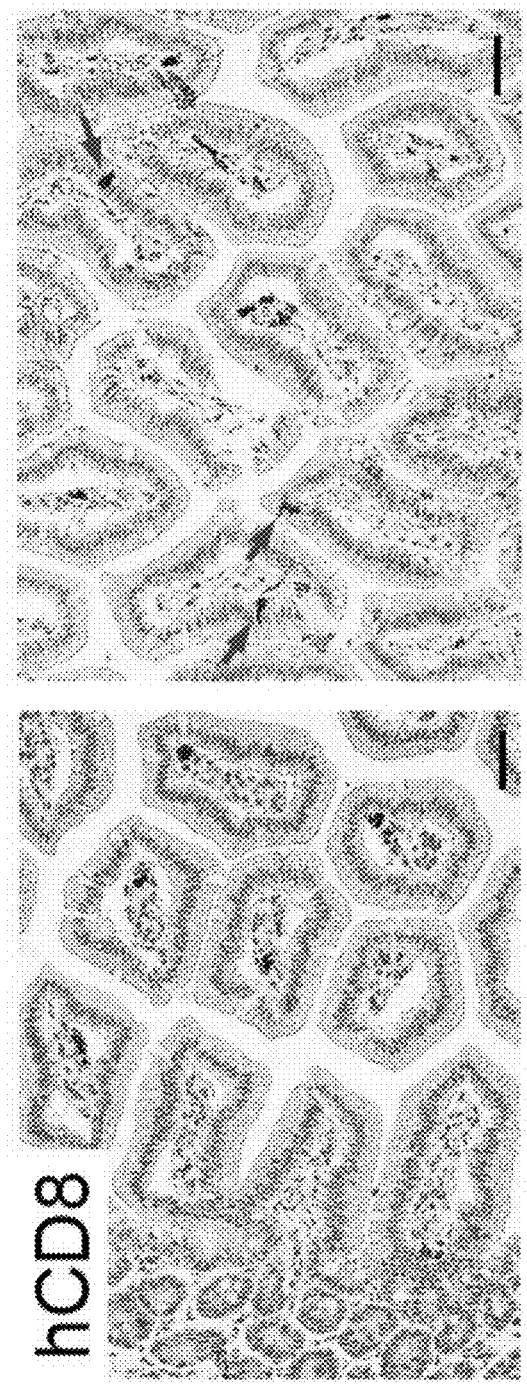
FIG. 18E provides images of immunohistochemical staining of hCD8 in the small intestine of SRG and SRG-15 (mouse 2) mice. The arrows indicate hCD8⁻ IELs. The pictures are representative of three mice per group.

Similar to the SRG-15 engrafted mouse 1, in SRG-15 engrafted mouse 2, FACS analysis revealed a higher proportion of human CD45$^+$ cells in the IEL fraction of SRG-15 mice compared to SRG mice (FIG. 18A). In addition, while the number of LPLs was not significantly changed between SRG and SRG-15 (mouse 2) mice, a significant increase in IELs was seen in SRG-15 (mouse 2) mice relative to SRG mice (FIG. 18B). The composition of hCD3+ cells in the small intestine of SRG-15 mice (mouse 2) is provided in FIG. 18C and shows a greater proportion of hCD8+ relative to hCD4+ cells. The phenotypic characteristics of hCD3+ hCD8+ T cells in the spleen and small intestine of SRG-15 mice (mouse 2) are provided in FIG. 18D. Immunohistochemical analysis, as illustrated in FIG. 18E, demonstrated that the human CD8+ IELs were located in the epithelial cell layer of the small intestine of SRG-15 mice (mouse 2) (as designated by the arrows in FIG. 18E), while very few intraepithelial lymphocytes were found in SRG mice.

Figure 19A:
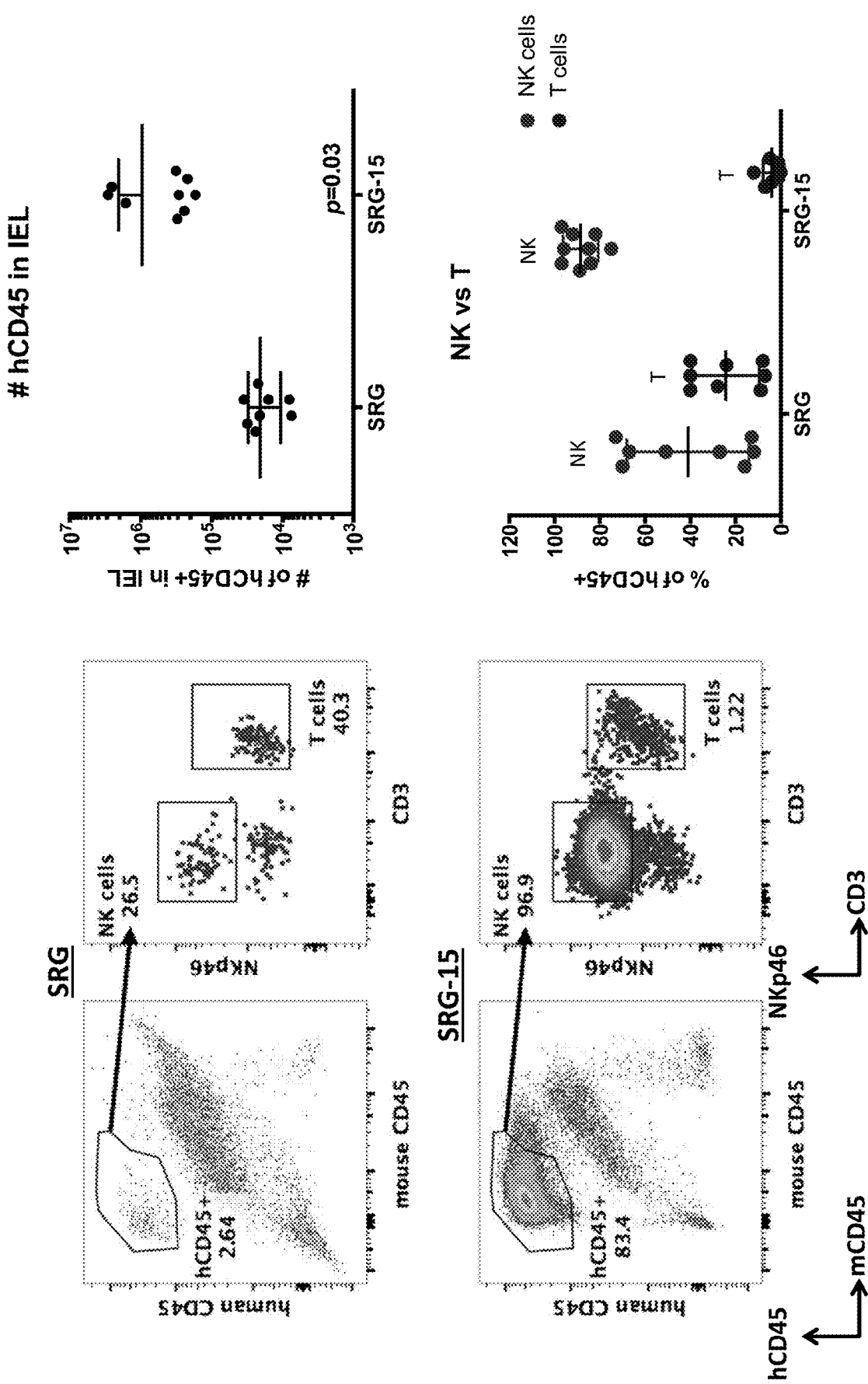
FIG. 19A provides plots and graphs showing the distribution and the number of hCD45+ cells in the intraepithelial lymphocyte populations of SRG and SRG-15 mice and the relative percentages of NK cells and T cells in the populations of hCD45+ cells in the intraepithelial lymphocyte populations of SRG and SRG-15 (mouse 2) mice.
Figure 19B:
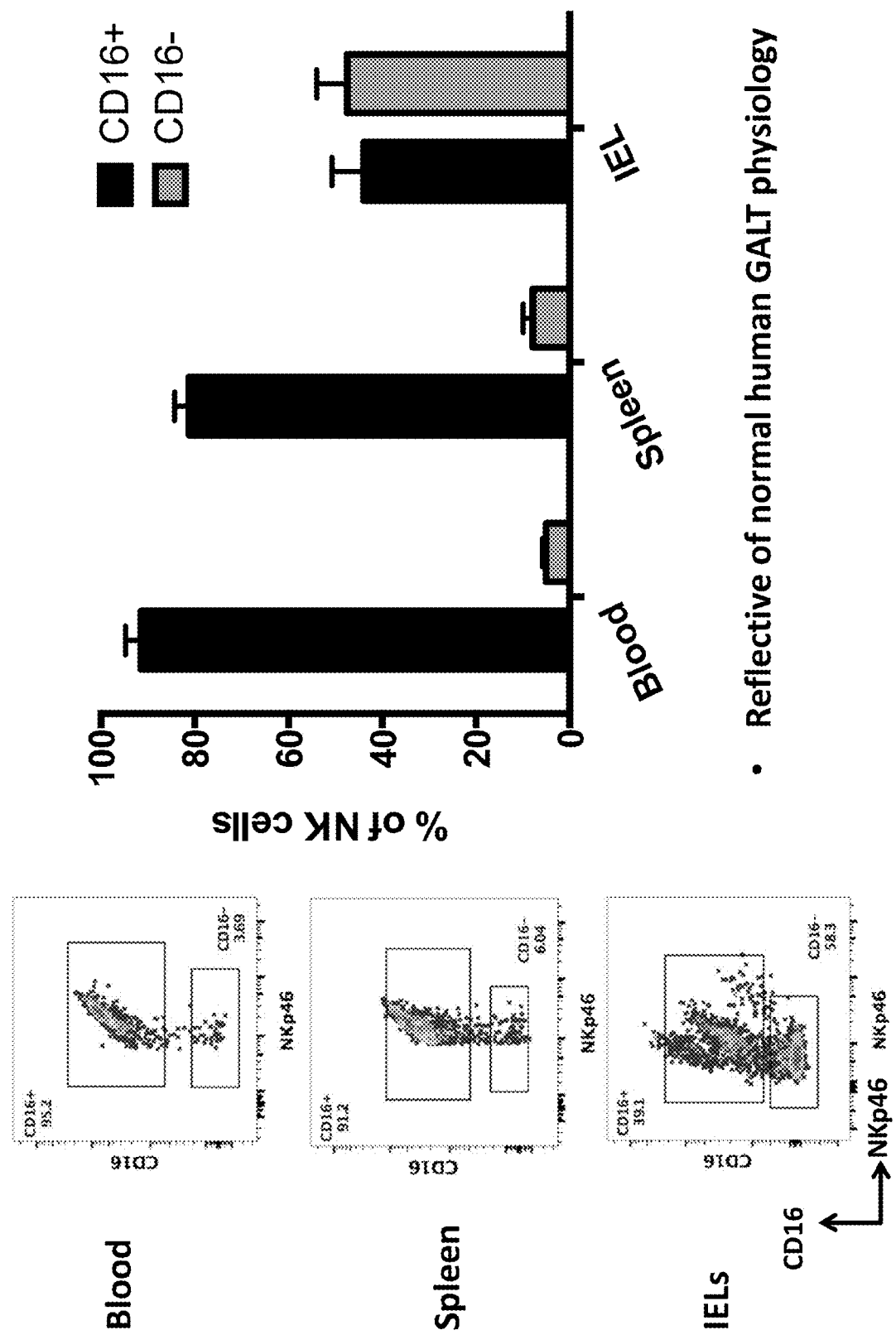
FIG. 19B provides plots and graphs showing the distribution and percentage of CD16+ and CD16− NK cells in intraepithelial lymphocytes of SRG-15 mice (mouse 2) as compared with blood and spleen.
Figure 20A:
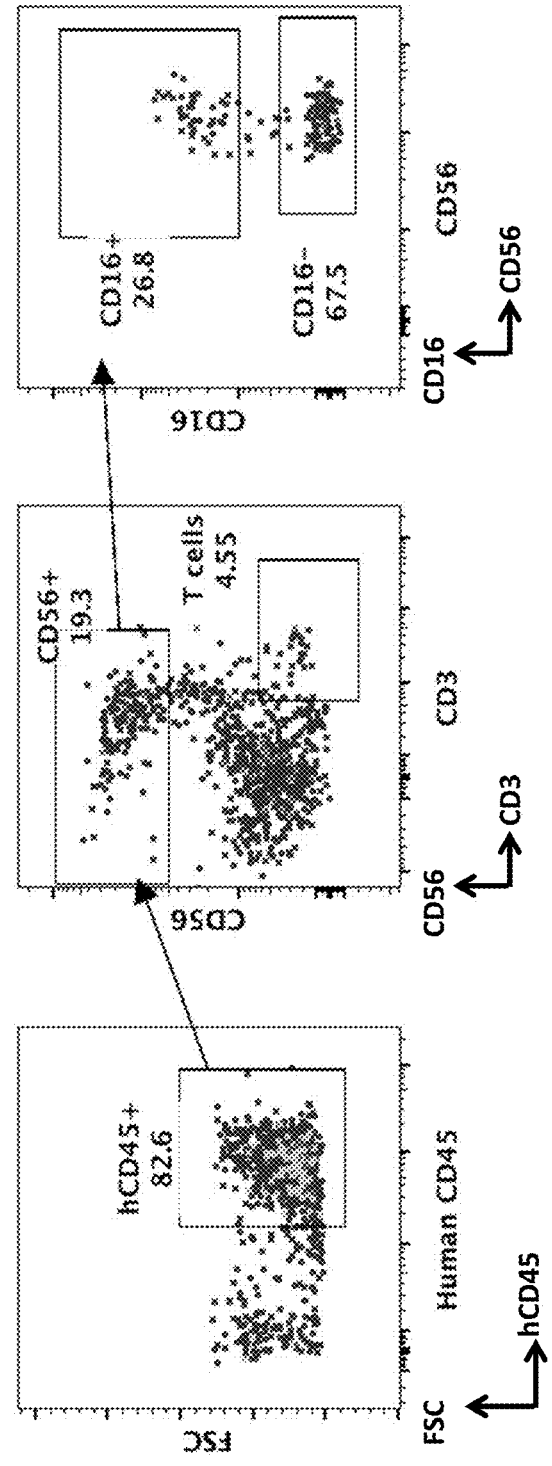
FIGS. 20A and 20B provides plots and graphs demonstrating the presence of discernible Peyer's Patches containing predominantly hCD45+ cells in SRG-15 mice (mouse 2).
Figure 20B:
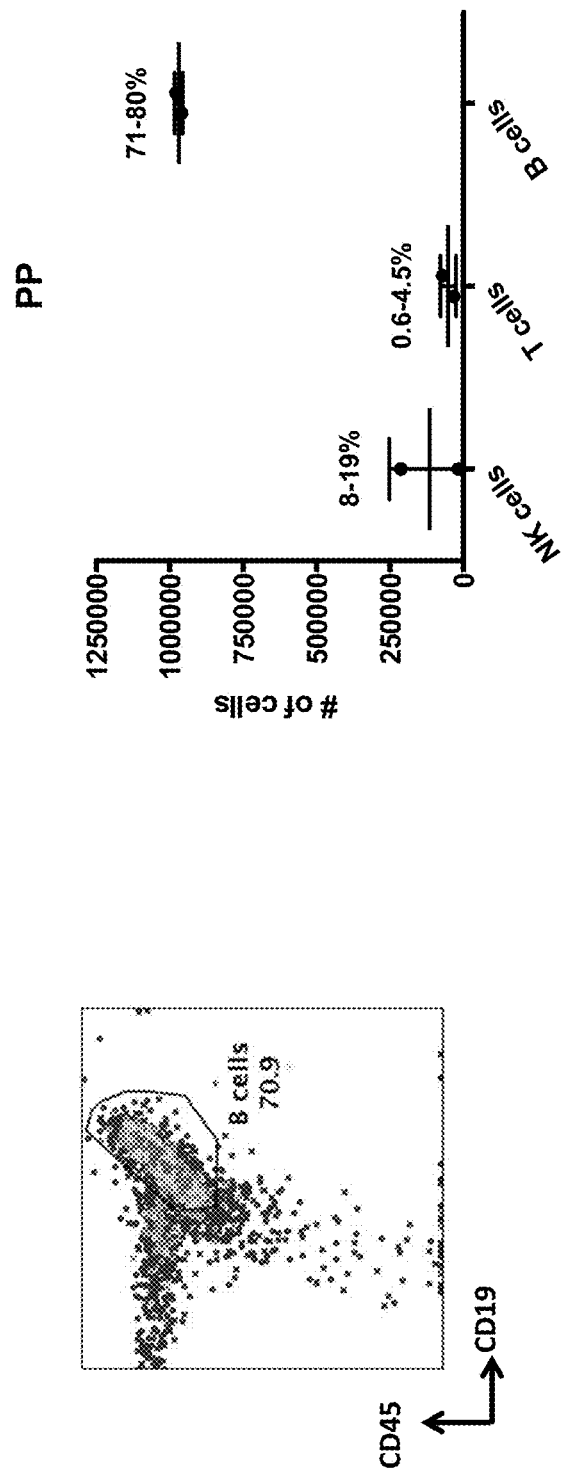

As discussed above with respect to FIGS. 18A and 18B, in SRG-15 engrafted mouse 2, greater gut-associated lymphoid tissue (GALT) resident intraepithelial human lymphocyte reconstitution (IELs) was observed compared to SRG mice (FIGS. 19A and 19C). Interestingly, the majority of the human lymphocytes observed were human NK cells. As expected for normal human GALT physiology, the majority of of NK cells in the SRG-15 mouse 2 in both blood and spleen were cytotoxic NK cells (CD16+), while in IEL, there was a comparable distribution of CD16+ versus CD16− NK cells (FIG. 19B). There were no changes in the number of lamina propria lymphocytes between the engrafted SRG and SRG-15 mice (FIG. 19C). Unlike engrafted SRG-15 mouse 1, in engrafted SRG-15 mouse 2 a greater proportion of human CD3+ CD8+ IELs expressed human CD103 marker. Peyer's patches were completely absent in SRG mice but they were present in the SRG-15 mouse 2 and were populated with human lymphocytes as shown in FIGS. 20A and 20B.

Example 5: Determining the Functional Role of Human Tissue-Resident T Cells in SRG-15 Mice During Viral Infections To test whether tissue-resident T cells in SRG-15 mice have a functional relevance during homeostasis, it was determined whether the increased number of human CD8+ IELs in SRG-15 mice induces characteristic changes in the composition of the mouse gut microbiota.

Materials and Methods

Neonate mice are irradiated sub-lethally without anesthesia 3-5 days post birth with 160 cGy and returned to their mothers for rest. 4-12 hours post irradiation these neonates are transplanted with CD34+ huHSCs in 25 μl PBS intrahepatically (i.h.) using a 30 G needle.

Figure 21A:
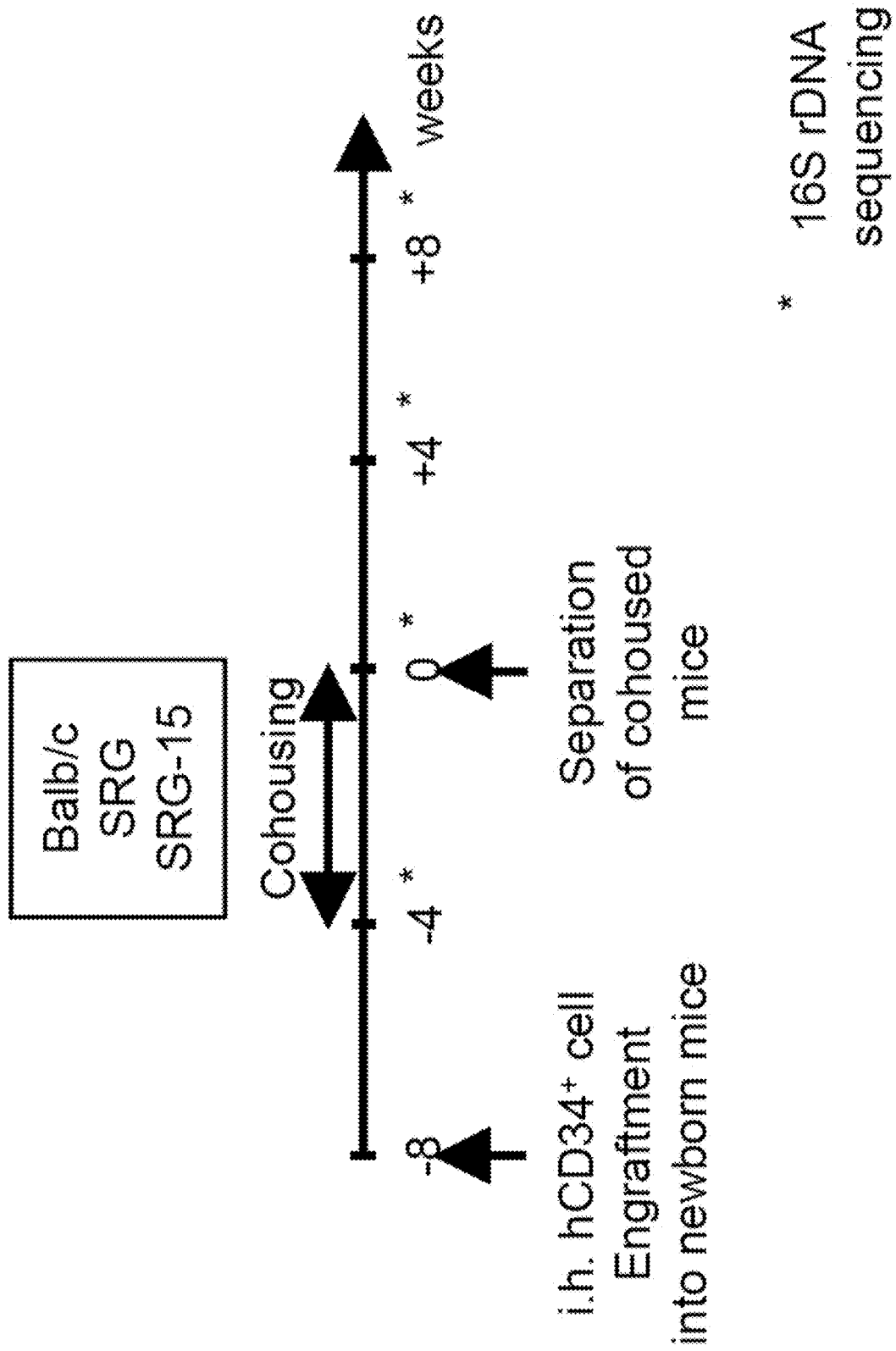
FIG. 21A provides a timeline for cohousing and feces sample collection for gut microbiota sequencing.

Four weeks post engraftment, SRG-15 mice were cohoused for four weeks with SRG and donor Balb/c mice to equalize the gut microbiota between the different strains. The mice were then separated and fecal samples were collected and analyzed by 16S rRNA sequencing. FIG. 21A provides a timeline for cohousing and feces sample collection for gut microbiota sequencing.

Results

Figure 22:
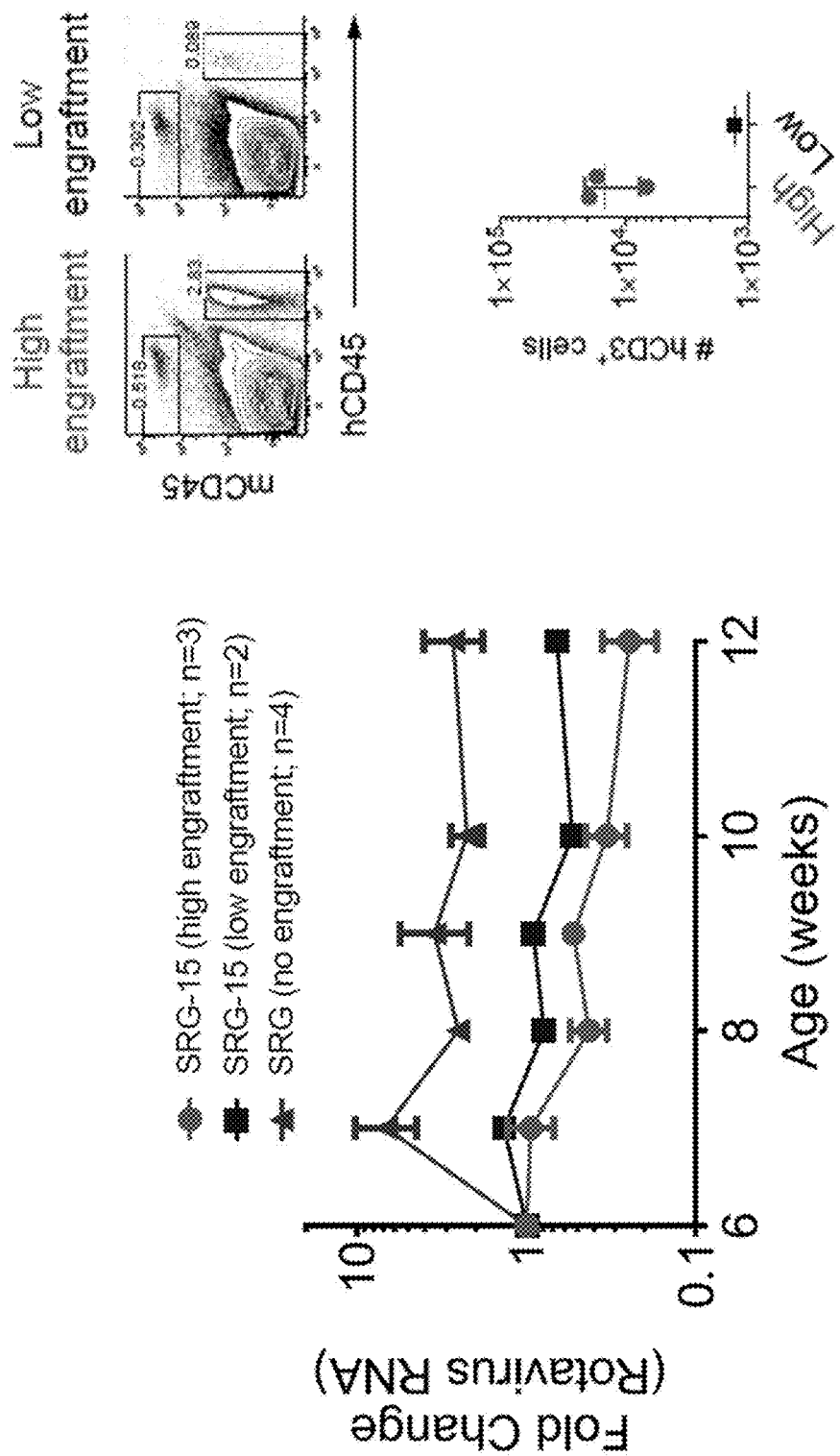
FIG. 22 illustrates the functional relevance of human tissue-resident T cells in SRG-15 mice. More specifically, FIG. 22 provides a graph demonstrating the functional relevance of human IELs in clearing acute rotavirus infection.

As illustrated in 21B, for mouse 1, the results show that there were no significant changes between engrafted SRG-15 and SRG mice after cohousing, indicating that the developing human CD8+ IELs do not induce major changes during steady state conditions. Additional experiments were conducted to determine whether CD8+ IELs, which are sufficient to clear acute rotavirus infection, can clear rotavirus infection in engrafted SRG-15 mice. As shown in FIG. 22, the results indicated that acute rotavirus infection can be cleared in engrafted SRG-15 mice but not in non-engrafted SRG mice.

Example 6: Analysis of NK Cell Subsets in SRG-15 Mice (Mouse 2) and Humans

NK cell subsets in SRG-15 (mouse 2) mice were characterized for various phenotypic markers and compared with humans.

Materials and Methods

NK cell subsets were detected via Cytometry by Time-of-Flight (CyTOF), as described generally in Yao et al. *J. of Immunological Methods* 415 (2014) 1-5, and analyzed using ViSNE (el-AD et al. *Nat. Biotechnol.* 2013 June; 31(6):545-52doi: 10.1038/nbt.2594. Epub 2013 May 19.

Results

FIG. 23A provides ViSNE plots showing CyTOF-based analysis of 33 parameters of $CD56^{bright}$ $CD16^-$ and $CD56^{dim}$ $CD16^+$ NK cell subsets in humans (n=20) and SRG-15 mice (mouse 2) (n=9). Each dot represents a single cell.

Figure 23B:
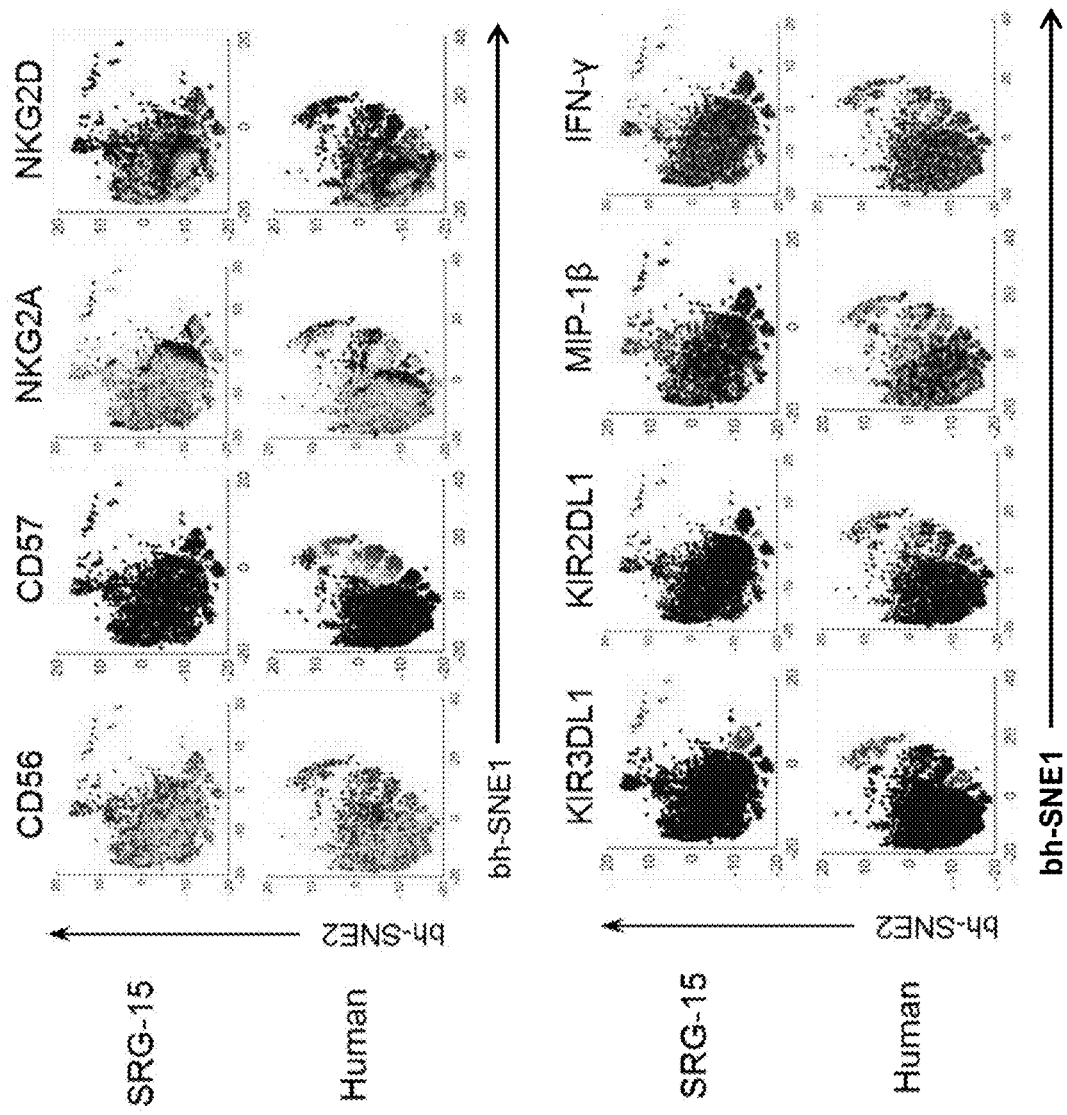
FIG. 23B provides ViSNE plots showing the expression intensity of eight selected markers on $CD56^{bright}$ $CD16^-$ NK cells in humans (n=20) and SRG-15 mice (mouse 2) (n=9).

FIG. 23B provides ViSNE plots showing the expression intensity of eight selected markers on $CD56^{bright}$ $CD16^-$ NK cells in humans (n=20) and SRG-15 mice (mouse 2) (n=9).

Figure 23C:
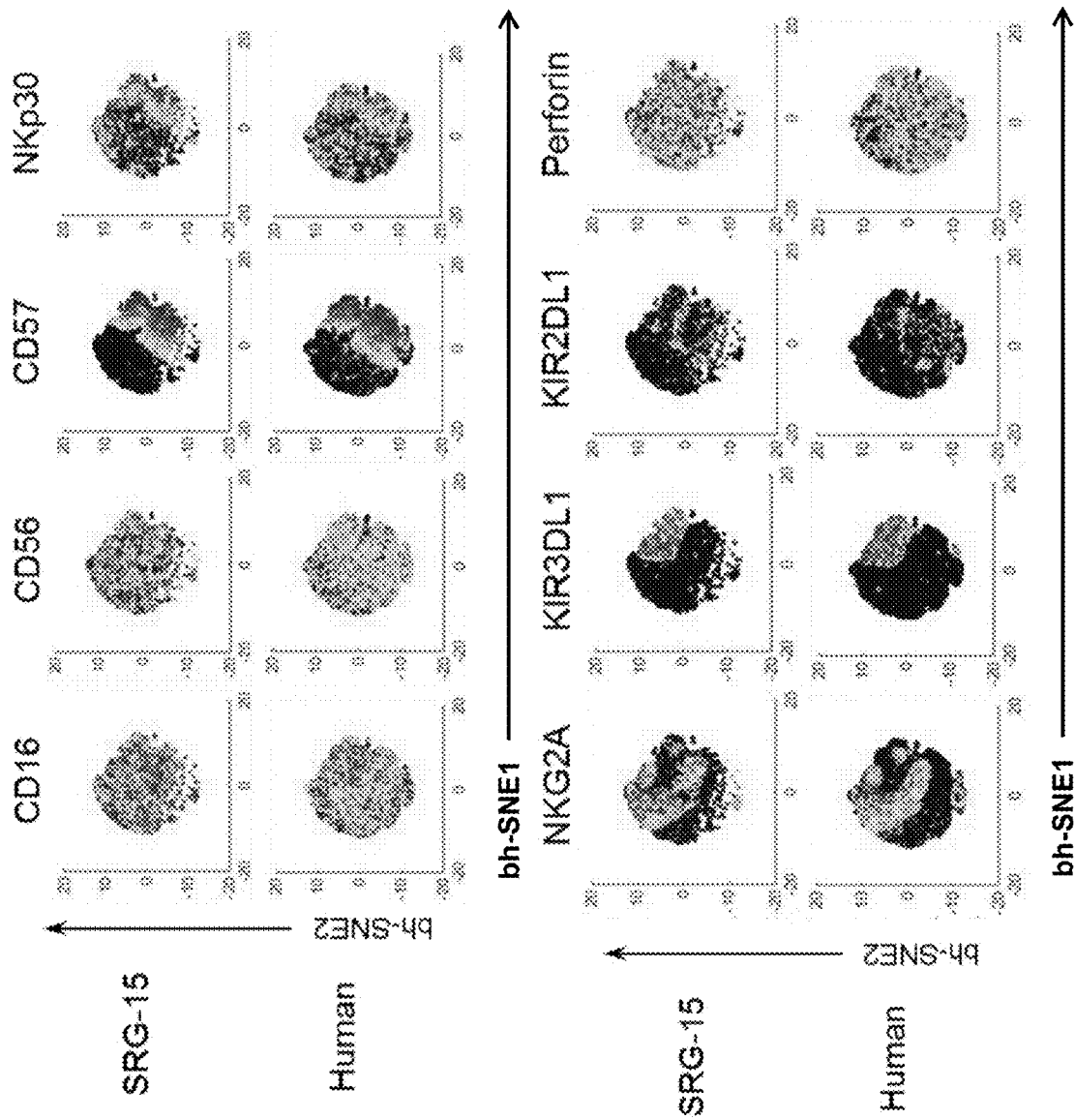
FIG. 23C ViSNE plots showing the expression intensity of eight selected markers on $CD56^{dim}$ $CD16^+$ NK cells in humans (n=20) and SRG-15 mice (n=9).

FIG. 23C ViSNE plots showing the expression intensity of eight selected markers on $CD56^{dim}$ $CD16^+$ NK cells in humans (n=20) and SRG-15 mice (n=9). This multi-dimensional single-cell analysis of 33 key molecules of human NK cells indicate that the human NK cells that develop in SRG-15 mice are highly comparable to human NK cells in healthy individuals.

Example 7: Cytotoxic Capacity of NK Cells from SRG-15 Mice

Materials and Methods

For in vitro NK cytotoxicity studies, isolated splenic NK cells from human HSC-engrafted SRG and SRG-15 mice (mouse 2) were treated overnight with human IL-2. The next day, NK cells were cultured with CFSE-labeled, NK-susceptible K562 target cells at varying effector to target ratios (E:T). After 5 hr co-culture, killing of K562 cells was measured by FACS analysis of viability dye Topro3 uptake by K562 cells (gated on CFSE+ cells to distinguish K562 and then analysis of percent positive for Topro3).

Additionally, for in vitro antibody-dependent cellular cytotoxicity (ADCC) studies, isolated splenic NK cells from human HSC-engrafted SRG and SRG-15 mice were treated overnight with human IL-2. The next day, NK cells were cultured with CFSE-labeled Raji target cells at varying effector to target ratios (E:T). Raji cells were pre-treated with anti-CD20 (Rituximab) or control IgG. After 5 hr co-culture, killing of Raji cells was measured by FACS analysis of viability dye Topro3 uptake by Raji cells (gated on CFSE+ cells and then analysis of percent positive for Topro3).

For in vivo NK cell activation studies, human HSC-engrafted SRG and SRG-15 mice (mouse 2) were injected intra-peritoneally with 50 μg poly IC. Mice were pre-bled (before poly IC injection) and 18 hours after poly IC injection. Human CD45+ NKp46+ (NK cells) were analyzed for activation marker CD69 expression by FACS pre- and post-poly IC administration.

Results

Figure 24A:
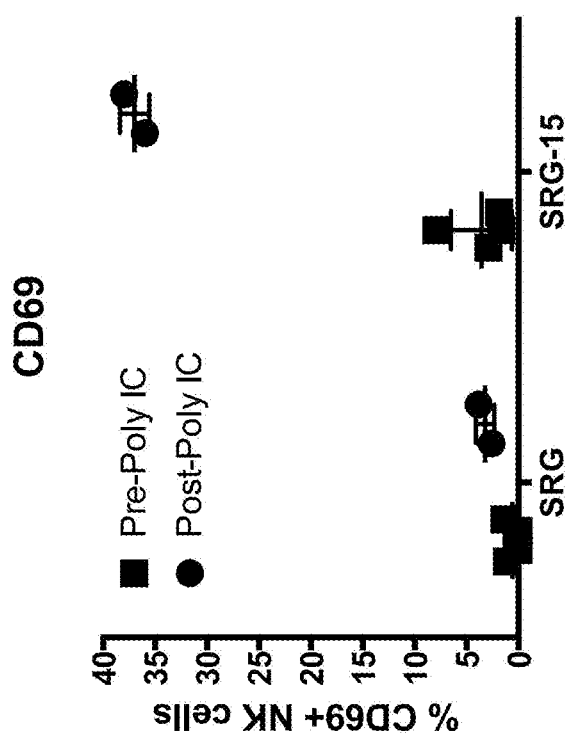
FIG. 24A provides a graph showing the percentage of blood NK cells in SRG vs SRG-15 (mouse 2) mice that are CD69+ before and after poly-IC injection.
Figure 24C:
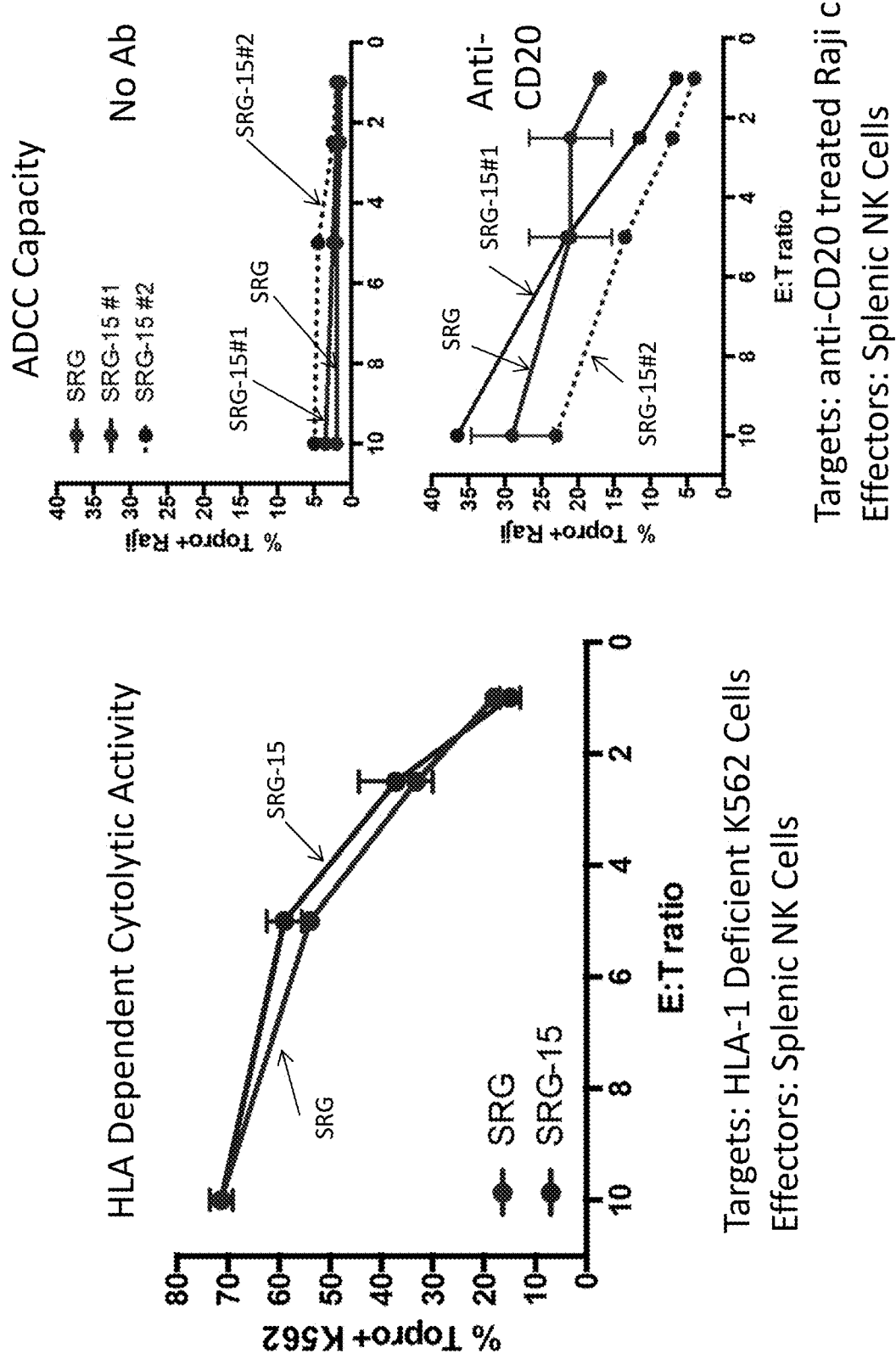
FIG. 24C provides graphs showing the cytolytic capacity of splenic NK cells from SRG and SRG-15 (mouse 2) mice either against HLA class I deficient K562 cells (left) or against Raji cells in the absence (top right) or the presence (bottom right) of anti-CD20 antibody. SRG-15 #1 and SRG-15 #2 represent two different NK cell preparations from SRG-15 (mouse 2) littermates.

In a classical NK cytotoxicity study, classical NK target HLA class I deficient K562 cells were subject to killing by activated NK cells from SRG or SRG-15 mice (mouse 2). As shown in FIG. 24C (left) splenic NK cells from SRG and SRG-15 mice showed comparable cytolytic capacity with respect to K562 cells when normalized for number.

NK cells are typically responsible for anti-CD20 antibody mediated ADCC against B cell leukemias and lymphomas (see, e.g., J. Golay et al. *Haematologica* 2003; 88:1002-12). In order to demonstrate the ability of NK cells from SRG-15 engrafted mice to facilitate anti-CD20 mediated ADCC, splenic NK cells from both SRG and SRG-15 mice were tested and shown to exhibit comparable antibody-dependent cellular toxicity (ADCC) activity against anti-CD20 treated Raji cells when normalized for cell number (FIG. 24C (right)).

Figure 8:
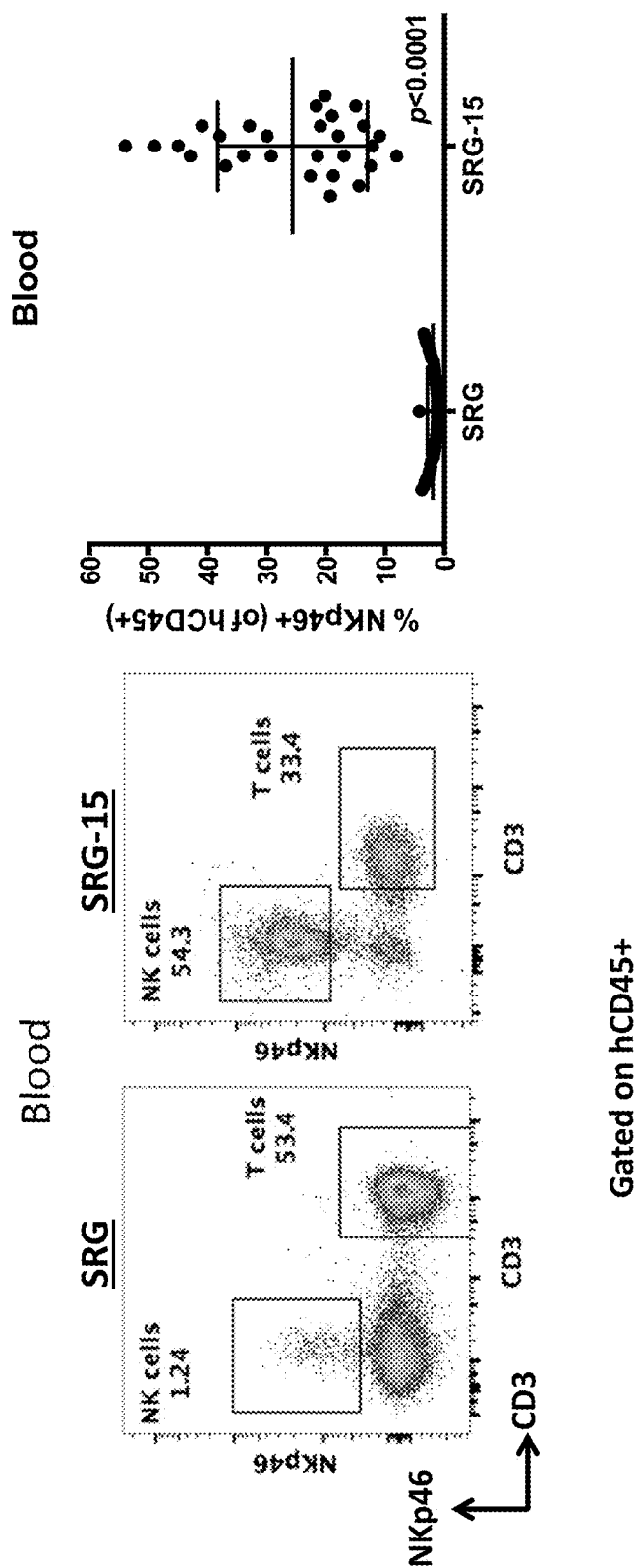
FIG. 8 provides plots (left) showing human T and NK cell distribution in SRG and SRG-15 (mouse 2) mice in blood (gated on human CD45+ cells (hematopoietic cells) and NKp46+ cells (NK cells); and a graph (right) showing the percentage of the hCD45+ cells that are NKp46+ cells in the blood of engrafted SRG-15 mice.

As depicted, e.g., in FIGS. 8 and 9, there is a significant upregulation of NK cells in both spleen and blood of SRG-15 animals. The capacity for activation of NK cells in SRG-15 mice was tested by measuring CD69 marker activation after a poly-IC injection. As shown in FIG. 24A, the percentage of NK cells positive for the activation marker CD69 was increased in SRG-15 mice relative to SRG mice. As SRG-15 NK cells were shown to mediate ADCC comparable to SRG NK cells in vitro under normalized conditions, the ability of SRG-15 NK cells to exhibit a greater activated phenotype in vivo, as well as greater numbers of NK cells in SRG-15 mice, suggests that SRG-15 mice may be a suitable in vivo model to study human NK cell ADCC.

Example 8: IFNγ Production from SRG and SRG-15 Derived NK Cells

Materials and Methods

NK cells were isolated from pooled splenocytes of SRG or SRG-15 mice (3 spleens per group) and NK cells were isolated using EasySep Human NK enrichment kit (StemCell Technologies; Cat #19055).

NK cells were also isolated from healthy human PBMCs. NK cells were treated overnight with 10 ng/mL human IL-2. The next day, cells were stimulated overnight with 10 ng/mL human IL-12p70 or 2 mg/mL poly I:C or left untreated. The next day, supernatant was harvested and IFNg levels assessed using Human IFNg Quantikine ELISA kit (R&D systems; Cat #DIF50). NK cell purity was analyzed by FACS and IFNg levels normalized as picograms (pg) produced by individual NK cells. Statistical analysis was performed using ANOVA test.

Results

As shown in FIG. 24B, SRG and SRG-15 derived NK cells have comparable IFNγ secretion, but less than human PBMC-derived NK cells upon IL-12p70 treatment.

Example 9: Human NK Cells Inhibit Tumor Growth in SRG-15 Mice

The ability of human NK cells to infiltrate human tumor xenografts and inhibit tumor growth in SRG-15 mice (mouse 2) was tested.

Materials and Methods

Rituximab was injected i.p. every other day (started at day 14 post s.c. injection of 5 million Raji cells). Tumor growth was assessed by caliper measurement and the volume was calculated using the following formula: tumor volume=0.5× (length×width^2). Data were pooled from 2 independent experiments. Statistical analysis was performed using unpaired, two-tailed Mann-Whitney U-test comparing engrafted, untreated SRG-15 and engrafted, RTX-treated SRG-15 mice ($*P<0.05$).

The s.c. tumor was crushed and digested using Collagenase D (1 hour, 37 C). The recovered cells, including tumor and immune cells were analyzed by an LSRII flow cytometer.

Results

Figure 25B:
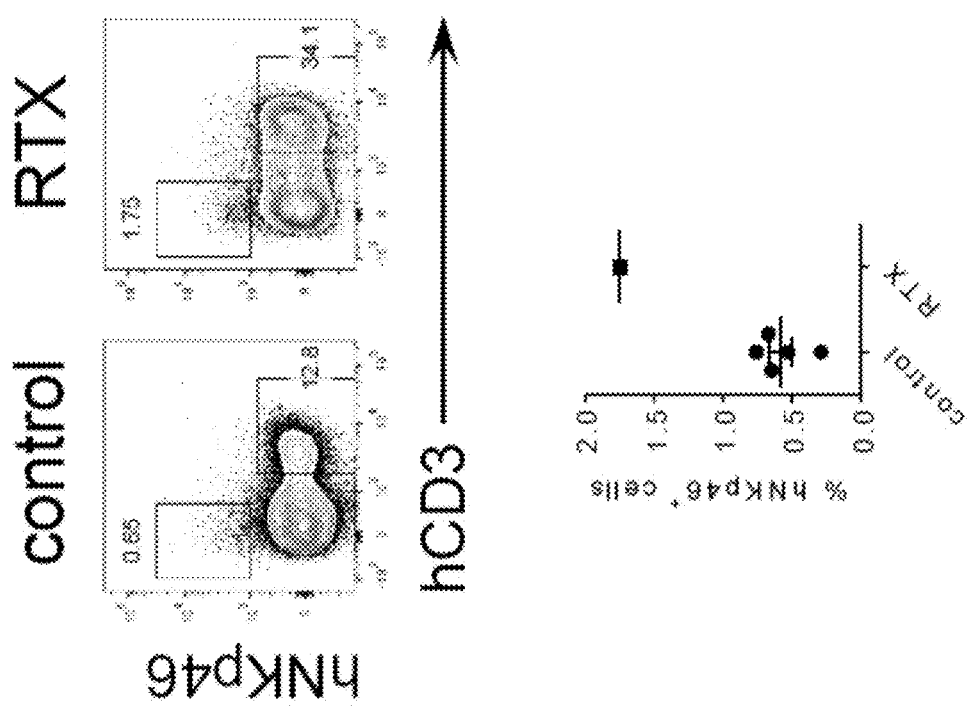
FIG. 25B provides plots and a graph showing the frequency of human NK cells and T cells in human tumor xenografts of untreated (n=5) and RTX-treated SRG-15 mice (n=1). All data are shown as mean±s.e.m. Statistical analyses were performed using unpaired, two-tailed Mann-Whitney U-test (***P<0.001).
Figure 25C:
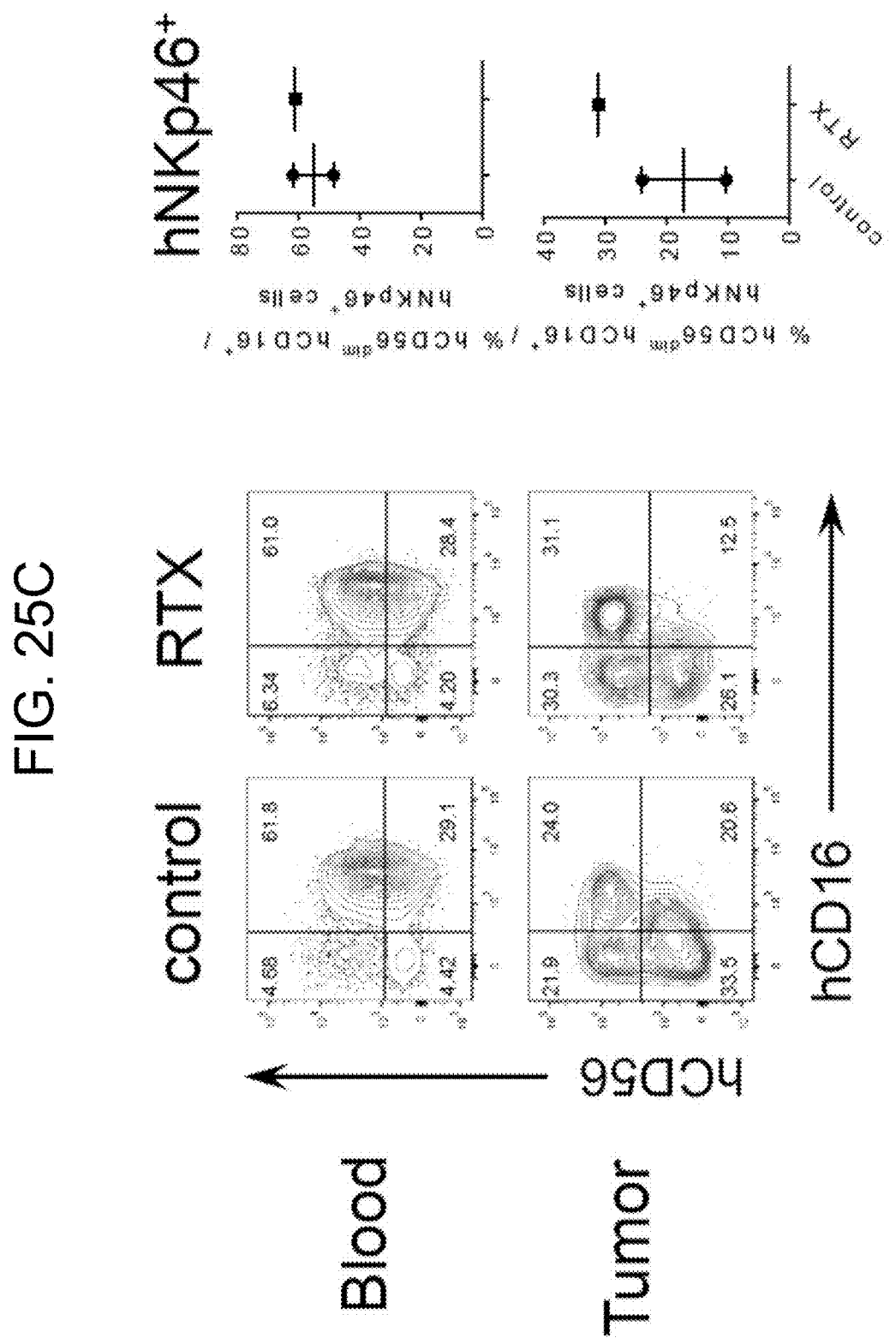
FIG. 25C provides plots and graphs showing human NK cell subsets in the blood and tumor of untreated (n=2) and RTX-treated SRG-15 mice (n=1). All data are shown as mean±s.e.m. Statistical analyses were performed using unpaired, two-tailed Mann-Whitney U-test (***P<0.001).

As shown in FIG. 25A, human NK cells in SRG-15 mice inhibit tumor growth following treatment with rituximab (RTX). FIG. 25B, shows the frequency of human NK cells and T cells in human tumor xenografts of untreated (n=5) and RTX-treated SRG-15 mice (n=1). FIG. 25C, shows human NK cell subsets in the blood and tumor of untreated (n=2) and RTX-treated SRG-15 mice (n=1).

Example 10: Additional Materials and Methods Utilized in Connection with the Above Examples Human $CD34^+$ cell isolation and injection. Human $CD34^+$ cell isolation and injection was performed according to the methods described, for example, in Rongvaux A, Willinger T, Martinek J et al. *Nat Biotechnol* 2014; 32:364-372.

Flow cytometric analysis of human cell populations. Flow cytometric analysis of human cell populations was performed as described in Strowig T, Rongvaux A, Rathinam C et al. *Proc Natl Acad Sci USA* 2011; 108:13218-13223, and in Rongvaux A, Willinger T, Martinek J et al. *Nat Biotechnol* 2014; 32:364-372.

Histology. Tissue was fixed overnight in 4% paraformaldehyde, transferred to 70% ethanol and embedded in paraffin.

Quantitative RT-PCR. Quantitative RT-PCR was performed as described in Rongvaux A, Willinger T, Martinek J et al. *Nat Biotechnol* 2014; 32:364-372.

16S rRNA sequencing. 16S rRNA sequencing was performed as described in Palm N W, de Zoete M R, Cullen T W et al. *Cell* 2014; 158:1000-1010.

Viral infections. Rotavirus and influenza virus were obtained and applied in the subject methods.

Statistical analysis. Statistical significance was performed with Prism 6 software (GraphPad), using two-tailed unpaired Student's t-test.

FACS antibodies were obtained BD Biosciences and BioLegend.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

Additional Sequence Information

```
LOCUS       NM_001040022 4201 bp mRNA linear PRI 15-MAR-2015
DEFINITION  Homo sapiens signal-regulatory protein alpha (SIRPA),
            transcript variant 1, mRNA.
ACCESSION   NM_001040022
VERSION     NM_001040022.1 GI:91105763
SOURCE      Homo sapiens (human)
[SEQ ID NO: 11]
   1 tccggcccgc acccacccc aagagggggcc ttcagctttg gggctcagag gcacgacctc
  61 ctggggaggg ttaaaaggca gacgcccccc cgcccccgc gccccgcgc cccgactcct
 121 tcgccgcctc cagcctctcg ccagtgggaa gcggggagca gccgcgcggc cggagtccgg
 181 aggcgagggg aggtcggccg caacttcccc ggtccacctt aagaggacga tgtagccagc
 241 tcgcagcgct gaccttagaa aaacaagttt gcgcaaagtg gagcggggac ccggcctctg
 301 ggcagccccg gcggcgcttc cagtgccttc cagccctcgc gggcggcgca gccgcggccc
 361 atggagcccg ccggcccggc cccggccgc ctcgggccgc tgctctgcct gctgctcgcc
 421 gcgtcctgcg cctggtcagg agtggcgggt gaggaggagc tgcaggtgat tcagcctgac
 481 aagtccgtgt tggttgcagc tggagagaca gccactctgc gctgcactgc gacctctctg
 541 atccctgtgg ggcccatcca gtggttcaga ggagctggac caggccggga attaatctac
 601 aatcaaaaag aaggccactt cccccgggta caactgtttt cagacctcac aaagagaaac
 661 aacatggact tttccatccg catcggtaac atcaccccag cagatgccgg cacctactac
 721 tgtgtgaagt tccggaaagg gagccccgat gacgtggagt ttaagtctgg agcaggcact
 781 gagctgtctg tgcgcgccaa accctctgcc cccgtggtat cgggccctgc ggcgagggcc
 841 acacctcagc acacagtgag cttcacctgc gagtcccacg gcttctcacc cagagacatc
 901 accctgaaat ggttcaaaaa tgggaatgag ctctcagact ccagaccaa cgtggacccc
 961 gtaggagaga gcgtgtccta cagcatccac agcacagcca aggtggtgct gacccgcgag
1021 gacgttcact ctcaagtcat ctgcgaggtg gcccacgtca ccttgcaggg ggaccctctt
1081 cgtgggactg ccaacttgtc tgagaccatc cgagttccac ccaccttgga ggttactcaa
1141 cagcccgtga gggcagagaa ccaggtgaat gtcacctgcc aggtgaggaa gttctacccc
1201 cagagactac agctgacctg gttggagaat ggaaacgtgt cccggacaga aacggcctca
1261 accgttacag agaacaagga tggtacctac aactggatga gctggctcct ggtgaatgta
1321 tctgcccaca gggatgatgt gaagctcacc tgccaggtgg agcatgacgg gcagccagcg
1381 gtcagcaaaa gccatgacct gaaggtctca gcccacccga aggagcaggg ctcaaatacc
1441 gccgctgaga acactggatc taatgaacgg aacatctata ttgtggtggg tgtggtgtgc
1501 accttgctgg tggccctact gatggcggcc ctctacctcg tccgaatcag acagaagaaa
1561 gcccagggct ccacttcttc tacaaggttg catgagcccg agaagaatgc cagagaaata
1621 acacaggaca caaatgatat cacatatgca gacctgaacc tgcccaaggg gaagaagcct
1681 gctccccagg ctgcggagcc caacaaccac acggagtatg ccagcattca gaccagcccg
1741 cagcccgcgt cggaggacac cctcacctat gctgacctgg acatggtcca cctcaaccgg
1801 accccaagc agccggcccc caagcctgag ccgtccttct cagagtacgc cagcgtccag
1861 gtccccgagga agtgaatggg accgtggttt gctctagcac ccatctctac gcgctttctt
1921 gtcccacagg gagccgccgt gatgagcaca gccaacccag ttcccggagg gctggggcgg
```

```
1981   tgcaggctct gggacccagg ggccagggtg gctcttctct ccccacccct ccttggctct
2041   ccagcacttc ctgggcagcc acggccccct cccccacat  tgccacatac ctggaggctg
2101   acgttgccaa accagccagg gaaccaacct gggaagtggc cagaactgcc tggggtccaa
2161   gaactcttgt gcctccgtcc atcaccatgt gggttttgaa gaccctcgac tgcctccccg
2221   atgctccgaa gcctgatctt ccagggtggg gaggagaaaa tcccacctcc cctgacctcc
2281   accacctcca ccaccaccac caccaccacc accaccacta ccaccaccac ccaactgggg
2341   ctagagtggg gaagatttcc cctttagatc aaactgcccc ttccatggaa aagctggaaa
2401   aaaactctgg aacccatatc caggcttggt gaggttgctg ccaacagtcc tggcctcccc
2461   catccctagg ctaaagagcc atgagtcctg gaggaggaga ggacccctcc caaaggactg
2521   gagacaaaac cctctgcttc cttgggtccc tccaagactc cctggggccc aactgtgttg
2581   ctccacccgg acccatctct cccttctaga cctgagcttg cccctccagc tagcactaag
2641   caacatctcg ctgtggacgc ctgtaaatta ctgagaaatg tgaaacgtgc aatcttgaaa
2701   ctgaggtgtt agaaaacttg atctgtggtg ttttgttttg ttttttttct taaaacaaca
2761   gcaacgtgat cttggctgtc tgtcatgtgt tgaagtccat ggttgggtct tgtgaagtct
2821   gaggtttaac agtttgttgt cctggaggga ttttcttaca gcgaagactt gagttcctcc
2881   aagtcccaga accccaagaa tgggcaagaa ggatcaggtc agccactccc tggagacaca
2941   gccttctggc tgggactgac ttggccatgt tctcagctga gccacgcggc tggtagtgca
3001   gccttctgtg accccgctgt ggtaagtcca gcctgcccag ggctgctgag ggctgcctct
3061   tgacagtgca gtcttatcga gacccaatgc ctcagtctgc tcatccgtaa agtggggata
3121   gtgaagatga caccctcccc caccacctct cataagcact ttaggaacac acagagggta
3181   gggatagtgg ccctggccgt ctatcctacc cctttagtga ccgccccat  cccggctttc
3241   tgagctgatc cttgaagaag aaatcttcca tttctgctct caaaccctac tgggatcaaa
3301   ctggaataaa ttgaagacag ccagggggat ggtgcagctg tgaagctcgg gctgattccc
3361   cctctgtccc agaaggttgg ccagagggtg tgacccagtt acccttaac  ccccacccctt
3421   ccagtcgggt gtgagggcct gaccgggccc agggcaagca gatgtcgcaa gccctattta
3481   ttcagtcttc actataactc ttagagttga gacgctaatg ttcatgactc ctggccttgg
3541   gatgcccaag ggatttctgg ctcaggctgt aaaagtagct gagccatcct gcccattcct
3601   ggaggtccta caggtgaaac tgcaggagct cagcatagac ccagctctct gggggatggt
3661   cacctggtga tttcaatgat ggcatccagg aattagctga gccaacagac catgtggaca
3721   gctttggcca gagctcccgt gtggcatctg ggagccacag tgacccagcc acctggctca
3781   ggctagttcc aaattccaaa agattggctt gtaaaccttc gtctccctct cttttaccca
3841   gagacagcac atacgtgtgc acacgcatgc acacacacat tcagtatttt aaaagaatgt
3901   tttcttggtg ccatttcat  tttattttat ttttaattc  ttggaggggg aaataaggga
3961   ataaggccaa ggaagatgta tagctttagc tttagcctgg caacctggag aatccacata
4021   ccttgtgtat tgaaccccag gaaaaggaag aggtcgaacc aaccctgcgg aaggagcatg
4081   gtttcaggag tttattttaa gactgctggg aaggaaacag gccccatttt gtatatagtt
4141   gcaacttaaa cttttggct  tgcaaaatat ttttgtaata aagatttctg ggtaataatg
4201   a
```

[SEQ ID NO: 12]
Translation = MEPAGPAPGRLGPLLCLLLAASCAWSGVAGEEELQVIQPDKSVL
VAAGETATLRCTATSLIPVGPIQWFRGAGPGRELIYNQKEGHFPRVTTVSDLTKRNNM
DFSIRIGNITPADAGTYYCVKFRKGSPDDVEEKSGAGTELSVRAKPSAPVVSGPAARA
TPQHTVSFTCESHGFSPRDITLKWFKNGNELSDFQTNVDPVGESVSYSIHSTAKVVLT
REDVHSQVICEVAHVTLQGDPLRGTANLSETIRVPPTLEVTQQPVRAENQVNVTCQVR
KFYPQRLQLTWLENGNVSRTETASTVTENKDGTYNWMSWLLVNVSAHRDDVKLTCQVE
HDGQPAVSKSHDLKVSAHPKEQGSNTAAENTGSNERNIYIVVGVVCTLLVALLMAALY
LVRIRQKKAQGSTSSTRLHEPEKNAREITQDTNDITYADLNLPKGKKPAPQAAEPNNH
TEYASIQTSPQPASEDTLTYADLDMVELNRTPKQPAPKPEPSFSEYASVQVPRK LOCUS        NM_001040023 4109 bp mRNA linear PRI 15-MAR-2015

DEFINITION   *Homo sapiens* signal-regulatory protein alpha (SIRPA),
             Transcript variant 2, mRNA.

ACCESSION    NM_001040023

VERSION      NM_001040023.1 GI:91105766

SOURCE       *Homo sapiens* (human)

[SEQ ID NO: 13]
```
   1 ctctctggcc gccctggct ttatttctcg cgcgcttggg gtctctccca gtctccgtct
  61 ctccatttct cctgggggc ggggaggggg ggtctccaaa aaccgcggcg gcggcggcgg
 121 ccgctccagg cgcccgttcc ggagtcgggg ggaggcccag ccgggagggg ggaaggggg
 181 gagccttagt catttccccg ctccagcctg ctcccgcccg agcgcgcact cacggccgct
 241 ctccctcctc gctccgcagc cgcggcccat ggagcccgcc ggcccggccc cggccgcct
 301 cgggccgctg ctctgcctgc tgctcgccgc gtcctgcgcc tggtcaggag tggcgggtga
 361 ggaggagctg caggtgattc agcctgacaa gtccgtgttg gttgcagctg gagagacagc
 421 cactctgcgc tgcactgcga cctctctgat ccctgtgggg cccatccagt ggttcagagg
 481 agctggacca ggccgggaat taatctcaa tcaaaaagaa ggccacttcc ccgggtaac
 541 aactgtttca gacctcacaa agagaaacaa catggacttt tccatccgca tcggtaacat
 601 cacccagca gatgccggca cctactactg tgtgaagttc cggaaaggga gccccgatga
 661 cgtggagttt aagtctggag caggcactga gctgtctgtg cgcgccaaac cctctgcccc
 721 cgtggtatcg ggccctgcgg cgagggccac acctcagcac acagtgagct tcacctgcga
 781 gtcccacggc ttctcacccca gagacatcac cctgaaatgg ttcaaaaatg gaatgagct
 841 ctcagacttc cagaccaacg tggaccccgt aggagagagc gtgtcctaca gcatccacag
 901 cacagccaag gtggtgctga cccgcgagga cgttcactct caagtcatct gcgaggtggc
 961 ccacgtcacc ttgcagggg accctcttcg tgggactgcc aacttgtctg agaccatccg
1021 agttccaccc accttggagg ttactcaaca gcccgtgagg gcagagaacc aggtgaatgt
1081 cacctgccag gtgaggaagt tctaccccca gagactacag ctgacctggt tggagaatgg
1141 aaacgtgtcc cggacagaaa cggcctcaac cgttacagag aacaaggatg tacctacaa
1201 ctggatgagc tggctcctgg tgaatgtatc tgcccacagg atgatgtga agctcacctg
1261 ccaggtggag catgacgggc agccagcggt cagcaaaagc catgacctga aggtctcagc
1321 ccacccgaag gagcagggct caaataccgc cgctgagaac actggatcta atgaacggaa
1381 catctatatt gtggtgggtg tggtgtgcac cttgctggtg ccctactga tggcggccct
1441 ctacctcgtc cgaatcagac agaagaaagc ccagggctcc acttcttcta caaggttgca
1501 tgagcccgag aagaatgcca gagaaataac acaggacaca atgatatca catatgcaga
1561 cctgaacctg cccaagggga agaagcctgc tccccaggct gcggagccca acaaccacac
1621 ggagtatgcc agcattcaga ccagcccgca gccgcgtcg gaggacaccc tcacctatgc
```

```
1681  tgacctggac atggtccacc tcaaccggac ccccaagcag ccggccccca agcctgagcc
1741  gtccttctca gagtacgcca gcgtccaggt cccgaggaag tgaatgggac cgtggtttgc
1801  tctagcaccc atctctacgc gctttcttgt cccacaggga gccgccgtga tgagcacagc
1861  caacccagtt cccggagggc tggggcggtg caggctctgg gacccagggg ccagggtggc
1921  tcttctctcc ccacccctcc ttggctctcc agcacttcct gggcagccac ggccccctcc
1981  ccccacattg ccacatacct ggaggctgac gttgccaaac cagccaggga accaacctgg
2041  gaagtggcca gaactgcctg gggtccaaga actcttgtgc ctccgtccat caccatgtgg
2101  gttttgaaga ccctcgactg cctccccgat gctccgaagc ctgatcttcc agggtgggga
2161  ggagaaaatc ccacctcccc tgacctccac cacctccacc accaccacca ccaccaccac
2221  caccactacc accaccaccc aactgggggct agagtgggga agatttcccc tttagatcaa
2281  actgcccctt ccatggaaaa gctggaaaaa aactctggaa cccatatcca ggcttggtga
2341  ggttgctgcc aacagtcctg gcctccccca tccctaggct aaagagccat gagtcctgga
2401  ggaggagagg acccctccca aaggactgga gacaaaaccc tctgcttcct tgggtccctc
2461  caagactccc tggggcccaa ctgtgttgct ccacccggac ccatctctcc cttctagacc
2521  tgagcttgcc cctccagcta gcactaagca acatctcgct gtggacgcct gtaaattact
2581  gagaaatgtg aaacgtgcaa tcttgaaact gaggtgttag aaaacttgat ctgtggtgtt
2641  ttgttttgtt tttttctta aaacaacagc aacgtgatct tggctgtctg tcatgtgttg
2701  aagtccatgg ttgggtcttg tgaagtctga ggtttaacag tttgttgtcc tggagggatt
2761  ttcttacagc gaagacttga gttcctccaa gtcccagaac cccaagaatg ggcaagaagg
2821  atcaggtcag ccactccctg gagacacagc cttctggctg ggactgactt ggccatgttc
2881  tcagctgagc cacgcggctg gtagtgcagc cttctgtgac cccgctgtgg taagtccagc
2941  ctgcccaggg ctgctgaggg ctgcctcttg acagtgcagt cttatcgaga cccaatgcct
3001  cagtctgctc atccgtaaag tggggatagt gaagatgaca cccctcccca ccacctctca
3061  taagcacttt aggaacacac agagggtagg gatagtggcc ctggccgtct atcctacccc
3121  tttagtgacc gcccccatcc cggctttctg agctgatcct tgaagaagaa atcttccatt
3181  tctgctctca aaccctactg ggatcaaact ggaataaatt gaagacagcc aggggatgg
3241  tgcagctgtg aagctcgggc tgattccccc tctgtcccag aaggttggcc agagggtgtg
3301  acccagttac cctttaaccc ccacccttcc agtcgggtgt gagggcctga ccgggcccag
3361  ggcaagcaga tgtcgcaagc cctatttatt cagtcttcac tataactctt agagttgaga
3421  cgctaatgtt catgactcct ggccttggga tgcccaaggg atttctggct caggctgtaa
3481  aagtagctga gccatcctgc ccattcctgg aggtcctaca ggtgaaactg caggagctca
3541  gcatagaccc agctctctgg gggatggtca cctggtgatt tcaatgatgg catccaggaa
3601  ttagctgagc caacagacca tgtgacagc tttggccaga gctcccgtgt ggcatctggg
3661  agccacagtg acccagccac ctggctcagg ctagttccaa attccaaaag attggcttgt
3721  aaaccttcgt ctccctctct tttacccaga gacagcacat acgtgtgcac acgcatgcac
3781  acacacattc agtatttaa aagaatgttt tcttggtgcc attttcattt tatttattt
3841  tttaattctt ggaggggggaa ataagggaat aaggccaagg aagatgtata gctttagctt
3901  tagcctggca acctggagaa tccacatacc ttgtgtattg aaccccagga aaaggaagag
3961  gtcgaaccaa ccctgcggaa ggagcatggt ttcaggagtt tattttaaga ctgctgggaa
```

| 4021 | ggaaacaggc cccattttgt atatagttgc aacttaaact ttttggcttg caaaatattt |
| 4081 | ttgtaataaa gatttctggg taataatga |

[SEQ ID NO: 12]
Translation = MEPAGPAPGRLGPLLCLLLAASCAWSGVAGEEELQVIQPDKSVL
VAAGETATLRCTATSLIPVGPIQWFRGAGPGRELIYNQKEGHFPRVTTVSDLTKRNNM
DFSIRIGNITPADAGTYYCVKFRKGSPDDVEEKSGAGTELSVRAKPSAPVVSGPAARA
TPQHTVSFTCESHGFSPRDITLKWFKNGNELSDFQTNVDPVGESVSYSIHSTAKVVLT
REDVHSQVICEVAHVTLQGDPLRGTANLSETIRVPPTLEVTQQPVRAENQVNVTCQVR
KFYPQRLQLTWLENGNVSRTETASTVTENKDGTYNWMSWLLVNVSAHRDDVKLTCQVE
HDGQPAVSKSHDLKVSAHPKEQGSNTAAENTGSNERNIYIVVGVVCTLLVALLMAALY
LVRIRQKKAQGSTSSTRLHEPEKNAREITQDTNDITYADLNLPKGKKPAPQAAEPNNH
TEYASIQTSPQPASEDTLTYADLDMVELNRTPKQPAPKPEPSFSEYASVQVPRK

| LOCUS | NM_080792 3868 bp mRNA linear PRI 15-MAR-2015 |
| DEFINITION | *Homo sapiens* signal-regulatory protein alpha (SIRPA), Transcript variant 3, mRNA. |
| ACCESSION | NM_080792 NM_004648 |
| VERSION | NM_080792.2 GI:91105786 |
| SOURCE | *Homo sapiens* (human) |

[SEQ ID NO: 14]
| 1 | cgctcgctcg cagagaagcc gcggcccatg gagcccgccg gcccggcccc cggccgcctc |
| 61 | gggccgctgc tctgcctgct gctcgccgcg tcctgcgcct ggtcaggagt ggcgggtgag |
| 121 | gaggagctgc aggtgattca gcctgacaag tccgtgttgg ttgcagctgg agagacagcc |
| 181 | actctgcgct gcactgcgac ctctctgatc cctgtggggc ccatccagtg gttcagagga |
| 241 | gctggaccag gccgggaatt aatctacaat caaaagaag gccacttccc ccgggtaaca |
| 301 | actgtttcag acctcacaaa gagaaacaac atggactttt ccatccgcat cggtaacatc |
| 361 | accccagcag atgccggcac ctactactgt gtgaagttcc ggaagggag ccccgatgac |
| 421 | gtggagttta gtctggagc aggcactgag ctgtctgtgc gcgccaaacc ctctgccccc |
| 481 | gtggtatcgg gccctgcgg gagggccaca cctcagcaca cagtgagctt cacctgcgag |
| 541 | tcccacggct ctcacccag agacatcacc ctgaaatggt tcaaaaatgg gaatgagctc |
| 601 | tcagacttcc agaccaacgt ggacccgta ggagagagcg tgtcctacag catccacagc |
| 661 | acagccaagg tggtgctgac cgcgaggac gttcactctc aagtcatctg cgaggtggcc |
| 721 | cacgtcacct tgcagggga ccctcttcgt gggactgcca acttgtctga ccatccga |
| 781 | gttccaccca ccttggaggt tactcaacag cccgtgaggg cagagaacca ggtgaatgtc |
| 841 | acctgccagg tgaggaagtt ctaccccag agactacagc tgacctggtt ggagaatgga |
| 901 | aacgtgtccc ggacagaaac ggcctcaacc gttacagaga caaggatgg tacctacaac |
| 961 | tggatgagct ggctcctggt gaatgtatct gcccacaggg atgatgtgaa gctcacctgc |
| 1021 | caggtggagc atgacgggca gccagcggtc agcaaaagcc atgacctgaa ggtctcagcc |
| 1081 | caccccgaagg agcagggctc aaataccgcc gctgagaaca ctggatctaa tgaacggaac |
| 1141 | atctatattg tggtgggtgt ggtgtgcacc ttgctggtgg ccctactgat ggcggccctc |
| 1201 | tacctcgtcc gaatcagaca gaagaaagcc cagggctcca cttcttctac aaggttgcat |
| 1261 | gagcccgaga gaatgccag agaaataaca caggacacaa atgatatcac atatgcagac |
| 1321 | ctgaacctgc caagggaa gaagcctgct cccaggctg cggagcccaa caaccacacg |
| 1381 | gagtatgcca gcattcagac cagcccgcag ccgcgtcgg aggacaccct cacctatgct |
| 1441 | gacctggaca tggtccacct caaccgacc cccaagcagc cggccccaa gcctgagccg |
| 1501 | tccttctcag agtacgccag cgtccaggtc ccgaggaagt gaatgggacc gtggtttgct |

-continued

```
1561  ctagcaccca tctctacgcg ctttcttgtc ccacagggag ccgccgtgat gagcacagcc
1621  aacccagttc ccggagggct ggggcggtgc aggctctggg acccagggge cagggtggct
1681  cttctctccc caccctcct  tggctctcca gcacttcctg ggcagccacg gcccctccc
1741  cccacattgc cacatacctg gaggctgacg ttgccaaacc agccagggaa ccaacctggg
1801  aagtggccag aactgcctgg ggtccaagaa ctcttgtgcc tccgtccatc accatgtggg
1861  ttttgaagac cctcgactgc ctccccgatg ctccgaagcc tgatcttcca gggtggggag
1921  gagaaaatcc cacctcccct gacctccacc acctccacca ccaccaccac caccaccacc
1981  accactacca ccaccaccca actggggcta gagtgggggaa gatttcccct ttagatcaaa
2041  ctgcccccttc catggaaaag ctggaaaaaa actctggaac ccatatccag gcttggtgag
2101  gttgctgcca acagtcctgg cctcccccat ccctaggcta aagagccatg agtcctggag
2161  gaggagagga cccctcccaa aggactggag acaaaaccct ctgcttcctt gggtccctcc
2221  aagactccct ggggcccaac tgtgttgctc cacccggacc catctctccc ttctagacct
2281  gagcttgccc ctccagctag cactaagcaa catctcgctg tggacgcctg taaattactg
2341  agaaatgtga aacgtgcaat cttgaaactg aggtgttaga aaacttgatc tgtggtgttt
2401  tgttttgttt ttttcttaa acaacagca acgtgatctt ggctgtcgt catgtgttga
2461  agtccatggt tgggtcttgt gaagtctgag gtttaacagt ttgttgtcct ggagggattt
2521  tcttacagcg aagacttgag ttcctccaag tcccagaacc ccaagaatgg caagaagga
2581  tcaggtcagc cactccctgg agacacagcc ttctggctgg gactgacttg gccatgttct
2641  cagctgagcc acgcggctgg tagtgcagcc ttctgtgacc ccgctgtggt aagtccagcc
2701  tgcccagggc tgctgagggc tgcctcttga cagtgcagtc ttatcgagac ccaatgcctc
2761  agtctgctca tccgtaaagt ggggatagtg aagatgacac ccctccccac cacctctcat
2821  aagcacttta ggaacacaca gagggtaggg atagtggccc tggccgtcta tcctacccct
2881  ttagtgaccg ccccccatccc ggctttctga gctgatcctt gaagaagaaa tcttccattt
2941  ctgctctcaa accctactgg gatcaaactg gaataaattg aagacagcca gggggatggt
3001  gcagctgtga agctcgggct gattcccccet ctgtcccaga aggttggcca gagggtgtga
3061  cccagttacc cttttaacccc caccettcca gtcgggtgtg agggcctgac cgggcccagg
3121  gcaagcagat gtcgcaagcc ctatttattc agtcttcact ataactctta gagttgagac
3181  gctaatgttc atgactcctg gccttgggat gcccaaggga tttctggctc aggctgtaaa
3241  agtagctgag ccatcctgcc cattcctgga ggtcctacag gtgaaactgc aggagctcag
3301  catagaccca gctctctggg ggatggtcac ctggtgattt caatgatggc atccaggaat
3361  tagctgagcc aacagaccat gtggacagct ttggccagag ctcccgtgtg gcatctggga
3421  gccacagtga cccagccacc tggctcaggc tagttccaaa ttccaaaaga ttggcttgta
3481  aaccttcgtc tccctctctt ttacccagag acagcacata cgtgtgcaca cgcatgcaca
3541  cacacattca gtattttaaa agaatgtttt cttggtgcca ttttcatttt attttatttt
3601  ttaattcttg gagggggaaa taagggaata aggccaagga agatgtatag ctttagcttt
3661  agcctggcaa cctggagaat ccacatacct tgtgtattga acccccaggaa aaggaagagg
3721  tcgaaccaac cctgcggaag gagcatggtt tcaggagttt attttaagac tgctgggaag
3781  gaaacaggcc ccattttgta tatagttgca acttaaactt tttggcttgc aaaatatttt
3841  tgtaataaag atttctgggt aataatga
```

[SEQ ID NO: 12]
Translation = MEPAGPAPGRLGPLLCLLLAASCAWSGVAGEEELQVIQPDKSVL
VAAGETATLRCTATSLIPVGPIQWFRGAGPGRELIYNQKEGHFPRVTTVSDLTKRNNM
DFSIRIGNITPADAGTYYCVKFRKGSPDDVEFKSGAGTELSVRAKPSAPVVSGPAARA
TPQHTVSFTCESHGFSPRDITLKWFKNGNELSDFQTNVDPVGESVSYSIHSTAKVVLT
REDVHSQVICEVAHVTLQGDPLRGTANLSETIRVPPTLEVTQQPVRAENQVNVTCQVR
KFYPQRLQLTWLENGNVSRTETASTVTENKDGTYNWMSWLLVNVSAHRDDVKLTCQVE
HDGQPAVSKSHDLKVSAHPKEQGSNTAAENTGSNERNIYIVVGVVCTLLVALLMAALY
LVRIRQKKAQGSTSSTRLHEPEKNAREITQDTNDITYADLNLPKGKKPAPQAAEPNNH
TEYASIQTSPQPASEDTLTYADLDMVHLNRTPKQPAPKPEPSFSEYASVQVPRK LOCUS           NM_007547  4031 bp  mRNA   linear  ROD  15-FEB-2015
DEFINITION      Mus musculus signal-regulatory protein alpha (Sirpa),
                Transcript variant 1, mRNA.
ACCESSION       NM_007547 NM_011208
VERSION         NM_007547.4 GI:597084939
SOURCE          Mus musculus (house mouse)

[SEQ ID NO: 15]
       1 cgggaaggtg cgggcgcgag gaggggcgc tcggccgggc cgccctcgcg ctggcctcgc
      61 gacggctccg cacagcccgc actcgctctg cgagctgtcc ccgctcgcgc ttgctctccg
     121 atctccgtcc ccgctccctc tccctcttcc tctccccctc tttccttctc cctcgctatc
     181 cgctcccccg cccccgtgcc tctggctctg cgcctggctc cctcgggtcc gctccccttt
     241 cccgccggcc tggccggcg tcacgctccc ggagtctccc cgctcggcgc cgtctcattg
     301 tgggaggggg tcagatcacc ccgccgggcg gtggcgctgg ggggcagcgg aggggagggg
     361 gccttagtcg ttcgcccgcg ccgcccgccc gctgccgag cgcgctcacc gccgctctcc
     421 ctccttgctc tgcagccgcg gcccatggag cccgccggcc cggcccctgg ccgcctaggg
     481 ccgctgctgc tctgcctgct gctctccgcg tcctgtttct gtacaggagc acggggaag
     541 gaactgaagg tgactcagcc tgagaaatca gtgtctgttg ctgctgggga ttcgaccgtt
     601 ctgaactgca cttttgacctc cttgttgccg gtgggaccca ttaggtggta cagaggagta
     661 gggccaagcc ggctgttgat ctacagtttc gcaggagaat acgttcctcg aattagaaat
     721 gtttcagata ctactaagag aaacaatatg gactttttcca tccgtatcag taatgtcacc
     781 ccagcagatg ctggcatcta ctactgtgtg aagttccaga aggatcatc agagcctgac
     841 acagaaatac aatctggagg gggaacagag gtctatgtac tcgccaaacc ttctccaccg
     901 gaggtatccg gcccagcaga caggggcata cctgaccaga agtgaacttc cacctgcaag
     961 tctcatggct tctctcccg gaatatcacc ctgaagtggt tcaaagatgg caagaactc
    1021 caccccttgg agaccaccgt gaaccctagt ggaaagaatg tctcctacaa catctccagc
    1081 acagtcaggg tggtactaaa ctccatggat gttaattcta aggtcatctg cgaggtagcc
    1141 cacatcacct ggatagaag ccctcttcgt gggattgcta acctgtctaa cttcatccga
    1201 gtttcaccca ccgtgaaggt caccccaacag tccccgacgt caatgaacca ggtgaacctc
    1261 acctgccggg ctgagaggtt ctaccccgag atctccagc tgatctggct ggagaatgga
    1321 aacgtatcac ggaatgacac gcccaagaat ctcacaaaga cacggatgg gacctataat
    1381 tacacaagct tgttcctggt gaactcatct gctcatagag aggacgtggt gttcacgtgc
    1441 caggtgaagc acgaccaaca gccagcgatc acccgaaacc ataccgtgct gggatttgcc
    1501 cactcgagtg atcaaggag catgcaaacc ttccctgata ataatgctac ccacaactgg
    1561 aatgtcttca tcggtgtggg cgtggcgtgt gctttgctcg tagtcctgct gatggctgct
    1621 ctctacctcc tccggatcaa acagaagaaa gccaagggt caacatcttc cacacggttg

```
1681  cacgagcccg agaagaacgc cagggaaata acccagatcc aggacacaaa tgacatcaac 1741  gacatcacat acgcagacct gaatctgccc aaagagaaga agcccgcacc ccgggcccct 1801  gagcctaaca accacacaga atatgcaagc attgagacag gcaaagtgcc taggccagag 1861  gataccctca cctatgctga cctggacatg gtccacctca gccgggcaca gccagccccc 1921  aagcctgagc catctttctc agagtatgct agtgtccagg tccagaggaa gtgaatgggg 1981  ctgtggtctg tactaggccc catccccaca agttttcttg tcctacatgg agtggccatg 2041  acgaggacat ccagccagcc aatcctgtcc ccagaaggcc aggtggcacg ggtcctagga 2101  ccagggtaa gggtggcctt tgtcttccct ccgtggctct caacacctc ttgggcaccc 2161  acgtcccctt cttccggagg ctgggtgttg cagaaccaga gggcgaactg gagaaagctg 2221  cctggaatcc aagaagtgtt gtgcctcggc ccatcactcg tgggtctgga tcctggtctt 2281  ggcaacccca ggttgcgtcc ttgatgttcc agagcttggt cttctgtgtg gagaagagct 2341  caccatctct acccaacttg agctttggga ccagactccc tttagatcaa accgccccat 2401  ctgtggaaga actacaccag aagtcagcaa gttttcagcc aacagtgctg gcctcccac 2461  ctcccaggct gactagccct ggggagaagg aaccctctcc tcctagacca gcagagactc 2521  cctgggcatg ttcagtgtgg ccccacctcc cttccagtcc cagcttgctt cctccagcta 2581  gcactaactc agcagcatcg ctctgtggac gcctgtaaat tattgagaaa tgtgaactgt 2641  gcagtcttaa agctaaggtg ttagaaaatt tgatttatgc tgtttagttg ttgttgggtt 2701  tcttttcttt ttaatttctt tttctttttt gattttttt ctttccctta aacaacagc 2761  agcagcatct tggctctttg tcatgtgttg aatggttggg tcttgtgaag tctgaggtct 2821  aacagtttat tgtcctggaa ggattttctt acagcagaaa cagattttt tcaaattccc 2881  agaatcctga ggaccaagaa ggatccctca gctgctactt ccagcaccca gcgtcactgg 2941  gacgaaccag gccctgttct tacaaggcca catggctggc cctttgcctc catggctact 3001  gtggtaagtg cagccttgtc tgacccaatg ctgacctaat gttggccatt ccacattgag 3061  gggacaaggt cagtgatgcc cccttcact cacaagcact tcagaggcat gcagagagaa 3121  gggacactcg gccagctctc tgaggtaatc agtgcaagga ggagtccgtt ttttgccagc 3181  aaacctcagc aggatcacac tggaacagaa cctggtcata cctgtgacaa cacagctgtg 3241  agccagggca aaccacccac tgtcactggc tcgagagtct gggcagaggc tctgaccctc 3301  cacccttta actggatgcc ggggcctggc tgggcccaat gccaagtggt tatggcaacc 3361  ctgactatct ggtcttaaca tgtagctcag gaagtggagg cgctaatgtc cccaatccct 3421  ggggattcct gattccagct attcatgtaa gcagagccaa cctgcctatt tctgtaggtg 3481  cgactgggat gttaggagca cagcaaggac ccagctctgt agggctggtg acctgatact 3541  tctcataatg gcatctagaa gttaggctga gttggcctca ctggcccagc aaaccagaac 3601  ttgtctttgt ccgggccatg ttcttgggct gtcttctaat ccaaagggt tggttggtaa 3661  agctccaccc ccttctcctc tgcctaaaga catcacatgt gtatacacac acgggtgtat 3721  agatgagtta aaagaatgtc ctcgctggca tcctaatttt gtcttaagtt ttttggagg 3781  gagaaaggaa caaggcaagg gaagatgtgt agctttggct ttaaccaggc agcctggggg 3841  ctcccaagcc tatggaaccc tggtacaaag aagagaacag aagcgccctg tgaggagtgg
```

```
3901   gatttgtttt tctgtagacc agatgagaag gaaacaggcc ctgttttgta catagttgca 3961   acttaaaatt tttggcttgc aaaatatttt tgtaataaag atttctgggt aacaataaaa 4021   aaaaaaaaaa a
```

[SEQ ID NO: 16]
Translation = MEPAGPAPGRLGPLLLCLLLSASCFCTGATGKELKVTQPEKSVS
VAAGDSTVLNCTLTSLLPVGPIRWYRGVGPSRLLIYSFAGEYVPRIRNVSDTTKRNNM
DFSIRISNVTPADAGIYYCVKFQKGSSEPDTEIQSGGGTEVYVLAKPSPPEVSGPADR
GIPDQKVNFTCKSHGESPRNITLKWFKDGQELHPLETTVNPSGKNVSYNISSTVRVVL
NSMDVNSKVICEVAHITLDRSPLRGIANLSNFIRVSPTVKVTQQSPTSMNQVNLTCRA
ERFYPEDLQLIWLENGNVSRNDTPKNLTKNTDGTYNYTSLELVNSSAHREDVVETCQV
KHDQQPAITRNHTVLGFAHSSDQGSMQTFPDNNATHNWNVFIGVGVACALLVVLLMAA
LYLLRIKQKKAKGSTSSTRLHEPEKNAREITQIQDTNDINDITYADLNLPKEKKPAPR
APEPNNHTEYASIETGKVPRPEDTLTYADLDMVHLSRAQPAPKPEPSFSEYASVQVQR
K

```
LOCUS        NM_001177647  3377 bp  mRNA  linear  ROD 15-FEB-2015

DEFINITION   Mus musculus signal-regulatory protein alpha (Sirpa),
             Transcript variant 3, mRNA.

ACCESSION    NM_001177647

VERSION      NM_001177647.2  GI:597436949

SOURCE       Mus musculus (house mouse)
```

[SEQ ID NO: 17]
```
   1   cgggaaggtg cgggcgcgag gaggggcgc tcggccgggc cgccctcgcg ctggcctcgc 61   gacggctccg cacagcccgc actcgctctg cgagctgtcc ccgctcgcgc ttgctctccg 121   atctccgtcc ccgctccctc tccctcttcc tctcccctc tttccttctc cctcgctatc 181   cgctccccg ccccgtgcc tctggctctg cgcctggctc cctcgggtcc gctccccttt 241   cccgccggcc tggccgggc tcacgctccc ggagtctccc cgctcggcgg cgtctcattg 301   tgggagggg tcagatcacc ccgccgggcg gtggcgctgg ggggcagcgg aggggaggg 361   gccttagtcg ttcgcccgcg ccgcccgccc gctgccgag cgcgctcacc gccgctctcc 421   ctccttgctc tgcagccgcg gcccatggag ccgccggcc cggcccctgg ccgcctaggg 481   ccgctgctgc tctgcctgct gctctccgcg tcctgttct gtacaggagc cacggggaag 541   gaactgaagg tgactcagcc tgagaaatca gtgtctgttg ctgctgggga ttcgaccgtt 601   ctgaactgca cttttgacctc cttgttgccg gtgggaccca ttaggtggta cagaggagta 661   gggccaagcc ggctgttgat ctacagtttc gcaggagaat acgttcctcg aattagaaat 721   gtttcagata ctactaagag aaacaatatg gactttttcca tccgtatcag taatgtcacc 781   ccagcagatg ctggcatcta ctactgtgtg aagttccaga aggatcatc agagcctgac 841   acagaaatac aatctggagg gggaacagag gtctatgtac tcgataataa tgctacccac 901   aactggaatg tcttcatcgg tgtgggcgtg gcgtgtgctt tgctcgtagt cctgctgatg 961   gctgctctct acctcctccg gatcaaacag aagaaagcca aggggtcaac atcttccaca 1021   cggttgcacg agcccgagaa gaacgccagg gaaataaccc agatccagga cacaaatgac 1081   atcaacgaca tcacatacgc agacctgaat ctgccaaag agaagaagcc cgcaccccgg 1141   gcccctgagc ctaacaacca cacagaatat gcaagcattg agacaggcaa agtgcctagg 1201   ccagaggata ccctcaccta tgctgacctg acatggtcc acctcagccg ggcacagcca 1261   gccccaagc ctgagccatc tttctcagag tatgctagtg tccaggtcca gaggaagtga 1321   atggggctgt ggtctgtact aggccccatc cccacaagtt ttcttgtcct acatggagtg 1381   gccatgacga ggacatccag ccagccaatc ctgtccccag aaggccaggt ggcacgggtc
```

```
1441   ctaggaccag gggtaagggt ggcctttgtc ttccctccgt ggctcttcaa cacctcttgg 1501   gcacccacgt ccccttcttc cggaggctgg gtgttgcaga accagagggc gaactggaga 1561   aagctgcctg gaatccaaga agtgttgtgc ctcggcccat cactcgtggg tctggatcct 1621   ggtcttggca accccaggtt gcgtccttga tgttccagag cttggtcttc tgtgtggaga 1681   agagctcacc atctctaccc aacttgagct ttgggaccag actcccttta gatcaaaccg 1741   ccccatctgt ggaagaacta caccagaagt cagcaagttt tcagccaaca gtgctggcct 1801   ccccacctcc caggctgact agccctgggg agaaggaacc ctctcctcct agaccagcag 1861   agactccctg ggcatgttca gtgtggcccc acctcccttc cagtcccagc ttgcttcctc 1921   cagctagcac taactcagca gcatcgctct gtggacgcct gtaaattatt gagaaatgtg 1981   aactgtgcag tcttaaagct aaggtgttag aaaatttgat ttatgctgtt tagttgttgt 2041   tgggtttctt ttctttttaa tttctttttc tttttgatt tttttctttc cccttaaaac 2101   aacagcagca gcatcttggc tctttgtcat gtgttgaatg gttgggtctt gtgaagtctg 2161   aggtctaaca gtttattgtc ctggaaggat tttcttacag cagaaacaga ttttttttcaa 2221   attcccagaa tcctgaggac caagaaggat ccctcagctg ctacttccag cacccagcgt 2281   cactgggacg aaccaggccc tgttcttaca aggccacatg gctggccctt tgcctccatg 2341   gctactgtgg taagtgcagc cttgtctgac ccaatgctga cctaatgttg gccattccac 2401   attgagggga caaggtcagt gatgccccc ttcactcaca agcacttcag aggcatgcag 2461   agagaaggga cactcggcca gctctctgag gtaatcagtg caaggaggag tccgttttt 2521   gccagcaaac ctcagcagga tcacactgga acagaacctg gtcatacctg tgacaacaca 2581   gctgtgagcc agggcaaacc acccactgtc actggctcga gagtctgggc agaggctctg 2641   accctccacc ctttaaactg gatgccgggg cctggctggg cccaatgcca agtggttatg 2701   gcaaccctga ctatctggtc ttaacatgta gctcaggaag tggaggcgct aatgtcccca 2761   atccctgggg attcctgatt ccagctattc atgtaagcag agccaacctg cctatttctg 2821   taggtgcgac tgggatgtta ggagcacagc aaggacccag ctctgtaggg ctggtgacct 2881   gatacttctc ataatggcat ctagaagtta ggctgagttg gcctcactgg cccagcaaac 2941   cagaacttgt ctttgtccgg ccatgttct tgggctgtct tctaattcca aagggttggt 3001   tggtaaagct ccaccccctt ctcctctgcc taaagacatc acatgtgtat acacacacgg 3061   gtgtatagat gagttaaaag aatgtcctcg ctggcatcct aattttgtct taagtttttt 3121   tggagggaga aaggaacaag gcaagggaag atgtgtagct ttggctttaa ccaggcagcc 3181   tgggggctcc caagcctatg gaaccctggt acaaagaaga gaacagaagc gccctgtgag 3241   gagtgggatt tgttttttctg tagaccagat gagaaggaaa caggccctgt tttgtacata 3301   gttgcaactt aaaattttg gcttgcaaaa tattttgta ataaagattt ctgggtaaca 3361   ataaaaaaaa aaaaaaa
```

[SEQ ID NO: 18]
Translation = MEPAGPAPGRLGPLLLCLLLSASCFCTGATGKELKVTQPEKSVS
VAAGDSTVLNCTLTSLLPVGPIRWYRGVGPSRLLIYSFAGEYVPRIRNVSDTTKRNNM
DFSIRISNVTPADAGIYYCVKFQKGSSEPDTEIQSGGGTEVVLDNNATHNWNVFIGV
GVACALLVVLLMAALYLLRIKQKKAKGSTSSTRLHEPEKNAREITQIQDTNDINDITY
ADLNLPKEKKPAPRAPEPNNHTEYASIETGKVPRPEDTLTYADLDMVHLSRAQPAPKP
EPSFSEYASVQVQRK LOCUS        NM_001291019 4043 bp mRNA linear ROD 15-FEB-2015

DEFINITION   *Mus musculus* signal-regulatory protein alpha (Sirpa),
             transcript variant 4, mRNA.

ACCESSION    NM_001291019 XM_006498985

VERSION      NM_001291019.1 GI:597436868

SOURCE       *Mus musculus* (house mouse)

[SEQ ID NO: 19]

```
   1 cgggaaggtg cgggcgcgag gaggggcgc tcggccgggc cgccctcgcg ctggcctcgc
  61 gacggctccg cacagcccgc actcgctctg cgagctgtcc ccgctcgcgc ttgctctccg
 121 atctccgtcc ccgctccctc tccctcttcc tctcccctc tttccttctc cctcgctatc
 181 cgctcccccg cccccgtgcc tctggtctg cgcctggctc cctcgggtcc gctccccttt
 241 cccgccggcc tggcccggcg tcacgctccc ggagtctccc cgctcggcgg cgtctcattg
 301 tgggaggggg tcagatcacc ccgccgggcg gtggcgctgg ggggcagcgg aggggaggg
 361 gccttagtcg ttcgcccgcg ccgcccgccc gcctgccgag cgcgctcacc gccgctctcc
 421 ctccttgctc tgcagccgcg gcccatggag cccgccggcc cggcccctgg ccgcctaggg
 481 ccgctgctgc tctgcctgct gctctccgcg tcctgtttct gtacaggagc cacggggaag
 541 gaactgaagg tgactcagcc tgagaaatca gtgtctgttg ctgctgggga ttcgaccgtt
 601 ctgaactgca cttgacctc cttgttgccg gtgggaccca ttaggtggta cagaggagta
 661 gggccaagcc ggctgttgat ctacagtttc gcaggagaat acgttcctcg aattagaaat
 721 gtttcagata ctactaagag aaacaatatg gacttttcca tccgtatcag taatgtcacc
 781 ccagcagatg ctggcatcta ctactgtgtg aagttccaga aaggatcatc agagcctgac
 841 acagaaatac aatctggagg gggaacagag gtctatgtac tcgccaaacc ttctccaccg
 901 gaggtatccg gcccagcaga caggggcata cctgaccaga aagtgaactt cacctgcaag
 961 tctcatggct ctctccccg gaatatcacc ctgaagtggt tcaaagatgg caagaactc
1021 cacccttgg agaccaccgt gaaccctagt ggaaagaatg tctcctacaa catctccagc
1081 acagtcaggg tggtactaaa ctccatggat gttaattcta aggtcatctg cgaggtagcc
1141 cacatcacct tggatagaag ccctcttcgt gggattgcta acctgtctaa cttcatccga
1201 gtttcaccca ccgtgaaggt cacccaacag tccccgacgt caatgaacca ggtgaacctc
1261 acctgccggg ctgagaggtt ctaccccgag atctccagc tgatctggct ggagaatgga
1321 aacgtatcac ggaatgacac gcccaagaat ctcacaaaga cacggatgg gacctataat
1381 tacacaagct tgttcctggt gaactcatct gctcatagag aggacgtggt gttcacgtgc
1441 caggtgaagc acgaccaaca gccagcgatc acccgaaacc ataccgtgct gggatttgcc
1501 cactcgagtg atcaaggag catgcaaacc ttccctgata ataatgctac ccacaactgg
1561 aatgtcttca tcggtgtggg cgtggcgtgt gctttgctcg tagtcctgct gatggctgct
1621 ctctacctcc tccgatcaa acagaagaaa gccaaggggt caacatcttc cacacggttg
1681 cacgagcccg agaagaacgc cagggaaata acccaggtac agtctttgat ccaggacaca
```

```
1741  aatgacatca acgacatcac atacgcagac ctgaatctgc ccaaagagaa gaagcccgca
1801  ccccgggccc ctgagcctaa caaccacaca gaatatgcaa gcattgagac aggcaaagtg
1861  cctaggccag aggatacect cacctatgct gacctggaca tggtccacct cagccgggca
1921  cagccagccc caagcctga gccatctttc tcagagtatg ctagtgtcca ggtccagagg
1981  aagtgaatgg ggctgtggtc tgtactaggc cccatcccca caagttttct tgtcctacat
2041  ggagtggcca tgacgaggac atccagccag ccaatcctgt ccccagaagg ccaggtggca
2101  cgggtcctag gaccaggggt aagggtggcc tttgtcttcc ctccgtggct cttcaacacc
2161  tcttgggcac ccacgtcccc ttcttccgga ggctgggtgt tgcagaacca gagggcgaac
2221  tggagaaagc tgcctggaat ccaagaagtg ttgtgcctcg cccatcact cgtgggtctg
2281  gatcctggtc ttggcaaccc caggttgcgt ccttgatgtt ccagagcttg tcttctgtg
2341  tggagaagag ctcaccatct ctacccaact tgagctttgg gaccagactc cctttagatc
2401  aaaccgcccc atctgtggaa gaactacacc agaagtcagc aagttttcag ccaacagtgc
2461  tggcctcccc acctcccagg ctgactagcc tggggagaa ggaaccctct cctcctagac
2521  cagcagagac tccctgggca tgttcagtgt ggccccacct cccttccagt cccagcttgc
2581  ttcctccagc tagcactaac tcagcagcat cgctctgtgg acgcctgtaa attattgaga
2641  aatgtgaact gtgcagtctt aaagctaagg tgttagaaaa tttgatttat gctgtttagt
2701  tgttgttggg tttctttttct ttttaattttc ttttcctttt ttgattttttt ttctttccct
2761  taaaacaaca gcagcagcat cttggctctt tgtcatgtgt tgaatggttg ggtcttgtga
2821  agtctgaggt ctaacagttt attgtcctgg aaggattttc ttacagcaga aacagatttt
2881  tttcaaattc ccagaatcct gaggaccaag aaggatccct cagctgctac ttccagcacc
2941  cagcgtcact gggacgaacc aggccctgtt cttacaaggc cacatggctg gcccctttgcc
3001  tccatggcta ctgtggtaag tgcagccttg tctgacccaa tgctgaccta atgttggcca
3061  ttccacattg aggggacaag gtcagtgatg cccccttca ctcacaagca cttcagaggc
3121  atgcagagag aagggacact cggccagctc tctgaggtaa tcagtgcaag gaggagtccg
3181  ttttttgcca gcaaacctca gcaggatcac actggaacag aacctggtca tacctgtgac
3241  aacacagctg tgagccaggg caaaccaccc actgtcactg gctcgagagt ctgggcagag
3301  gctctgaccc tccacccttt aaactggatg ccggggcctg gctgggccca atgccaagtg
3361  gttatggcaa ccctgactat ctggtcttaa catgtagctc aggaagtgga ggcgctaatg
3421  tccccaatcc ctggggattc ctgattccag ctattcatgt aagcagagcc aacctgccta
3481  tttctgtagg tgcgactggg atgttaggag cacagcaagg acccagctct gtagggctgg
3541  tgacctgata cttctcataa tggcatctag aagttaggct gagttggcct cactggccca
3601  gcaaaccaga acttgtcttt gtccgggcca tgttcttggg ctgtcttcta attccaaagg
3661  gttggttggt aaagctccac cccttctcc tctgcctaaa gacatcacat gtgtatacac
3721  acacgggtgt atagatgagt taaaagaatg tcctcgctgg catcctaatt ttgtcttaag
3781  ttttttgga gggagaaagg aacaaggcaa gggaagatgt gtagctttgg ctttaaccag
3841  gcagcctggg ggctcccaag cctatggaac cctggtacaa agaagagaac agaagcgccc
3901  tgtgaggagt gggatttgtt tttctgtaga ccagatgaga aggaaacagg ccctgttttg
3961  tacatagttg caacttaaaa ttttggctt gcaaaatatt tttgtaataa agatttctgg
4021  gtaacaataa aaaaaaaaaa aaa
```

[SEQ ID NO: 20]
Translation = MEPAGPAPGRLGPLLLCLLLSASCFCTGATGKELKVTQPEKSVS
VAAGDSTVLNCTLTSLLPVGPIRWYRGVGPSRLLIYSFAGEYVPRIRNVSDTTKRNNM
DFSIRISNVTPADAGIYYCVKFQKGSSEPDTEIQSGGGTEVVLAKPSPPEVSGPADR
GIPDQKVNFTCKSHGFSPRNITLKWFKDGQELHPLETTVNPSGKNVSYNISSTVRVVL
NSMDVNSKVICEVAHITLDRSPLRGIANLSNFIRVSPTVKVTQQSPTSMNQVNLTCRA
ERFYPEDLQLIWLENGNVSRNDTPKNLTKNTDGTYNYTSLFLVNSSAHREDVVFTCQV
KHDQQPAITRNHTVLGFAHSSDQGSMQTFPDNNATHNWNVFIGVGVACALLVVLLMAA
LYLLRIKQKKAKGSTSSTRLHEPEKNAREITQVQSLIQDTNDINDITYADLNLPKEKK
PAPRAPEPNNHTEYASIETGKVPRPEDTLTYADLDMVHLSRAQPAPKPEPSFSEYASV
QVQRK LOCUS           NM_001291020 3845 bp mRNA linear ROD 15-FEB-2015
DEFINITION      Mus musculus signal-regulatory protein alpha (Sirpa),
                transcript variant 5, mRNA.
ACCESSION       NM_001291020 XM_006498984
VERSION         NM_001291020.1 GI:597436945
KEYWORDS        RefSeq.
SOURCE          Mus musculus (house mouse)

[SEQ ID NO: 21]
     1 aagctcccct gccgcgggca gcctcttgcc cactggagtc taaggactgg ccgggtgaga
    61 ggccgagacc aggggggcgat cggccgccac ttccccagtc caccttaaga ggaccaagta
   121 gccagcccgc cgcgccgacc tcagaaaaac aagtttgcgc aaagtggtgc gcggccagcc
   181 tctgggcaga gggagcggtg cttccaccgc ctggcagccc tgcgcgcggc ggcgcagccg
   241 cggcccatgg agcccgccgg cccggccccct ggccgcctag ggccgctgct gctctgcctg
   301 ctgctctccg cgtcctgttt ctgtacagga gccacgggga aggaactgaa ggtgactcag
   361 cctgagaaat cagtgtctgt tgctgctggg gattcgaccg ttctgaactg cactttgacc
   421 tccttgttgc cggtgggacc cattaggtgg tacagaggag tagggccaag ccggctgttg
   481 atctacagtt tcgcaggaga atacgttcct cgaattagaa atgtttcaga tactactaag
   541 agaaacaata tggactttc catccgtatc agtaatgtca ccccagcaga tgctggcatc
   601 tactactgtg tgaagttcca gaaaggatca tcagagcctg acacagaaat acaatctgga
   661 gggggaacag aggtctatgt actcgccaaa ccttctccac cggaggtatc cggcccagca
   721 gacaggggca tacctgacca gaaagtgaac ttcacctgca gtctcatgg cttctctccc
   781 cggaatatca ccctgaagtg gttcaaagat gggcaagaac tccaccccttggagaccacc
   841 gtgaacccta gtggaaagaa tgtctcctac aacatctcca gcacagtcag ggtggtacta
   901 aactccatgg atgttaattc taaggtcatc tgcgaggtag cccacatcac cttggataga
   961 agccctcttc gtgggattgc taacctgtct aacttcatcc gagtttcacc caccgtgaag
  1021 gtcacccaac agtccccgac gtcaatgaac caggtgaacc tcacctgccg ggctgagagg
  1081 ttctaccccg aggatctcca gctgatctgg ctggagaatg gaacgtatc acggaatgac
  1141 acgccaagaa tctcacaaa gaacacggat gggacctata attacacaag cttgttcctg
  1201 gtgaactcat ctgctcatag agaggacgtg gtgttcacgt gccaggtgaa gcacgaccaa
  1261 cagccagcga tcacccgaaa ccataccgtg ctgggatttg cccactcgag tgatcaaggg
  1321 agcatgcaaa ccttccctga taataatgct acccacaact ggaatgtctt catcggtgtg
  1381 ggcgtggcgt gtgctttgct cgtagtcctg ctgatggctg ctctctacct cctccggatc
  1441 aaacagaaga aagccaaggg gtcaacatct tccacacggt tgcacgagcc cgagaagaac
  1501 gccagggaaa taacccaggt acagtctttg atccaggaca caaatgacat caacgacatc

```
1561  acatacgcag acctgaatct gcccaaagag aagaagcccg caccccgggc ccctgagcct
1621  aacaaccaca cagaatatgc aagcattgag acaggcaaag tgcctaggcc agaggatacc
1681  ctcacctatg ctgacctgga catggtccac ctcagccggg cacagccagc ccccaagcct
1741  gagccatctt tctcagagta tgctagtgtc caggtccaga ggaagtgaat ggggctgtgg
1801  tctgtactag gccccatccc cacaagtttt cttgtcctac atggagtggc catgacgagg
1861  acatccagcc agccaatcct gtccccagaa ggccaggtgg cacgggtcct aggaccaggg
1921  gtaagggtgg cctttgtctt ccctccgtgg ctcttcaaca cctcttgggc acccacgtcc
1981  ccttcttccg gaggctgggt gttgcagaac cagagggcga actggagaaa gctgcctgga
2041  atccaagaag tgttgtgcct cggcccatca ctcgtgggtc tggatcctgg tcttggcaac
2101  cccaggttgc gtccttgatg ttccagagct tggtcttctg tgtggagaag agctcaccat
2161  ctctacccaa cttgagcttt gggaccagac tcccttaga tcaaaccgcc ccatctgtgg
2221  aagaactaca ccagaagtca gcaagttttc agccaacagt gctggcctcc ccacctccca
2281  ggctgactag ccctggggag aaggaaccct ctcctcctag accagcagag actccctggg
2341  catgttcagt gtggccccac ctcccttcca gtcccagctt gcttcctcca gctagcacta
2401  actcagcagc atcgctctgt ggacgcctgt aaattattga gaaatgtgaa ctgtgcagtc
2461  ttaaagctaa ggtgttagaa aatttgattt atgctgttta gttgttgttg ggtttctttt
2521  cttttaatt tctttttctt ttttgatttt ttttctttcc cttaaaacaa cagcagcagc
2581  atcttggctc tttgtcatgt gttgaatggt tgggtcttgt gaagtctgag gtctaacagt
2641  ttattgtcct ggaaggattt tcttacagca gaaacagatt tttttcaaat tcccagaatc
2701  ctgaggacca agaaggatcc ctcagctgct acttccagca cccagcgtca ctgggacgaa
2761  ccaggccctg ttcttacaag gccacatggc tggcccttg cctccatggc tactgtggta
2821  agtgcagcct tgtctgaccc aatgctgacc taatgttggc cattccacat tgaggggaca
2881  aggtcagtga tgcccccctt cactcacaag cacttcagag gcatgcagag agaagggaca
2941  ctcggccagc tctctgaggt aatcagtgca aggaggagtc cgttttttgc cagcaaacct
3001  cagcaggatc acactggaac agaacctggt catacctgtg acaacacagc tgtgagccag
3061  ggcaaaccac ccactgtcac tggctcgaga gtctgggcag aggctctgac cctccaccct
3121  ttaaactgga tgccggggcc tggctgggcc caatgccaag tggttatggc aaccctgact
3181  atctggtctt aacatgtagc tcaggaagtg gaggcgctaa tgtccccaat ccctggggat
3241  tcctgattcc agctattcat gtaagcagag ccaacctgcc tatttctgta ggtgcgactg
3301  ggatgttagg agcacagcaa ggacccagct ctgtagggct ggtgacctga tacttctcat
3361  aatggcatct agaagttagg ctgagttggc ctcactggcc cagcaaacca gaacttgtct
3421  ttgtccgggc catgttcttg ggctgtcttc taattccaaa gggttggttg gtaaagctcc
3481  accccttct cctctgccta aagacatcac atgtgtatac acacacgggt gtatagatga
3541  gttaaaagaa tgtcctcgct ggcatcctaa ttttgtctta agttttttg gagggagaaa
3601  ggaacaaggc aagggaagat gtgtagcttt ggctttaacc aggcagcctg ggggctccca
3661  agcctatgga accctggtac aaagaagaga acagaagcgc cctgtgagga gtgggatttg
3721  ttttttctgta gaccagatga gaaggaaaca ggccctgttt tgtacatagt tgcaacttaa
3781  aattttttggc ttgcaaaata tttttgtaat aaagatttct gggtaacaat aaaaaaaaaa
3841  aaaaa
```

[SEQ ID NO: 20]
Translation = MEPAGPAPGRLGPLLLCLLLSASCFCTGATGKELKVTQPEKSVS
VAAGDSTVLNCTLTSLLPVGPIRWYRGVGPSRLLIYSFAGEYVPRIRNVSDTTKRNNM
DFSIRISNVTPADAGIYYCVKFQKGSSEPDTEIQSGGGTEVYVLAKPSPPEVSGPADR
GIPDQKVNFTCKSHGFSPRNITLKWFKDGQELHPLETTVNPSGKNVSYNISSTVRVVL
NSMDVNSKVICEVAHITLDRSPLRGIANLSNFIRVSPTVKVTQQSPTSMNQVNLTCRA
ERFYPEDLQLIWLENGNVSRNDTPKNLTKNTDGTYNYTSLFLVNSSAHREDVVFTCQV
KHDQQPAITRNHTVLGFAHSSDQGSMQTFPDNNATHNWNVFIGVGVACALLVVLLMAA
LYLLRIKQKKAKGSTSSTRLHEPEKNAREITQVQSLIQDTNDINDITYADLNLPKEKK
PAPRAPEPNNHTEYASIETGKVPRPEDTLTYADLDMVHLSRAQPAPKPEPSFSEYASV
QVQRK LOCUS           NM_001291021 3389 bp mRNA linear ROD 15-FEB-2015

DEFINITION      *Mus musculus* signal-regulatory protein alpha (Sirpa),
                Transcript variant 6, mRNA.

ACCESSION       NM_001291021 XM_006498987

VERSION         NM_001291021.1 GI:597436920

SOURCE          *Mus musculus* (house mouse)

[SEQ ID NO: 22]
```
   1 cgggaaggtg cgggcgcgag gaggggcgc tcggccgggc cgccctcgcg ctggcctcgc
  61 gacggctccg cacagcccgc actcgctctg cgagctgtcc ccgctcgcgc ttgctctccg
 121 atctccgtcc ccgctccctc tccctcttcc tctccccctc tttccttctc cctcgctatc
 181 cgctccccg cccccgtgcc tctggtctg cgcctggctc cctcgggtcc gctcccctt
 241 cccgccggcc tggcccggcg tcacgctccc ggagtctccc cgctcggcgg cgtctcattg
 301 tgggaggggg tcagatcacc ccgccgggcg gtggcgctgg ggggcagcgg aggggaggg
 361 gccttagtcg ttcgcccgcg ccgcccgccc gcctgccgag cgcgctcacc gccgctctcc
 421 ctccttgctc tgcagccgcg gcccatggag cccgccggcc cggcccctgg ccgcctaggg
 481 ccgctgctgc tctgcctgct gctctccgcg tcctgtttct gtacaggagc cacggggaag
 541 gaactgaagg tgactcagcc tgagaaatca gtgtctgttg ctgctgggga ttcgaccgtt
 601 ctgaactgca cttttgacctc cttgttgccg gtgggaccca ttaggtggta cagaggagta
 661 gggccaagcc ggctgttgat ctacagtttc gcaggagaat acgttcctcg aattagaaat
 721 gtttcagata ctactaagag aaacaatatg gacttttcca tccgtatcag taatgtcacc
 781 ccagcagatg ctggcatcta ctactgtgtg aagttccaga aaggatcatc agagcctgac
 841 acagaaatac aatctggagg gggaacagag gtctatgtac tcgataataa tgctacccac
 901 aactggaatg tctttcatcg tgtgggcgtg gcgtgtgctt tgctcgtagt cctgctgatg
 961 gctgctctct acctcctccg gatcaaacag aagaaagcca aggggtcaac atcttccaca
1021 cggttgcacg agcccgagaa gaacgccagg gaaataaccc aggtacagtc tttgatccag
1081 gacacaaatg acatcaacga catcacatac gcagacctga atctgcccaa agagaagaag
1141 cccgcacccc gggcccctga gcctaacaac cacacagaat atgcaagcat tgagacaggc
1201 aaagtgccta ggccagagga taccctcacc tatgctgacc tggacatggt ccacctcagc
1261 cgggcacagc cagcccccaa gcctgagcca tctttctcag agtatgctag tgtccaggtc
1321 cagaggaagt gaatggggct gtggtctgta ctaggcccca tccccacaag ttttcttgtc
1381 ctacatggag tggccatgac gaggacatcc agccagccaa tcctgtcccc agaaggccag
1441 gtggcacggg tcctaggacc aggggtaagg gtggcctttg tcttccctcc gtggctcttc
1501 aacacctctt gggcacccac gtccccttct tccggaggct gggtgttgca gaaccagagg
1561 gcgaactgga gaaagctgcc tggaatccaa gaagtgttgt gcctcggccc atcactcgtg
```

-continued

```
1621  ggtctggatc ctggtcttgg caaccccagg ttgcgtcctt gatgttccag agcttggtct 1681  tctgtgtgga agagagctca ccatctctac ccaacttgag ctttgggacc agactccctt 1741  tagatcaaac cgccccatct gtggaagaac tacaccagaa gtcagcaagt tttcagccaa 1801  cagtgctggc ctccccacct cccaggctga ctagccctgg ggagaaggaa ccctctcctc 1861  ctagaccagc agagactccc tgggcatgtt cagtgtggcc ccacctccct tccagtccca 1921  gcttgcttcc tccagctagc actaactcag cagcatcgct ctgtggacgc ctgtaaatta 1981  ttgagaaatg tgaactgtgc agtcttaaag ctaaggtgtt agaaaatttg atttatgctg 2041  tttagttgtt gttgggtttc ttttcttttt aatttctttt tcttttttga ttttttttct 2101  ttcccttaaa acaacagcag cagcatcttg gctctttgtc atgtgttgaa tggttgggtc 2161  ttgtgaagtc tgaggtctaa cagtttattg tcctggaagg attttcttac agcagaaaca 2221  gattttttc aaattcccag aatcctgagg accaagaagg atccctcagc tgctacttcc 2281  agcacccagc gtcactggga cgaaccaggc cctgttctta caaggccaca tggctggccc 2341  tttgcctcca tggctactgt ggtaagtgca gccttgtctg acccaatgct gacctaatgt 2401  tggccattcc acattgaggg gacaaggtca gtgatgcccc ccttcactca caagcacttc 2461  agaggcatgc agagagaagg gacactcggc cagctctctg aggtaatcag tgcaaggagg 2521  agtccgtttt ttgccagcaa acctcagcag gatcacactg aacagaacc tggtcatacc 2581  tgtgacaaca cagctgtgag ccagggcaaa ccacccactg tcactggctc gagagtctgg 2641  gcagaggctc tgaccctcca ccctttaaac tggatgccgg ggcctggctg ggcccaatgc 2701  caagtggtta tggcaaccct gactatctgg tcttaacatg tagctcagga agtggaggcg 2761  ctaatgtccc caatccctgg ggattcctga ttccagctat tcatgtaagc agagccaacc 2821  tgcctatttc tgtaggtgcg actgggatgt taggagcaca gcaaggaccc agctctgtag 2881  ggctggtgac ctgatacttc tcataatggc atctagaagt taggctgagt tggcctcact 2941  ggcccagcaa accagaactt gtctttgtcc gggccatgtt cttgggctgt cttctaattc 3001  caaagggttg gttggtaaag ctccacccc ttctcctctg cctaaagaca tcacatgtgt 3061  atacacacac gggtgtatag atgagttaaa agaatgtcct cgctggcatc taattttgt 3121  cttaagtttt tttggaggga gaaaggaaca aggcaaggga agatgtgtag ctttggcttt 3181  aaccaggcag cctgggggct cccaagccta tggaaccctg gtacaaagaa gagaacagaa 3241  gcgccctgtg aggagtggga tttgtttttc tgtagaccag atgagaagga aacaggccct 3301  gttttgtaca tagttgcaac ttaaaatttt tggcttgcaa atatttttg taataaagat 3361  ttctgggtaa caataaaaaa aaaaaaaa
```

[SEQ ID NO: 23]
Translation = MEPAGPAPGRLGPLLLCLLLSASCFCTGATGKELKVTQPEKSVS
VAAGDSTVLNCTLTSLLPVGPIRWYRGVGPSRLLIYSFAGEYVPRIRNVSDTTKRNNM
DFSIRISNVTPADAGIYYCVKFQKGSSEPDTEIQSGGGTEVYVLDNNATHNWNVFIGV
GVACALLVVLLMAALYLLRIKQKKAKGSTSSTRLHEPEKNAREITQVQSLIQDTNDIN
DITYADLNLPKEKKPAPRAPEPNNHTEYASIETGKVPRPEDTLTYADLDMVHLSRAQP
APKPEPSFSEYASVQVQRK LOCUS           NM_001291022 3020 bp mRNA linear ROD 15-FEB-2015

DEFINITION      *Mus musculus* signal-regulatory protein alpha (Sirpa),
                Transcript variant 7, mRNA.

ACCESSION       NM_001291022

VERSION         NM_001291022.1 GI:597436963

SOURCE          *Mus musculus* (house mouse)

[SEQ ID NO: 24]

```
   1 cgggaaggtg cgggcgcgag gaggggcgc tcggccgggc cgccctcgcg ctggcctcgc
  61 gacggctccg cacagcccgc actcgctctg cgagctgtcc ccgctcgcgc ttgctctccg
 121 atctccgtcc ccgctccctc tccctcttcc tctccccctc tttccttctc cctcgctatc
 181 cgctcccccg cccccgtgcc tctggtctg cgcctggctc cctcgggtcc gctcccctt
 241 cccgccggcc tggcccggcg tcacgctccc ggagtctccc cgctcggcgg cgtctcattg
 301 tgggagggg tcagatcacc ccgccgggcg gtggcgctgg ggggcagcgg aggggaggg
 361 gccttagtcg ttcgcccgcg ccgcccgccc gcctgccgag cgcgctcacc gccgctctcc
 421 ctccttgctc tgcagccgcg gcccatggag cccgccggcc cggcccctgg ccgcctaggg
 481 ccgctgctgc tctgcctgct gctctccgcg tcctgtttct gtacagataa taatgctacc
 541 cacaactgga atgtcttcat cggtgtgggc gtggcgtgtg ctttgctcgt agtcctgctg
 601 atggctgctc tctacctcct ccggatcaaa cagaagaaag ccaagggtc aacatcttcc
 661 acacggttgc acgagcccga gaagaacgcc agggaaataa cccagatcca ggacacaaat
 721 gacatcaacg acatcacata cgcagacctg aatctgccca agagaagaa gcccgcaccc
 781 cgggcccctg agcctaacaa ccacacagaa tatgcaagca ttgagacagg caaagtgcct
 841 aggccagagg atacccctcac ctatgctgac ctggacatgg tccacctcag ccgggcacag
 901 ccagccccca agcctgagcc atctttctca gagtatgcta gtgtccaggt ccagaggaag
 961 tgaatgggc gtggtctgt actaggcccc atccccacaa gttttcttgt cctacatgga
1021 gtggccatga cgaggacatc cagccagcca atcctgtccc cagaaggcca ggtggcacgg
1081 gtcctaggac caggggtaag ggtggcctttt gtcttccctc cgtggctctt caacacctct
1141 tgggcaccca cgtccccttc ttccggaggc tgggtgttgc agaaccagag ggcgaactgg
1201 agaaagctgc ctggaatcca agaagtgttg tgcctcggcc catcactcgt gggtctggat
1261 cctggtcttg gcaacccag gttgcgtcct tgatgttcca gagcttggtc ttctgtgtgg
1321 agaagagctc accatctcta cccaacttga gctttgggac cagactccct ttagatcaaa
1381 ccgccccatc tgtggaagaa ctacaccaga agtcagcaag ttttcagcca acagtgctgg
1441 cctccccacc tcccaggctg actagccctg gggagaagga accctctcct cctagaccag
1501 cagagactcc ctgggcatgt tcagtgtggc cccactcccc ttccagtccc agcttgcttc
1561 ctccagctag cactaactca gcagcatcgc tctgtggacg cctgtaaatt attgagaaat
1621 gtgaactgtg cagtcttaaa gctaaggtgt tagaaaattt gatttatgct gtttagttgt
1681 tgttgggttt cttttctttt taatttcttt ttcttttttg atttttttc tttcccttaa
```

-continued

```
1741  aacaacagca gcagcatctt ggctctttgt catgtgttga atggttgggt cttgtgaagt
1801  ctgaggtcta acagtttatt gtcctggaag gattttctta cagcagaaac agattttttt
1861  caaattccca gaatcctgag gaccaagaag gatccctcag ctgctacttc cagcacccag
1921  cgtcactggg acgaaccagg ccctgttctt acaaggccac atggctggcc ctttgcctcc
1981  atggctactg tggtaagtgc agccttgtct gacccaatgc tgacctaatg ttggccattc
2041  cacattgagg ggacaaggtc agtgatgccc ccttcactc acaagcactt cagaggcatg
2101  cagagagaag ggacactcgg ccagctctct gaggtaatca gtgcaaggag gagtccgttt
2161  tttgccagca aacctcagca ggatcacact ggaacagaac ctggtcatac ctgtgacaac
2221  acagctgtga gccagggcaa accacccact gtcactggct cgagagtctg ggcagaggct
2281  ctgaccctcc acccttaaa ctggatgccg gggcctggct gggcccaatg ccaagtggtt
2341  atggcaaccc tgactatctg gtcttaacat gtagctcagg aagtggaggc gctaatgtcc
2401  ccaatccctg gggattcctg attccagcta ttcatgtaag cagagccaac ctgcctattt
2461  ctgtaggtgc gactgggatg ttaggagcac agcaaggacc cagctctgta gggctggtga
2521  cctgatactt ctcataatgg catctagaag ttaggctgag ttggcctcac tggcccagca
2581  aaccagaact tgtctttgtc cgggccatgt tcttgggctg tcttctaatt ccaaagggtt
2641  ggttggtaaa gctccacccc cttctcctct gcctaaagac atcacatgtg tatacacaca
2701  cgggtgtata gatgagttaa aagaatgtcc tcgctggcat cctaattttg tcttaagttt
2761  ttttggaggg agaaaggaac aaggcaaggg aagatgtgta gctttggctt taaccaggca
2821  gcctggggc tcccaagcct atggaaccct ggtacaaaga agagaacaga agcgccctgt
2881  gaggagtggg atttgttttt ctgtagacca gatgagaagg aaacaggccc tgttttgtac
2941  atagttgcaa cttaaaattt ttggcttgca aaatattttt gtaataaaga tttctgggta
3001  acaataaaaa aaaaaaaaa
```

[SEQ ID NO: 25]
Translation = MEPAGPAPGRLGPLLLCLLLSASCFCTDNNATHNWNVFIGVVA
CALLVVLLMAALYLLRIKQKKAKGSTSSTRLHEPEKNAREITQIQDINDINDITYADL
NLPKEKKPAPRAPEPNNHTEYASIETGKVPRPEDILTYADLDMVHLSRAQPAPKPEPS
FSEYASVQVQRK

| | |
|---|---|
| LOCUS | NM_009020 3393 bp mRNA linear ROD 15-FEB-2015 |
| DEFINITION | *Mus musculus* recombination activating gene 2 (Rag2), mRNA. |
| ACCESSION | NM_009020 |
| VERSION | NM_009020.3 GI:144227233 |
| SOURCE | *Mus musculus* (house mouse) |

[SEQ ID NO: 26]
```
   1  actctaccct gcagccttca gcttggcaca aactaaacag tgactcttcc ccaagtgccg
  61  agtttaattc ctggcttggc cgaaaggatt cagagaggga taagcagccc ctctggcctt
 121  cagtgccaaa ataagaaaga gtatttcaca tccacaagca ggaagtacac ttcataccctc
 181  tctaagataa aagacctatt cacaatcaaa aatgtccctg cagatggtaa cagtgggtca
 241  taacatagcc ttaattcaac caggcttctc acttatgaat tttgatggcc aagttttctt
 301  ctttggccag aaaggctggc ctaagagatc ctgtcctact ggagtctttc attttgatat
 361  aaaacaaaat catctcaaac tgaagcctgc aatcttctct aaagattcct gctacctccc
 421  acctcttcgt tatccagcta cttgctcata caaggcagc atagactctg acaagcatca
 481  atatatcatt cacggaggga aaacaccaaa caatgagctt tccgataaga tttatatcat
```

```
 541  gtctgtcgct tgcaagaata acaaaaaagt tactttccgt tgcacagaga aagacttagt
 601  aggagatgtc cctgaaccca gatacggcca ttccattgac gtggtgtata gtcgagggaa
 661  aagcatgggt gttctctttg gaggacgttc atacatgcct tctacccaga gaaccacaga
 721  aaaatggaat agtgtagctg actgcctacc ccatgttttc ttgatagatt ttgaatttgg
 781  gtgtgctaca tcatatattc tcccagaact tcaggatggg ctgtcttttc atgtttctat
 841  tgccagaaac gataccgttt atattttggg aggacactca cttgccagta atatacgccc
 901  tgctaacttg tatagaataa gagtggacct tccectgggt accccagcag tgaattgcac
 961  agtcttgcca ggaggaatct ctgtctccag tgcaatcctc actcaaacaa acaatgatga
1021  atttgttatt gtgggtggtt atcagctgga aaatcagaaa aggatggtct gcagccttgt
1081  ctctctaggg gacaacacga ttgaaatcag tgagatggag actcctgact ggacctcaga
1141  tattaagcat agcaaaatat ggtttggaag caacatggga aacgggacta ttttccttgg
1201  cataccagga gacaataagc aggctatgtc agaagcattc tatttctata ctttgagatg
1261  ctctgaagag gatttgagtg aagatcagaa aattgtctcc aacagtcaga catcaacaga
1321  agatcctggg gactccactc cctttgaaga ctcagaggaa ttttgtttca gtgctgaagc
1381  aaccagtttt gatggtgacg atgaatttga cacctacaat gaagatgatg aagatgacga
1441  gtctgtaacc ggctactgga taacatgttg ccctacttgt gatgttgaca tcaatacctg
1501  ggttccgttc tattcaacgg agctcaataa acccgccatg atctattgtt ctcatgggga
1561  tgggcactgg gtacatgccc agtgcatgga tttggaagaa cgcacactca tccacttgtc
1621  agaaggaagc aacaagtatt attgcaatga acatgtacag atagcaagag cattgcaaac
1681  tcccaaaaga accccccct tacaaaaacc tccaatgaaa tccctccaca aaaaaggctc
1741  tgggaaagtc ttgactcctg ccaagaaatc cttccttaga agactgtttg attaatttag
1801  caaaagcccc tcagactcag gtatattgct ctctgaatct actttcaatc ataaacatta
1861  ttttgatttt tgtttactga aatctctatg ttatgtttta gttatgtgaa ttaagtgctg
1921  ttgtgattta ttgttaagta taactattct aatgtgtgtt ttttaacatc ttatccagga
1981  atgtcttaaa tgagaaatgt tatacagttt tccattaagg atatcagtga taaagtatag
2041  aactcttaca ttattttgta acaatctaca tattgaatag taactaaata ccaataaata
2101  aactaatgca caaaaagtta agttcttttg tgtaataagt agcctatagt tggtttaaac
2161  agttaaaacc aacagctata tcccacacta ctgctgttta taaattttaa ggtggcctct
2221  ggtttatact tatgagcaga attatatata ttggtcaata ccatgaagaa aaatttaatt
2281  ctatatcaag ccaggcatgg tgatggtgat acatgcctgt aatcctggca cttaggaagt
2341  ggaagaagga agtttgtgag tttgatgctt gttgaggtat gaccttttgc tatgtattgt
2401  agtgtatgag ccccaagacc tgcttgaccc agagacaaga gagtccacac atagatccaa
2461  gtaatgctat gtgaccttgc ccccgggtta cttgtgatta ggtgaataaa gatgtcaaca
2521  gccaatagct gggcagaaga gccaaaagtg gggattgagg gtaccctggc ttgatgtagg
2581  aggagaccat gaggaaaggg gagaaaaaag tgatggagga ggagaaagat gccatgagct
2641  aggagttaag aaagcatggc catgagtgct ggccaattgg agttaagagc agcccagatg
2701  aaacatagta agtaataact cagggttatc gatagaaaat agatttagt gccgtactct
2761  ccccagccct agagctgact atggcttact gtaaatataa agtttgtatg tgtcttttat
2821  ccaggaacta aatggtcaaa ggtggagtag aaactctgga ttgggattaa atttttctac
```

-continued

```
2881   aacaaatgct ggcctgggct agattttatc tcatatccga aggctgacag aacacagagc 2941   actggtaaca ttgccacctg ccatgcacaa agacctgagt ctaatactgt ggacattttc 3001   ttgaagtatc tacatgtact tctggagtga aaacatattc caacaatatg cctttgttta 3061   aatcactcac tcactttggg ccctcacatt atatcctttc aaaatcaatg gttcacccct 3121   ttgaaaatgc ttagccatag tccctcatct tccttaaaga cagttgtcat ctctggaaat 3181   agtcacatgt cattcaaggt ccaatactgt gcagctctga agtatggcat taccacttta 3241   agtgaaaagt gaaatatgaa catgagctca gacaaaggtt tgggactatc actctcaagg 3301   aggctctact gctaagtcct gaactgcttt cacatgaata cagaaattat aacaaaaaat 3361   atgtaatcaa taaaagaaa actttcatat tcc
```

[SEQ ID NO: 27]
Translation = MSLQMVTVGHNIALIQPGFSLMNFDGQVFFFGQKGWPKRSCPTG
VFHFDIKQNHLKLKPAIFSKDSCYLPPLRYPATCSYKGSIDSDKHQYIIHGGKTPNNE
LSDKIYIMSVACKNNKKVTFRCTEKDLVGDVPEPRYGHSIDVVYSRGKSMGVLFGGRS
YMPSTQRTTEKWNSVADCLPHVFLIDFEFGCATSYILPELQDGLSFHVSIARNDTVYI
LGGHSLASNIRPANLYRIRVDLPLGTPAYNCTVLPGGISVSSAILTQTNNDEFVIVGG
YQLENQKRMVCSLVSLGDNTIEISEMETPDWTSDIKHSKIWFGSNMGNGTIFLGIPGD
NKQAMSEAFYFYTLRCSEEDLSEDQKIVSNSQTSTEDPGDSTPFEDSEEFCFSAEATS
FDGDDEFDTYNEDDEDDESVTGYWITCCPTCDVDINTWVPFYSTELNKPAMIYCSHGD
GHWVHAQCMDLEERTLIHLSEGSNKYYCNEHVQIARALQTPKRNPPLQKPPMKSLHKK
GSGKVLTPAKKSFLRRLFD

```
LOCUS       NM_013563  1612 bp mRNA linear ROD 15-FEB-2015
DEFINITION  Mus musculus interleukin 2 receptor, gamma chain (Il2rg),
            mRNA.
ACCESSION   NM_013563
VERSION     NM_013563.3  GI:118129799
SOURCE      Mus musculus (house mouse)
```

[SEQ ID NO: 28]
```
   1   gacacagact acacccagag aaagaagagc aagcaccatg ttgaaactat tattgtcacc 61   tagatccttc ttagtccttc agctgctcct gctgagggca gggtggagct ccaaggtcct 121   catgtccagt gcgaatgaag acatcaaagc tgatttgatc ctgacttcta cagcccctga 181   acacctcagt gctcctactc tgccccttcc agaggttcag tgctttgtgt tcaacataga 241   gtacatgaat tgcacttgga atagcagttc tgagcctcag caaccaacc tcacgctgca 301   ctataggtac aaggtatctg ataataatac attccaggag tgcagtcact atttgttctc 361   caaagagatt acttctggct gtcagataca aaagaagat atccagctct accagacatt 421   tgttgtccag ctccaggacc ccagaaacc cagaggcga gctgtacaga agctaaacct 481   acagaatctt gtgatcccac gggctccaga aaatctaaca ctcagcaatc tgagtgaatc 541   ccagctagag ctgagatgga aaagcagaca tattaaagaa cgctgtttac aatacttggt 601   gcagtaccgg agcaacagag atcgaagctg gacggaacta atagtgaatc atgaacctag 661   attctccctg cctagtgtgg atgagctgaa acgtacaca tttcgggttc ggagccgcta 721   taacccaatc tgtggaagtt ctcaacagtg gagtaaatgg agccagcctg tccactgggg 781   gagtcatact gtagaggaga tccttccttt gtttgcactg gaagctgtgc ttatccctgt 841   tggcaccatg gggttgatta ttaccctgat ctttgtgtac tgttggttgg aacgaatgcc 901   tccaattccc cccatcaaga atctagagga tctggttact gaataccaag gaacttttc 961   ggcctggagt ggtgtgtcta aagggctgac tgagagtctg cagccagact acagtgaacg 1021   gttctgccac gtcagcgaga ttcccccaa aggaggggcc ctaggagagg ggcctggagg 1081   ttctccttgc agcctgcata gcccttactg gcctccccca tgttattctc tgaagccgga
```

```
1141 agcctgaaca tcaatccttt gatggaacct caaagtccta tagtcctaag tgacgctaac 1201 ctcccctact caccttggca atctggatcc aatgctcact gccttccctt ggggctaagt 1261 ttcgatttcc tgtcccatgt aactgctttt ctgttccata tgccctactt gagagtgtcc 1321 cttgccctct ttccctgcac aagccctccc atgcccagcc taacaccttt ccactttctt 1381 tgaagagagt cttaccctgt agcccagggt ggctgggagc tcactatgta ggccaggttg 1441 gcctccaact cacaggctat cctcccacct ctgcctcata agagttgggg ttactggcat 1501 gcaccaccac acccagcatg gtccttctct tttataggat ctccctccc tttttctacc 1561 tatgattcaa ctgtttccaa atcaacaaga aataaagttt taaccaatg at
```

[SEQ ID NO: 29]
Translation = MLKLLLSPRSFLVLQLLLLRAGWSSKVLMSSANEDIKADLILTS
TAPEHLSAPTLPLPEVQCFVFNIEYMNCTWNSSSEPQATNLILHYRYKVSDNNTFQEC
SHYLFSKEITSGCQIQKEDIQLYQTFVVQLQDPQKPQRRAVQKLNLQNLVIPRAPENL
ILSNLSESQLELRWKSRHIKERCLQYLVLVQYRSNRDRSWIELIVNHEPRFSLPSVDELK
RYTFRVRSRYNPICGSSQQWSKWSQPVHWGSHIVEENPSLFALEAVLIPVGIMGLIIT
LIFVYCWLERMPPIPPIKNLEDLVTEYQGNFSAWSGVSKGLIESLQPDYSERFCHVSE
IPPKGGALGEGPGGSPCSLHSPYWPPPCYSLKPEA

```
LOCUS       NM_000585 2012 bp mRNA linear PRI 15-MAR-2015
DEFINITION  Homo sapiens interleukin 15 (IL15), transcript variant
            3, mRNA.
ACCESSION   NM_000585
VERSION     NM_000585.4 GI:323098327
SOURCE      Homo sapiens (human)
```

[SEQ ID NO: 30]
```
   1 gttgggactc cgggtggcag gcgcccgggg gaatcccagc tgactcgctc actgccttcg 61 aagtccggcg ccccccggga gggaactggg tggccgcacc ctcccggctg cggtggctgt 121 cgcccccccac cctgcagcca ggactcgatg gagaatccat tccaatatat ggccatgtgg 181 ctctttggag caatgttcca tcatgttcca tgctgctgac gtcacatgga gcacagaaat 241 caatgttagc agatagccag cccatacaag atcgtattgt attgtaggag gcattgtgga 301 tggatggctg ctggaaaccc cttgccatag ccagctcttc ttcaatactt aaggatttac 361 cgtggctttg agtaatgaga atttcgaaac cacatttgag aagtatttcc atccagtgct 421 acttgtgttt acttctaaac agtcattttc taactgaagc tggcattcat gtcttcattt 481 tgggctgttt cagtgcaggg cttcctaaaa cagaagccaa ctgggtgaat gtaataagtg 541 atttgaaaaa aattgaagat cttattcaat ctatgcatat tgatgctact ttatatacgg 601 aaagtgatgt tcaccccagt tgcaaagtaa cagcaatgaa gtgctttctc ttggagttac 661 aagttatttc acttgagtcc ggagatgcaa gtattcatga tacagtagaa aatctgatca 721 tcctagcaaa caacagtttg tcttctaatg ggaatgtaac agaatctgga tgcaaagaat 781 gtgaggaact ggaggaaaaa aatattaaag aattttttgca gagttttgta catattgtcc 841 aaatgttcat caacacttct tgattgcaat tgattctttt taaagtgttt ctgttattaa 901 caaacatcac tctgctgctt agacataaca aaacactcgg catttcaaat gtgctgtcaa 961 aacaagtttt tctgtcaaga agatgatcag accttggatc agatgaactc ttagaaatga 1021 aggcagaaaa atgtcattga gtaatatagt gactatgaac ttctctcaga cttactttac 1081 tcatttttt aatttattat tgaaattgta catatttgtg gaataatgta aatgttgaa 1141 taaaatatg tacaagtgtt gtttttttaag ttgcactgat attttacctc ttattgcaaa 1201 atagcatttg tttaagggtg atagtcaaat tatgtattgg tggggctggg taccaatgct
```

```
1261  gcaggtcaac agctatgctg gtaggctcct gccagtgtgg aaccactgac tactggctct
1321  cattgacttc cttactaagc atagcaaaca gaggaagaat tgttatcag taagaaaaag
1381  aagaactata tgtgaatcct cttctttata ctgtaattta gttattgatg tataaagcaa
1441  ctgttatgaa ataaagaaat tgcaataact ggcatataat gtccatcagt aaatcttggt
1501  ggtggtggca ataataaact tctactgata ggtagaatgg tgtgcaagct tgtccaatca
1561  cggattgcag gccacatgcg gcccaggaca actttgaatg tggcccaaca caaattcata
1621  aactttcata catctcgttt ttagctcatc agctatcatt agcggtagtg tatttaaagt
1681  gtggcccaag acaattcttc ttattccaat gtggcccagg gaaatcaaaa gattggatgc
1741  ccctggtata gaaaactaat agtgacagtg ttcatatttc atgctttccc aaatacaggt
1801  attttatttt cacattcttt ttgccatgtt tatataataa taagaaaaaa ccctgttgat
1861  ttgttggagc cattgttatc tgacagaaaa taattgttta tattttttgc actacactgt
1921  ctaaaattag caagctctct tctaatggaa ctgtaagaaa gatgaaatat ttttgtttta
1981  ttataaattt atttcacctt aaaaaaaaaa aa
```

[SEQ ID NO: 31]
Translation = MRISKPHLRSISIQCYLCLLLNSHFLTEAGIHVFILGCFSAGLP
KTEANWVNVISDLKKIEDLIQSMHIDATLYTESDVHPSCKVTAMKCFLLELQVISLES
GDASIHDTVENLIILANNSLSSNGNVTESGCKECEELEEKNIKEFLQSFVHIVQMFIN
TS

| | | |
|---|---|---|
| LOCUS | NM_172175 2333 bp mRNA linear PRI 15-MAR-2015 | |
| DEFINITION | Homo sapiens interleukin 15 (IL15), transcript variant 2, mRNA. | |
| ACCESSION | NM_172175 | |
| VERSION | NM_172175.2 GI:323098328 | |
| SOURCE | Homo sapiens (human) | |

[SEQ ID NO: 32]
```
   1  gttgggactc cgggtggcag gcgcccgggg gaatcccagc tgactcgctc actgccttcg
  61  aagtccggcg ccccccggga gggaactggg tggccgcacc ctccggctg cggtggctgt
 121  cgccccccac cctgcagcca ggactcgatg gagaatccat tccaatatat ggccatgtgg
 181  ctctttggag caatgttcca tcatgttcca tgctgctgac gtcacatgga gcacagaaat
 241  caatgttagc agatagccag cccatacaag atcgttttca actagtggcc ccactgtgtc
 301  cggaattgat gggttcttgg tctcactgac ttcaagaatg aagccgcgga ccctcgcggt
 361  gagtgttaca gctcttaagg tggcgcatct ggagtttgtt ccttctgatg ttcggatgtg
 421  ttcggagttt cttccttctg gtgggttcgt ggtctcgctg gctcaggagt gaagctacag
 481  accttcgcgg aggcattgtg atggatggc tgctggaaac ccttgccat agccagctct
 541  tcttcaatac ttaaggattt accgtggctt gagtaatga atttcgaa accacatttg
 601  agaagtattt ccatccagtg ctacttgtgt ttacttctaa acagtcattt tctaactgaa
 661  gctggcattc atgtcttcat tttgggatgc agctaatata cccagttggc caaagcacc
 721  taacctatag ttatataatc tgactctcag ttcagttta ctctactaat gccttcatgg
 781  tattgggaac catagatttg tgcagctgtt tcagtgcagg gcttcctaaa acagaagcca
 841  actgggtgaa tgtaataagt gatttgaaaa aaattgaaga tcttattcaa tctatgcata
 901  ttgatgctac tttatatacg gaaagtgatg ttcaccccag ttgcaaagta acagcaatga
 961  agtgctttct cttggagtta caagttattc cacttgagtc cggagatgca agtattcatg
```

-continued

```
1021  atacagtaga aaatctgatc atcctagcaa acaacagttt gtcttctaat gggaatgtaa
1081  cagaatctgg atgcaaagaa tgtgaggaac tggaggaaaa aaatattaaa gaattttgc
1141  agagttttgt acatattgtc caaatgttca tcaacacttc ttgattgcaa ttgattcttt
1201  ttaaagtgtt tctgttatta acaaacatca ctctgctgct tagacataac aaaacactcg
1261  gcatttcaaa tgtgctgtca aaacaagttt ttctgtcaag aagatgatca gaccttggat
1321  cagatgaact cttagaaatg aaggcagaaa aatgtcattg agtaatatag tgactatgaa
1381  cttctctcag acttacttta ctcatttttt taatttatta ttgaaattgt acatatttgt
1441  ggaataatgt aaaatgttga ataaaaatat gtacaagtgt tgttttttaa gttgcactga
1501  tattttacct cttattgcaa aatagcattt gtttaagggt gatagtcaaa ttatgtattg
1561  gtggggctgg gtaccaatgc tgcaggtcaa cagctatgct ggtaggctcc tgccagtgtg
1621  gaaccactga ctactggctc tcattgactt ccttactaag catagcaaac agaggaagaa
1681  tttgttatca gtaagaaaaa gaagaactat atgtgaatcc tcttctttat actgtaattt
1741  agttattgat gtataaagca actgttatga aataaagaaa ttgcaataac tggcatataa
1801  tgtccatcag taaatcttgg tggtggtggc aataataaac ttctactgat aggtagaatg
1861  gtgtgcaagc ttgtccaatc acggattgca ggccacatgc ggcccaggac aactttgaat
1921  gtggcccaac acaaattcat aaactttcat acatctcgtt tttagctcat cagctatcat
1981  tagcggtagt gtatttaaag tgtggcccaa gcaattctt cttattccaa tgtggcccag
2041  ggaaatcaaa agattggatg ccctggtat agaaaactaa tagtgacagt gttcatattt
2101  catgctttcc caaatacagg tattttattt tcacattctt tttgccatgt ttatataata
2161  ataaagaaaa accctgttga tttgttggag ccattgttat ctgacagaaa ataattgttt
2221  atattttttg cactacactg tctaaaatta gcaagctctc ttctaatgga actgtaagaa
2281  agatgaaata ttttgttttt attataaatt tatttcaccct taaaaaaaaa aaa
```

[SEQ ID NO: 33]
Translation = MVLGTIDLCSCFSAGLPKTEANWVNVISDLKKIEDLIQSMHIDA
TLYTESDVHPSCKVTAMKCFLLELQVISLESGDASIHDTVENLIILANNSLSSNGNVT
ESGCKECEELEEKNIKEFLQSFVHIVQMFINTS

```
LOCUS           NM_008357 1297 bp mRNA linear ROD 15-FEB-2015
DEFINITION      Mus musculus interleukin 15 (Il15), transcript variant
                1, mRNA.
ACCESSION       NM_008357
VERSION         NM_008357.2  GI:363000959
SOURCE          Mus musculus (house mouse)
```

[SEQ ID NO: 34]
```
  1  ttcttgacca agacttcaat actcagtggc actgtattcc ccttctgtcc agccactctt
 61  ccccagagtt ctcttcttca tcctcccct tgcagagtag ggcagcttgc aggtcctcct
121  gcaagtctct cccaattctc tgcgcccaaa agactgcag tgcatctcct acgcgctgc
181  agggaccttg ccagggcagg actgccccg cccagttgca gagttggacg aagacgggat
241  cctgctgtgt ttggaaggct gagttccaca tctaacagct cagagaggtc aggaaagaat
301  ccaccttgac acatggccct ctggctcttc aaagcactgc ctcttcatgg tccttgctgg
361  tgaggtcctt aagaacacag aaacccatgt cagcagataa ccagcctaca ggaggccaag
421  aagagttctg gatggatggc agctggaagc ccatcgccat agccagctca tcttcaacat
481  tgaagctctt acctgggcat taagtaatga aaattttgaa accatatatg aggaatacat
```

-continued

```
 541 ccatctcgtg ctacttgtgt ttccttctaa acagtcactt tttaactgag gctggcattc
 601 atgtcttcat tttgggctgt gtcagtgtag gtctccctaa aacagaggcc aactggatag
 661 atgtaagata tgacctggag aaaattgaaa gccttattca atctattcat attgacacca
 721 ctttatacac tgacagtgac tttcatccca gttgcaaagt tactgcaatg aactgctttc
 781 tcctggaatt gcaggttatt ttacatgagt acagtaacat gactcttaat gaaacagtaa
 841 gaaacgtgct ctaccttgca aacagcactc tgtcttctaa caagaatgta gcagaatctg
 901 gctgcaagga atgtgaggag ctggaggaga aaaccttcac agagttttg caaagcttta
 961 tacgcattgt ccaaatgttc atcaacacgt cctgactgca tgcgagcctc ttccgtgttt
1021 ctgttattaa ggtacctcca cctgctgctc agaggcagca cagctccatg catttgaaat
1081 ctgctgggca aactaagctt cctaacaagg ataatgag ccacttggat cacatgaaat
1141 cttggaaatg aagagaggaa aagagctcgt ctcagactta ttttgcttg cttattttta
1201 atttattgct tcatttgtac atatttgtaa tataacagaa gatgtggaat aaagttgtat
1261 ggatattta tcaattgaaa tttaaaaaaa aaaaaaa
```

[SEQ ID NO: 35]
Translation = MKILKPYMRNTSISCYLCFLLNSHFLTEAGIHVFILGCVSVGLP
KTEANWIDVRYDLEKIESLIQSIHIDTTLYTDSDFHPSCKVTAMNCFLLELQVILHEY
SNMTLNETVRNVLYLANSTLSSNKNVAESGCKECEELEEKTFTEFLQSFIRIVQMFIN
TS

| | |
|---|---|
| LOCUS | NM_001254747 1287 bp mRNA linear ROD 15-FEB-2015 |
| DEFINITION | *Mus musculus* interleukin 15 (Il15), transcript variant 2, mRNA. |
| ACCESSION | NM_001254747 |
| VERSION | NM_001254747.1 GI:363000983 |
| SOURCE | *Mus musculus* (house mouse) |

[SEQ ID NO: 36]
```
   1 ttcttgacca agacttcaat actcagtggc actgtattcc ccttctgtcc agccactctt
  61 ccccagagtt ctcttcttca tcctccccct tgcagagtag ggcagcttgc aggtcctcct
 121 gcaagtctct cccaattctc tgcgcccaaa agactgcag tgcatctcct acgcgctgc
 181 agggaccttg ccagggcagg actgcccccg cccagttgca gagttggacg aagacgggat
 241 cctgctgtgt ttggaaggct gagttccaca tctaacagct cagagagaat ccaccttgac
 301 acatggccct ctggctcttc aaagcactgc ctcttcatgg tccttgctgg tgaggtcctt
 361 aagaacacag aaacccatgt cagcagataa ccagcctaca ggaggccaag aagagttctg
 421 gatggatggc agctggaagc ccatcgccat agccagctca tcttcaacat tgaagctctt
 481 acctgggcat taagtaatga aaattttgaa accatatatg aggaatacat ccatctcgtg
 541 ctacttgtgt ttccttctaa acagtcactt tttaactgag gctggcattc atgtcttcat
 601 tttgggctgt gtcagtgtag gtctccctaa aacagaggcc aactggatag atgtaagata
 661 tgacctggag aaaattgaaa gccttattca atctattcat attgacacca ctttatacac
 721 tgacagtgac tttcatccca gttgcaaagt tactgcaatg aactgctttc tcctggaatt
 781 gcaggttatt ttacatgagt acagtaacat gactcttaat gaaacagtaa gaaacgtgct
 841 ctaccttgca aacagcactc tgtcttctaa caagaatgta gcagaatctg gctgcaagga
 901 atgtgaggag ctggaggaga aaaccttcac agagttttg caaagcttta tacgcattgt
 961 ccaaatgttc atcaacacgt cctgactgca tgcgagcctc ttccgtgttt ctgttattaa
1021 ggtacctcca cctgctgctc agaggcagca cagctccatg catttgaaat ctgctgggca
```

```
1081   aactaagctt cctaacaagg agataatgag ccacttggat cacatgaaat cttggaaatg 1141   aagagaggaa aagagctcgt ctcagactta tttttgcttg cttattttta atttattgct 1201   tcatttgtac atatttgtaa tataacagaa gatgtggaat aaagttgtat ggatatttta 1261   tcaattgaaa tttaaaaaaa aaaaaaa
```

[SEQ ID NO: 35]
Translation = MKILKPYMRNTSISCYLCFLLNSHFLTEAGIHVFILGCVSVGLP
KTEANWIDVRYDLEKIESLIQSIHIDTTLYTDSDFHPSCKVTAMNCFLLELQVILHEY
SNMTLNETVRNVLYLANSTLSSNKNVAESGCKECEELEEKTFTEFLQSFIRIVQMFIN
TS

That which is claimed is:

1. A genetically modified mouse, comprising:
   a null mutation in the mouse SIRPα gene at the mouse SIRPα gene locus and a nucleic acid sequence encoding a human SIRPα protein incorporated into the genome of the genetically modified mouse and operably linked to an endogenous mouse SIRPα gene promoter at the mouse SIRPα gene locus; and
   a null mutation in the mouse IL-15 gene at the mouse IL-15 gene locus and a nucleic acid sequence encoding a human IL-15 protein incorporated into the genome of the genetically modified mouse and is operably linked to an endogenous mouse IL-15 gene promoter at the mouse IL-15 gene locus,
   wherein the genetically modified mouse expresses the human SIRPα protein and the human IL-15 protein, and
   wherein the genetically modified mouse is immunodeficient and comprises a Rag2 gene knock-out and an IL2rg gene knock-out, a Rag2 gene knock-out, or an IL2rg gene knock-out.

2. The genetically modified mouse according to claim 1, wherein the null mutation is a deletion of at least mouse SIRPα exons 2-4 and wherein the genetically modified mouse is heterozygous for the allele comprising the nucleic acid sequence encoding the human SIRPα protein.

3. The genetically modified mouse according to claim 1, wherein the null mutation is a deletion of at least mouse SIRPα exons 2-4 and wherein the genetically modified mouse is homozygous for the allele comprising the nucleic acid sequence encoding the human SIRPα protein.

4. The genetically modified mouse according to claim 1, wherein the human SIRPα protein is a functional fragment of a full length human SIRPα protein.

5. The genetically modified mouse according to claim 4, wherein the functional fragment comprises an extracellular domain of human SIRPα.

6. The genetically modified mouse according to claim 1, wherein the human IL-15 protein is a functional fragment of a full-length human IL-15 protein.

7. The genetically modified mouse according to claim 1, wherein the null mutation is a deletion of at least mouse IL-15 exons 5-8, wherein the genetically modified mouse is heterozygous for the allele comprising the nucleic acid sequence encoding the human IL-15 protein.

8. The genetically modified mouse according to claim 1, wherein the null mutation is a deletion of at least mouse IL-15 exons 5-8, wherein the genetically modified mouse is homozygous for the allele comprising the nucleic acid sequence that encodes the human IL-15 protein.

9. The genetically modified mouse according to claim 1, wherein the genetically modified mouse comprises an engraftment of human hematopoietic cells.

10. The genetically modified mouse according to claim 9, wherein the genetically modified mouse comprises an infection with a human pathogen.

11. The genetically modified mouse according to claim 10, wherein the human pathogen activates, induces and/or targets T cells.

12. The genetically modified mouse according to claim 10, wherein the human pathogen activates, induces and/or targets natural killer (NK) cells.

13. The genetically modified mouse according to claim 10, wherein the human pathogen is a pathogen that infects human intestine or the human lung.

14. An animal engraftment model, comprising a genetically modified mouse comprising:
   a null mutation in the mouse SIRPα gene at the mouse SIRPα gene locus and a nucleic acid sequence incorporated into the genome of the genetically modified mouse, which sequence encodes a human SIRPα protein and is operably linked to an endogenous mouse SIRPα gene promoter at the mouse SIRPα gene locus;
   a null mutation in the mouse IL-15 gene at the mouse IL-15 gene locus and a nucleic acid sequence incorporated into the genome of the genetically modified mouse, which sequence encodes a human IL-15 protein and is operably linked to an endogenous mouse IL-15 gene promoter at the mouse IL-15 gene locus; and
   an engraftment of human hematopoietic cells, wherein the genetically modified mouse (i) expresses the human SIRPα protein and the human IL-15 protein, and (ii) comprises human intraepithelial lymphocytes (IELs) in the lung or small intestine and Peyer's patches of the genetically modified mouse,
   wherein the genetically modified mouse is immunodeficient and comprises a Rag2 gene knock-out and an IL2rg gene knock-out, a Rag2 gene knock-out, or an IL2rg gene knock-out.

15. The engraftment model according to claim 14, wherein the null mutation is a deletion of at least mouse SIRPα exons 2-4, wherein the genetically modified mouse is heterozygous for the allele comprising the nucleic acid sequence that encodes the human SIRPα protein.

16. The engraftment model according to claim 14, wherein the null mutation is a deletion of at least mouse SIRPα exons 2-4, wherein the genetically modified mouse is homozygous for the allele comprising the nucleic acid sequence that encodes the human SIRPα protein.

17. The engraftment model according to claim 14, wherein the human SIRPα protein is a functional fragment of a full length human SIRPα protein and the human IL-15 protein is a functional fragment of a full-length human IL-15 protein.

18. The engraftment model according to claim 17, wherein the functional fragment comprises an extracellular domain of human SIRPα.

19. The engraftment model according to claim 14, wherein the null mutation is a deletion of at least mouse IL-15 exons 5-8, wherein the genetically modified mouse is heterozygous for the allele comprising the nucleic acid sequence that encodes the human IL-15 protein.

20. The engraftment model according to claim 14, wherein the null mutation is a deletion of at least mouse IL-15 exons 5-8, wherein the genetically modified mouse is homozygous for the allele comprising the nucleic acid sequence that encodes the human IL-15 protein.

* * * * *

UNITED STATES PATENT AND TRADEMARK OFFICE
CERTIFICATE OF CORRECTION

PATENT NO. : 11,576,356 B2
APPLICATION NO. : 16/782708
DATED : February 14, 2023
INVENTOR(S) : Dietmar Herndler-Brandstetter et al.

It is certified that error appears in the above-identified patent and that said Letters Patent is hereby corrected as shown below:

On the Title Page

Item [71], replace "Regeneren" with --Regeneron--

In the Specification

Column 3, Line 26, replace "an an" with --an--

Column 3, Line 27, replace "an an" with --an--

Column 3, Line 38, replace "the the" with --the--

Column 3, Line 41-42, replace "the the" with --the--

Column 3, Line 46, replace "the the" with --the--

Column 3, Line 50, replace "the the" with --the--

Column 5, Line 16, replace "an an" with --an--

Column 5, Line 17, replace "an an" with --an--

Column 6, Line 52, replace "an an" with --an--

Column 6, Line 53, replace "an an" with --an--

Column 15, Line 12, replace "hCD8-" with --hCD8+--

Column 41, Line 54, replace "cytoxicity" with --cytotoxicity--

Signed and Sealed this
Twenty-seventh Day of June, 2023

Katherine Kelly Vidal
*Director of the United States Patent and Trademark Office*

Column 60, Line 37, replace "CD9+" with --CD8+--

Column 60, Line 50, replace "11-15" with --IL-15--

Column 63, Line 50, replace "IL-15mRNA" with --IL-15 mRNA--

Column 65, Line 21, replace "the the" with --the--

Column 67, Line 14, replace "of of" with --of--